(12) United States Patent
Trullinger et al.

(10) Patent No.: US 9,006,446 B2
(45) Date of Patent: *Apr. 14, 2015

(54) PESTICIDAL COMPOSITIONS

(71) Applicant: Dow AgroSciences LLC, Indianapolis, IN (US)

(72) Inventors: Tony K. Trullinger, Westfield, IN (US); Ricky Hunter, Westfield, IN (US); Negar Garizi, Westfield, IN (US); Maurice C. H. Yap, Zionsville, IN (US); Ann M. Buysse, Carmel, IN (US); Dan Pernich, Indianapolis, IN (US); Timothy C. Johnson, Indianapolis, IN (US); Kristy Bryan, Carmel, IN (US); Carl Deamicis, Indianapolis, IN (US); Yu Zhang, Carmel, IN (US); Noormohamed M. Niyaz, Indianapolis, IN (US); CaSandra Lee McLeod, Indianapolis, IN (US); Ronald Ross, Jr., Zionsville, IN (US); Yuanming Zhu, Carmel, IN (US); Peter Lee Johnson, Indianapolis, IN (US); Joseph D. Eckelbarger, Carmel, IN (US); Marshall H. Parker, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/676,746

(22) Filed: Nov. 14, 2012

(65) Prior Publication Data
US 2013/0072382 A1   Mar. 21, 2013

Related U.S. Application Data

(63) Continuation of application No. 12/773,062, filed on May 4, 2010, now Pat. No. 8,350,044.

(60) Provisional application No. 61/175,659, filed on May 5, 2009.

(51) Int. Cl.
| | |
|---|---|
| *C07D 417/04* | (2006.01) |
| *C07D 417/14* | (2006.01) |
| *C07D 213/02* | (2006.01) |
| *A61K 31/445* | (2006.01) |
| *A01N 43/54* | (2006.01) |
| *A01N 43/78* | (2006.01) |
| *A01N 43/40* | (2006.01) |

(52) U.S. Cl.
CPC .............. *A01N 43/78* (2013.01); *C07D 417/04* (2013.01); *C07D 417/14* (2013.01); *A01N 43/40* (2013.01)

(58) Field of Classification Search
None
See application file for complete search history.

(56) References Cited

U.S. PATENT DOCUMENTS

| | | | |
|---|---|---|---|
| 4,080,457 A | 3/1978 | Harrison et al. | |
| 4,260,765 A | 4/1981 | Harrison et al. | |
| 4,536,506 A | 8/1985 | Marcoux et al. | |
| 5,556,859 A * | 9/1996 | Johnson | 514/256 |
| 5,597,836 A * | 1/1997 | Hackler et al. | 514/352 |
| 5,817,677 A | 10/1998 | Linz et al. | |
| 2002/0013326 A1 | 1/2002 | Tiebes et al. | |
| 2002/0083111 A1 | 6/2002 | Row et al. | |
| 2005/0176710 A1 | 8/2005 | Schwink et al. | |
| 2008/0004301 A1 | 1/2008 | Tamaki et al. | |
| 2011/0098287 A1 | 4/2011 | Bretschneider et al. | |
| 2011/0118290 A1 | 5/2011 | Bretschneider et al. | |
| 2011/0166129 A1 | 7/2011 | Machacek et al. | |
| 2011/0166143 A1 | 7/2011 | Bretschneider et al. | |
| 2011/0212949 A1 | 9/2011 | Bretschneider et al. | |
| 2011/0275583 A1 | 11/2011 | Bretschneider et al. | |
| 2011/0319428 A1 | 12/2011 | Fulein et al. | |
| 2012/0053146 A1 | 3/2012 | Parker et al. | |
| 2012/0095023 A1 | 4/2012 | Bretschneider et al. | |
| 2012/0110701 A1 | 5/2012 | Garizi et al. | |
| 2012/0110702 A1 | 5/2012 | Yap et al. | |

FOREIGN PATENT DOCUMENTS

| | | |
|---|---|---|
| EP | 97323 A2 | 4/1984 |
| EP | 1 321 463 A1 | 6/2003 |
| JP | 2003212864 A | 7/2003 |
| WO | 03072102 A1 | 9/2003 |
| WO | 2004041813 A1 | 5/2004 |
| WO | 2005074875 A2 | 8/2005 |
| WO | 2006023462 A1 | 3/2006 |
| WO | 2007087427 A2 | 8/2007 |
| WO | 2008005457 A2 | 1/2008 |
| WO | 2008090382 A1 | 7/2008 |
| WO | 2010129497 | 6/2010 |
| WO | 2010129497 | 11/2010 |
| WO | 2012000896 A2 | 1/2012 |
| WO | 2012052412 A1 | 4/2012 |

* cited by examiner

*Primary Examiner* — Nyeemah A Grazier
(74) *Attorney, Agent, or Firm* — Carl D. Corvin

(57) ABSTRACT

This document discloses molecules having the following formula ("Formula I"):

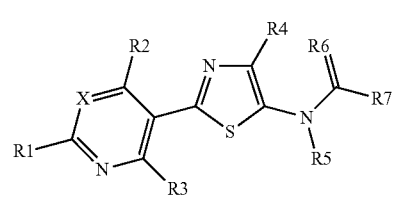

Formula I

10 Claims, No Drawings

PESTICIDAL COMPOSITIONS

CROSS-REFERENCE TO RELATED APPLICATIONS

This application claims priority from U.S. provisional application 61/175,659 filed on 5 May 2009. The entire content of this provisional application is hereby incorporated by reference into this application. This application claims priority from U.S. non-provisional application Ser. No. 12/773,062 filed on 4 May 2009. The entire content of this non-provisional application is hereby incorporated by reference into this application.

FIELD OF THE INVENTION

The invention disclosed in this document is related to the field of processes to produce molecules that are useful as pesticides (e.g., acaricides, insecticides, molluscicides, and nematicides), such molecules, and processes of using such molecules to control pests.

BACKGROUND OF THE INVENTION

Pests cause millions of human deaths around the world each year. Furthermore, there are more than ten thousand species of pests that cause losses in agriculture. The worldwide agricultural losses amount to billions of U.S. dollars each year.

Termites cause damage to all kinds of private and public structures. The world-wide termite damage losses amount to billions of U.S. dollars each year.

Stored food pests eat and adulterate stored food. The world-wide stored food losses amount to billions of U.S. dollars each year, but more importantly, deprive people of needed food.

There is an acute need for new pesticides. Certain pests are developing resistance to pesticides in current use. Hundreds of pest species are resistant to one or more pesticides. The development of resistance to some of the older pesticides, such as DDT, the carbamates, and the organophosphates, is well known. But resistance has even developed to some of the newer pesticides.

Therefore, for many reasons, including the above reasons, a need exists for new pesticides.

DEFINITIONS

The examples given in the definitions are generally non-exhaustive and must not be construed as limiting the invention disclosed in this document. It is understood that a substituent should comply with chemical bonding rules and steric compatibility constraints in relation to the particular molecule to which it is attached.

"Acaricide Group" is defined under the heading "ACARICIDES".

"AI Group" is defined after the place in this document where the "Herbicide Group" is defined.

"alkenyl" means an acyclic, unsaturated (at least one carbon-carbon double bond), branched or unbranched, substituent consisting of carbon and hydrogen, for example, vinyl, allyl, butenyl, pentenyl, hexenyl, heptenyl, octenyl, nonenyl, and decenyl.

"alkenyloxy" means an alkenyl further consisting of a carbon-oxygen single bond, for example, allyloxy, butenyloxy, pentenyloxy, hexenyloxy, heptenyloxy, octenyloxy, nonenyloxy, and decenyloxy.

"alkoxy" means an alkyl further consisting of a carbon-oxygen single bond, for example, methoxy, ethoxy, propoxy, isopropoxy, 1-butoxy, 2-butoxy, isobutoxy, tert-butoxy, pentoxy, 2-methylbutoxy, 1,1-dimethylpropoxy, hexoxy, heptoxy, octoxy, nonoxy, and decoxy.

"alkyl" means an acyclic, saturated, branched or unbranched, substituent consisting of carbon and hydrogen, for example, methyl, ethyl, propyl, isopropyl, 1-butyl, 2-butyl, isobutyl, tert-butyl, pentyl, 2-methylbutyl, 1,1-dimethylpropyl, hexyl, heptyl, octyl, nonyl, and decyl.

"alkynyl" means an acyclic, unsaturated (at least one carbon-carbon triple bond, and any double bonds), branched or unbranched, substituent consisting of carbon and hydrogen, for example, ethynyl, propargyl, butynyl, pentynyl, hexynyl, heptynyl, octynyl, nonynyl, and decynyl.

"alkynyloxy" means an alkynyl further consisting of a carbon-oxygen single bond, for example, pentynyloxy, hexynyloxy, heptynyloxy, octynyloxy, nonynyloxy, and decynyloxy.

"aryl" means a cyclic, aromatic substituent consisting of hydrogen and carbon, for example, phenyl, naphthyl, and biphenyl.

"cycloalkenyl" means a monocyclic or polycyclic, unsaturated (at least one carbon-carbon double bond) substituent consisting of carbon and hydrogen, for example, cyclobutenyl, cyclopentenyl, cyclohexenyl, cycloheptenyl, cyclooctenyl, cyclodecenyl, norbornenyl, bicyclo[2.2.2]octenyl, tetrahydronaphthyl, hexahydronaphthyl, and octahydronaphthyl.

"cycloalkenyloxy" means a cycloalkenyl further consisting of a carbon-oxygen single bond, for example, cyclobutenyloxy, cyclopentenyloxy, cyclohexenyloxy, cycloheptenyloxy, cyclooctenyloxy, cyclodecenyloxy, norbornenyloxy, and bicyclo[2.2.2]octenyloxy.

"cycloalkyl" means a monocyclic or polycyclic, saturated substituent consisting of carbon and hydrogen, for example, cyclopropyl, cyclobutyl, cyclopentyl, cyclohexyl, cycloheptyl, cyclooctyl, cyclodecyl, norbornyl, bicyclo[2.2.2]octyl, and decahydronaphthyl.

"cycloalkoxy" means a cycloalkyl further consisting of a carbon-oxygen single bond, for example, cyclopropyloxy, cyclobutyloxy, cyclopentyloxy, cyclohexyloxy, cycloheptyloxy, cyclooctyloxy, cyclodecyloxy, norbornyloxy, and bicyclo[2.2.2]octyloxy.

"cyclohaloalkyl" means a monocyclic or polycyclic, saturated substituent consisting of carbon halo, and hydrogen, for example, 1-chlorocyclopropyl, 1-chlorocyclobutyl, and 1-dichlorocyclopentyl.

"Fungicide Group" is defined under the heading "FUNGICIDES".

"halo" means fluoro, chloro, bromo, and iodo.

"haloalkyl" means an alkyl further consisting of, from one to the maximum possible number of, identical or different, halos, for example, fluoromethyl, difluoromethyl, trifluoromethyl, 1-fluoroethyl, 2-fluoroethyl, 2,2,2-trifluoroethyl, chloromethyl, trichloromethyl, and 1,1,2,2-tetrafluoroethyl.

"Herbicide Group" is defined under the heading "HERBICIDES." "heterocyclyl" means a cyclic substituent that may be fully saturated, partially unsaturated, or fully unsaturated, where the cyclic structure contains at least one carbon and at least one heteroatom, where said heteroatom is nitrogen, sulfur, or oxygen, for example, benzofuranyl, benzoisothiazolyl, benzoisoxazolyl, benzoxazolyl, benzothienyl, benzothiazolyl cinnolinyl, furanyl, indazolyl, indolyl, imidazolyl, isoindolyl, isoquinolinyl, isothiazolyl, isoxazolyl, 1,3,4-oxadiazolyl, oxazolinyl, oxazolyl, phthalazinyl, pyrazinyl, pyrazolinyl, pyrazolyl, pyridazinyl, pyridyl, pyrimidinyl, pyrrolyl, quinazolinyl, quinolinyl, quinoxalinyl, 1,2,3,4-tetrazolyl, thiazolinyl, thiazolyl, thienyl, 1,2,3-triazinyl, 1,2,4-triazinyl, 1,3,5-triazinyl, 1,2,3-triazolyl, and 1,2,4-triazolyl.

"Insecticide Group" is defined under the heading "INSECTICIDES".

"Nematicide Group" is defined under the heading "NEMATICIDES".

"Synergist Group" is defined under the heading "SYNERGISTIC MIXTURES AND SYNERGISTS".

DETAILED DESCRIPTION OF THE INVENTION

This document discloses molecules having the following formula ("Formula I"):

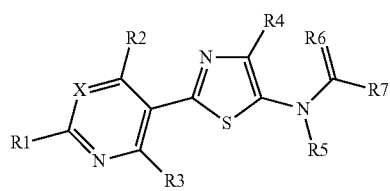

Formula I wherein:
(a) X is N or CR8;
(b) R1 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R1, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(c) R2 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R2, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(d) R3 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R3, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(e) R4 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(f) R5 is H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl)S(O)$_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_6$-$C_{20}$ aryl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9;

wherein each said R5, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, R9 aryl (each of which that can be substituted, may optionally be substituted with R9)

optionally R5 and R7 can be connected in a cyclic arrangement, where optionally such arrangement can have one or more heteroatoms selected from O, S, or, N, in the cyclic structure connecting R5 and R7;

(g) R6 is O, S, NR9, or NOR9;

(h) R7 is substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, OR9S(O)$_n$R9, C(=X1)R9, C(=X1)OR9, R9C(=X1)OR9, R9X2C(=X1)R9X2R9, C(=X1)N(R9)$_2$, N(R9)$_2$, N(R9)(R9S(O)$_n$R9), N(R9)C(=X1)R9, SR9, S(O)$_n$OR9, R9S(O)$_n$R9, $C_1$-$C_6$alkylOC(=O)$C_1$-$C_6$alkyl, $OC_1$-$C_6$ alkyl $C_1$-$C_{20}$ heterocyclyl, $C_1$-$C_6$alkyl$C_1$-$C_{20}$ heterocyclyl, $C_1$-$C_6$, alkylS(=N—CN)($C_1$-$C_6$alkyl), $C_1$-$C_6$alkylS(O)(=N—CN)($C_1$-$C_6$alkyl), $C_1$-$C_6$alkylS(O)$_n$($C_1$-$C_6$alkyl$C_1$-$C_{20}$heterocyclyl), $C_1$-$C_6$alkylS(O)(=N—CN)($C_1$-$C_6$ alkyl-$C_1$-$C_{20}$heterocyclyl), $C_1$-$C_6$alkylNH(C(=O)OC_1$-$C_6$ alkyl), $C_1$-$C_6$ alkylC(=O)O$C_1$-$C_6$ alkyl, $C_1$-$C_6$alkyl($C_6$-$C_{20}$aryl)NH(C(=O)O$C_1$-$C_6$alkyl), $C_1$-$C_6$alkyl(S—$C_1$-$C_6$ alkyl)NH(C(=O)O$C_1$-$C_6$alkyl), $C_1$-$C_6$alkyl(S—$C_1$-$C_6$alkyl-$C_6$-$C_{20}$aryl)NH(C(=O)O$C_1$-$C_6$alkyl), $C_1$-$C_6$ alkyl(NHC(=O)O$C_1$-$C_6$alkyl$C_6$-$C_{20}$ aryl)NH(C(=O)O$C_1$-$C_6$alkyl), $C_1$-$C_6$alkyl(O$C_1$-$C_6$alkyl$C_6$-$C_{20}$aryl)NH(C(=O)O$C_1$-$C_6$alkyl), $C_1$-$C_6$alkylN($C_1$-$C_6$alkyl)(C(=O)O$C_1$-$C_6$alkyl), $C_1$-$C_6$alkylNH($C_1$-$C_6$alkyl), $C_6$-$C_{20}$arylS$C_1$-$C_6$haloalkyl, $C_1$-$C_6$alkyl-N($C_1$-$C_6$ alkyl)(C(=O)$C_1$-$C_6$alkyl$C_6$-$C_{20}$aryl), $C_1$-$C_6$alkylN($C_1$-$C_6$alkyl)($C_1$-$C_6$alkyl), $C_1$-$C_6$alkylN($C_1$-$C_6$ alkyl)(S(O)$_n$$C_1$-$C_6$ alkyl), $C_1$-$C_6$ alkylN($C_1$-$C_6$ alkyl)(S(O)$_n$$C_1$-$C_6$ alkenyl$C_6$-$C_{20}$ aryl), $C_1$-$C_6$alkylN($C_1$-$C_6$ alkyl)(C(=O)$C_1$-$C_{20}$ heterocyclyl), $C_1$-$C_6$alkylN($C_1$-$C_6$alkyl)(C(=O)O$C_1$-$C_6$ alkyl$C_6$-$C_{20}$aryl), NH($C_1$-$C_6$ alkylS(O)$_n$$C_1$-$C_6$alkyl), NH($C_1$-$C_6$ alkylS(O)$_n$$C_6$-$C_{20}$ aryl), $C_1$-$C_6$alkyl(S(O)$_n$$C_1$-$C_6$ alkyl)(C(=O)$C_1$-$C_6$alkylS(O)$_n$($C_1$-$C_6$ alkyl), or R9S(O)$_n$(NZ)R9, wherein each said R7, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9), C(=X1)R9, C(=X1)OR9, C(=X1)N(R9)$_2$, =X2, N(R9)$_2$, S(=X2)$_n$R9, R9S(O)$_n$R9, S(O)$_n$N(R9)$_2$;

(i) R8 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$R9, S(O)$_n$OR9, or R9S(O)$_n$R9, wherein each said R8, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);

(j) R9 (each independently) is H, CN, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, S(O)$_n$$C_1$-$C_6$ alkyl, N($C_1$-$C_6$alkyl)$_2$, wherein each said R9, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OC$_1$-$C_6$ alkyl, OC$_1$-$C_6$ haloalkyl, S(O)$_n$$C_1$-$C_6$alkyl, S(O)$_n$O$C_1$-$C_6$ alkyl, $C_6$-$C_{20}$ aryl, or $C_1$-$C_{20}$ heterocyclyl;

(k) n is 0, 1, or 2;
(l) X1 is (each independently) O or S;
(m) X2 is (each independently) O, S, =NR9, or =NOR9; and
(n) Z is CN, NO$_2$, $C_1$-$C_6$ alkyl(R9), C(=X1)N(R9)$_2$.

In another embodiment of this invention:
(a) X is N or CR8;
(b) R1 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R1, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);

(c) R2 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R2, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);

(d) R3 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R3, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);

(e) R4 is H, F, Cl, Br, I, CN, NO$_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R4, which is substituted, has one or more substituents selected from F, Cl, Br, I, CN, NO$_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or C$_6$-C$_{20}$ aryl, (each of which that can be substituted, may optionally be substituted with R9);

(f) R5 is H, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, C$_1$-C$_6$ alkyl C$_6$-C$_{20}$ aryl (wherein the alkyl and aryl can independently be substituted or unsubstituted), C(=X2)R9, C(=X1)X2R9, R9X2C(=X1)R9, R9X2R9, or R9X2C(=X1)X2R9;

wherein each said R5, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, or C$_6$-C$_{20}$ aryl, R9 aryl (each of which that can be substituted, may optionally be substituted with R9)

optionally R5 and R7 can be connected in a cyclic arrangement, where optionally such arrangement can have one or more heteroatoms selected from O, S, or, N, in the cyclic structure connecting R5 and R7;

(g) R6 is O, S, NR9, or NOR9;

(h) R7 is substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, OR9, OR9S(O)$_n$R9, C(=X1)R9, C(=X1)OR9, R9C(=X1)OR9, R9X2C(=X1)R9X2R9, C(=X1)N(R9)$_2$, N(R9)$_2$, N(R9)(R9S(O)$_n$R9), N(R9)C(=X1)R9, SR9, S(O)$_n$OR9, R9S(O)$_n$R9, or R9S(O)$_n$(NZ)R9, wherein each said R7, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, or C$_6$-C$_{20}$ aryl, (each of which that can be substituted, may optionally be substituted with R9)

(i) R8 is H, F, Cl, Br, I, CN, NO$_2$, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9, wherein each said R8, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OR9, S(O)$_n$OR9, or C$_6$-C$_{20}$ aryl (each of which that can be substituted, may optionally be substituted with R9);

(j) R9 (each independently) is H, CN, substituted or unsubstituted C$_1$-C$_6$ alkyl, substituted or unsubstituted C$_2$-C$_6$ alkenyl, substituted or unsubstituted C$_1$-C$_6$ alkoxy, substituted or unsubstituted C$_2$-C$_6$ alkenyloxy, substituted or unsubstituted C$_3$-C$_{10}$ cycloalkyl, substituted or unsubstituted C$_3$-C$_{10}$ cycloalkenyl, substituted or unsubstituted C$_6$-C$_{20}$ aryl, wherein each said R9, which is substituted, has one or more substituents selected from F, Cl, Br, I, CN, NO$_2$, C$_1$-C$_6$ alkyl, C$_2$-C$_6$ alkenyl, C$_1$-C$_6$ haloalkyl, C$_2$-C$_6$ haloalkenyl, C$_1$-C$_6$ haloalkyloxy, C$_2$-C$_6$ haloalkenyloxy, C$_3$-C$_{10}$ cycloalkyl, C$_3$-C$_{10}$ cycloalkenyl, C$_3$-C$_{10}$ halocycloalkyl, C$_3$-C$_{10}$ halocycloalkenyl, OC$_1$-C$_6$ alkyl, OC$_1$-C$_6$ haloalkyl, S(O)$_n$OC$_1$-C$_6$ alkyl, C$_6$-C$_{20}$ aryl;

(k) n is 0, 1, or 2;

(l) X1 is (each independently) O or S;

(m) X2 is (each independently) O, S, =NR9, or =NOR9; and (n) Z is CN, NO$_2$, C$_1$-C$_6$ alkyl(R9), C(=X1)N(R9)$_2$.

In another embodiment of the invention X is preferably CR8.

In another embodiment of this invention R1 is preferably H, F, Cl, or C$_1$-C$_6$ alkoxy.

In another embodiment of this invention R1 is more preferably H, F, Cl, or OCH$_3$.

In another embodiment of this invention R1 is even more preferably H,

In another embodiment of this invention R2 and R3 are preferably H.

In another embodiment of this invention R4 is H, F, Cl, Br, I, CN, C$_1$-C$_6$ alkyl, C$_1$-C$_6$ haloalkyl, C$_2$-C$_6$ alkenyl, C$_6$-C$_{20}$ aryl, C(=O)O(C$_1$-C$_6$ alkyl), or S(C$_1$-C$_6$ alkyl).

In another embodiment of this invention R4 is preferably H, C$_1$, CF$_3$, CH$_3$, CH$_2$CH$_3$, CH(CH$_3$)$_2$, SCH$_3$, C(=O)OCH$_2$CH$_3$, or phenyl.

In another embodiment of this invention R4 is more preferably H, Cl, or CH$_3$.

In another embodiment of this invention R4 is even more preferably Cl.

In another embodiment of this invention R5 is preferably C(=O)(C$_1$-C$_6$ alkyl)S(O)$_n$(C$_1$-C$_6$ alkyl), C(=O)(C$_1$-C$_6$ alkyl)C(=O)O(C$_1$-C$_6$ alkyl), (C$_1$-C$_6$ alkyl)OC(=O)(C$_6$-C$_{20}$ aryl), (C$_1$-C$_6$ alkyl)OC(=O)(C$_1$-C$_6$ alkyl), C$_1$-C$_6$ alkyl-(C$_3$-C$_{10}$ cyclohaloalkyl), or (C$_1$-C$_6$ alkenyl)C(=O)O(C$_1$-C$_6$ alkyl).

In another embodiment of this invention R5 is more preferably C(=O)CH(CH$_3$)CH$_2$SCH$_3$, C(=O)CH$_2$CH$_2$SCH$_3$, C(=O)CH$_2$CH$_2$C(O)OCH$_3$, C(=O)C(CH$_3$)$_2$CH$_2$SCH$_3$, CH$_2$OC(=O)-phenyl, CH$_2$C(=O)CH$_2$CH$_2$CH$_3$, C(=O)CH(CH$_3$)SCH$_3$, CH$_2$(2,2-difluorocyclopropyl), or CH$_2$CH=CHC(=O)OCH$_3$.

In another embodiment of this invention R5 is preferably H, C$_1$-C$_6$ alkyl, C$_1$-C$_6$ alkyl-C$_6$-C$_{20}$ aryl, C$_2$-C$_6$ alkenyl, C(=O)(C$_1$-C$_6$ alkyl), (C$_1$-C$_6$ alkyl)O(C$_1$-C$_6$ alkyl), (C$_1$-C$_6$ alkyl)O(C$_1$-C$_6$ alkyl)(C$_6$-C$_{20}$ aryl), C(=O)O(C$_1$-C$_6$ alkyl), C(=O)(C$_2$-C$_6$ alkenyl), C$_1$-C$_6$ alkyl(substituted C$_6$-C$_{20}$ aryl), C$_1$-C$_6$ haloalkyl, C$_1$-C$_6$ alkyl-(C$_3$-C$_{10}$ cycloalkyl), (C$_3$-C$_{10}$ cycloalkyl)O(C$_1$-C$_6$ alkyl) or (C$_1$-C$_6$ alkyl)S(O)$_n$(C$_1$-C$_6$ alkyl).

In another embodiment of this invention R5 is more preferably H, CH$_3$, CH$_2$CH$_3$, CH(CH$_3$)$_2$, CH$_2$CH(CH$_3$)$_2$, CH$_2$-phenyl, C(=O)CH(CH$_3$)$_2$, C(=O)OC(CH$_3$)$_3$, C(=O)CH$_3$, $CH_2OCH_3$, $C(O)CH=CH_2$, $CH_2$-phenyl-$OCH_3$, $CH_2OCH_2$-phenyl, $CH_2CH_2CH_3$, $CH_2CH_2F$, $CH_2CH=CH_2$, $CH_2CH_2OCH_3$, $CH_2$cyclopropyl, $CH_2CH=CHCH_3$, cyclopropyl-O—$CH_2CH_3$, $CH_2CH_2SCH_3$, or $CH_2CH_2S(O)_2CH_3$.

In another embodiment of this invention R5 is even more preferably H, $CH_3$, $CH_2CH_3$, $CH(CH_3)_2$, $CH_2CH(CH_3)_2$, or $CH_2CH_2CH_3$.

In another embodiment of this invention R6 is preferably O, S, or $N(C_1-C_6$ alkyl).

In another embodiment of this invention R6 is more preferably O, S, or $NCH_2CH_3$.

In another embodiment of this invention R6 is even more preferably O.

In another embodiment of this invention R7 is furyl. In another embodiment of this invention R7 is substituted furyl wherein the substituted furyl has one or more substituents selected from $C(=O)C_1-C_6$ alkyl, $(C_1-C_6$ alkyl)-$S(O)_n$—$(C_1-C_6$ alkyl), and tetrahydrofuran.

In another embodiment of this invention R7 is oxazolyl. In another embodiment of this invention R7 is substituted oxazolyl wherein the substituted oxazolyl has one or more $C_1-C_6$ alkyls.

In another embodiment of this invention R7 is piperidinyl. In another embodiment of this invention R7 is substituted piperidinyl wherein said substituted piperidinyl has one or more substituents selected from $C_1-C_6$ alkyl, $C(=O)OC_1-C_6$ alkyl, $C(=S)NH(C_3-C_{10}$ cycloalkyl), $C(=O)C_1-C_6$ haloalkyl, $C(O)OC_1-C_6$ alkyl$OC_1-C_6$ alkyl, $S(O)_n(C_1-C_6$ alkyl) and $C(=O)C_1-C_6$ alkyl.

In another embodiment of this invention R7 is pyrazolyl. In another embodiment of this invention R7 is substituted pyrazolyl wherein said substituted pyrazolyl has one or more substituents selected from $C_1-C_6$ alkyl, $C_6-C_{20}$ aryl, $C_1-C_6$ haloalkyl, and $S(O)_nN(C_1-C_6$ alkyl$)_2$.

In another embodiment of this invention R7 is pyridazinyl. In another embodiment of this invention R7 is substituted pyridazinyl wherein said substituted pyridazinyl has one or more substituents selected from (=O) and $C_1-C_6$ alkyl.

In another embodiment of this invention R7 is pyridyl. In another embodiment of this invention R7 is substituted pyridyl wherein said substituted pyridyl has one or more $C_1-C_6$ alkyls.

In another embodiment of this invention R7 is pyrrolidinyl. In another embodiment of this invention R7 is substituted pyrrolidinyl wherein said substituted pyrrolidinyl has one or more $C(=O)OC(CH_3)_3$.

In another embodiment of this invention R7 is thiazolyl. In another embodiment of this invention R7 is substituted thiazolyl wherein said substituted thiazolyl has one or more substituents selected from $C_1-C_6$ alkyl and $C_1-C_6$ haloalkyl.

In another embodiment of this invention R7 is thienyl. In another embodiment of this invention R7 is preferably tetrahydrothienyl, thienyl$C(=O)(C_1-C_6$ alkyl), or tetrahydrothienyl-1-oxide. In another embodiment of this invention R7 is more preferably thienyl$C(=O)CH_3$.

In another embodiment of this invention, R7 is $C_1-C_6$alkyl$OC(=O)C_1-C_6$alkyl, $OC_1-C_6$alkyl$C_1-C_{20}$heterocyclyl, $C_1-C_6$alkyl$C_1-C_{20}$heterocyclyl, $C_1-C_6$alkyl$S(=N—CN)(C_1-C_6$alkyl), $C_1-C_6$alkyl$S(O)(=N—CN)(C_1-C_6$alkyl), $C_1-C_6$alkyl$S(O)_n(C_1-C_6$ alkyl-$C_1-C_{20}$heterocyclyl), $C_1-C_6$alkyl$S(O)(=N—CN)(C_1-C_6$alkyl$C_1-C_{20}$heterocyclyl), $C_1-C_6$alkyl$NH(C(=O)OC_1-C_6$alkyl), $C_1-C_6$alkyl$C(=O)OC_1-C_6$alkyl, $C_1-C_6$alkyl$(C_6-C_{20}$aryl)$NH(C(=O)OC_1-C_6$alkyl), $C_1-C_6$alkyl$(SC_1-C_6$alkyl)$NH(C(=O)OC_1-C_6$alkyl), $C_1-C_6$alkyl$(SC_1-C_6$alkyl$C_6-C_{20}$ aryl)$NH(C(=O)OC_1-C_6$alkyl), $C_1-C_6$alkyl$(NHC(=O)OC_1-C_6$alkyl-$C_6-C_{20}$ aryl)$NH(C(=O)OC_1-C_6$alkyl), $C_1-C_6$alkyl$(O—C_1-C_6$alkyl$C_6-C_{20}$ aryl)$NH(C(=O)OC_1-C_6$alkyl), $C_1-C_6$alkyl$N(C_1-C_6$ alkyl)$(C(=O)OC_1-C_6$alkyl), $C_1-C_6$alkyl$NH(C_1-C_6$ alkyl), $C_6-C_{20}$ aryl$SC_1-C_6$haloalkyl, $C_1-C_6$alkyl$N(C_1-C_6$alkyl)$(C(=O)C_1-C_6$alkyl$C_6-C_{20}$aryl), $C_1-C_6$alkyl$N(C_1-C_6$alkyl)$(C_1-C_6$alkyl), $C_1-C_6$alkyl$N(C_1-C_6$ alkyl)$(S(O)_nC_1-C_6$alkyl), $C_1-C_6$alkyl$N(C_1-C_6$ alkyl)$(S(O)_nC_1-C_6$alkenyl$C_6-C_{20}$aryl), $C_1-C_6$alkyl$N(C_1-C_6$alkyl)$(C(=O)C_1-C_{20}$hetertoaryl), $C_1-C_6$alkyl$N(C_1-C_6$alkyl)$(C(=O)OC_1-C_6$alkyl$C_6-C_{20}$aryl), $NH(C_1-C_6$alkyl$S(O)_nC_1-C_6$alkyl), $NH(C_1-C_6$alkyl$S(O)_nC_6-C_{20}$aryl), or $C_1-C_6$alkyl$(S(O)_nC_1-C_6$alkyl)$(C(=O)C_1-C_6$ alkyl$S(O)_n(C_1-C_6$alkyl).

In another embodiment of this invention, R7 is more preferably $CH(CH_3)CH_2S(=N—CN)CH_3$, $CH(CH_3)CH_2S(O)(=N—CN)CH_3$, $CH(CH_3)CH_2SCH_2$(chloropyridyl), $CH(CH_3)CH_2S(O)(=N—CN)CH_2$(chloropyridyl), $CH(CH_3)NHC(=O)OC(CH_3)_3$, $CH_2CH_2C(=O)OCH_3$, $CH_2NHC(=O)OC(CH_3)_3$, $CH(CH_2$-phenyl)$NHC(=O)OC(CH_3)_3$, $CH(CH_2CH_2SCH_3)NHC(=O)OC(CH_3)_3$, $CH(CH_3)NHC(=O)OC(CH_3)_3$, $CH(CH_2CH_2CH_3)NHC(=O)OC(CH_3)_3$, $CH(CH_2SCH_2$-phenyl)$NHC(=O)OC(CH_3)_3$, $CH(CH_2CH_2CH_2CH_2NHC(=O)OCH_2$-phenyl)$NHC(=O)OC(CH_3)_3$, $CH(CH(CH_3)OCH_2$-phenyl)$NHC(=O)OC(CH_3)_3$, $CH_2(CH_3)N(CH_3)C(=O)OC(CH_3)_3$, $CH_2(CH_3)NH(CH_3)$, phenyl-S—$CHF_2$, $CH_2N(CH_3)C(=O)CH(CH_3)$pyrazolyl, $CH_2N(CH_3)(S(O)_2CH_3)$, $CH_2N(CH_3)(CH_3)$, $CH_2N(CH_3)(S(O)_2CH=CH$-phenyl), $CH_2N(CH_3)(C(=O)$thienyl), $CH(CH_3)N(CH_3)(C(O)OCH_2$-phenyl), $NHCH_2CH_2SCH_3$, $NHCH_2CH_2S$(chlorophenyl), $CH_2$thienyl, or $CH(CH_3)CH_2(3,5$-dimethyltriazolyl).

In another embodiment of this invention R7 is preferably $C_1-C_6$ alkyl, $C_1-C_6$ haloalkyl, $C_1-C_6$ alkenyl, $O(C_1-C_6$ alkyl), $(C_1-C_6$ alkyl)$S(O)_n(C_1-C_6$ alkyl), $(C_1-C_6$ alkyl)$S(O)_n(C_1-C_6$ alkyl$(C_6-C_{20}$ aryl)), $(C_1-C_6$ alkyl)$C(=O)O(C_1-C_6$ alkyl), $O(C_1-C_6$ alkyl)$S(O)_n(C_1-C_6$ alkyl), $NH(C_1-C_6$ alkyl)$S(O)_n(C_1-C_6$ alkyl), $N(C_1-C_6$ alkyl)$(C_1-C_6$ alkyl-$S(O)_nC_1-C_6$ alkyl, $(C_1-C_6$ alkyl)$S(O)_n(C_1-C_6$ alkenyl), $O(C_1-C_6$ haloalkyl), N(unsubstituted $C_1-C_6$ alkyl)(unsubstituted $C_1-C_6$ alkyl), $C_1-C_6$ alkyl$S(O)_n(C_1-C_6$ alkenyl), $O(C_3-C_{10}$ cycloalkyl), $O(C_1-C_6$ alkyl)$O(C_1-C_6$ alkyl), $C_1-C_6$ alkyl-$(C_6-C_{20}$ aryl), (unsubstituted $C_1-C_6$ alkyl)$S(O)_n$(unsubstituted $C_6-C_{20}$ aryl), NH(aryl), $C_3-C_{10}$ cycloalkyl, $NH(C_1-C_6$ alkyl), or $(C_6-C_{20}$ aryl)$S(O)_n(C_1-C_6$ alkyl).

In another embodiment of this invention R7 is more preferably $CH_3$, $CF_3$, $OC(CH_3)_3$, $CH(CH_3)CH_2SCH_3$, $C(CH_3)_2CH_2SCH_3$, $CH_2CH_2SCH_3$, $CH(CH_3)_2$, $C(CH_3)_3$, $CH_2CF_3$, $CH_2CH_2C(=O)OCH_3$, $OCH_2CH_2SCH_3$, $OCH_2CH_3$, $CH_2CH_2S(O)CH_3$, $CH(CH_3)CH_2S(O)CH_3$, $C(CH_3)_2CH_2S(O)CH_3$, $NHCH_2CH_2S(O)CH_3$, $N(CH_3)(CH_2CH_2S(O)CH_3)$, $OCH_2CH_2S(O)CH_3$, $C(CH_3)_2CH_2S(O)CH_3$, $CH(CH_3)CH_2S(O)CH_3$, $CH_2CH_2S(O)CH_3$, $CH_2CH_2S(O)_2CH_3$, $C(CH_3)_2CH_2S(O)_2CH_3$, $CH(CH_3)CH_2S(O)_2CH_3$, $NHCH(CH_3)CH_2CH_3$, $NHCH_2CH_2SCH_3$, $N(CH_3)CH_2CH_2SCH_3$, $CH(CH_3)CH_2SCH_2CH=CH_2$, $CH(CH_3)$ CH$_2$SCH$_2$-phenyl, OC(CH$_3$)$_2$CF$_3$, OC(CH$_3$)$_2$CH$_2$CH$_2$CH$_3$, O(methylcyclohexyl), OC(CH$_3$)$_2$CH$_2$OCH$_3$, OCH$_2$-phenyl, OCH$_3$, CH=CH$_2$, CH$_2$CH$_2$CH$_2$Cl, CH$_2$C(CH$_3$)$_2$SCH$_3$, CH(CH$_3$)CH(CH$_3$)SCH$_3$, cyclopropyl-SCH$_3$, CH$_2$CH(CH$_3$)SCH$_3$, CH(CH$_3$)CH$_2$S(O)$_n$CH$_2$CH=CH$_2$, CH(CH$_3$)C(=O)OCH$_2$CH$_3$, CH$_2$CH(CH$_3$)S(O)CH$_3$, OC(CH$_3$)$_2$CH$_2$OCH$_3$, CH$_2$CH$_2$SCH$_2$-phenyl, CH$_2$CH$_2$SCH$_2$-phenyl, CH$_2$CH$_2$SCH$_2$CH$_3$, CH$_2$CH$_2$SCH(CH$_3$)$_2$, CH(CH$_3$)SCH$_3$, O-cyclohexyl, OCH(CH$_3$)CH$_2$CH$_2$CH$_3$, OCH(CH$_3$)CF$_3$, OCH$_2$CH$_2$OCH$_3$, NHCH(CH$_3$)$_2$, NHCH$_2$CH$_2$CH$_3$, CH$_2$CH$_2$cyclopropyl, CH$_2$cyclopropyl, CH$_2$CH$_2$CH=CHCH$_3$, CH$_2$CH$_2$CH=CHCH$_3$, C$_4$F$_9$, NHCH$_2$CH$_3$, SCH$_2$CH$_2$CH$_2$CH$_3$, OCH(CH$_3$)CH$_2$CH$_2$CH$_3$, OCH$_2$CH$_2$CH$_2$CH$_3$, CH$_2$CF$_3$, NHcyclopropyl, CH=CH$_2$CH$_3$, CH(CH$_3$)(chlorophenyl), C(CH$_3$)CH$_2$S(O)CH$_3$, C(CH$_3$)CH$_2$SCH$_3$, CH(=CH$_2$)CH$_2$CH$_3$, CH$_2$CH$_2$C(=O)OCH$_3$, CH$_2$SCH$_2$CH$_3$, CH$_2$SCH$_3$, CH$_2$CH$_2$CH$_2$SCH$_3$, OCH$_2$CF$_3$, NH-(chlorophenyl), phenyl-S(O)—CH$_3$, CH$_2$C(CH$_3$)$_2$(SCH$_3$), CH(CH$_3$)CHOCH$_3$, CH$_2$CH(CH$_3$)SCH$_3$, CH$_2$CH(CH$_3$)$_2$SCH$_3$, CH$_2$CH$_2$CH$_2$CH$_3$, CH(CH$_3$)CH$_2$CH$_3$, 1-methyl-2,2-dichlorocyclopropyl, CH(CH$_2$CH$_3$)CH$_2$SCH$_3$, CH(CH$_2$CH$_3$)CH$_2$S(O)CH$_3$, or CH(CH$_3$)CH(CH$_3$)S(O)CH$_3$.

In another embodiment of this invention R7 is even more preferably CH(CH$_3$)CH$_2$SCH$_3$, C(CH$_3$)$_2$CH$_2$SCH$_3$, CH$_2$CH$_2$SCH$_3$, CH(CH$_3$)$_2$, C(CH$_3$)$_3$, CH$_2$CH$_2$S(O)CH$_3$, C(CH$_3$)$_2$CH$_2$S(O)CH$_3$, CH(CH$_3$)CH$_2$S(O)CH$_3$, CH$_2$CH$_2$S(O)$_2$CH$_3$, C(CH$_3$)$_2$CH$_2$S(O)$_2$CH$_3$, CH(CH$_3$)CH$_2$S(O)$_2$CH$_3$, CH(CH$_3$)CH$_2$SCH$_2$CH=CH$_2$, CH$_2$C(CH$_3$)$_2$SCH$_3$, CH(CH$_3$)CH(CH$_3$)SCH$_3$, CH$_2$CH(CH$_3$)SCH$_3$, CH(CH$_3$)CH$_2$S(O)$_n$CH$_2$CH=CH$_2$, CH$_2$CH(CH$_3$)S(O)CH$_3$, CH$_2$CH$_2$SCH$_2$CH$_3$, CH$_2$CH$_2$SCH(CH$_3$)$_2$, CH(CH$_3$)SCH$_3$, CH$_2$SCH$_2$CH$_3$, CH$_2$SCH$_3$, CH$_2$CH$_2$CH$_2$SCH$_3$, CH$_2$CH(CH$_3$)SCH$_3$, CH$_2$CH(CH$_3$)$_2$SCH$_3$, CH(CH$_2$CH$_3$)CH$_2$SCH$_3$, CH(CH$_2$CH$_3$)CH$_2$S(O)CH$_3$, or CH(CH$_3$)CH(CH$_3$)S(O)CH$_3$.

In another embodiment of this invention R8 is H, F, Cl, Br, CN, C$_1$-C$_6$ alkyl, C$_1$-C$_6$ alkoxy, C(=O)O(C$_1$-C$_6$ alkyl), or S(O)$_n$(C$_1$-C$_6$ alkyl). In another embodiment of this invention R8 is preferably H, F, Cl, Br, CN, CH$_3$, OCH$_3$, S(O)$_2$CH$_3$, or C(=O)OCH$_2$CH$_3$.

In another embodiment of this invention R8 is even more preferably H or F.

In another embodiment of this invention:
(a) X is CR8;
(b) R1 is H;
(c) R2 is H;
(d) R3 is H;
(e) R4 is C$_1$ or CH$_3$;
(f) R5 is H or unsubstituted C$_1$-C$_6$ alkyl;
(g) R6 is O;
(h) R7 is (unsubstituted C$_1$-C$_6$ alkyl)S(O)$_n$(unsubstituted C$_1$-C$_6$ alkyl), (unsubstituted C$_1$-C$_6$ alkyl)S(O)$_n$(unsubstituted C$_1$-C$_6$ alkenyl), O(unsubstituted C$_1$-C$_6$ alkyl), (C$_1$-C$_6$ alkyl);
(i) R8 is H or F; and
(k) n is 0, 1, or 2.

In another embodiment of this invention:
(a) X is CR8;
(b) R1 is H;
(c) R2 is H;
(d) R3 is H;
(e) R4 is Cl;
(f) R5 is unsubstituted C$_1$-C$_6$ alkyl;
(g) R6 is O;
(h) R7 is (unsubstituted C$_1$-C$_6$ alkyl)S(O)$_n$(unsubstituted C$_1$-C$_6$ alkyl);
(i) R8 is H or F; and
(k) n is 0, 1, or 2.

While the embodiments have been expressed, other embodiments and combinations of these expressed embodiments and other embodiments are possible.

The following scheme illustrates approaches to generating aminothiazoles. In step a of Scheme I, treatment of a carboxylic acid of Formula IIa, such as nicotinic acid wherein R1, R2, R3 and X are as previously defined, with oxalyl chloride in the presence of a catalytic amount of N,N-dimethylformamide (DMF) in a polar aprotic solvent such as 1,2-dichloroethane (DCE) provides the corresponding acid chloride of Formula IIb. In step b of Scheme I, a commercially available carboxylic acid of Formula IIa, such as nicotinic acid, can be treated with an amino acid ester of Formula III (R4=H) such as glycine methyl ester hydrochloride, in the presence of p-toluenesulfonyl chloride, a catalytic amount of benzyltriethylammonium chloride and an inorganic base, such as potassium carbonate, in a solvent such as chloroform to afford the amide ester of Formula IVa. Alternatively, the amide ester IVa can be accessed as in step c of Scheme I, where an acid chloride of Formula IIb is allowed to react with an amino acid ester of Formula III (R4=H, CH$_3$, phenyl, or isopropyl) such as glycine or (±)-alanine methyl ester hydrochloride, in the presence of a tertiary amine base such as triethylamine and in a polar aprotic solvent such as DCE or acetonitrile. In step d of Scheme I and in the event wherein R3 is a halogen and R1, R2, R4 and X are as previously defined, the halogen can be removed reductively using hydrogen in the presence of a catalyst, such as palladium hydroxide on carbon, in a polar protic solvent such as methanol to give compounds of Formula IVb, where R3 is H. In step e of Scheme I, reaction of the amide esters of Formula IVa and IVb, wherein R1, R2, R3, R4 and X are as previously defined, with an amine such as methylamine in a polar protic solvent like ethyl alcohol affords the diamides of Formula V, which upon treatment with phosphorus pentasulfide (step g) or Lawesson's reagent (step h) may yield aminothiazoles of Formula VIIa. In the event wherein X is CR8 and R4 is H, the diamide of Formula V, which upon treatment with Lawesson's reagent, may provide the bis-thioamide of Formula VI as in step i of Scheme I. Cyclization to yield the aminothiazole of Formula VIIb is accomplished in two steps, by reaction of the bis-thioamide of Formula VI with trifluoroacetic anhydride as in step j, followed by hydrolysis with sodium hydroxide in a polar protic solvent such as methyl alcohol, as in step k of Scheme I. Alternatively, cyclization to yield the aminothiazole of Formula VIIc, where R4=Cl is accomplished in three steps, by reaction of the bis-thioamide of Formula VI with trifluoroacetic anhydride as in step j, followed by chlorination with a chlorinating agent such as N-chlorosuccinimide in a polar aprotic solvent such as acetonitrile as in step 1, and hydrolysis with potassium carbonate in a polar protic solvent such as methyl alcohol, as in step m of Scheme I.

Scheme I

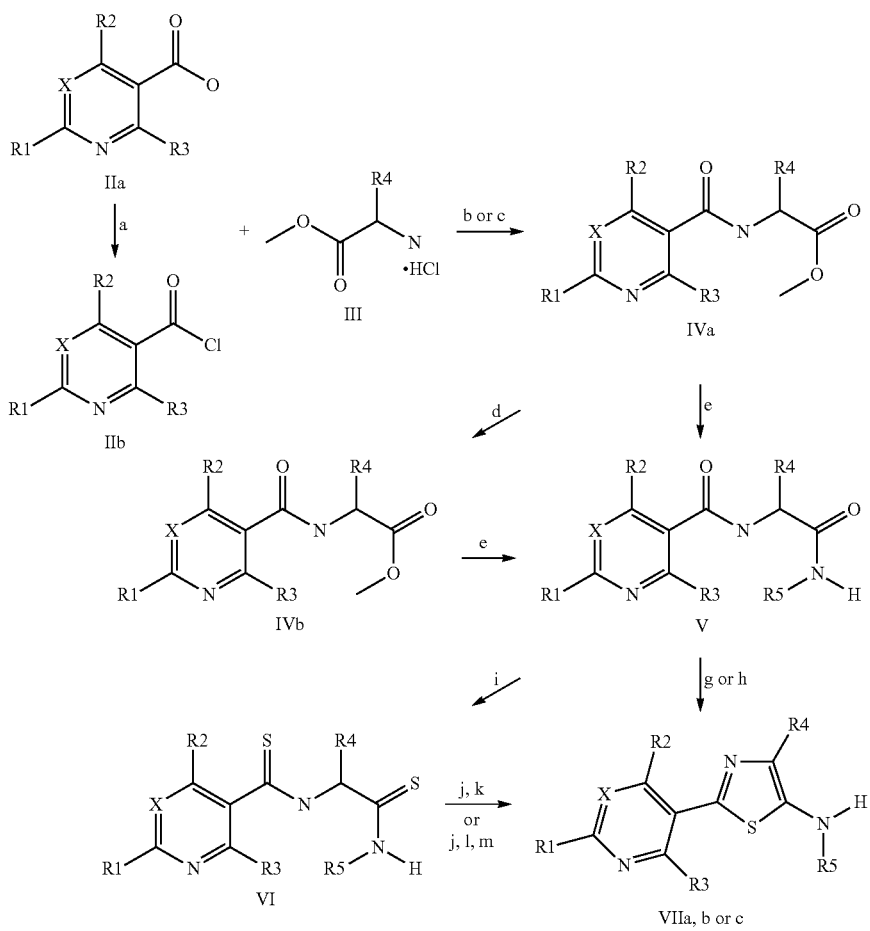

Another approach to substituted aminothiazoles is illustrated in Scheme II. In step a, the thiazole ester of Formula Xa is formed in one step by reaction of a commercially available thioamide of Formula VIIIa, wherein R1, R2, R3 and X are as previously defined, with a β-ketoester of Formula IXa such as 2-chloro-4,4,4-trifluoro-3-oxobutyric acid ethyl ester, wherein R4 is as previously defined, under microwave irradiation conditions in the presence of a base, such as triethylamine, and in a solvent such as ethyl alcohol. Saponification of the ester can be accomplished as in step b of Scheme II using a base such as sodium hydroxide in a solvent such as aqueous methyl alcohol to give the acid of Formula XIa. In step c of Scheme II, the tert-butyl carbamate (shown) or other carbamate of Formula XIIa is formed by reaction of the acid of Formula XIa with diphenyl phosphoryl azide (DPPA) and the appropriate alcohol with heating. Alkylation of the carbamate nitrogen with an alkyl halide such as iodomethane, in the presence of a base such as sodium hydride and in a polar aprotic solvent such as N,N-dimethylformamide (DMF) may yield the compounds of Formula XIIIa as shown in step d of Scheme II. Finally in step e of Scheme II, deprotection of the amine in the presence of an acid, such as trifluoroacetic acid (TFA), may afford the aminothiazole of Formula VIId.

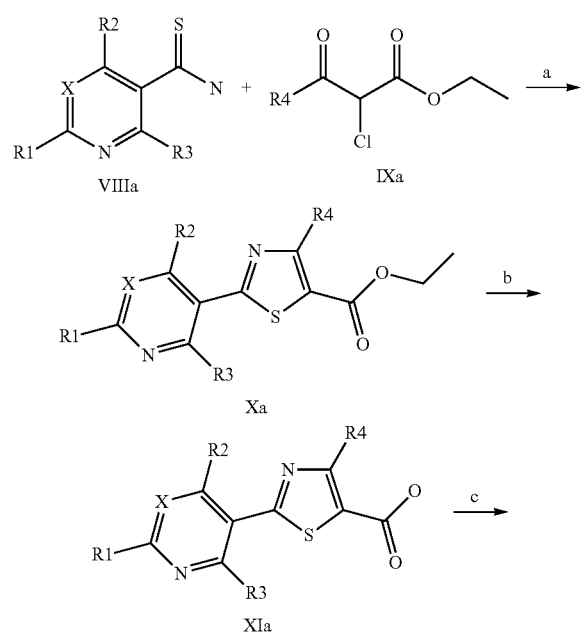

Scheme II

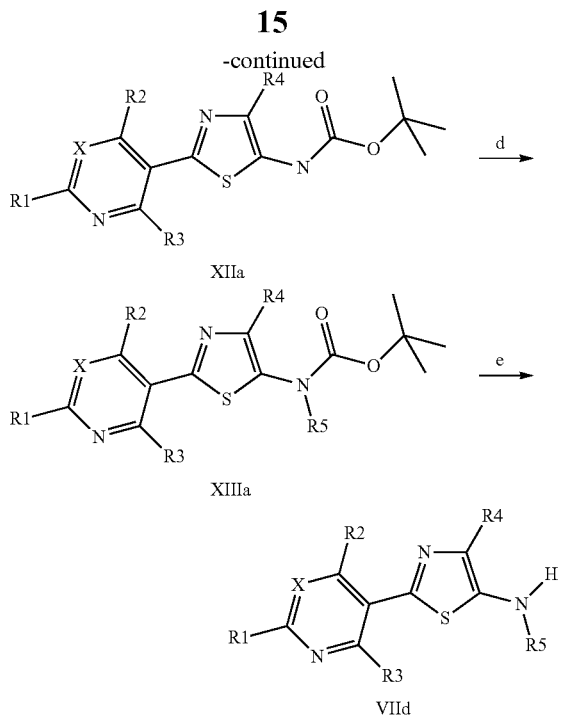

Yet another approach to aminothiazoles is through coupling of the desired amine-protected thiazole and the heterocycle as in Scheme III. In step a, a 2-halo-4-substituted thiazole-5-carboxylic acid ethyl ester of Formula XIVa, wherein R4 is as previously defined, is hydrolyzed under basic conditions, such as with lithium hydroxide hydrate, in a solvent system such as aqueous tetrahydrofuran (THF) to afford the corresponding acid of Formula XVa. Compounds of Formula XVa are transformed to the acyl azide of Formula XVIa by reaction with diphenyl phosphoryl azide as in step b of Scheme III. In step c of Scheme III, a Curtius rearrangement, followed by the trapping of the resulting isocyanate with tert-butyl alcohol, affords the tert-butyloxycarbonyl (Boc) protected 5-amino thiazole of Formula XVIIa, wherein R4 is as previously defined. Alkylation of the carbamate functionality with an alkyl halide such as iodomethane, in the presence of a base such as sodium hydride and in a polar aprotic solvent such as DMF yields the alkyl carbamate of Formula XVIIIa, as shown as step d in Scheme III. In step e of Scheme III, compounds of Formula XVIIa or XVIIIa, wherein R4 and R5 are as previously defined, can be allowed to react under Suzuki coupling conditions with a boronic acid of Formula XIXa, wherein X, R1, R2 and R3 are as previously defined, to provide the heterocycle-coupled thiazole of Formula XIIIb. In the event that R5 is not H, the Boc-group can be removed under acidic conditions such as trifluoroacetic acid (TFA) in a polar aprotic solvent like dichloromethane to give compounds of Formula VIIe as in step f of Scheme III. When R5 is H, the Boc-group can be removed under acidic conditions such as methanolic hydrochloric acid to yield compounds of Formula VIIf as in step g of Scheme III. In step h, when R4 is H, compounds of Formula XVIIIb can be converted to compounds of Formula XVIIIa, wherein R4 is specifically a halogen. This can be accomplished by treatment of XVIIIb with a halogenating reagent such as N-chlorosuccinimide or N-bromosuccinimide, in a polar aprotic solvent such as acetonitrile to afford 4-halo-thiazole of Formula XVIIIa.

Scheme III

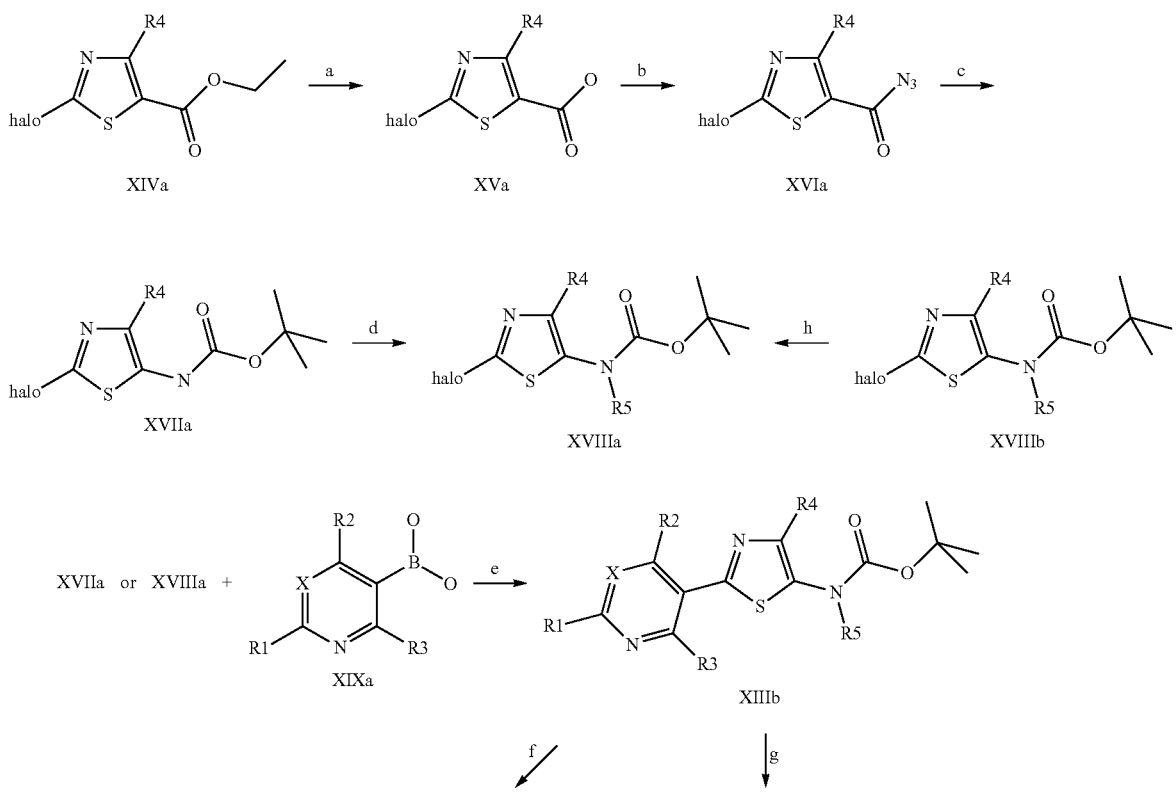

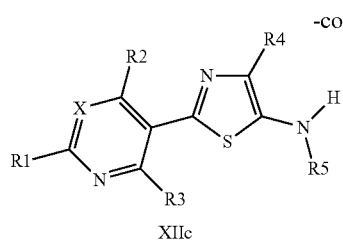

XIIc

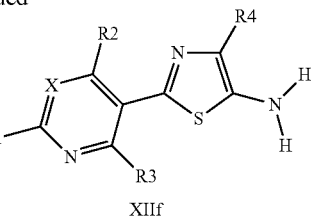

XIIf

In step a of Scheme IV, the compounds of Formula XVIIIc, wherein R4 is as previously defined and R5 is H, can be treated with an acid chloride of Formula XXa, wherein R6 is O and R7 is as previously defined, in the presence of a base such as triethylamine in a polar aprotic solvent such as dichloroethane (DCE) to yield compounds of Formula XXI. In step b of Scheme IV the Boc group can be removed under acidic conditions, such as trifluoroacetic acid in a polar aprotic solvent such a dichloromethane (DCM) to provide compounds of Formula XXII. The acid chlorides used in the acylation reactions herein are either commercially available or can be synthesized by those skilled in the art. In step c of Scheme IV, the compounds of Formula XXII can undergo alkylation with an alkyl halide such as iodomethane, in the presence of a base such as sodium hydride or potassium carbonate and in a polar aprotic solvent such as N,N-dimethylformamide (DMF) to yield the alkylated compounds of Formula XXIII. In step d of Scheme IV, compounds of Formula XXII or XXIII, wherein R4, R5, R6 and R7 are as previously defined, can be allowed to react under Suzuki coupling conditions with a boronic acid of Formula XIXb, wherein X, R1, R2 and R3 are as previously defined, to provide the heterocycle-coupled thiazole of Formula Ia.

Scheme IV

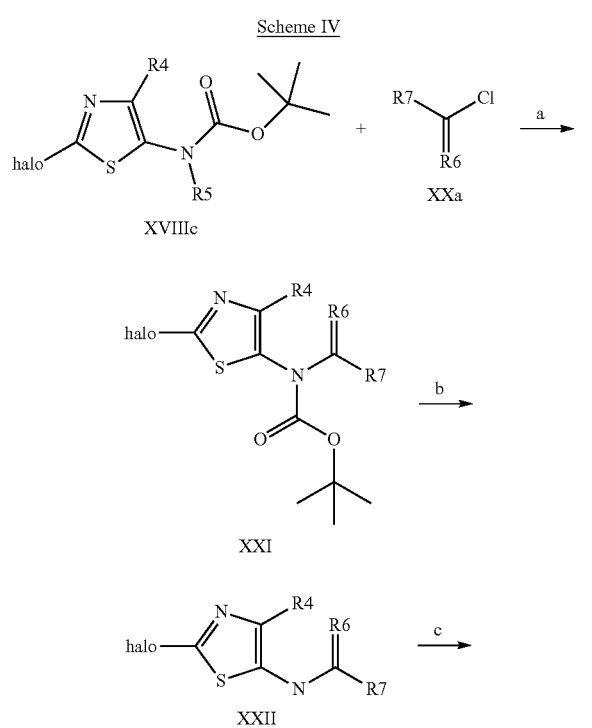

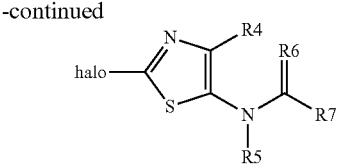

XXIII

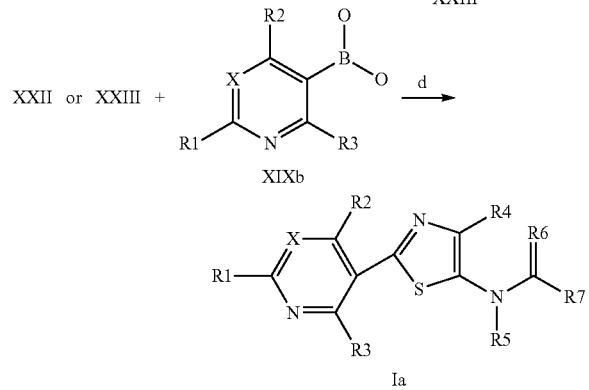

In step a of Scheme V, compounds of Formula VIIa-k, wherein X, R1, R2, R3, R4 and R5 are as previously defined, can be treated with an acid chloride of Formula XXb, wherein R6 is O and R7 is as previously defined, in the presence of a base such as triethylamine in a polar aprotic solvent such as dichloroethane (DCE) to yield compounds of Formula Ib.

Scheme V

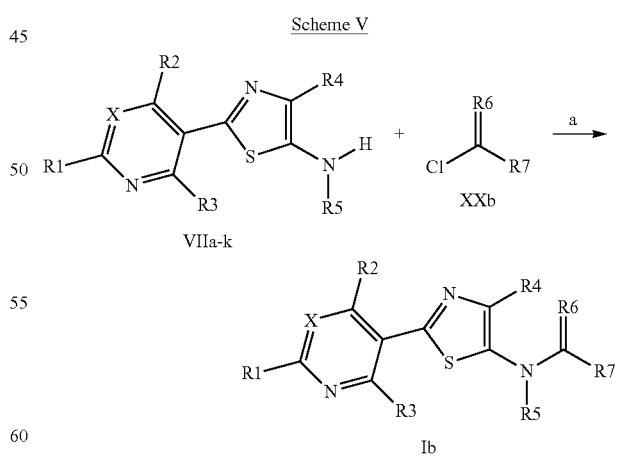

In step a of Scheme VI, ureas and carbamates are made from the aminothiazoles of Formula VIIa-k. Compounds of Formula VIIa-k, wherein X, R1, R2, R3, R4 and R5 are as previously defined, are allowed to react with phosgene to provide the intermediate carbamoyl chloride. In steps b and c of Scheme VI, the carbamoyl chloride is treated with an amine or alcohol, respectively, to generate an urea of Formula Ic or a carbamate of Formula Id, respectively. Alkylation of the urea nitrogen of compounds of Formula Ic with an alkyl halide such as iodomethane, in the presence of a base such as sodium hydride and in a polar aprotic solvent such as N,N-dimethylformamide (DMF) yields compounds of Formula Ie as shown in step d of Scheme VI.

R3, R4 and R5 are as previously defined, is treated with an oxidant such as sodium perborate tetrahydrate in a polar protic solvent such as glacial acetic acid to give the sulfoxide of Formula Ig as in step a of Scheme VII. The sulfoxide of Formula Ig can be further oxidized to the sulfone of Formula Ih by sodium perborate tetrahydrate in a polar protic solvent such as glacial acetic acid as in step b of Scheme VII. Alter-

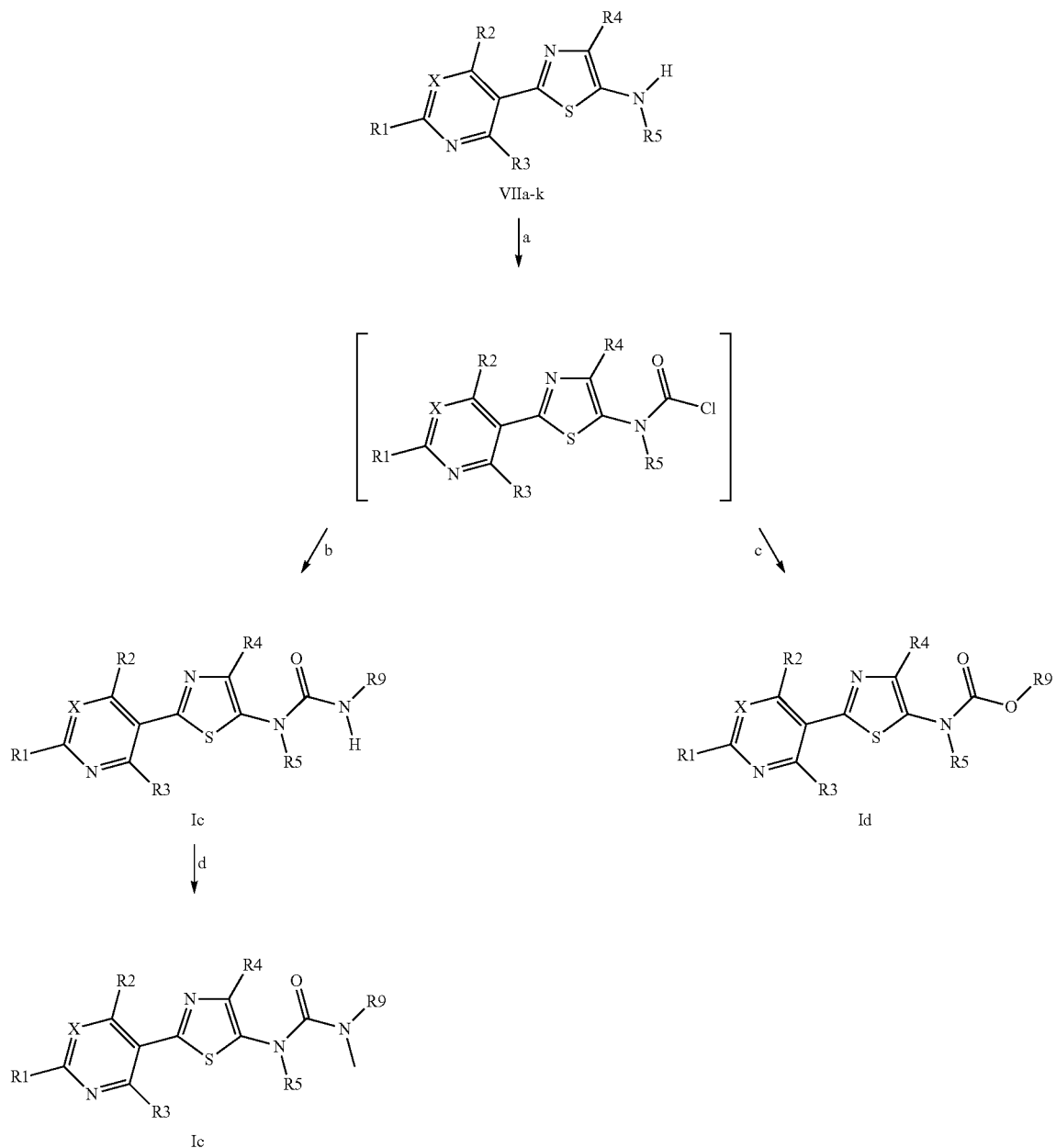

Oxidation of the sulfide to the sulfoxide or sulfone is accomplished as in Scheme VII where (~) can be any number of atoms and bonds previously mentioned within the scope of this invention. The sulfide of Formula If, wherein X, R1, R2, natively, the sulfone of Formula Ih can be generated in a one-step procedure from the sulfide of Formula If by using the aforementioned conditions with ≥2 equivalents of sodium perborate tetrahydrate, as in step c of Scheme VII.

Scheme VII

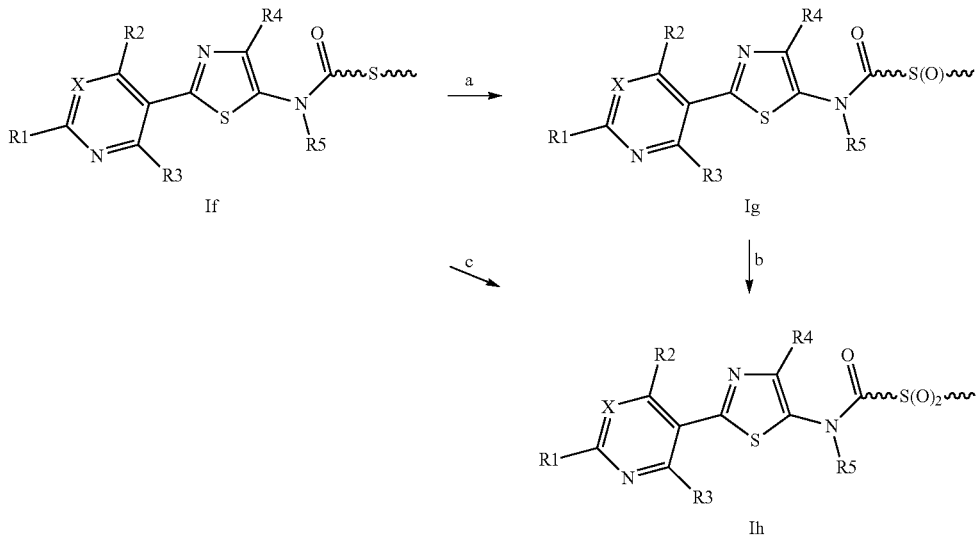

In step a of Scheme VIII, compounds of Formula XIIb, wherein X, R1, R2, R3 and R4 are as previously defined, can be treated with an acid chloride of Formula XXc, wherein R6 is O and R7 are as previously defined, in the presence of a base such as triethylamine in a polar aprotic solvent such as dichloroethane (DCE) to yield compounds of Formula XXIV. In step b of Scheme VIII the Boc group of XXIV can be removed under acidic conditions, such as trifluoroacetic acid (TFA) in a polar aprotic solvent such a dichloromethane to provide compounds of Formula II. Alkylation of the amide functionality with an alkyl halide such as benzoic acid chloromethyl ester, in the presence of a base such as sodium hydride and in a polar aprotic solvent such as N,N-dimethylformamide (DMF) yields alkyl amide of Formula Ij, as shown in step c of Scheme VIII.

Scheme VIII

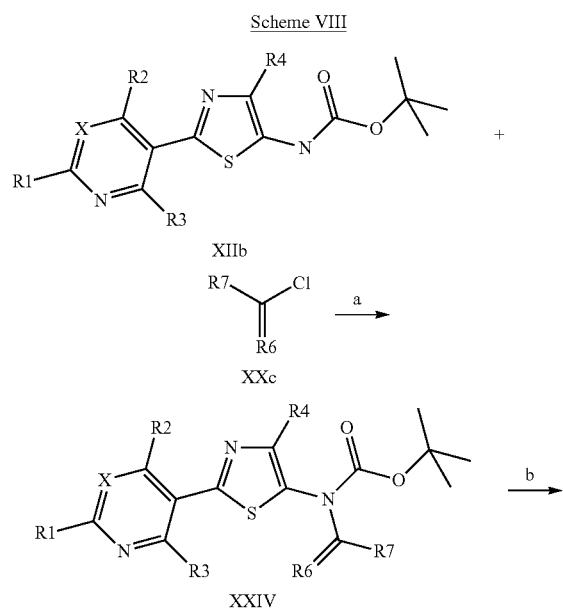

-continued

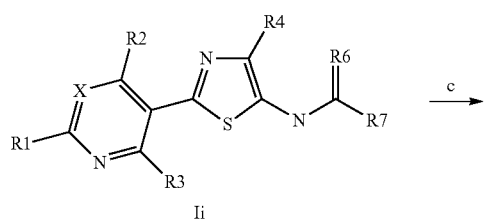

In step a of Scheme IX, compounds of Formula XIIIc, wherein X, R1, R2, R3 and R5 are as previously defined, can be treated with an electrophilic source of halogen, such as N-bromosuccinimide or N-iodosuccinimide in a polar aprotic solvent such as acetonitrile to yield compounds of Formula XIIId, wherein R4 is limited to halogens. Palladium-catalyzed cross coupling reactions such as the Stille coupling on compounds of Formula XIIId can be performed as in step b using a palladium catalyst such as bis(triphenylphosphine)palladium(II)chloride in a polar aprotic solvent such as dioxane to yield carbamates of Formula XXV. Also, compounds of the formula XIIIe, where R4 is a cyano group, can be prepared by treating the compound of the formula XIIId with CuCN in a solvent such as N,N-dimethylformamide (DMF) at a suitable temperature as in step c.

Scheme IX

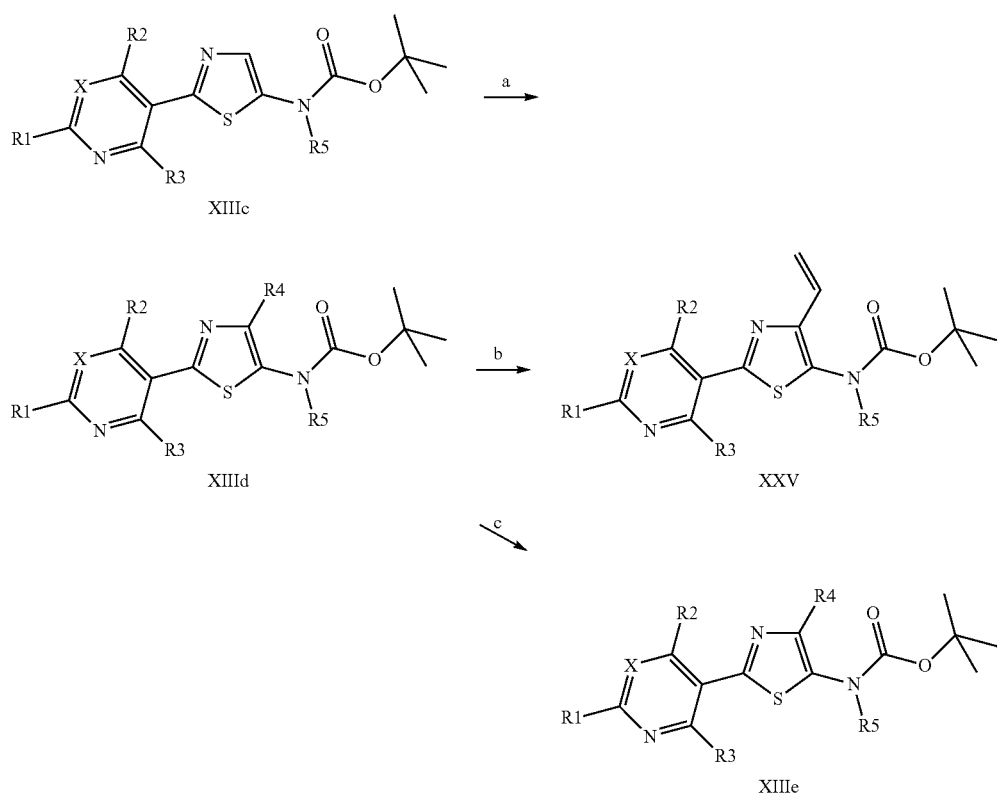

In step a of Scheme X, the compound of Formula XVIIb where R4 is H can be treated with BOC-anhydride in the presence of a base such as triethylamine in a polar aprotic solvent such as tetrahydrofuran (THF) to yield compounds of Formula XXV. Next, as in step b, compounds of Formula XXV can be allowed to react under Suzuki coupling conditions with a boronic acid of Formula XIXc, wherein X, R1, R2, R3 and R4 are as previously defined, to provide the heterocycle-coupled thiazole of Formula XXVI. In step c, compounds of Formula XXVI can be treated with an electrophilic source of halogen, such as Selectfluor™, in a mixture of polar aprotic solvents such as acetonitrile and N,N-dimethylformamide (DMF) to yield compounds of Formula XXVII, wherein R4 is limited to halogens. Finally, one of the BOC-groups can be removed under acidic conditions such as trifluoroacetic acid (TFA) in a polar aprotic solvent such as dichloromethane (DCM) to yield compounds of Formula XIIc as in step d of Scheme X, where R1, R2, R3 and R4 are as previously defined.

Scheme X

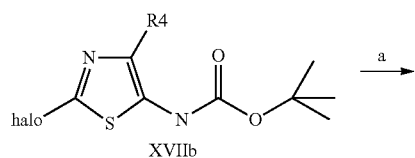

-continued

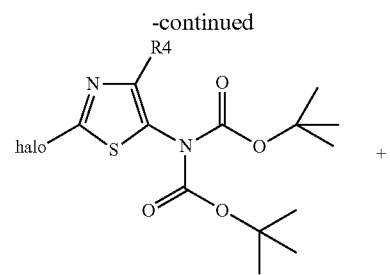

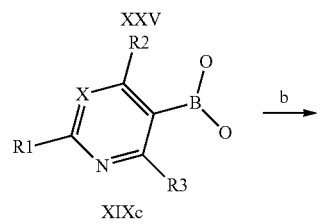

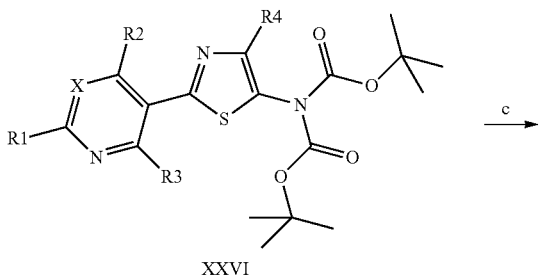

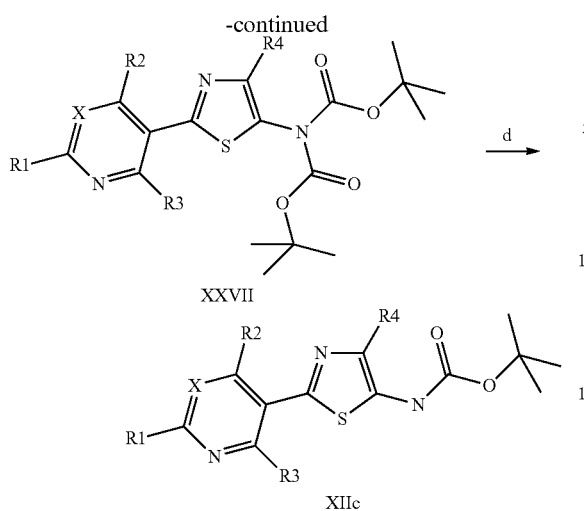

XXVII

XIIc

Oxidation of the sulfide to the sulfoximine is accomplished as in Scheme XI. The sulfide of Formula Ik, wherein X, R1, R2, R3, R4 and R5 are as previously defined, is oxidized as in step a with iodobenzene diacetate in the presence of cyanamide in a polar aprotic solvent such as methylene chloride (DCM) to give sulfilimine of the Formula Im. The sulfilimine of Formula Im may be further oxidized to the sulfoximine of Formula In with mCPBA in the presence of a base such as potassium carbonate in a protic polar solvent system such as ethanol and water as in step b of Scheme XI.

Scheme XI

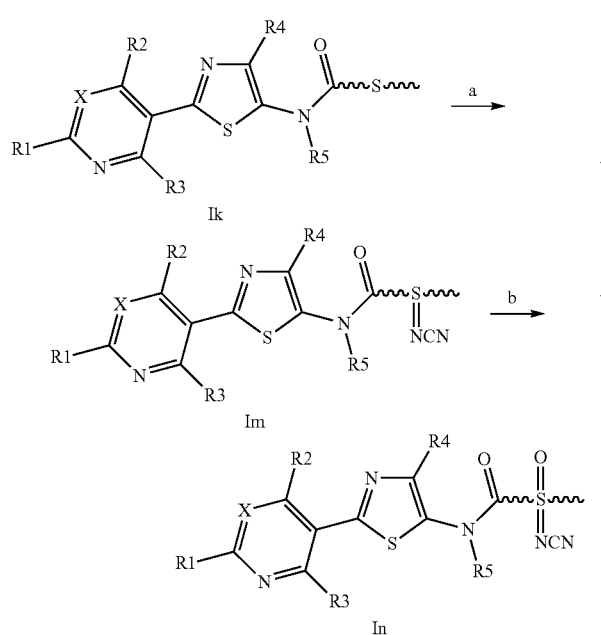

Ik

Im

In

In step a of Scheme XII, the compound of Formula VIIIb, wherein X, R1, R2 and R3 are as previously defined, can be treated with ethyl bromopyruvate in a polar protic solvent such as ethanol to yield compounds of Formula XXVIII. In step b of Scheme XII, the 5-bromothiazole of Formula XXIX is formed by reaction of the thiazole ester of Formula XXVIII with a base such as potassium bis(trimethylsilyl)amide and N-bromosuccinimide in a polar aprotic solvent such as THF.

In step c, the bromine is displaced with sodium azide in a solvent system such as N,N-dimethylformamide (DMF)/H$_2$O. The resultant azide was thermally reduced (75° C.) to give the 5-aminothiazole of Formula XXX in Scheme XII.

Scheme XII

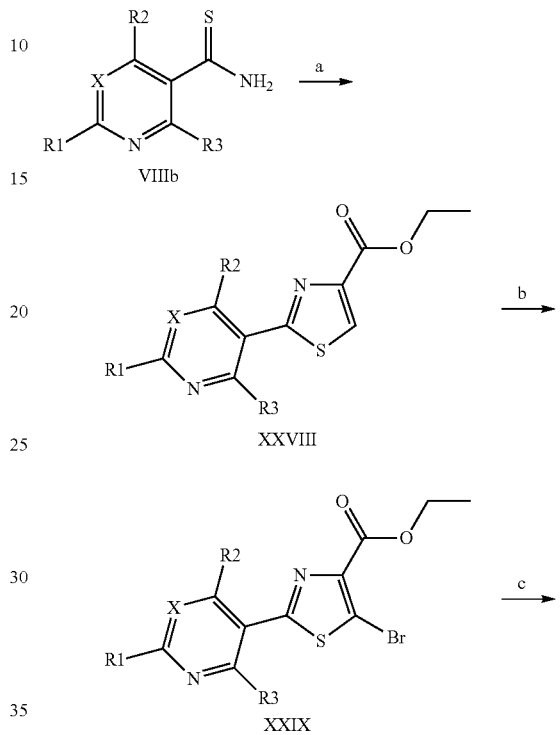

VIIIb

XXVIII

XXIX

XXX

In step a of Scheme XIII, the thioamide Iq is prepared from the amide of Formula Ip. The compound of Formula Ip, wherein X, R1, R2, R3, R4, R5 and R7 are as previously defined, is allowed to react under microwave irradiation conditions with Lawesson's reagent in a solvent such as dioxane to give the thioamide of Formula Iq in Scheme XIII Scheme XIII

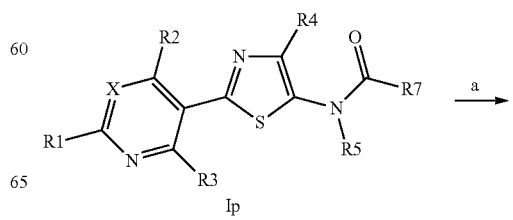

Ip

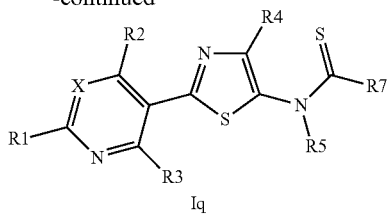

In step a of Scheme XIV, compounds of Formula VIIg, wherein X, R1, R2, R3, R4, and R5 are as previously defined, can be treated with substituted isothiocyanates of Formula XXXI where R9 is as previously defined, in refluxing dioxane to yield compounds of Formula Ir. In step b of Scheme XIV, the S-alkylated pseudothioureas of Formula Is can be formed by treating thioureas of Formula Ir with alkylating agents in refluxing ethanol under basic conditions, wherein each R9 can be the same or different.

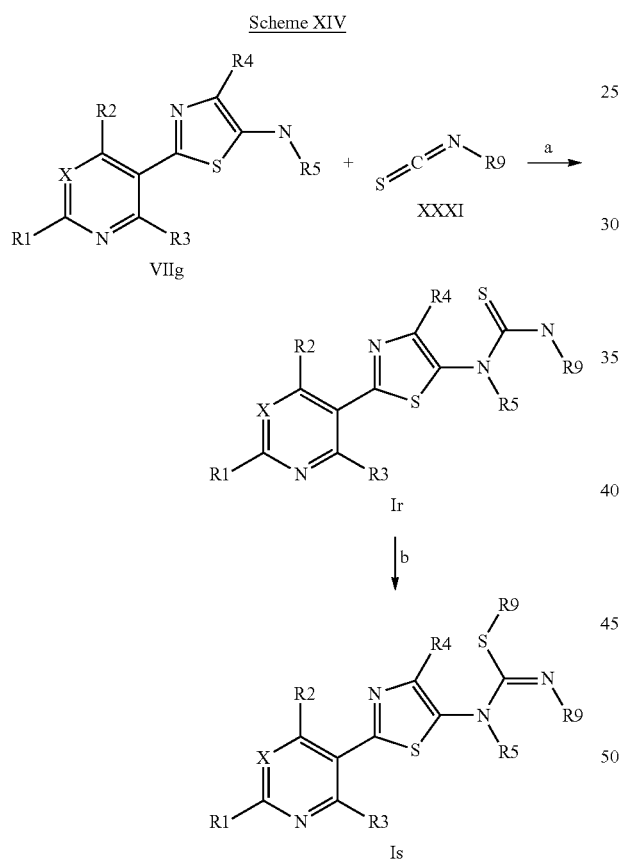

In step a of Scheme XV, the compound of Formula XXXV wherein R4 is as defined previously, can be allowed to react under Suzuki coupling conditions with a boronic acid of Formula XIXd, wherein R1, R2, R3 and X are as defined previously to provide the heterocycle-coupled thiazole of Formula XXII. In step b of Scheme XV, compounds of the Formula XXXII, wherein R1, R2, R3, R4 and X are as defined previously, can be converted to compounds of the Formula XXXIIIa, wherein R1, R2, R3, R4 and X are as defined previously by treatment with a nitrating reagent such as a mixture of fuming nitric acid and concentrated sulfuric acid at a suitable temperature. In step c, compounds of Formula XXXIIIa, wherein R1, R2, R3, and X are as defined previously and R4 is a leaving group such as chloro, can be treated with a nucleophile such as sodium thiomethoxide to produce the compounds of Formula XXXIIIb, wherein R1, R2, R3, and X are as defined previously and R4 is thioalkyl. In step d, compounds of Formula XXXIIIb can be converted to compounds of Formula VIIh, wherein R1, R2, R3, R4 and X are as defined previously and R5 is H, by treatment with molecular hydrogen in the presence of a catalyst such as Pd on C and an acid such as acetic acid in a solvent such as ethyl acetate.

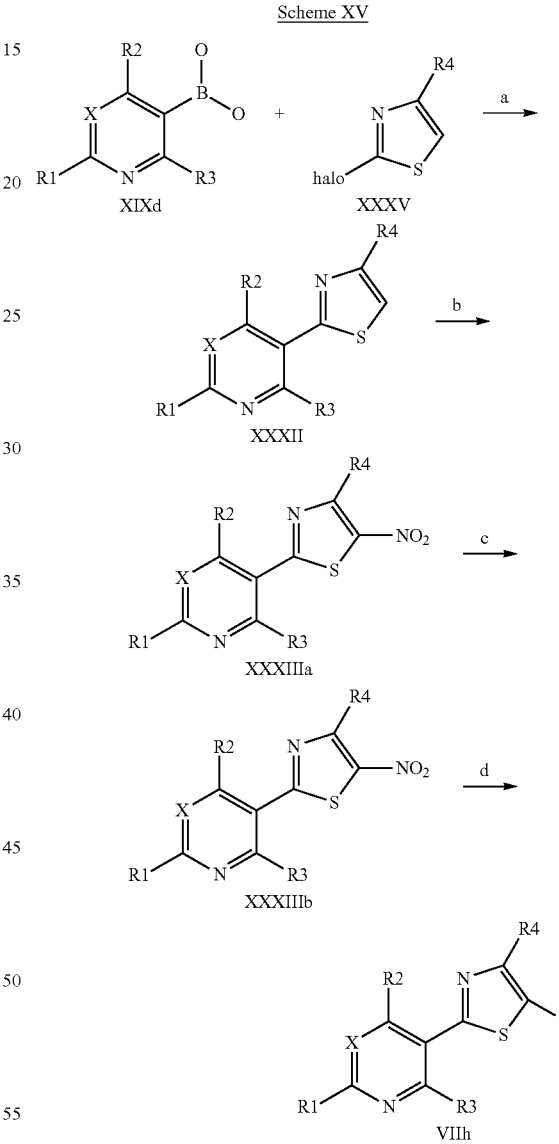

In step a of Scheme XVI, compounds of Formula VIIi, wherein X, R1, R2, R3, R4 and R5 are as previously defined, can be treated with an acid of Formula XXXIV, wherein R6 is O and R7 is as previously defined, in the presence of a coupling reagent such as 1-(3-dimethylaminopropyl)-3-ethylcarbodiimide hydrochloride (EDC.HCl) and a base such as N,N-dimethylaminopyridine (DMAP) in a polar aprotic solvent such as dichloroethane (DCE) to yield compounds of Formula It.

Scheme XVI

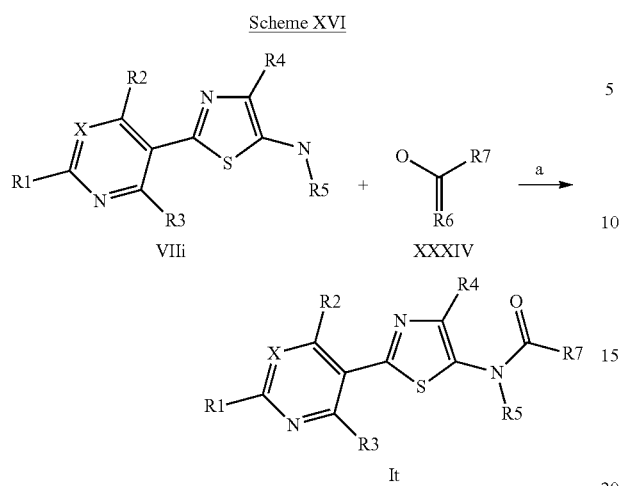

Another approach to substituted aminothiazoles is illustrated in Scheme XVII. In step a, the thiazole ester of Formula Xb is formed in one step by reaction of a commercially available thioamide of Formula VIIIb, wherein R1, R2, R3 and X are as previously defined, with a β-ketoester of Formula IXb such as ethyl 2-chloro-3-oxobutanoate, wherein R4 is as previously defined, and heating to 70-80° C. in a solvent such as ethyl alcohol. Saponification of the ester can be accomplished as in step b of Scheme XVII using a base such as lithium hydroxide in a solvent such as tetrahydrofuran (THF) to give the acid of Formula XIb. In step c of Scheme XVII, the tert-butyl carbamate of Formula XIIc is formed by reaction of the acid of Formula XIb with a chlorinating agent such as thionyl chloride to give the acid chloride, treatment of the acid chloride with sodium azide in a biphasic solution such as dichloroethane (DCE) and water to give the acyl azide, and then heating the acyl azide in tert-butanol as solvent. Alkylation of the carbamate nitrogen with an alkyl halide such as iodomethane, in the presence of a base such as sodium hydride and in a polar aprotic solvent such as N,N-dimethylformamide (DMF) may yield the compounds of Formula XIIIf as shown in step d of Scheme XVII. Finally in step e of Scheme XVII, deprotection of the amine in the presence of an acid, such as 4M HCl in dioxane, affords the aminothiazole as the HCl salt as in Formula VIIj.

Scheme XVII

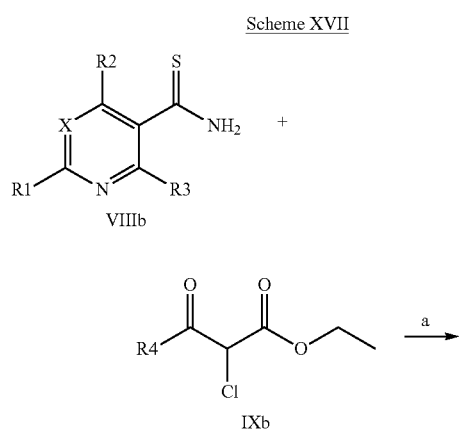

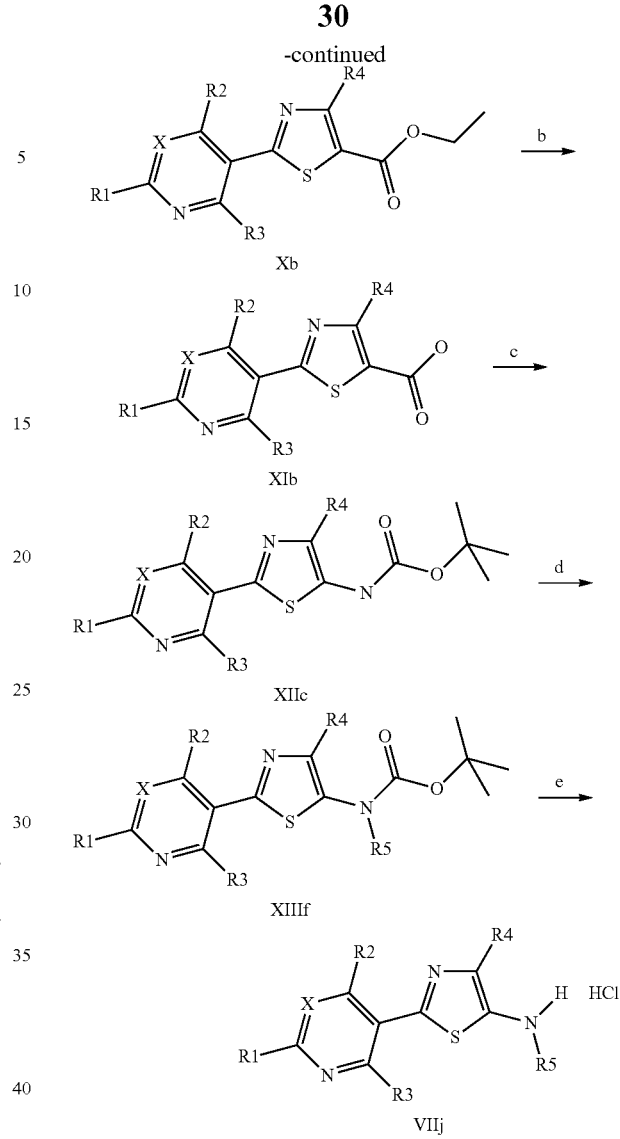

Another approach to aminothiazoles is through coupling of the desired amine-protected thiazole and the heterocycle as in Scheme XVIII. In step a, a 2-halo-4-substituted thiazole-5-carboxylic acid ethyl ester of Formula XIVb, wherein R4 is as previously defined, is hydrolyzed under basic conditions, such as lithium hydroxide hydrate, in a solvent system such as aqueous tetrahydrofuran (THF) to afford the corresponding acid of Formula XVb. Compounds of Formula XVb are transformed to the tert-butyl carbamate of Formula XVIIc by reaction with diphenyl phosphoryl azide in tert-butanol as solvent in the presence of a base such as triethylamine as in step b of Scheme XVIII. Alkylation of the carbamate functionality with an alkyl halide such as iodomethane, in the presence of a base such as sodium hydride and in a polar aprotic solvent such as N,N-dimethylformamide (DMF) yields the alkyl carbamate of Formula XVIIId, as shown in step c of Scheme XVIII. In step d of Scheme XVIII, compounds of Formula XVIIc or XVIIId, wherein R4 and R5 are as previously defined, can be allowed to react under Suzuki coupling conditions with a boronic acid of Formula XIXe, wherein X, R1, R2 and R3 are as previously defined, to provide the heterocycle-coupled thiazole of Formula XIIIg. In the event that R5 is as previously defined, the Boc-group can be removed under acidic conditions such as 4M HCl in dioxane to give compounds of Formula VIIk as in step e of Scheme XVIII.

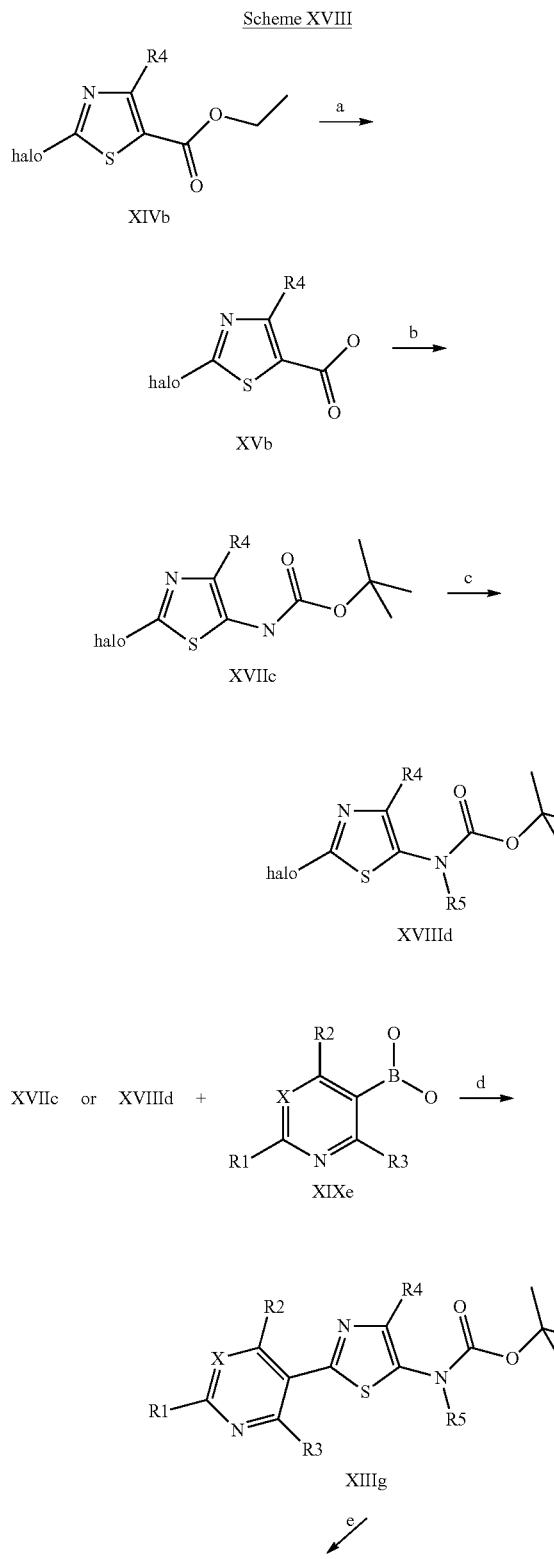

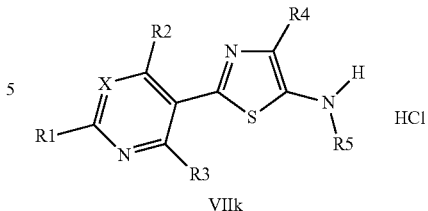

In step a of Scheme XIX, compounds of Formula VIIa-k, wherein X, R1, R2, R3, R4 and R5 are as previously defined, can be treated with an acid chloride of Formula XXd, wherein R6 is O and R7 is as previously defined, in the presence of a catalyst such as N,N-dimethylaminopyridine (DMAP) and a base such as pyridine in a polar aprotic solvent such as dichloromethane (DCM) to yield compounds of Formula Iv.

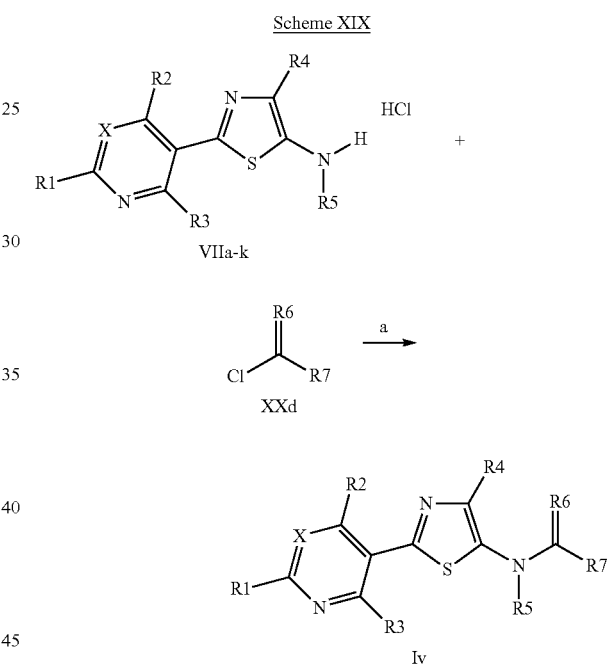

In step a of Scheme XX, compounds of Formula XXXVI can be treated with an electrophilic source of halogen such as N-chlorosuccinimide in a polar aprotic solvent such as acetonitrile to yield compounds of Formula XXXVII. The Boc-group in compounds of Formula XXXVII can be removed under acidic conditions such as trifluoroacetic acid (TFA) in a polar aprotic solvent such as dichloromethane as in step b to give compounds of Formula XXXVIII. In step c compounds of Formula XXXVIII can be treated with 3-methylsulfanyl-propionyl chloride in the presence of a base such as N,N-dimethyl amino-pyridine in a polar aprotic solvent such as dichloroethane (DCE) to yield compounds of Formula XXXIX. In step d compounds of Formula XXXVIII can be treated with 2-methyl-3-methylsulfanyl-propionyl chloride in the presence of a base such as N,N-dimethylamino-pyridine in a polar aprotic solvent such as dichloroethane (DCE) to yield compounds of Formula XXXX.

Scheme XX

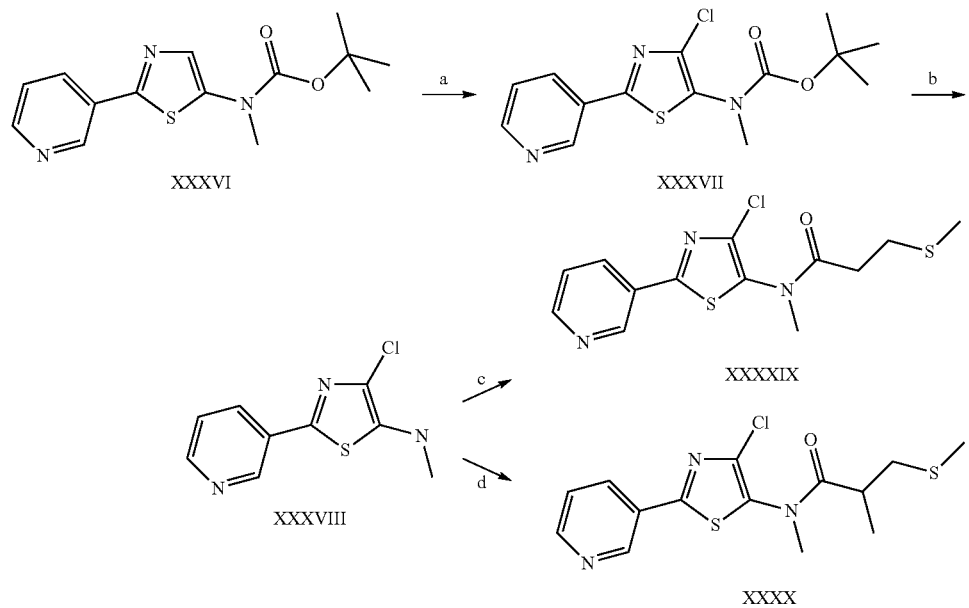

In step a of Scheme XXI, compounds of Formula XXXI can be treated with an electrophilic source of halogen such as N-chlorosuccinimide in a polar aprotic solvent such as acetonitrile to yield compounds of Formula XXXXII. The Boc-group in compounds of Formula XXXXII can be removed under acidic conditions such as trifluoroacetic acid (TFA) in a polar aprotic solvent such as dichloromethane (DCM) as in step b to give compounds of Formula XXXXIII. In step c compounds of Formula XXXXIII can be treated with 3-methylsulfanyl-propionyl chloride in the presence of a base such as N,N-dimethyl amino-pyridine in a polar aprotic solvent such as dichloroethane (DCE) to yield compounds of Formula XXXXIV. In step d compounds of Formula XXXXIII can be treated with 2-methyl-3-methylsulfanyl-propionyl chloride in the presence of a base such as N,N-dimethylamino-pyridine in a polar aprotic solvent such as dichloroethane (DCE) to yield compounds of Formula XXXXV.

Scheme XXI

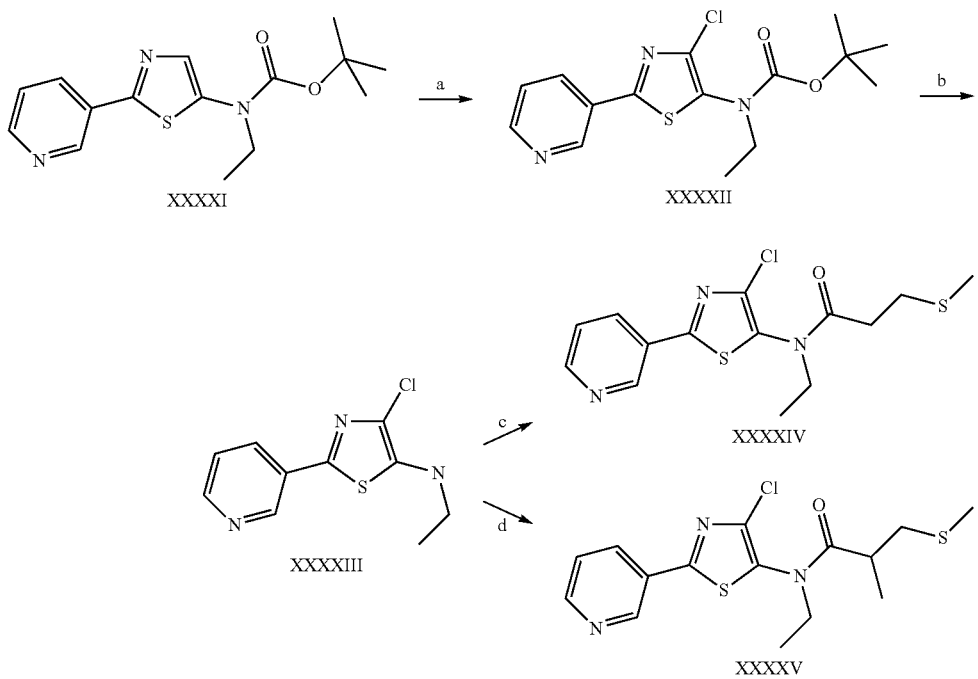

EXAMPLES

The examples are for illustration purposes and are not to be construed as limiting the invention disclosed in this document to only the embodiments disclosed in these examples.

Starting materials, reagents and solvents which were obtained from commercial sources were used without further purification. Anhydrous solvents were purchased as Sure/Seal™ from Aldrich and were used as received. Melting points were obtained on a Thomas Hoover Unimelt capillary melting point apparatus or an OptiMelt Automated Melting Point System from Stanford Research Systems and are uncorrected. Molecules are given their known names, named according to naming programs within ISIS Draw, ChemDraw or ACD Name Pro. If such programs are unable to name a molecule, the molecule is named using conventional naming rules. All NMR are in ppm ($\delta$) and were recorded at 300, 400 or 600 MHz unless otherwise stated.

Example 1

Preparation of [(pyridine-3-carbonyl)-amino]-acetic acid methyl ester

Method A

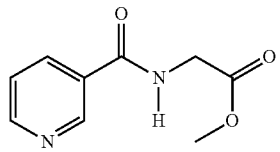

An ice-cold suspension of the hydrochloride salt of nicotinoyl chloride (5 grams (g), 28 millimoles (mmol)) in dichloroethane (DCE, 150 milliliters (mL)) was treated with glycine methyl ester hydrochloride (3.7 g, 29 mmol) in portions, followed by dropwise addition of triethylamine ($Et_3N$, 15.6 mL, 0.111 moles (mol)) via syringe. The reaction mixture was allowed to come to room temperature under nitrogen over 14 hours (h), washed with water (2×100 mL), brine (100 mL), dried over magnesium sulfate ($MgSO_4$) and purified by silica gel chromatography (ethyl acetate/hexanes gradient) to yield an orange solid (1.8 g, 33%). The aqueous washings of the crude reaction mixture were saturated with sodium chloride (NaCl), extracted with dichloromethane ($CH_2Cl_2$) and purified by silica gel chromatography (ethyl acetate/hexanes gradient) to yield a yellow solid (1.6 g, 29%; total yield 3.4 g, 62%): mp 66-68° C.; $^1H$ NMR (300 MHz, $CDCl_3$) $\delta$ 9.04 (d, J=2.2 Hz, 1H), 8.76 (dd, J=4.8, 1.5 Hz, 1H), 8.15 (dt, J=8.1, 1.8 Hz, 1H), 7.42 (dd, J=8.1, 4.8 Hz, 1H), 6.84 (br s, 1H), 4.28 (d, J=5.2 Hz, 2H), 3.82 (s, 3H); ESIMS m/z 195 (M+1).

Method B

A mixture of nicotinic acid (10 g, 81 mmol), p-toluenesulfonyl chloride (17 g, 89 mmol), benzyltriethylammonium chloride (1.85 g, 8.1 mmol), and potassium carbonate ($K_2CO_3$, 44.9 g, 320 mmol) in chloroform ($CHCl_3$, 500 mL) was stirred mechanically at 40° C. for 1 h. Glycine methyl ester hydrochloride (10.2 g, 81 mmol) and $K_2CO_3$ (11.2 g, 80 mmol) were then added and stirred at 50° C. for 90 minutes (min). The reaction mixture was filtered through Celite® and the filtrate was concentrated under reduced pressure. The crude product was purified by silica gel column chromatography (2% methanol/ethyl acetate) to give the desired product as an orange gum which solidified upon standing at room temperature (4.7 g, 30%): $^1H$ NMR (400 MHz, $CDCl_3$) $\delta$ 9.04 (d, J=2.2 Hz, 1H), 8.76 (dd, J=4.8, 1.5 Hz, 1H), 8.15 (dt, J=8.1, 1.8 Hz, 1H), 7.42 (dd, J=8.1, 4.8 Hz, 1H), 6.84 (br s, 1H), 4.28 (d, J=5.2 Hz, 2H), 3.87 (s, 3H); ESIMS m/z 195 (M+1).

Example 2

Preparation of 2-[(pyridine-3-carbonyl)-amino]-propionic acid methyl ester

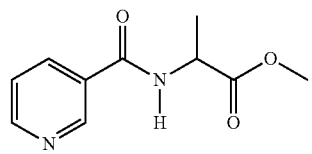

(±)-Alanine methyl ester hydrochloride salt (35.2 g, 280 mmol) and $Et_3N$ (58.5 mL, 420 mmol) were sequentially added to a stirred solution of nicotinoyl chloride (19.8 g, 140 mmol) in acetonitrile (800 mL) and stirred at ambient temperature for 10 min and then 80° C. for 2 h. The reaction mixture was poured into a separatory funnel containing brine and ethyl acetate. The biphasic mixture was separated, and the organic layer was washed one time with brine, dried over $MgSO_4$, filtered and concentrated to dryness. The crude product was triturated in 80% ethyl acetate/hexanes overnight at ambient temperature. The solids were removed by filtration over Celite® and the filtrate was concentrated in vacuo to give the desired product as a clear brown oil (20 g, 69%): $^1H$ NMR (300 MHz, $CDCl_3$) $\delta$ 9.04 (d, J=2.2 Hz, 1H), 8.75 (dd, J=4.9, 1.4 Hz, 1H), 8.13 (dt, J=7.7, 1.9 Hz, 1H), 7.40 (dd, J=8.0, 4.9 Hz, 1H), 6.92 (br s, 1H), 4.82 (m, 1H), 3.81 (s, 3H), 1.55 (d, J=7.1 Hz, 3H); ESIMS m/z 209 (M+1), m/z 207 (M−1).

Example 3

Preparation of [(2-chloro-5-fluoropyridine-3-carbonyl)-amino]-acetic acid methyl ester

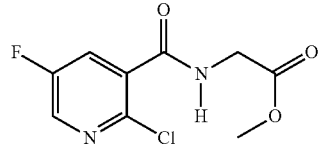 [SMILES: COC(=O)CNC(=O)c1cc(F)cnc1Cl]

To a solution of 2-chloro-5-fluoro-nicotinic acid (21.9 g, 124 mmol) in DCE (300 mL) were added oxalyl chloride (21.5 mL, 249 mmol) and then a drop of N,N-dimethylformamide (DMF). After the vigorous bubbling subsided (ca 5 min), the reaction mixture was heated to 65° C. for 1 h. The reaction solvents were removed in vacuo to afford the acid chloride as a yellow oil which was used directly in the next step. The freshly made acid chloride was dissolved in 1,4-dioxane (300 mL), and the solution was cooled to 0° C. in an ice bath. Glycine methyl ester hydrochloride (16.3 g, 130 mmol) and then $Et_3N$ (50 mL, 370 mmol) were added. After stirring for 10 min, the solution was allowed to warm to ambient temperature and was then heated to reflux for 1.5 h. LC-MS analysis of a quenched aliquot (water/ethyl acetate) showed incomplete conversion to the desired product so additional glycine methyl ester hydrochloride (15 g, 130 mmol), Et₃N (20 mL, 143 mmol), and 1,4-dioxane (200 mL) were added, and the reaction mixture was heated at reflux overnight. LC-MS analysis of a quenched aliquot (water/ethyl acetate) showed no starting material and 74% of the desired product. The reaction mixture was cooled and then added to a separatory funnel containing water and ethyl acetate. After separating the layers, the organic layer was washed with water and brine. To the initial aqueous layer was added salt and then ethyl acetate. After separation, the organic layer was washed with water and brine. The combined organic layers were dried over MgSO₄, filtered, and concentrated in vacuo. The crude material was purified via silica gel chromatography (40% to 70% ethyl acetate/hexanes) to afford a brown oil (20.5 g, 67%): ¹H NMR (300 MHz, CDCl₃) δ 8.36 (d, J=3.0 Hz, 1H), 7.92 (dd, J=7.7, 3.0 Hz, 1H), 7.32 (br s, 1H), 4.27 (d, J=5.2 Hz, 2H), 3.82 (s, 3H); ESIMS m/z 247 (M+1), m/z 245 (M−1).

Example 4

Preparation of [(5-fluoropyridine-3-carbonyl)-amino]-acetic acid methyl ester

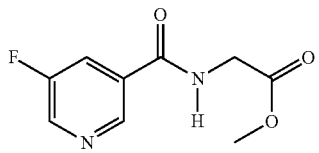

To a solution of [(2-chloro-5-fluoropyridine-3-carbonyl)-amino]-acetic acid methyl ester (4.65 g, 18.9 mmol) in methanol (200 mL) in a Parr vessel was added Et₃N (3.15 mL, 22.6 mmol) and palladium hydroxide on carbon (1.5 g, 20 wt % Pd, moisture 60%). The vessel was evacuated and then put under an atmosphere of hydrogen (initial pressure 42 psi). After 5 min the hydrogen pressure was 14 psi. The catalyst was removed via suction filtration over Celite® and then the filtrate was concentrated. Purification by silica gel chromatography (0 to 100% ethyl acetate/hexanes) afforded a light yellow solid (3.83 g, 95%): mp 80-82° C.; ¹H NMR (300 MHz, CDCl₃) δ 8.84 (s, 1H), 8.62 (d, J=2.7 Hz, 1H), 7.87 (m, 1H), 7.00 (br s, 1H), 4.27 (d, J=5.3 Hz, 2H), 3.82 (s, 3H); ESIMS m/z 213 (M+1).

Example 5

Preparation of N-methylcarbamoylmethyl-nicotinamide

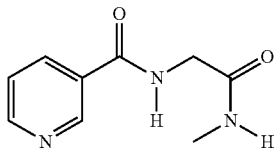

A suspension of [(pyridine-3-carbonyl)-amino]-acetic acid methyl ester (1.5 g, 7.7 mmol) and methylamine (33 wt % in absolute ethanol, 3.86 mL, 38.6 mmol) in ethanol (8 mL) was heated at 55° C. in a Parr reactor for 6 h. The mixture was cooled and then concentrated under reduced pressure to yield the product as a iridescent beige plates (1.41 g, 94%): ¹H NMR (300 MHz, DMSO-d₆) δ 9.05 (d, J=2.2 Hz, 1H), 9.00 (t, J=5.8 Hz, 1H), 8.77 (d, J=4.0 Hz, 1H), 8.23 (br d, J=8.1 Hz, 1H), 7.90 (q, J=4.1 Hz, 1H), 7.53 (dd, J=7.7, 4.7 Hz, 1H), 3.86 (d, J=5.8 Hz, 2H), 2.61 (d, J=4.4 Hz, 3H); IR (KBr) 3314, 1641 cm⁻¹; ESIMS m/z 194 (M+1).

Example 6

Preparation of N-(1-methylcarbamoyl-ethyl)nicotinamide

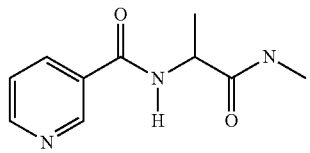

To a solution of 2-[(pyridine-3-carbonyl)-amino]-propionic acid methyl ester (10.4 g, 50 mmol) in ethanol (50 mL) was added methylamine (24 g, 33 wt % solution in ethanol, 250 mmol). The reaction mixture was heated at 55° C. for 45 min. The solvents were removed in vacuo and the residue was recrystallized from hot ethyl acetate and hexanes. The yellow crystals thus obtained were washed with cold ethyl acetate and dried to give the desired product (5.2 g, 50%): ¹H NMR (300 MHz, DMSO-d₆) δ 9.05 (br s, 1H), 8.77-8.70 (m, 2H), 8.24 (m, 2H), 7.89 (br s, 1H), 7.50 (m, 1H), 2.59 (d, J=4.7 Hz, 3H), 1.33 (d, J=7.4 Hz, 3H); ESIMS m/z 208.1 (M+1), m/z 206.1 (M−1).

Example 7

Preparation of 5-fluoro-N-methylcarbamoylmethyl-nicotinamide

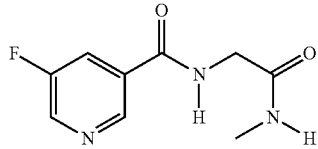

To a solution of [(5-fluoropyridine-3-carbonyl)-amino]-acetic acid methyl ester (2.96 g, 14.0 mmol) in ethanol (15 mL) was added methylamine (1.5 g, 33 wt % solution in ethanol, 70 mmol). This clear solution was then immediately put onto a 55° C. heating mantle for 10 min at which time the product had precipitated out of solution. The mixture was filtered in vacuo and the precipitate was washed with ethanol. The filtrate was concentrated and recrystallized from hot ethanol. This process was repeated again to give a white fluffy material (2.11 g, 72%): mp 201-202° C.; ¹H NMR (300 MHz, DMSO-d₆) δ 9.10 (m, 1H), 8.93 (s, 1H), 8.76 (d, J=2.5 Hz, 1H), 8.10

(m, 1H), 7.95 (br s, 1H), 3.86 (d, J=5.8 Hz, 2H), 2.61 (d, J=4.4 Hz, 3H); ESIMS m/z 212 (M+1), m/z 210 (M−1).

Example 8

Preparation of methyl-(2-pyridin-3-yl-thiazol-5-yl)-amine

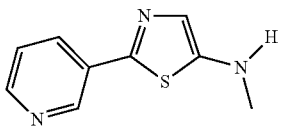

A suspension of phosphorus pentasulfide (1.73 g, 7.8 mmol) and N-methylcarbamoylmethyl-nicotinamide (1 g, 5 mmol) in dry toluene (10 mL) was stirred at reflux under nitrogen for 16 h. The mixture was cooled to room temperature and then dry pyridine (4 mL) was added. The mixture was stirred at reflux under nitrogen for 8 h, then it was cooled to room temperature and the organic layer was removed. The dark residue was treated with hot saturated aqueous sodium bicarbonate (Na$_2$CO$_3$, 40 mL) and the aqueous layer was extracted with ethyl acetate (2×50 mL). The combined organic extracts were washed with brine (50 mL), dried over magnesium sulfate (MgSO$_4$), and purified by silica gel chromatography (1% methanol in dichloromethane) to yield a brown amorphous solid (0.22 g, 22%): mp 141-146° C.; $^1$H NMR (300 MHz, CDCl$_3$) δ 8.97 (d, J=2.4 Hz, 1H), 8.53 (dd, J=5.0, 1.8 Hz, 1H), 8.06 (ddd, J=7.2, 3.3, 0.6 Hz, 1H), 7.31 (ddd, J=5.5, 4.7, 0.5 Hz, 1H), 6.96 (s, 1H), 2.97 (d, J=5.0 Hz, 3H); ESIMS m/z 192 (M+1).

Example 9

Preparation of methyl-(4-methyl-2-pyridin-3-yl-thiazol-5-yl)-amine

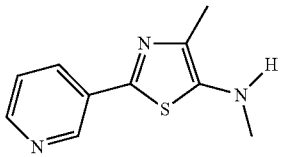

To a 10 mL microwave vessel containing DCE (5 mL) was added N-(1-methylcarbamoyl-ethyl)nicotinamide (207 mg, 1.0 mmol) followed by Lawesson's reagent (2,4-bis-(4-methoxyphenyl)-1,3-dithia-2,4-diphosphetane 2,4-disulfide, 404 mg, 1.0 mmol) in one portion. The heterogeneous mixture was heated in a microwave for 5 min at 130° C. The reaction mixture was partitioned between CH$_2$Cl$_2$ and saturated aqueous sodium bicarbonate (NaHCO$_3$). The layers were separated and the organic layer was washed once with brine. The solution was dried over MgSO$_4$, filtered and concentrated in vacuo. The crude material was purified by silica gel column chromatography (ethyl acetate) to give the desired product as an orange solid (141 mg, 68%): mp 84-87° C.; $^1$H NMR (300 MHz, CDCl$_3$) δ 8.98 (d, J=1.7 Hz, 1H), 8.51 (dd, J=4.9, 1.7 Hz, 1H), 8.08 (dt, J=8.0, 1.7 Hz, 1H), 7.29 (m, 1H), 3.00 (s, 3H), 2.30 (s, 3H); ESIMS m/z 206.4 (M+1), m/z 204.2 (M−1).

Example 10

Preparation of 2,2,2-trifluoro-N-[2-(5-fluoropyridin-3-yl)-thiazol-5-yl]-N-methyl-acetamide (Compound 1)

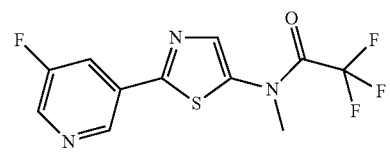 [SMILES: CN(C(=O)C(F)(F)F)c1cnc(-c2cncc(F)c2)s1]

To a 10 mL microwave tube was added 5-fluoro-N-methyl-carbamoylmethyl-nicotinamide (211 mg, 1.00 mmol), 4 Å molecular sieves (100 mg, spheres), Lawesson's reagent (404 mg, 1.00 mmol) and then toluene (5 mL). The tube was capped and heated to 130° C. for 30 seconds via microwave irradiation. The resulting orange solution was diluted with CH$_2$Cl$_2$ and filtered to remove the sieves. This solution was concentrated in vacuo to a semi-solid. To this crude material was added CH$_2$Cl$_2$ (2 mL) and trifluoroacetic anhydride (2 mL). Gas evolution was noted immediately. After stirring for 2 h at room temperature, the solvents were removed in vacuo. The residue was partitioned between CH$_2$Cl$_2$ and pH 7.0 buffer. The layers were separated and the buffer was extracted with CH$_2$Cl$_2$. The combined organic extracts were dried over MgSO$_4$, filtered, and concentrated in vacuo. Purification by silica gel chromatography (0 to 100% ethyl acetate/hexanes) afforded the product as a white solid (282 mg, 92%): mp 168-170° C.; $^1$H NMR (300 MHz, CDCl$_3$) mixture of isomers δ 8.98 and 8.95 (2 br s, 1H), 8.55 and 8.54 (m and app d, J=2.4 Hz, 1H), (dt, J=9.0 Hz, 2.2 Hz, 1H), 7.80 (s, 1H), 3.75 and 3.47 (2 s, 3H); ESIMS m/z 306 (M+1).

The following compounds were made via the methods in the previous examples.

2,2,2-Trifluoro-N-methyl-N-(2-pyridin-3-yl-thiazol-5-yl)-acetamide (Compound 2)

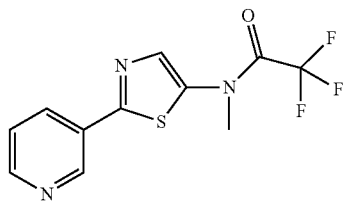 [SMILES: CN(C(=O)C(F)(F)F)c1cnc(-c2cccnc2)s1]

Purification by silica gel chromatography (0 to 100% ethyl acetate/hexanes) afforded the product as an orange solid (1.13 g, 65%): mp 154-158° C.; ESIMS m/z 306.4 (M+1).

N-(4-Ethyl-2-pyridin-3-yl-thiazol-5-yl)-2,2,2-trifluoro-N-methyl-acetamide (Compound 3)

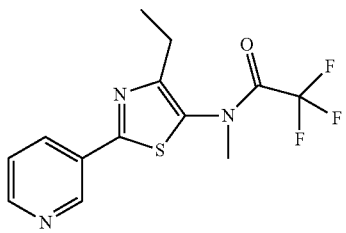 [SMILES: CCc1nc(-c2cccnc2)sc1N(C)C(=O)C(F)(F)F]

The compound was isolated after purification via silica gel chromatography eluting with an ethyl acetate/hexanes gradient to yield an amber gum (0.98 g, 63%): IR (thin film) 1717 cm$^{-1}$; ESIMS m/z 318.21 (M+3).

2,2,2-Trifluoro-N-methyl-N-(4-phenyl-2-pyridin-3-yl-thiazol-5-yl)-acetamide (Compound 4)

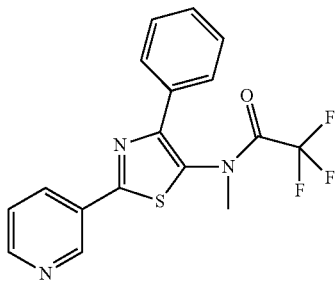 [SMILES: CN(C(=O)C(F)(F)F)c1sc(-c2cccnc2)nc1-c1ccccc1]

The compound was isolated after purification via silica gel chromatography eluting with a gradient of ethyl acetate in hexanes to yield an amorphous yellow solid (0.17 g, 31%): IR (thin film) 1674 cm$^{-1}$; ESIMS m/z 365.4 (M+2).

N-Ethyl-2,2,2-trifluoro-N-(4-phenyl-2-pyridin-3-yl-thiazol-5-yl)-acetamide (Compound 5)

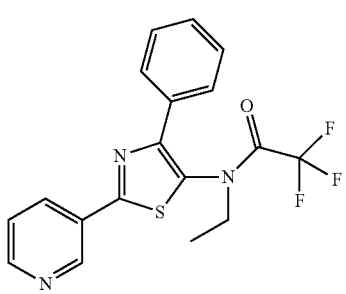 [SMILES: CCN(C(=O)C(F)(F)F)c1sc(-c2cccnc2)nc1-c1ccccc1]

The compound was isolated after purification via silica gel chromatography (ethyl acetate in hexanes) to yield a yellow solid (0.89 g, 75%): mp 81-92° C.; IR (KBr) 1713 cm$^{-1}$; ESIMS m/z 379.4 (M+2).

Example 11

N-(4-Chloro-2-pyridin-3-yl-thiazol-5-yl)-2,2,2-trifluoro-N-methyl-acetamide (Compound 6)

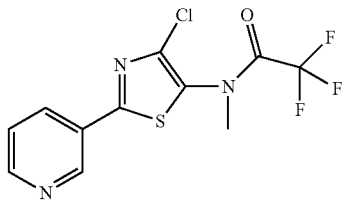 [SMILES: CN(C(=O)C(F)(F)F)c1sc(-c2cccnc2)nc1Cl]

A suspension of 2,2,2-trifluoro-N-methyl-N-(2-pyridin-3-yl-thiazol-5-yl)-acetamide (1.0 g, 3.5 mmol) and N-chlorosuccinimide (0.557 g, 4.2 mmol) in acetonitrile (30 mL) was heated to 63° C. under nitrogen for 3 h. The reaction mixture was cooled to room temperature and it was treated with additional N-chlorosuccinimide (0.557 g, 4.2 mmol) and heated to 35° C. under nitrogen for 2 h. The reaction mixture was cooled and concentrated under reduced pressure. The residue was redissolved in dichloromethane (80 mL) and washed with water (70 mL). The aqueous layer was re-extracted with methylene chloride (100 mL). The combined organic layers were washed with water (50 mL) and brine (50 mL), dried over sodium sulfate, filtered, concentrated under reduced pressure and purified using reverse phase chromatography. The product eluted with a gradient of acetonitrile in water. The desired product was isolated as a thick brown gum (0.337 g, 30%): $^1$H NMR (400 MHz, CDCl$_3$) δ 9.12 (br, 1H), 8.75 (br, 1H), 8.22 (d, J=7.9 Hz, 1H), 7.28 (br, 1H), 3.40 (s, 3H); $^{19}$F NMR (376 MHz, CDCl$_3$) δ−69.3; ESIMS m/z 324.3 (M+2); IR (thin film) 1772 cm$^{-1}$.

Example 12

Synthesis of (4-chloro-2-pyridin-3-yl-thiazol-5-yl)-methyl-amine

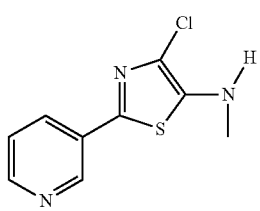

A solution of N-(4-chloro-2-pyridin-3-yl-thiazol-5-yl)-2,2,2-trifluoro-N-methyl-acetamide (0.337 g, 1 mmol) in ice-cold methanol (18 mL) was treated with potassium carbonate (0.434 g, 3.1 mmol) and stirred under nitrogen for 20 min. The solids were removed by filtration, and the filtrate was concentrated under reduced pressure and it was adsorbed onto silica gel. Purification by silica gel chromatography eluting with a gradient of ethyl acetate in hexanes afforded a bright yellow solid (0.195 g, 82%): mp 79° C. (dec); $^1$H NMR (400 MHz, CDCl$_3$) δ 8.97 (d, J=2.1 Hz, 1H), 8.55 (dd, J=4.8, J=1.5 Hz, 1H), 8.08 (ddd, J=8.1, 2.0, 2.0 Hz, 1H), 7.32 (dd, J=8.1, 4.8 Hz, 1H), 4.07 (br m, 1H), 3.03 (d, J=5.3 Hz, 3H); ESIMS m/z 228.23 (M+2); IR 1540 cm$^{-1}$.

Example 13

Preparation of 2-pyridin-3-yl-4-trifluoromethyl-thiazole-5-carboxylic acid ethyl ester

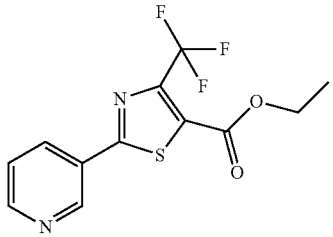 [SMILES: CCOC(=O)c1sc(-c2cccnc2)nc1C(F)(F)F]

To a 20 mL microwave tube was added thionicotinamide (0.552 g, 4.0 mmol), ethanol (15 mL) and 2-chloro-4,4,4-trifluoro-3-oxo-butyric acid ethyl ester (1.75 g, 8 mmol). The tube was capped and heated in a microwave at 150° C. for 10 min. The reaction mixture was cooled to ambient temperature and Et$_3$N (1.7 mL, 12 mmol) was added. The tube was capped and heated in a microwave at 130° C. for 1 min. After cooling to ambient temperature the solvent was evaporated and the crude reaction mixture was directly subjected to silica gel chromatography (0 to 100% ethyl acetate/hexanes) to give the desired product as an orange oil which subsequently solidified (0.885 g, 73%): IR (KBr) 2988, 1737, 1712 cm$^{-1}$; $^1$H NMR (300 MHz, CDCl$_3$) δ 9.21 (dd, J=2.5, 0.8 Hz, 1H), 8.77 (dd, J=5.0, 1.7 Hz, 1H), 8.33 (dt, J=8.0, 2.2 Hz, 1H), 7.47 (ddd, J=11.8, 4.7, 0.8 Hz, 1H), 4.45 (q, J=14.3, 7.1 Hz, 2H), 1.44 (t, J=7.1 Hz, 3H); ESIMS m/z 303 (M+1).

Example 14

Preparation of 2-pyridin-3-yl-4-trifluoromethyl-thiazole-5-carboxylic acid

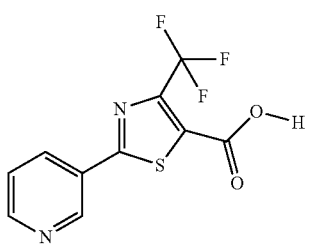 [SMILES: O=C(O)c1sc(-c2cccnc2)nc1C(F)(F)F]

To a solution of 2-pyridin-3-yl-4-trifluoromethyl-thiazole-5-carboxylic acid ethyl ester (13.9 g, 46 mmol, ca. 85% pure) in methanol (150 mL) was added an aqueous solution of sodium hydroxide (total volume 75 mL, 140 mmol), and the mixture was stirred for 40 min. Upon addition of 2 N HCl (70 mL, ca pH=3) to the reaction mixture, a precipitate was formed. Water (300 mL) was then added and the heterogeneous mixture was filtered under reduced pressure. The precipitate was rinsed further with water and dried in vacuo to give the desired product as an off-white solid (7.37 g, 58%): mp 209° C.; $^1$H NMR (300 MHz, DMSO-d$_6$) δ 9.21 (d, J=2.5 Hz, 1H), 8.77 (dd, J=4.9, 1.7 Hz, 1H), 8.41 (dt, J=8.0, 1.7 Hz, 1H), 7.60 (dd, J=8.0, 4.9 Hz, 1H), 3.4 (br s, 1H); ESIMS m/z 276.2 (M+1).

Example 15

Preparation of (2-pyridin-3-yl-4-trifluoromethyl-thiazol-5-yl)-carbamic acid tert-butyl ester (Compound 7)

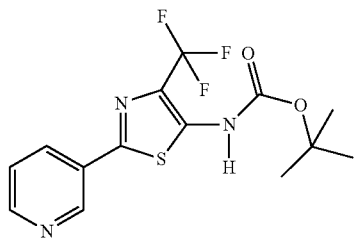 [SMILES: CC(C)(C)OC(=O)Nc1sc(-c2cccnc2)nc1C(F)(F)F]

To 2-pyridin-3-yl-4-trifluoromethyl-thiazole-5-carboxylic acid (6.33 g, 23.1 mmol) in toluene/tert-butyl alcohol (100 mL each) was added Et$_3$N (3.21 mL, 23.1 mmol) and diphenyl phosphoryl azide (5 mL, 23.1 mmol). The reaction mixture was stirred at room temperature for 5 min and then heated at 95° C. for 4 h. The mixture was cooled to room temperature and the solvents were removed under reduced pressure. The crude product was purified by silica gel column chromatography (0 to 100% ethyl acetate/hexanes) to give the desired product as a white solid (4.7 g, 59%): mp 145-147° C.; $^1$H NMR (300 MHz, CDCl$_3$) δ 9.11 (dd, J=2.5, 0.8 Hz, 1H), 8.67 (dd, J=5.0, 1.7 Hz, 1H), 8.22 (ddd, J=8.0, 2.5, 1.7 Hz, 1H), 7.58 (br s, 1H), 7.39 (ddd, J=8.0, 4.7, 0.8 Hz, 1H), 1.59 (s, 9H); ESIMS m/z 346.5 (M+1), m/z 344.2 (M−1).

The following compounds were made via the methods in the previous examples.

(4-Methyl-2-pyrimidin-5-yl-thiazol-5-yl)-carbamic acid tert-butyl ester (Compound 8)

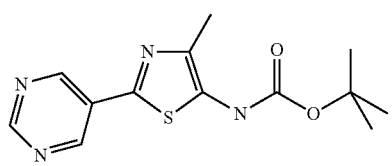 [SMILES: Cc1nc(-c2cncnc2)sc1NC(=O)OC(C)(C)C]

The compound was isolated after purification via silica gel column chromatography (0 to 100% ethyl acetate/hexanes) to give the desired product as a light yellow solid (0.25 g, 86%): mp 155° C.; ESIMS m/z 292.83 (M+1).

(4-Methyl-2-pyridin-3-yl-thiazol-5-yl)-carbamic acid tert-butyl ester (Compound 9)

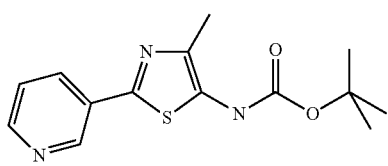 [SMILES: Cc1nc(-c2cccnc2)sc1NC(=O)OC(C)(C)C]

The compound was isolated after purification via silica gel column chromatography (0 to 100% ethyl acetate/hexanes) to yield a yellow solid (4.15 g, 61%): mp 146-148° C.; ESIMS m/z 292.5 (M+1).

Example 16

Preparation of methyl-(2-pyridin-3-yl-4-trifluoromethyl-thiazol-5-yl)carbamic acid tert-butyl ester (Compound 10)

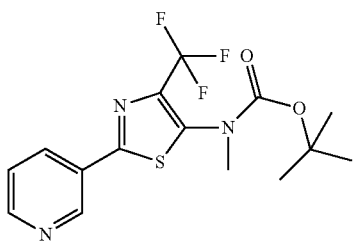 [SMILES: CN(C(=O)OC(C)(C)C)c1sc(-c2cccnc2)nc1C(F)(F)F]

To a solution of (2-pyridin-3-yl-4-trifluoromethyl-thiazol-5-yl)-carbamic acid tert-butyl ester (4.7 g, 13.6 mmol) in DMF (70 mL) at 0° C. was added sodium hydride (NaH, 0.65 g, 16.3 mmol, 60% dispersion in mineral oil) in one portion and the mixture was stirred for 50 min. Iodomethane (0.89 mL, 14.3 mmol) was added in one portion, and after 5 min the reaction mixture was warmed to room temperature and stirred for 5.5 h. Water and ethyl acetate were added, the resulting biphasic mixture was separated and the aqueous layer was extracted one time with ethyl acetate. The combined organic extracts were washed twice with brine, dried over MgSO$_4$, filtered and concentrated to dryness under reduced pressure. The crude product was purified by silica gel column chromatography (0 to 100% ethyl acetate/hexanes) to give the desired product as a clear orange oil (2.72 g, 56%); IR (KBr) 3428, 2981, 1728, 1561 cm$^{-1}$; $^1$H NMR (300 MHz, CDCl$_3$) δ 9.11 (d, J=2.5 Hz, 1H), 8.72 (dd, J=4.9, 1.1 Hz, 1H), 8.26 (dt, J=8.0, 1.7 Hz, 1H), 7.42 (dd, J=8.0, 4.9 Hz, 1H), 3.28 (s, 3H), 1.45 (s, 9H); ESIMS m/z 360.6 (M+1).

The following compounds were made via the methods in the previous examples.

Methyl-(4-methyl-2-pyrimidin-5-yl-thiazol-5-yl)-carbamic acid tert-butyl ester (Compound 11)

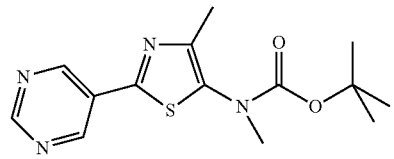 [SMILES: Cc1nc(-c2cncnc2)sc1N(C)C(=O)OC(C)(C)C]

The compound was isolated after purification by silica gel column chromatography (0 to 100% ethyl acetate/hexanes) to yield a white solid (0.66 g, 75%): ESIMS m/z 307.3 (M+1).

Ethyl-(4-methyl-2-pyridin-3-yl-thiazol-5-yl)-carbamic acid tert-butyl ester (Compound 12)

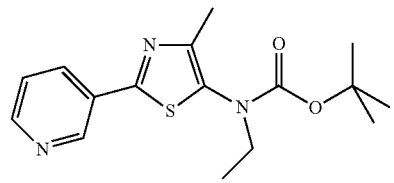 [SMILES: CCN(C(=O)OC(C)(C)C)c1sc(-c2cccnc2)nc1C]

The compound was isolated after purification via reverse-phase high-performance liquid chromatography (CH$_3$CN/H$_2$O) to yield an orange oil (0.16 g, 51%): IR (thin film) 1709 cm$^{-1}$; ESIMS m/z 320.3 (M+1).

Isopropyl-(4-methyl-2-pyridin-3-yl-thiazol-5-yl)-carbamic acid tert-butyl ester (Compound 13)

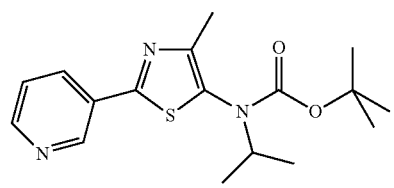 [SMILES: Cc1nc(-c2cccnc2)sc1N(C(=O)OC(C)(C)C)C(C)C]

The compound was isolated after purification via reverse-phase high-performance liquid chromatography (CH$_3$CN/H$_2$O) to yield a tan solid (0.15 g, 46%): mp 88-89° C.; ESIMS m/z 334.3 (M+1).

Isobutyl-(4-methyl-2-pyridin-3-yl-thiazol-5-yl)-carbamic acid tert-butyl ester (Compound 14)

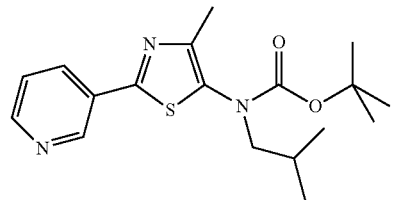 [SMILES: Cc1nc(-c2cccnc2)sc1N(CC(C)C)C(=O)OC(C)(C)C]

The compound was isolated after purification via reverse-phase high-performance liquid chromatography (CH₃CN/H₂O) to yield a brown solid (0.13 g, 37%): mp 87-88° C.; ESIMS m/z 348.3 (M+1).

Benzyl-(4-methyl-2-pyridin-3-yl-thiazol-5-yl)-carbamic acid tert-butyl ester (Compound 15)

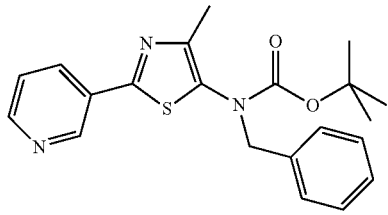 [SMILES: Cc1nc(-c2cccnc2)sc1N(Cc1ccccc1)C(=O)OC(C)(C)C]

The compound was isolated after purification via reverse-phase high-performance liquid chromatography (CH₃CN/H₂O) to yield a brown solid (0.25 g, 65%): mp 108-109° C.; ESIMS m/z 382.3 (M+1).

Example 17

Preparation of methyl-(2-pyridin-3-yl-4-trifluoromethyl-thiazol-5-yl)-amine

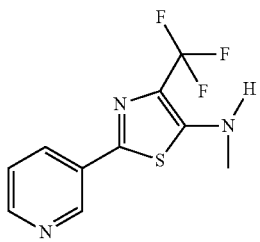 [SMILES: CNc1sc(-c2cccnc2)nc1C(F)(F)F]

To a solution of DCE (4 mL) was added methyl-(2-pyridin-3-yl-4-trifluoromethyl-thiazol-5-yl)-carbamic acid tert-butyl ester (0.616 g, 1.7 mmol) and trifluoroacetic acid (4 mL) and the mixture was stirred for 15 min. The solvents were removed under reduced pressure and the resulting residue was re-dissolved in DCE and aqueous saturated NaHCO₃. The biphasic mixture was separated and the aqueous layer was extracted three times with DCE. The organic extracts were combined, dried over MgSO₄, filtered and concentrated to dryness under reduced pressure. The crude product was purified by silica gel column chromatography (0 to 100% ethyl acetate/hexanes) to give the desired product as an off-white solid (0.357 g, 80%): mp 152-157° C.; $^1$H NMR (300 MHz, CDCl₃) δ 8.95 (d, J=2.3 Hz, 1H), 8.57 (dd, J=4.9, 1.7 Hz, 1H), 8.11 (dt, J=8.2, 2.3 Hz, 1H), 7.23 (ddd, J=7.9, 4.9, 0.7 Hz, 1H), 4.83 (br s, 1H), 3.05 (d, J=4.9 Hz, 3H); ESIMS m/z 260 (M+1), m/z 257.9 (M−1).

Example 18

Preparation of 2-bromo-4-methyl-thiazole-5-carboxylic acid

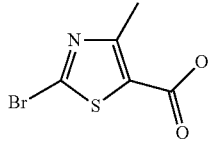

To a solution of 2-bromo-4-methyl-thiazole-5-carboxylic acid ethyl ester (3.0 g, 12 mmol) in tetrahydrofuran (THF, 50 mL) and water (5 mL) was added lithium hydroxide hydrate (1.0 g, 24 mmol). The reaction mixture was stirred at ambient temperature for 16 h. The reaction mixture was diluted with water and ethyl acetate. The aqueous layer was made acidic to pH 1 with 2 N hydrochloric acid (HCl) and then was extracted with ethyl acetate. The organic extracts were dried over sodium sulfate (Na₂SO₄), filtered and concentrated to provide product as an orange solid (2.6 g, 98%): mp 152-155° C.; $^1$H NMR (300 MHz, CDCl₃) δ 2.74 (s, 3H); ESIMS m/z 221 (M−1).

Example 19

Preparation of 2-bromo-4-methyl-thiazole-5-carbonyl-azide

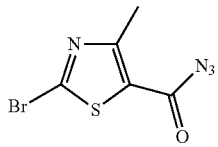

To a solution of 2-bromo-4-methyl-thiazole-5-carboxylic acid (5.0 g, 22.5 mmol) in toluene (100 mL) was added Et₃N (2.28 g, 22.5 mmol) followed by diphenyl phosphoryl azide (DPPA, 6.20 g, 22.5 mmol). The reaction mixture was stirred at ambient temperature for 4 h. The reaction mixture was concentrated and purified by silica gel chromatography (0-100% ethyl acetate/hexanes) to afford a brown solid (4.67 g, 84%): mp 86-89° C.; IR (KBr) 2183, 1672 cm$^{-1}$; $^1$H NMR (300 MHz, CDCl₃) δ 2.79 (s, 3H); ESIMS m/z 221 ((M-N₂)+2).

Example 20

Preparation of (2-bromo-4-methyl-thiazol-5-yl)-carbamic acid tert-butyl ester

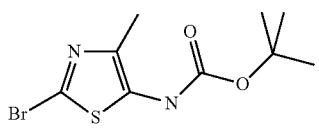

A solution of 2-bromo-4-methyl-thiazole-5-carbonyl-azide (3.0 g, 12.1 mmol) in toluene (80 mL) was heated to reflux and stirred for 2 h before tert-butyl alcohol (2 mL, 20.6 mmol) was added. The reaction mixture was further stirred at reflux for 1 h, then it was cooled and concentrated. Purification by silica gel chromatography (0-100% ethyl acetate/hexanes) afforded an off-white solid (3.4 g, 95%): mp 114-116° C.; $^1$H NMR (300 MHz, CDCl$_3$) δ 6.58 (br s, 1H), 2.29 (s, 3H), 1.54 (s, 9H); ESIMS m/z 295 (M+2).

Example 21

Preparation of (2-bromo-4-methyl-thiazol-5-yl)-methyl-carbamic acid tert-butyl ester

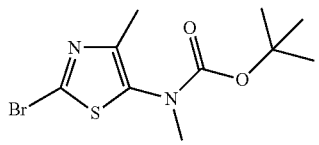 [SMILES: Cc1nc(Br)sc1N(C)C(=O)OC(C)(C)C]

To a solution of (2-bromo-4-methyl-thiazol-5-yl)-carbamic acid tert-butyl ester (2.93 g, 10 mmol) in DMF (50 mL) at 0° C. was added NaH (480 mg, 12 mmol, 60% dispersion in mineral oil) in one portion and the suspension was stirred for 1 h. Iodomethane (0.65 mL, 10.5 mmol) was added in one portion, and after 5 min the reaction mixture was warmed to ambient temperature and stirred for 5 h. Water and ethyl acetate were added and the resulting biphasic mixture was separated. The aqueous layer was extracted one time with ethyl acetate. The combined organic extracts were washed twice with brine, dried over Na$_2$SO$_4$, filtered and concentrated to dryness under reduced pressure. The crude product was purified by silica gel chromatography (0-100% ethyl acetate/hexanes) to give the desired product as a clear oil (1.66 g, 54%): IR (KBr) 1688 cm$^{-1}$; $^1$H NMR (300 MHz, CDCl$_3$) δ 2.98 (s, 3H), 2.29 (s, 3H), 1.54 (s, 9H); ESIMS m/z 309 (M+2).

Example 22

Preparation of [2-(6-chloropyridin-3-yl)-thiazol-5-yl]-methyl-carbamic acid tert-butyl ester (Compound 16)

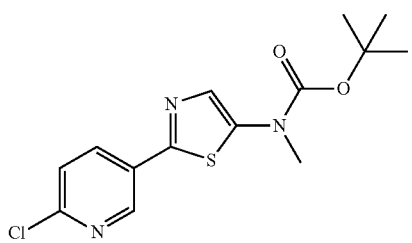 [SMILES: CN(C(=O)OC(C)(C)C)c1cnc(-c2ccc(Cl)nc2)s1]

To a suspension of 6-chloro-3-pyridine boronic acid (158 mg, 1.0 mmol) in toluene (4 mL) was added absolute ethanol (2 mL) followed by a 2.0 M solution of K$_2$CO$_3$ (1.0 mL). To this mixture was added (2-bromo-thiazol-5-yl)-methyl-carbamic acid tert-butyl ester (322 mg, 1.1 mmol) followed by tetrakis(triphenylphosphine)palladium(0) (58 mg, 0.05 mmol). The reaction mixture was heated to 100° C. for 16 h. The mixture was cooled and diluted with ethyl acetate. The organic layer was washed with saturated aqueous NaHCO$_3$, dried over Na$_2$SO$_4$, filtered and concentrated. The organic layer was purified by silica gel chromatography (0-100% ethyl acetate/hexanes) to afford an off-white solid (270 mg, 83%): mp 167-170° C.; $^1$H NMR (300 MHz, CDCl$_3$) δ 8.88 (br s, 1H), 8.16 (dd J=3.0, 8.0 Hz, 1H), 7.40 (d, J=7.0 Hz, 1H), 7.39 (s, 1H), 3.45 (s, 3H), 1.61 (s, 9H); ESIMS m/z 326 (M+1).

The following compound was made according to the procedure in Example 22.

N-[2-(5-chloropyridin-3-yl)-4-methyl-thiazol-5-yl]-2-methyl-3-methylsulfanyl-propionamide (Compound 17)

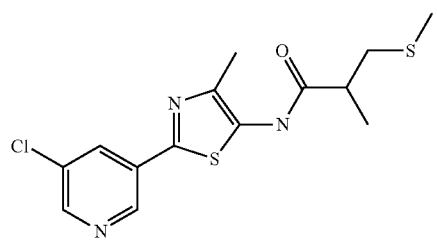 [SMILES: CSCC(C)C(=O)Nc1sc(-c2cncc(Cl)c2)nc1C]

The compound was isolated after purification via silica gel chromatography (0-100% ethyl acetate/hexanes) to afford a viscous brown oil (74 mg, 43%): IR (KBr) 3283, 2968, 2917, 1667, 1562 cm$^{-1}$; $^1$H NMR (300 MHz, CDCl$_3$) δ 8.96 (d, J=2.0 Hz, 1H), 8.58 (br s, 1H), 8.56 (d, J=2.0 Hz, 1H), 8.22 (t, J=2.0 Hz, 1H), 2.88 (m, 1H), 2.78 (m, 2H), 2.51 (s, 3H), 2.23 (s, 3H), 1.40 (d, J=6.0 Hz, 3H); ESIMS m/z 342 (M+1).

Example 23

Preparation of [2-(6-chloropyridin-3-yl)-thiazol-5-yl]-methyl-amine

To a solution of [2-(6-chloropyridin-3-yl)-thiazol-5-yl]-methyl-carbamic acid tert-butyl ester (90 mg, 0.27 mmol) in CH$_2$Cl$_2$ (2 mL) was added trifluoroacetic acid (2 mL), and the reaction mixture was stirred for 1 h at ambient temperature. The reaction was quenched with saturated aqueous NaHCO$_3$ and extracted with CH$_2$Cl$_2$. The organic layer was dried over Na$_2$SO$_4$, filtered, concentrated and purified by silica gel chromatography (0-100% ethyl acetate/hexanes) to afford a yellow oil (50 mg, 80%): IR (KBr) 2924, 1591, 1498 cm$^{-1}$; $^1$H NMR 300 MHz, CDCl$_3$) δ 8.71 (d, J=3.0 Hz, 1H), 8.00 (dd J=3.0, 8.0 Hz, 1H), 7.31 (d, J=7.0 Hz, 1H), 7.30 (s, 1H), 4.28 (br s, 1H), 3.05 (d, J=8.0 Hz, 3H); ESIMS m/z 226 (M+1).

Example 24

Preparation of 4-methyl-2-pyridin-3-yl-thiazol-5-ylamine

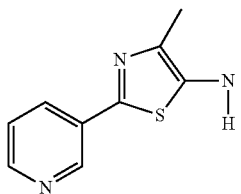

To (4-methyl-2-pyridin-3-yl-thiazol-5-yl)-carbamic acid tert-butyl ester (3.73 g, 12.8 mmol) in methanol (100 mL) at 0° C. was slowly added acetyl chloride (28 mL, 400 mmol). The flask was stoppered and removed from the ice bath. The reaction mixture was allowed to warm to ambient temperature and was stirred overnight. The resulting yellow heterogeneous solution was poured slowly into a separatory funnel containing ethyl acetate and saturated aqueous $NaHCO_3$. When the addition was complete, more saturated aqueous $NaHCO_3$ was added until the pH=7. The layers were separated, and the aqueous layer was extracted twice with ethyl acetate. The combined organic extracts were washed with brine, dried over $MgSO_4$, filtered, and concentrated under reduced pressure. The residue was purified via normal phase chromatography (0 to 100% ethyl acetate/hexanes) to afford the amino-thiazole as a yellow solid (1.66 g, 68%): mp 160-162° C.; $^1$H NMR (300 MHz, $CDCl_3$) δ 8.96 (d, J=2.3 Hz, 1H), 8.58 (dd, J=5.0, 1.7 Hz, 1H), 8.06 (dt, J=7.9, 2.3 Hz, 1H), 7.30 (dd, J=7.9, 5.0 Hz, 1H), 3.57 (br s, 2H), 2.32 (s, 3H); ESIMS m/z 192 (M+1).

Example 25

Preparation of N-(2-bromo-4-methyl-thiazol-5-yl)-2-methyl-3-methylsulfanyl-propionamide

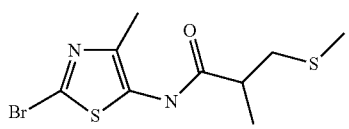

To a solution of (2-bromo-4-methyl-thiazol-5-yl)-carbamic acid tert-butyl ester (3.1 g, 10.57 mmol) in DCE (50 mL) was added $Et_3N$ (3.7 mL, 26.4 mmol) followed by 2-methyl-3-methylsulfanyl-propionyl chloride (2.42 g, 15.8 mmol). The reaction mixture was heated to 65° C. for 3 h. The mixture was cooled, diluted with DCE, washed with saturated aqueous ammonium chloride ($NH_4Cl$) and dried over $Na_2SO_4$. The crude product was dissolved in $CH_2Cl_2$ (30 mL) and trifluoroacetic acid (10 mL) was added. The reaction mixture was stirred at ambient temperature for 30 min. The reaction was quenched with saturated aqueous $NaHCO_3$ and extracted with $CH_2Cl_2$. The organic layer was dried over $Na_2SO_4$, filtered, concentrated and purified by silica gel chromatography (0-100% ethyl acetate/hexanes) to afford a clear oil (2.68 g, 82%): IR (KBr) 3282, 2966, 2916, 1668 $cm^{-1}$; $^1$H NMR (300 MHz, $CDCl_3$) δ 9.97 (br s, 1H), 4.17 (m, 3H), 3.79 (s, 3H), 3.59 (s, 3H), 2.76 (d, J=7.0 Hz, 3H); ESIMS m/z 311 (M+2).

Example 26

Preparation of N-[2-(5-fluoropyridin-3-yl)-thiazol-5-yl]-2,2,N-trimethyl-3-methylsulfanyl-propionamide (Compound 18)

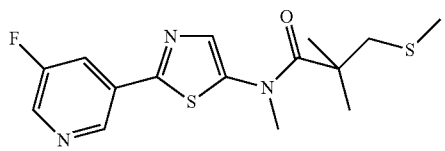 [SMILES: CSCC(C)(C)C(=O)N(C)c1cnc(-c2cncc(F)c2)s1]

To a solution of 2,2,2-trifluoro-N-[2-(5-fluoro-pyridin-3-yl)-thiazol-5-yl]-N-methyl-acetamide (244 mg, 0.80 mmol) in methanol (6 mL) was added an aqueous solution of sodium hydroxide (160 mg, 4 mmol, in 3 mL $H_2O$), and the mixture was stirred at room temperature for 45 min. To this solution was added pH 7.0 aqueous buffer and ethyl acetate. The layers were separated, and the aqueous layer was extracted with ethyl acetate. The combined organic extracts were dried over $MgSO_4$, filtered, and concentrated in vacuo. To this crude material was added DCE (5 mL), 4-dimethylaminopyridine (DMAP, 300 mg, 2.5 mmol) and then a solution of the 2,2-dimethyl-3-methylthiopropionyl chloride (250 mg, 1.5 mmol) in DCE (3.0 mL). This mixture was heated to 75° C. and stirred overnight. The heterogeneous mixture thus obtained was loaded directly onto a chromatographic column Silica gel chromatography (0 to 100% ethyl acetate/hexanes) afforded the product as a red solid (161 mg, 59%): mp 98-102° C.; $^1$H NMR (300 MHz, $CDCl_3$) δ 8.95 (app s, 1H), 8.51 (d, J=2.8 Hz, 1H), 7.98 (app dt, J=9.3, 2.5 Hz, 1H), 7.66 (s, 1H), 3.59 (s, 3H), 2.87 (s, 3H), 2.17 (s, 2H), 1.47 (s, 6H); ESIMS m/z 340 (M+1).

Example 27

Preparation of N-methyl-3-methylsulfanyl-N-(2-pyridin-3-yl-thiazol-5-yl)-propionamide (Compound 19)

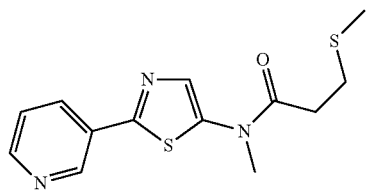 [SMILES: CSCCC(=O)N(C)c1cnc(-c2cccnc2)s1]

A solution of 3-methylsulfanyl-propionyl chloride (120 mg, 0.9 mmol) in DCE (1 mL) was pipetted at a dropwise rate into an ice-cold suspension of methyl-(2-pyridin-3-yl-thiazol-5-yl)-amine (114 mg, 0.6 mmol) in DCE (5 mL), and the mixture was stirred for 5 min before adding a solution of DMAP (80 mg, 0.6 mmol) in DCE (1 mL). The ice bath was removed after 30 min, and the mixture was stirred at reflux under nitrogen for 15 min. The reaction mixture was cooled, diluted with DCE (70 mL), washed with saturated aqueous $NaHCO_3$ (50 mL), dried over MgSO$_4$ and purified by silica gel chromatography (3:1 ethyl acetate/hexanes) to afford a fine yellow powder (131 mg, 75%): mp 116-118° C.; $^1$H NMR (400 MHz, DMSO-d$_6$) δ 9.08 (d, J=2.0 Hz, 1H), 8.61 (dd, J=4.8, 1.4 Hz, 1H), 8.24 (dt, J=9.8, 1.8 Hz, 1H), 7.81 (s, 1H), 7.51 (dd, J=7.7, 4.7 Hz, 1H), 3.56 (s, 3H), 3.02 (t, J=7.0 Hz, 2H), 2.76 (t, J=7.2 Hz, 2H), 2.12 (s, 3H); ESIMS m/z 294 (M+1).

Example 28

N-[2-(6-fluoropyridin-3-yl)-4-methyl-thiazol-5-yl]-2,2-dimethyl-3-methylsulfanyl-propionamide (Compound 20)

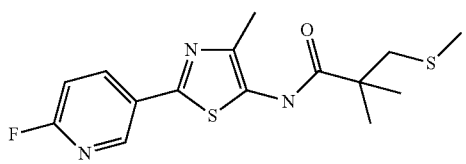 [SMILES: CSCC(C)(C)C(=O)Nc1sc(-c2ccc(F)nc2)nc1C]

To a solution of [2-(6-fluoropyridin-3-yl)-4-methyl-thiazol-5-yl]-carbamic acid tert-butyl ester (170 g, 0.55 mmol) in DCE (2.5 mL) was added Et$_3$N (0.19 mL, 1.37 mmol), followed by 2,2-dimethyl-3-methylsulfanyl-propionyl chloride (140 mg, 0.82 mmol). The reaction mixture was heated to 65° C. for 16 h. The mixture was cooled, diluted with DCE, washed with saturated aqueous NaHCO$_3$ and dried over Na$_2$SO$_4$. The crude product was dissolved in CH$_2$Cl$_2$ (2 mL), and trifluoroacetic acid (1 mL) was added. The reaction mixture was stirred at ambient temperature for 30 min. The reaction was quenched with saturated aqueous NaHCO$_3$ and extracted with CH$_2$Cl$_2$. The organic layer was dried over Na$_2$SO$_4$, filtered and concentrated. Silica gel chromatography (0-100% ethyl acetate/hexanes) afforded a yellow oil (142 mg, 76%): IR (KBr) 3284, 2969, 2918, 1668, 1562, 1498 cm$^{-1}$; $^1$H NMR (300 MHz, CDCl$_3$) δ 8.89 (bs, 1H), 8.72 (d, J=2.0 Hz, 1H), 8.27 (dt, J=8.0, 2.0 Hz, 1H), 6.99 (dd, J=8.0, 3.0 Hz 1H), 2.88 (s, 2H), 2.51 (s, 3H), 2.24 (s, 3H), 1.45 (s, 6H); ESIMS m/z 340 (M+1).

The following molecule, Compound 21, and Compounds 22-65 and 67-71 in Table 1 were made using the procedures disclosed above.

N-isobutyryl-N-(4-methyl-2-pyridin-3-yl-thiazol-5-yl)-isobutyramide (Compound 21)

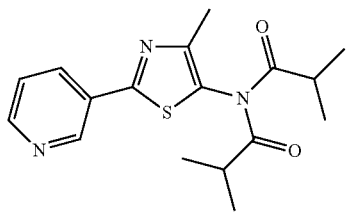 [SMILES: Cc1nc(-c2cccnc2)sc1N(C(=O)C(C)C)C(=O)C(C)C]

The compound was isolated after purification by silica gel chromatography (0-100% ethyl acetate/hexanes) as a yellow oil (150 mg, 90%): IR (KBr) 2974, 1721 cm$^{-1}$; $^1$H NMR (300 MHz, CDCl$_3$) δ 9.13 (d, J=2.0 Hz, 1H), 8.69 (dd, J=5.0, 3.0 Hz, 1H), 8.21 (dt, J=12.0, 2.0 Hz, 1H), 7.42 (dd, J=8.0, 5.0 Hz, 1H), 3.24 (septet, J=7.0 Hz, 2H), 2.32 (s, 3H), 1.24 (d, J=7.0 Hz, 12H); ESIMS m/z 332 (M+1).

Example 29

Preparation of [2-(5-fluoropyridin-3-yl)-thiazol-5-yl]-1-methyl-3-(2-methylsulfanyl-ethyl)urea (Compound 72)

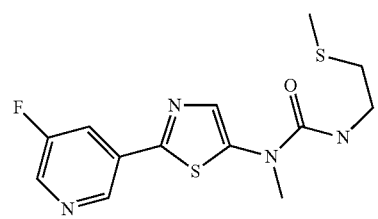 [SMILES: CSCCNC(=O)N(C)c1cnc(-c2cncc(F)c2)s1]

To a solution of [2-(5-fluoropyridin-3-yl)-thiazol-5-yl]-methyl-amine (0.4 g, 1.91 mmol) in DCE (5 mL) at 0° C. was added phosgene (1.3 mL, 2.5 mmol, 20 wt % solution in toluene). After 5 min, DMAP (0.5 g, 4.1 mmol) was added in one portion and the ice bath was removed. After another 5 min, the mixture was heated to reflux and stirred for 20 min. The reaction was cooled to ambient temperature and half of the solution was transferred to a vial and to this was added 2-(methylthio)ethanamine (0.183 g, 2.0 mmol) and DMAP (0.244 g, 2.0 mmol). The reaction was capped and heated at 80° C. overnight. The reaction was quenched upon addition of ethyl acetate and 0.1 N HCl. The layers were separated, and the organic layer was washed separately with saturated aqueous NaHCO$_3$ and brine. The ethyl acetate layer was dried over MgSO$_4$, filtered and concentrated under reduced pressure. The crude product was purified by silica gel column chromatography (0 to 100% ethyl acetate/hexanes) to give the desired product as an off-white solid (0.253 g, 81%): mp 117-119° C.; $^1$H NMR (300 MHz, CDCl$_3$) δ 8.94 (br s, 1H), 8.50 (d, J=2.7 Hz, 1H), 7.99-7.94 (m, 1H), 7.54 (s, 1H), 5.37 (m, 1H), 3.53 (q, J=11.8, 5.5 Hz, 2H), 3.43 (s, 3H), 2.72 (app t, J=6.6 Hz, 2H), 2.13 (s, 3H); ESIMS m/z 327.1 (M+H); m/z 325.0 (M−1).

The following molecule, Compound 73, was made using the procedures disclosed in Example 29.

3-sec-Butyl-1-[2-(5-fluoropyridin-3-yl)-thiazol-5-yl]-1-methyl-urea (Compound 73)

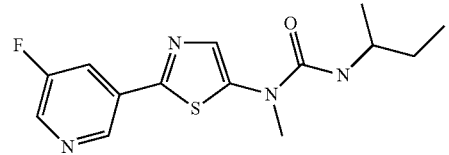 [SMILES: CCC(C)NC(=O)N(C)c1cnc(-c2cncc(F)c2)s1]

The compound was isolated after purification via silica gel chromatography (0 to 100% ethyl acetate/hexanes) to yield a yellow solid (0.07 g, 42%): mp 159-161° C.; ESIMS m/z 309 (M+1).

Example 30

Preparation of [2-(5-fluoropyridin-3-yl)-thiazol-5-yl]-1,3-dimethyl-3-(2-methylsulfanyl-ethyl)urea (Compound 74)

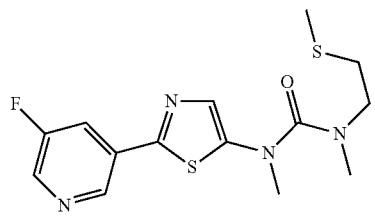 [SMILES: CSCCN(C)C(=O)N(C)c1cnc(-c2cncc(F)c2)s1]

To a solution of [2-(5-fluoropyridin-3-yl)-thiazol-5-yl]-1-methyl-3-(2-methylsulfanyl-ethyl)urea (173 mg, 0.53 mmol) in DMF (5 mL) cooled to 0° C. was added NaH (26 mg, 0.65 mmol, 60% dispersion in mineral oil) and the mixture was stirred for 30 min. To this was added iodomethane (47 µL, 0.75 mmol) and the reaction mixture was stirred for 1 h. The reaction was quenched by addition of ethyl acetate and 1 N HCl. The layers were separated, and the ethyl acetate layer was washed three times with water and once with brine, dried over MgSO$_4$, filtered and concentrated to dryness under reduced pressure to give the desired product as a yellow solid (0.110 g, 61%): mp 68-69° C.; $^1$H NMR (300 MHz, CDCl$_3$) δ 8.90 (s, 1H), 8.47 (d, J=2.8 Hz, 1H), 7.93 (dt, J=9.3, 2.2 Hz, 1H), 7.45 (s, 1H), 3.54 (t, J=6.9 Hz, 2H), 3.41 (s, 3H), 2.94 (s, 3H), 2.74 (t, J=7.1 Hz, 2H), 2.16 (s, 3H); ESIMS m/z 341.1 (M+1).

Example 31

Preparation of [2-(5-fluoropyridin-3-yl)-thiazol-5-yl]-methyl-carbamic acid 2-methylsulfanyl-ethyl ester (Compound 75)

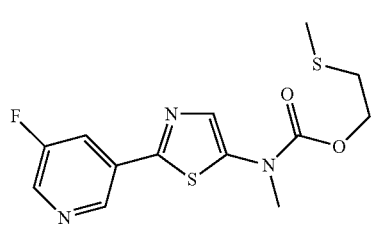 [SMILES: CSCCOC(=O)N(C)c1cnc(-c2cncc(F)c2)s1]

The carbamoyl chloride was formed as in Example 29. A 0.72 mmol solution of carbamoyl chloride in DCE was added to 2-(methylthio)ethanol (0.092 g, 1.0 mmol) and DMAP (0.122 g, 1.0 mmol) and heated at reflux overnight. The reaction was quenched upon addition of ethyl acetate and 0.1 N HCl. The layers were separated, and the organic layer was washed with saturated aqueous NaHCO$_3$ and brine. The ethyl acetate layer was dried over MgSO$_4$, filtered and concentrated to dryness under reduced pressure. The crude product was purified by silica gel column chromatography (0 to 100% ethyl acetate/hexanes) to give the desired product as a tan solid (0.102 g, 65%): mp 115-117° C.; $^1$H NMR (300 MHz, CDCl$_3$,) δ 8.90 (s, 1H), 8.46 (d, J=2.6 Hz, 1H), 7.92 (dt, J=9.2, 2.6 Hz, 1H), 7.45 (br s, 1H), 4.44 (t, J=6.9 Hz, 2H), 3.49 (s, 3H), 2.83 (t, J=6.6 Hz, 2H), 2.18 (s, 3H); ESIMS m/z 328.1 (M+1).

Compounds 76-77 were made using the procedures disclosed above.

[2-(5-Fluoropyridin-3-yl)-thiazol-5-yl]-methyl-carbamic acid ethyl ester (Compound 76)

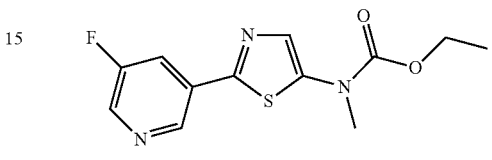

The compound was isolated after purification via silica gel chromatography (0 to 100% ethyl acetate/hexanes) to yield an off-white solid (0.067 g, 45%): mp 122-124° C.; ESIMS m/z 282.1 (M+1).

[2-(5-Fluoropyridin-3-yl)-thiazol-5-yl]-methyl-carbamic acid 5-nitro-furan-2-ylmethyl ester (Compound 77)

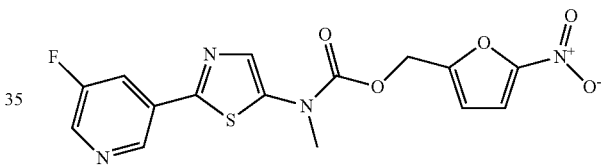

The compound was isolated after purification via silica gel chromatography (0 to 100% ethyl acetate/hexanes) to yield a brown solid (0.025 g, 28%): mp 95-99° C.; ESIMS m/z 379.1 (M+1).

Example 32

Preparation of N-[2-(5-fluoropyridin-3-yl)-thiazol-5-yl]-3-methanesulfinyl-N-methyl-propionamide (Compound 78)

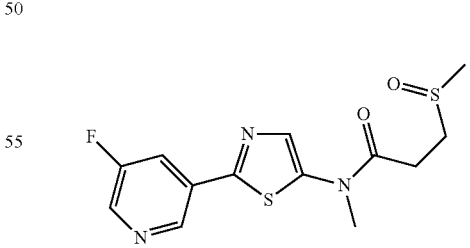

To N-[2-(5-fluoro-pyridin-3-yl)-thiazol-5-yl]-N-methyl-3-methylsulfanyl-propionamide (Compound 30, 44 mg, 0.14 mmol) in glacial acetic acid (1.5 mL) was added sodium perborate tetrahydrate (23 mg, 0.14 mmol), and the mixture was heated at 65° C. for 2 h. The reaction mixture was carefully poured into a separatory funnel containing saturated aqueous NaHCO$_3$ resulting in gas evolution. When the gas evolution had ceased, DCE was added and the layers were separated. The aqueous layer was extracted twice with DCE, and all the organic layers were combined, dried over MgSO₄, filtered and concentrated under reduced pressure to give the desired product as white solid (20 mg, 45%): mp 152-154° C.; ¹H NMR (300 MHz, CDCl₃) δ 8.95 (s, 1H), 8.59 (s, 0.3H), 8.49 (s, 0.7H), 7.98 (d, J=9.3 Hz, 1H), 7.73 (s, 0.3H), 7.62 (s, 0.7H), 3.64 (s, 2.1H), 3.36 (s, 0.9H), 3.40-2.70 (m, 4H), 2.69 (s, 2.1H), 2.61 (s, 0.9H); ESIMS m/z 328.1 (M+1), m/z 326.1 (M−1).

Compounds 79-94 in Table 1 were made using the procedures disclosed above.

Example 33

Preparation of 3-methanesulfonyl-N-methyl-N-(4-methyl-2-pyridin-3-yl-thiazol-5-yl)-propionamide (Compound 95)

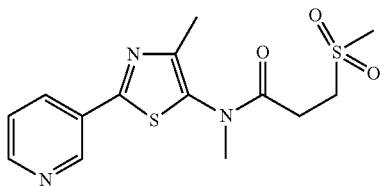 [SMILES: Cc1nc(-c2cccnc2)sc1N(C)C(=O)CCS(C)(=O)=O]

To N-methyl-N-(4-methyl-2-pyridin-3-yl-thiazol-5-yl)-3-methylsulfanyl-propionamide (Compound 19, 132 mg, 0.43 mmol) in glacial acetic acid (4.0 mL) was added sodium perborate tetrahydrate (165 mg, 1.07 mmol), and the mixture was heated at 65° C. for 16 h. The reaction mixture was carefully poured into a separatory funnel containing saturated aqueous NaHCO₃ resulting in gas evolution. When the gas evolution had ceased, dichloromethane was added and the layers were separated. The aqueous layer was extracted twice with dichloromethane, and all the organic layers were combined, dried over MgSO₄, filtered and concentrated under reduced pressure. The crude product was purified by silica gel column chromatography (0 to 10% methanol/dichloromethane) to give the desired product as a white oil (77 mg, 65%): IR (KBr) 2927, 1675 cm⁻¹; ¹H NMR (300 MHz, CDCl₃) δ 9.10 (d, J=2.0 Hz, 1H), 8.68 (dd, J=4.9, 1.7 Hz, 1H), 8.19 (dt, J=8.2, 2.0 Hz, 1H), 7.41 (dd, J=7.9, 4.9 Hz, 1H), 3.41 (t, J=6.9 Hz, 2H), 3.28 (s, 3H), 2.96 (s, 3H), 2.77 (t, J=7.3 Hz, 2H), 2.38 (s, 3H); ESIMS m/z 340.2 (M+1).

Compounds 96-101 were made using the procedures disclosed above.

Example 34

Preparation of [4-methyl-2-(5-methyl-pyridin-3-yl)-thiazol-5-yl]-(2-methyl-3-methylsulfanyl-propionyl)-carbamic acid tert-butyl ester (Compound 156)

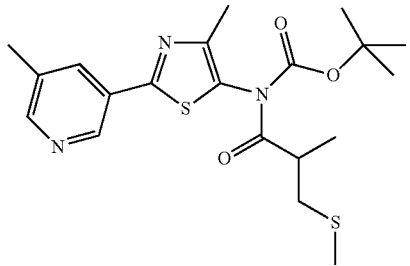 [SMILES: CSCC(C)C(=O)N(C(=O)OC(C)(C)C)c1sc(-c2cncc(C)c2)nc1C]

To a solution of [4-methyl-2-(5-methyl-pyridin-3-yl)-thiazol-5-yl]-carbamic acid tert-butyl ester (175 mg, 0.57 mmol) in dichloroethane (3 mL) was added triethylamine (0.2 mL, 1.44 mmol) followed by 2-methyl-3-methylsulfanyl-propionyl chloride (131 mg, 0.86 mmol). The reaction mixture was stirred at 65° C. for 16 hrs. The mixture was cooled, diluted with dichloroethane, washed with saturated aqueous NaHCO₃ and dried over Na₂SO₄, filtered and concentrated. The crude product was purified by silica gel chromatography (0 to 100% ethyl acetate/hexanes) to afford an orange oil (142 mg, 59%): IR (KBr) 1743, 1713 cm⁻¹; ¹H NMR (300 MHz, CDCl₃) δ 8.87 (d, J=2.0 Hz, 1H), 8.48 (s, 1H), 8.02 (s, 1H), 4.00-3.87 (m, 1H), 2.94 (dd, J=13.2, 8.3 Hz, 1H), 2.58 (dd, J=13.2, 6.1 Hz, 1H), 2.40 (s, 3H), 2.28 (s, 3H), 2.15 (s, 3H), 1.45 (s, 9H), 1.35 (d, J=6.8 Hz, 3H); ESIMS m/z 422 (M+1).

Example 35

Preparation of 2-methyl-N-[4-methyl-2-(5-methyl-pyridin-3-yl)-thiazol-5-yl]-3-methylsulfanyl-propionamide (Compound 171)

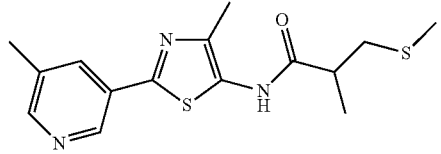

To a solution of [4-methyl-2-(5-methyl-pyridin-3-yl)-thiazol-5-yl]-(2-methyl-3-methylsulfanyl-propionyl)-carbamic acid tert-butyl ester (117 mg, 0.27 mmol) in dichloromethane (2 mL) was added trifluoroacetic acid (0.6 mL) and the reaction was stirred for 30 minutes at ambient temperature. The reaction was quenched with saturated aqueous NaHCO₃ and the mixture was extracted with dichloromethane. The organic layer was dried over Na₂SO₄, filtered and concentrated. The crude product was purified by silica gel chromatography (0 to 100% ethyl acetate/hexanes) to afford a yellow gum (75 mg, 85%): IR (KBr) 2973, 2920, 1711 cm⁻¹; ¹H NMR (300 MHz, CDCl₃) δ 8.89 (d, J=1.9 Hz, 1H), 8.43 (s, 1H), 8.00 (s, 1H), 2.91-2.69 (m, 3H), 2.47 (d, J=1.6 Hz, 3H), 2.39 (d, J=0.5 Hz, 3H), 2.19 (s, 3H), 2.13 (s, 1H), 1.37 (d, J=6.6 Hz, 3H); ESIMS m/z 322 (M+1).

Example 36

Benzoic acid [(2-methyl-3-methylsulfanyl-propionyl)-(4-methyl-2-pyridin-3-yl-thiazol-5-yl)-amino]-methyl ester (Compound 203)

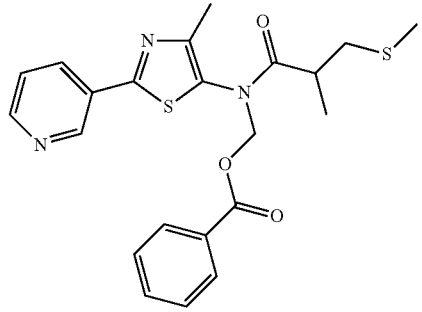 [SMILES: CSCC(C)C(=O)N(COC(=O)c1ccccc1)c1sc(-c2cccnc2)nc1C]

To a solution of 2-methyl-N-(4-methyl-2-pyridin-3-yl-thiazol-5-yl)-(3-methylsulfanyl-propionamide (200 mg, 0.65 mmol) in DMF (3.2 mL) was added sodium hydride (52 mg, 1.3 mmol) and the reaction was stirred for 30 min at ambient temperature. To the reaction mixture was added benzoic acid chloromethyl ester (221 mg, 1.3 mmol) and the reaction was stirred at ambient temperature for 16 h. The reaction was quenched with saturated aqueous NH₄Cl and the mixture was extracted with ethyl acetate. The organic layer was dried over Na₂SO₄, filtered and concentrated. The crude product was purified by silica gel chromatography (0 to 100% ethyl acetate/hexanes) to afford a light yellow oil (48 mg, 16%): IR (KBr) 1722, 1695 cm⁻¹; ¹H NMR (400 MHz, CDCl₃) δ 9.10 (s, 1H), 8.68 (d, J=3.6 Hz, 1H), 8.19 (d, J=7.4 Hz, 1H), 8.05 (d, J=7.3 Hz, 2H), 7.60 (t, J=7.4 Hz, 1H), 7.47 (t, J=7.7 Hz, 2H), 7.40 (dd, J=5.1, 2.2 Hz, 1H), 6.11 (t, J=10.8 Hz, 1H), 5.78 (dd, J=24.2, 9.4 Hz, 1H), 3.01-2.82 (m, 2H), 2.48 (s, 3H), 2.42 (s, 1H), 2.05 (t, J=6.3 Hz, 3H), 1.22 (d, J=6.5 Hz, 3H); ESIMS m/z 442 (M+1).

Example 37

Preparation of (4-bromo-2-pyridin-3-yl-thiazol-5-yl)-methyl-carbamic acid tert-butyl ester (Compound 242)

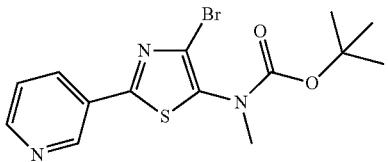

To a solution of methyl-(2-pyridin-3-yl-thiazol-5-yl)-carbamic acid tert-butyl ester (100 mg, 0.34 mmol) in acetonitrile (2 mL) was added N-bromosuccinimide (122 mg, 0.68 mmol) in one portion and the reaction mixture was stirred for 1 h. The reaction mixture was concentrated and the crude product was purified by silica gel chromatography (0 to 100% ethyl acetate/hexanes) to give the desired product as a white solid (81 mg, 64%): mp 88-91° C.; IR (KBr) 1715 cm⁻¹; ¹H NMR (300 MHz, CDCl₃) δ 9.11 (s, 1H), 8.70 (d, J=4.2 Hz, 1H), 8.28-8.17 (m, 1H), 7.42 (dd, J=8.1, 4.8 Hz, 1H), 3.27 (s, 3H), 1.48 (s, 9H); ESIMS m/z 372 (M+2).

Example 38

Preparation of tert-butyl 2-(5-fluoropyridin-3-yl)-4-iodothiazol-5-yl carbamate (Compound 481)

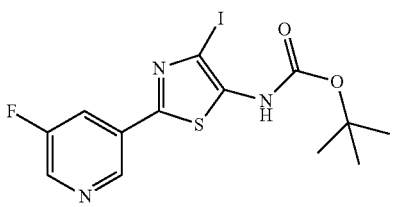 [SMILES: CC(C)(C)OC(=O)Nc1sc(-c2cncc(F)c2)nc1I]

To a solution of tert-butyl 2-(5-fluoropyridin-3-yl)thiazol-5-ylcarbamate (1.50 g, 5.08 mmol) in acetonitrile (50 mL) at 0° C. was added N-iodosuccinimide (2.40 g, 10.67 mmol). The mixture was stirred at 0° C. for 5 min and diluted with ethyl acetate and water. The organic phase was separated and rinsed with brine, dried over MgSO₄ and concentrated in vacuo to give a dark solid. This solid was passed through a bed of silica gel (100 g) eluting with 10% ether in hexanes (600 mL) to give tert-butyl 2-(5-fluoropyridin-3-yl)-4-iodothiazol-5-yl-carbamate as a pale yellow solid (1.80 g, 84% yield): mp 148-149° C.; ¹H NMR (300 MHz, CDCl₃) δ 8.87 (t, J=1.5 Hz, 1H), 8.47 (d, J=2.7 Hz, 1H), 7.93 (ddd, J=9.0, 2.5, 1.9 Hz, 1H), 7.08 (s, 1H), 1.57 (s, 9H). ESIMS m/z 422.1 (M+1), 420.2 (M−1).

Example 39

Preparation of tert-butyl 2-(5-fluoropyridin-3-yl)-4-iodothiazol-5-yl(methyl)carbamate (Compound 497)

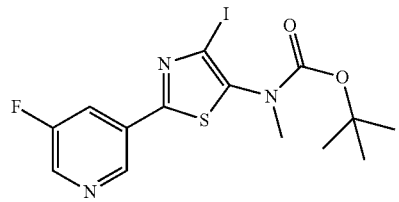 [SMILES: CN(C(=O)OC(C)(C)C)c1sc(-c2cncc(F)c2)nc1I]

To a solution of tert-butyl 2-(5-fluoropyridin-3-yl)-4-iodothiazol-5-ylcarbamate (1.20 g, 2.85 mmol) in DMF (5.7 mL) at 0° C. was added sodium hydride (125 mg, 3.13 mmol, 60% oil suspension) and the mixture was stirred at 0° C. for 10 min. To the yellow mixture was added iodomethane (0.49 g, 3.42 mmol) and the reaction mixture was stirred at 0° C. for 30 min. The ice-water bath was removed and the mixture was stirred for an additional 1 hour. The mixture was acidified with 0.1 N aq. HCl to neutral pH and diluted with ethyl acetate (100 mL) and aqueous sodium bicarbonate (5 mL). The organic phase was separated and rinsed with brine, dried over MgSO₄, filtered and concentrated in vacuo to give a yellow residue. This residue was purified on silica gel chromatography (6:4 hexane/ethyl acetate) to give tert-butyl 2-(5-fluoropyridin-3-yl)-4-iodothiazol-5-yl(methyl)carbamate as a pale yellow solid (1.13 g, 91%): mp 70-71° C.; ¹H NMR (300 MHz, CDCl₃) δ 8.87 (s, 1H), 8.53 (bs, 1H), 7.99 (d, J=0.9 Hz, 1H), 3.23 (s, 3H), 1.45 (s, 9H); ESIMS m/z 436.1 (M+1).

Example 40

Preparation of N-(4-cyano-2-(5-fluoropyridin-3-yl)thiazol-5-yl)-N-methyl-3-(methylthio)propanamide (Compound 495)

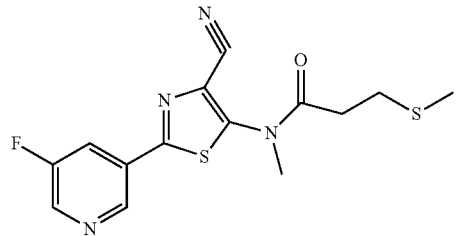 [SMILES: CSCCC(=O)N(C)c1sc(-c2cncc(F)c2)nc1C#N]

To a nitrogen-purged solution of tert-butyl 2-(5-fluoropyridin-3-yl)-4-iodothiazol-5-yl(methyl)carbamate (1.0 g, 2.298 mmol) in DMF (8 mL) was added CuCN (288 mg, 3.22 mmol) and the mixture was heated in a microwave at 120° C.

for 80 min. The mixture was diluted with ethyl acetate (75 mL) and successively washed with an aqueous solution (15 mL) of ethylene diamine (5% v/v), and brine, dried over MgSO$_4$ filtered, and concentrated on a rotary evaporator under vacuum to give a yellow solid, 2-(5-fluoropyridin-3-yl)-5-(methylamino)thiazole-4-carbonitrile. The solid was used in the preparation of N-(4-cyano-2-(5-fluoropyridin-3-yl)thiazol-5-yl)-N-methyl-3-(methylthio)propanamide. To a solution of crude 2-(5-fluoropyridin-3-yl)-5-(methylamino)thiazole-4-carbonitrile (200 mg, 0.83 mmol) in CH$_2$Cl$_2$ (2 mL) were added K$_2$CO$_3$ (178 mg, 1.28 mmol) and 3-(methylthio)propanoyl chloride (130 mg, 0.94 mmol) followed by dimethylaminopyridine (21 mg, 0.17 mmol). The mixture was stirred at room temperature for 36 h and diluted with ethyl acetate (20 mL) and saturated aqueous sodium bicarbonate (5 mL). The organic phase was separated and washed with brine, dried over MgSO$_4$ and concentrated in vacuo to give a brown gummy residue. This residue was purified by silica gel chromatography (6:4 hexane/ethyl acetate) to give N-(4-cyano-2-(5-fluoropyridin-3-yl)thiazol-5-yl)-N-methyl-3-(methylthio)propanamide as a pale yellow solid (164 mg, 57% yield): mp 97-98° C.; $^1$H NMR (300 MHz, CDCl$_3$) δ 8.98 (bs, 1H), 8.72 (d, J=2.7 Hz, 1H), 8.27 (dt, J=9.6, 1.8 Hz, 1H), 2.73 (t, J=7.5 Hz, 2H), 2.62 (t, J=7.62, 2H), 2.09 (s, 3H), 2.03 (s, 3H): ESIMS m/z 337.2 (M+1).

Example 41

Preparation of [2-(5-fluoro-pyridin-3-yl)-4-vinyl-thiazol-5-yl]-methyl-carbamic acid-tert-butyl ester (Compound 363)

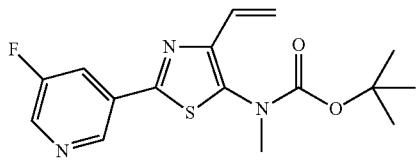 [SMILES: C=Cc1nc(-c2cncc(F)c2)sc1N(C)C(=O)OC(C)(C)C]

To a solution of [2-(5-fluoro-pyridin-3-yl)-4-bromo-thiazol-5-yl]-methyl-carbamic acid-tert-butyl ester (100 mg, 0.257 mmol) in anhydrous 1,4-dioxane (1.5 mL) was added vinyl tri-butyl tin (163 mg, 0.514 mmol). The solution was degassed prior to the addition of bis(triphenylphosphine)palladium(II) chloride (9 mg, 0.012 mmol). The reaction mixture was stirred at 100° C. for 3 hours. The mixture was concentrated and the product was purified via silica gel chromatography (0 to 100% ethyl acetate/hexanes) to afford a yellow oil (55 mg, 64%): IR (KBr) 1675 cm$^{-1}$; $^1$H NMR (300 MHz, CDCl$_3$) δ 8.89 (d, J=1.5 Hz, 1H), 8.50 (d, J=2.7 Hz, 1H), 7.99 (m, 1H), 6.58 (m, 1H), 6.22 (dd, J=14.0, 1.5 Hz, 1H), 5.51 (dd, J=8.0, 1.5 Hz, 1H), 3.22 (s, 3H), 1.43 (s, 9H); ESIMS m/z 336 (M+1).

Example 42

Preparation of di(tert-butyl) 2-bromo-1,3-thiazol-5-ylimidodicarbonate

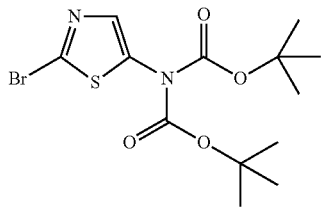 [SMILES: CC(C)(C)OC(=O)N(C(=O)OC(C)(C)C)c1cnc(Br)s1]

To a tetrahydrofuran (THF) (200 mL) solution of (2-bromo-thiazol-5-yl)-carbamic acid tert-butyl ester (19.8 g, 70.9 mmol) at 0° C. (ice bath) was added NaH (3.12 g, 78 mmol, 60% dispersion in mineral oil) in one portion. Gas evolution was observed. The reaction was stirred for 30 minutes. (Boc)$_2$O (17.0 g, 78 mmol) was added in one portion. The reaction was stirred for 5 minutes. The reaction vessel was pulled from the cooling bath and the reaction allowed to stir for 30 more minutes. Water and ethyl acetate were added to the reaction mixture. The layers were separated and the aqueous layer was extracted ethyl acetate (2×). The combined organic layers were dried over MgSO$_4$, filtered, and concentrated. Silica gel column chromatography (20 to 50% ethyl acetate/hexanes) afforded the final product as a white solid (25.0 g, 93% yield): mp 87-89° C.; $^1$H NMR (300 MHz, CDCl$_3$) δ 7.24 (s, 1H), 1.48 (s, 18H); ESIMS m/z 379, 381 (M+1).

Example 43

Preparation of di(tert-butyl) 2-(5-fluoropyridin-3-yl)-1,3-thiazol-5-ylimidodicarbonate (Compound 277)

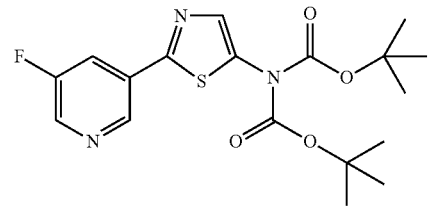 [SMILES: CC(C)(C)OC(=O)N(C(=O)OC(C)(C)C)c1cnc(-c2cncc(F)c2)s1]

To a 3-neck round bottom flask was added fluoropyridine boronic acid (4.55 g, 32.3 mmol), ethanol (54 mL), and aqueous K$_2$CO$_3$ solution (27 mL, 2.0 M, 53.8 mmol), followed by 50 mL toluene. To this mixture was added di(tert-butyl) 2-bromo-1,3-thiazol-5-ylimidodicarbonate (10.2 g, 26.9 mmol). Next, tetrakis(triphenylphosphine)palladium(0) (6.2 g, 5.4 mmol) was added in one portion. The flask was fitted with a reflux condenser and was heated to reflux. After 45 minutes, the reaction was cooled in an ice bath and partitioned between aqueous saturated NaHCO$_3$ and ethyl acetate. The layers were separated and the aqueous layer was extracted once with ethyl acetate. The combined organics were washed once with brine, dried over MgSO$_4$, filtered, and then concentrated. This solid was triturated with 20% ethyl acetate/hexanes. The solids were filtered off and the filtrate evaporated to provide a residue which was purified via silica gel column chromatography (0 to 100% ethyl acetate/hexanes) to afford the desired product as an off-white solid (7.74 g, 73% yield): mp 94-96° C.; $^1$H NMR (300 MHz, CDCl$_3$) δ 8.91 (app t, J=1.3 Hz, 1H), 8.52 (d, J=3.0 Hz, 1H), 7.96 (ddd, J=9.2, 3.0, 1.8 Hz, 1H), 7.66 (s, 1H), 1.48 (s, 18H); ESIMS m/z 396 (M+1).

Example 44

Preparation of di(tert-butyl) 4-fluoro-2-(5-fluoropyridin-3-yl)-1,3-thiazol-5-ylimidodicarbonate

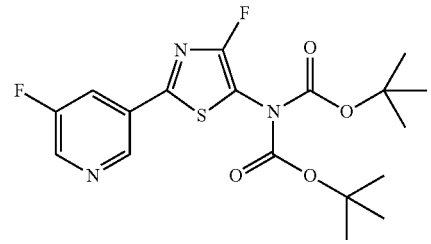 [SMILES: CC(C)(C)OC(=O)N(C(=O)OC(C)(C)C)c1sc(-c2cncc(F)c2)nc1F]

To a degassed solution of di(tert-butyl) 2-(5-fluoropyridin-3-yl)-1,3-thiazol-5-ylimidodicarbonate (1.0 g, 2.53 mmol) in anhydrous acetonitrile (20 mL) and DMF (10 mL) was added F-TEDA (SELECTFLUOR™) (1.8 g, 5.06 mmol). The reaction mixture was stirred at ambient temperature for 7 days. Water was added to the reaction mixture and the target extracted with ethyl acetate (2×). The organic layer was dried over sodium sulfate, was filtered and was concentrated. The crude mixture was purified via silica gel chromatography (0-100% ethyl acetate/hexanes) to afford a beige solid (860 mg, 82%): mp 143-143° C.; $^1$H NMR (300 MHz, CDCl$_3$) δ 8.87 (t, J=1.4 Hz, 1H), 8.54 (d, J=2.7 Hz, 1H), 7.91 (ddd, J=8.9, 2.7, 1.8 Hz, 1H), 1.48 (s, 18H); ESIMS m/z 414 (M+1).

Example 45

Preparation of [4-fluoro-2-(5-fluoro-pyridin-3-yl)-thiazol-5-yl]-carbamic acid tert-butyl ester (Compound 353)

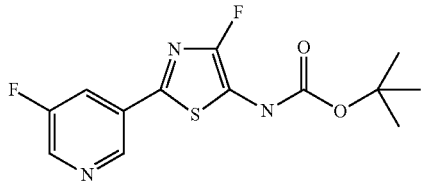 [SMILES: CC(C)(C)OC(=O)Nc1sc(-c2cncc(F)c2)nc1F]

To a solution of di(tert-butyl) 4-fluoro-2-(5-fluoropyridin-3-yl)-1,3-thiazol-5-ylimidodicarbonate (320 mg, 0.77 mmol) in DCM (7 mL) was added trifluoroacetic acid (TFA) (0.7 mL). The solution was stirred at room temperature for 10 minutes, before quenched slowly with saturated NaHCO$_3$ solution. The organic layer was separated and the aqueous layer was extracted with dichloromethane (DCM). The combined organic layer was dried over Na$_2$SO$_4$, filtered and purified by silica gel chromatography (0 to 100% ethyl acetate/hexanes) to give product as a pale yellow solid (166 mg, 68%): mp 188-191° C.; $^1$H NMR (300 MHz, CDCl$_3$) δ 8.84 (s, 1H), 8.46 (d, J=2.7 Hz, 1H), 7.85 (ddd, J=9.1, 2.6, 1.7 Hz, 1H), 6.92 (br s, 1H), 1.55 (s, 9H); ESIMS m/z 312 (M−1).

Example 46

Preparation of 2,3-diethyl-1-methyl-1-(4-methyl-2-pyridin-3-yl-thiazol-5-yl)-isothiourea (Compound 471)

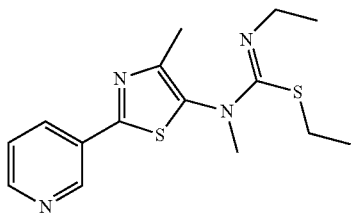 [SMILES: CC/N=C(\SCC)N(C)c1sc(-c2cccnc2)nc1C]

A solution of 3-ethyl-1-methyl-1-(4-methyl-2-(pyridin-3-yl)thiazol-5-yl)thiourea (70 mg, 0.239 mmol) and iodoethane (74.7 mg, 0.479 mmol) in ethanol (5 mL) was heated at 80° C. for 6 h in a sealed tube. Upon cooling the solvent was removed under reduced pressure and the residue purified via silica gel chromatography (0 to 100% ethyl acetate/hexanes) to furnish the title compound as a clear oil (30 mg, 39%): $^1$H NMR (400 MHz, CDCl$_3$) δ 9.10 (d, J=2.0 Hz, 1H), 8.64 (dd, J=4.6 Hz, 1.4 Hz, 1H), 8.20 (d, J=4.2 Hz, 1H), 7.41-7.37 (m, 1H), 3.63 (q, J=7.6 Hz, 2H), 3.22 (s, 3H), 2.72 (q, J=7.8 Hz, 2H), 2.38 (s, 3H), 1.28-1.17 (m, 6H); ESIMS m/z 321 (M+1).

Example 47

Preparation of 3-cyclopropyl-1-[2-(5-fluoro-pyridin-3-yl)-4-methyl-thiazol-5-yl]-1-methyl-thiourea (Compound 519)

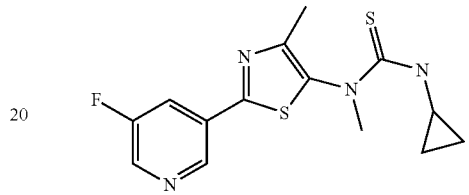

A solution of 2-(5-fluoropyridin-3-yl)-N,4-dimethylthiazol-5-amine (200 mg, 0.896 mmol) and isothiocyanatocyclopropane (266 mg, 2.69 mmol) in dioxane (10 mL) was heated at 100° C. for 24 h before the solvent was removed under reduced pressure. The residue was purified via silica gel chromatography (0 to 100% ethyl acetate/hexanes) to afford the title compound as a yellow solid (211 mg, 73%): mp 117-119° C.; $^1$H NMR (400 MHz, CDCl$_3$) δ 8.89 (s, 1H), 8.56 (d, J=2.8 Hz, 1H), 7.96 (dt, J=9.2 Hz, 2.4 Hz, 1H), 5.91 (br s, 1H), 3.62 (s, 3H), 3.04-2.99 (m, 1H), 2.31 (s, 3H), 0.89-0.81 (m, 2H), 0.57-0.48 (m, 2H); ESIMS m/z 323 (M+1).

Example 48

Preparation of ethyl 2-(pyridin-3-yl)thiazole-4-carboxylate

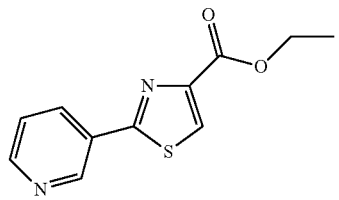 [SMILES: CCOC(=O)c1csc(-c2cccnc2)n1]

To a suspension of thionicotinamide (30.0 g, 217.1 mmol) in EtOH (400 mL) at room temperature was added ethyl bromopyruvate (90% technical, 30.6 mL, 219 mmol). The reaction mixture was heated to reflux and stirred for 2.5 days. The reaction mixture was cooled to room temperature and the precipitate that formed upon cooling was collected via vacuum filtration. The cake was rinsed twice with hexanes. This solid was added to a separatory funnel containing ethyl acetate and saturated aqueous NaHCO$_3$. The biphasic mixture was separated and the organic layer was washed with brine, dried over MgSO$_4$, filtered, and concentrated in vacuo. The crude product was purified using silica gel chromatography, (0 to 100% ethyl acetate/hexanes) to afford the desired product as a tan solid (24.1 g, 47%): mp 73-75° C.; $^1$H NMR (300 MHz, CDCl$_3$) δ 9.19 (dd, J=2.6, 1.0 Hz, 1H), 8.69 (dd, J=4.6, 1.6 Hz, 1H), 8.34 (dt, J=7.9, 1.6 Hz, 1H), 8.22 (s, 1H), 7.41 (ddd, J=7.9, 4.6, 1.0 Hz, 1H), 4.47 (q, J=6.9 Hz, 2H), 1.43 (t, J=6.9 Hz, 3H); ESIMS m/z 236.1 (M+2).

Example 49

Preparation of ethyl 5-bromo-2-(pyridin-3-yl)thiazole-4-carboxylate

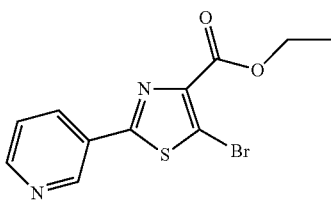 [SMILES: CCOC(=O)c1nc(-c2cccnc2)sc1Br]

A tetrahydrofuran (15 mL) solution of ethyl 2-(pyridin-3-yl)thiazole-4-carboxylate (1.17 g, 5.0 mmol) was added to −78° C. solution of potassium bis(trimethylsilyl)amide (12 mL, 6 mmol, 0.5 M in toluene) over 2 min. This reaction mixture was allowed to stir for 1.5 h and then was transferred via canula into a −78° C. solution of N-bromosuccinimide (1.35 g, 7.5 mmol) in tetrahydrofuran (5 mL). This mixture was stirred for 5 min and then the reaction vessel was removed from the cooling bath and allowed to warm to room temperature over 3 h. The reaction was quenched by pouring into a mixture of ether and water. The layers were separated and the aqueous layer was extracted twice with ethyl acetate. The combined organics were dried over MgSO₄, filtered, and the solvent was removed in vacuo. The residue was subjected to silica gel chromatography (0 to 100% ethyl acetate/hexanes) to give the desired product as a white solid (824 mg, 52%): ¹H NMR (300 MHz, CDCl₃) δ 9.09 (d, J=2.3 Hz, 1H), 8.71 (dd, J=4.9, 1.3 Hz, 1H), 8.25 (dt, J=8.2, 1.7 Hz, 1H), 7.41 (dd, J=7.9, 4.9 Hz, 1H), 4.48 (q, J=7.3 Hz, 2H), 1.46 (t, J=7.3 Hz, 3H); ESIMS m/z 315.0 (M+2).

Example 50

Preparation of ethyl 5-amino-2-(pyridin-3-yl)thiazole-4-carboxylate

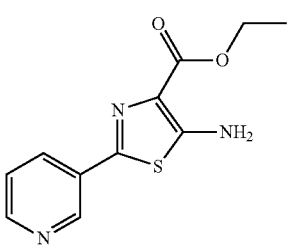 [SMILES: CCOC(=O)c1nc(-c2cccnc2)sc1N]

To a round bottom flask containing ethyl 5-bromo-2-(pyridin-3-yl)thiazole-4-carboxylate (2.5 g, 7.98 mmol) in DMF (26.6 ml)/water (13.3 ml) was carefully added sodium azide (2.59 g, 39.9 mmol) and stirred overnight at 75° C. The reaction was cooled to room temperature and poured into water which was extracted with ethyl acetate. The ethyl acetate layers were combined and washed with hexanes/water. The ethyl acetate extracts were dried (MgSO₄), filtered and concentrated to dryness. The crude material was purified by silica gel column chromatography (0 to 75% ethylacetate/hexanes) to give the desired product as a white solid (0.6 g, 30%) ¹H NMR (300 MHz, CDCl₃) δ 8.98 (s, 1H), 8.63 (d, 1H), 8.19 (d, 1H), 7.45-7.32 (m, 1H), 6.3 (s, 2H), 4.46 (q, 2H), 1.43 (t, 3H). ESIMS m/z 251.1 (M+2).

Example 51

Preparation of 3-[cyano(methyl)sulfonimidoyl]-N-[2-(5-fluoropyridin-3-yl)-4-methyl-1,3-thiazol-5-yl]-2-methylpropanamide (Compound 163)

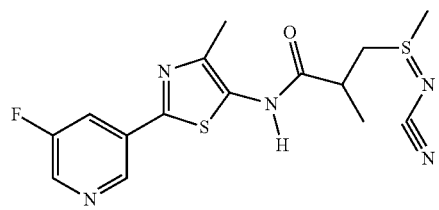 [SMILES: Cc1nc(-c2cncc(F)c2)sc1NC(=O)C(C)C/S(C)=N\C#N]

To a solution of N-[2-(5-fluoro-pyridin-3-yl)-4-methyl-thiazol-5-yl]-2-methyl-3-methylsulfanyl-propionamide (0.250 g, 0.76 mmol) in dichloromethane (3.07 ml) at 0° C. was added cyanamide (0.064 g, 1.53 mmol) and iodobenzenediacetate (0.272 g, 0.84 mmol) and subsequently stirred at room temperature for 1 hour. The reaction was concentrated to dryness. The crude material was purified by silica gel column chromatography (10% methanol/ethyl acetate) to give the desired product as a light yellow solid (0.220 g, 60%): mp 75-81° C.; ¹H NMR (400 MHz, CDCl₃) δ 9.85 (s, 1H), 8.94-8.70 (m, 1H), 8.57-8.34 (m, 1H), 8.07-7.77 (m, 1H), 3.69-3.40 (m, 2H), 3.22-3.00 (m, 1H), 2.92-2.77 (m, 3H), 2.50 (m, 3H), 1.49 (m, 3H); ESIMS m/z 363.9 (M−2).

Example 52-A

Preparation of 3-[cyano(methyl)sulfonimidoyl]-N-[2-(5-fluoropyridin-3-yl)-4-methyl-1,3-thiazol-5-yl]-2-methylpropanamide (Compound 164)

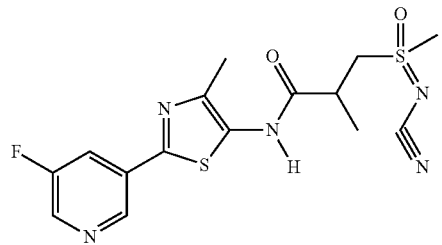 [SMILES: Cc1nc(-c2cncc(F)c2)sc1NC(=O)C(C)CS(C)(=O)=NC#N]

To a solution of 70% mCPBA (0.13 g, 0.61 mmol) in EtOH (2 ml) at 0° C. was added a solution of potassium carbonate (0.17 g, 1.23 mmol) in water (2 ml) and stirred for 20 minutes after which a solution of 3-[cyano(methyl)sulfonimidoyl]-N-[2-(5-fluoropyridin-3-yl)-4-methyl-1,3-thiazol-5-yl]-2-methylpropanamide (0.15 g, 0.41 mmol) in EtOH (2 ml) was added in one portion. The reaction was stirred for 1 h at 0° C. The excess mCPBA was quenched with 10% Na₂S₂O₃ and the reaction was concentrated to dryness. To the white solid was added dichloromethane and the mixture was filtered to remove solids. The filtrate was collected and concentrated to dryness. The crude material was purified by silica gel chromatography (100% ethyl acetate) to give the desired product as a light yellow solid (0.034 g, 22%): $^1$H NMR (400 MHz, CDCl$_3$) δ 8.87 (s, 1H), 8.53 (s, 1H), 8.45 (t, J=4.1 Hz, 1H), 7.93-7.85 (m, 1H), 3.74 (dd, J=14.2, 9.3 Hz, 1H), 3.38-3.25 (m, 1H), 3.14 (dd, J=14.2, 3.0 Hz, 1H), 3.01 (s, 3H), 2.47 (s, 3H), 1.48 (t, J=7.6 Hz, 3H).

Example 52-B

Preparation of 2-methyl-N-(4-methyl-2-pyridin-3-yl-thiazol-5-yl)-3-methylsulfanyl-thiopropionamide (Compound 180)

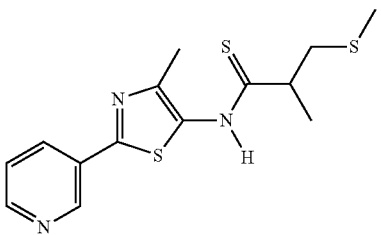 [SMILES: CSCC(C)C(=S)Nc1sc(-c2cccnc2)nc1C]

To a microwave reaction vessel was added 2-methyl-N-(4-methyl-2-pyridin-3-yl-thiazol-5-yl)3-methylsulfanyl-propionamide (0.10 g, 0.32 mmol) in dioxane and Lawesson's reagent (0.19 g, 0.48 mmol). The vessel was capped and heated in a Biotage Initiator microwave reactor for 1 min at 130° C., with external IR-sensor temperature monitoring from the side. The reaction was concentrated to dryness and the crude material was purified by silica gel chromatography (0 to 100% ethyl acetate/hexanes) to give the desired product as a yellow semi solid (0.019 g, 18%): $^1$H NMR (300 MHz, CDCl$_3$) δ 9.9 (m, 1H), 9.2 (d, 1H), 8.65 (d, 1H), 8.4 (m, 1H), 7.4 (m, 1H), 3.15 (m, 1H), 2.9 (m, 2H), 2.5 (s, 3H), 2.2 (s, 3H), 1.5 (d, 3H); ESIMS m/z 324.12 (M+1).

Example 53

Preparation of N-(4-chloro-2-pyridin-3-yl-thiazol-5-yl)-N-ethyl-2-methyl-3-methylsulfanyl-propionamide (Compound 316)

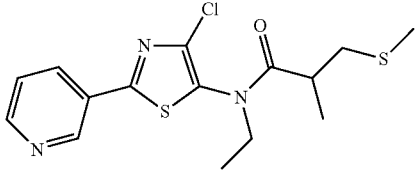 [SMILES: CCN(C(=O)C(C)CSC)c1sc(-c2cccnc2)nc1Cl]

To a solution of (4-chloro-2-pyridin-3-yl-thiazol-5-yl)-ethylamine (800 mg, 3.33 mmol) in dichloroethane (30 mL) was added 2-methyl-3-methylsulfanyl-propionic acid (prepared according to literature reference *J. Org. Chem.* 1996, 51, 1026-1029) (894 mg, 6.66 mmol) and N,N-dimethylaminopyridine (814 mg, 6.66 mmol) followed by triethylamine (0.2 mL, 1.44 mmol). To this was added 1-(3-dimethylaminopropyl)-3-ethylcarbodiimide hydrochloride (1.92 g, 9.99 mmol). The reaction mixture was stirred at ambient temperature for 16 h. The reaction mixture was concentrated and the crude product was purified by silica gel chromatography (0 to 100% ethyl acetate/hexanes) to afford a beige solid (715 mg, 60%): mp 79-81° C.; $^1$H NMR (300 MHz, CDCl$_3$) δ 9.11 (d, J=1.7 Hz, 1H), 8.71 (d, J=4.8 Hz, 1H), 8.27-8.13 (m, 1H), 7.42 (dd, J=8.0, 4.9 Hz, 1H), 3.90 (bs, 1H), 3.69 (bs, 1H), 2.80 (bs, 2H), 2.47 (bs, 1H), 2.02 (s, 3H), 1.21 (q, J=7.3 Hz, 6H); ESIMS m/z 356 (M+1).

Example 54

Preparation of 4-chloro-5-nitro-2-(pyridin-3-yl)thiazole

4-Chloro-2-(pyridin-3-yl)thiazole (1.00 g, 5.09 mmol) was placed in a dry flask and concentrated H$_2$SO$_4$ (2.50 g, 25.4 mmol) was added. The contents were cooled to 0° C., and fuming HNO$_3$ (641 mg, 10.17 mmol) was slowly added. The mixture was stirred at 40° C. for 3 h and cooled to room temperature. The contents were slowly added to an ice-cold saturated aqueous solution of NaHCO$_3$. The mixture was extracted with ethyl acetate (2×50 mL) and the extracts were combined, rinsed with brine and concentrated in vacuo to give 4-chloro-5-nitro-2-(pyridin-3-yl)thiazole as a peach-colored solid (985 mg, 80% yield): mp 110-112° C.; $^1$H NMR (300 MHz, CDCl$_3$) 9.18 (d, J=2.1 Hz, 1H), 8.81 (dd, J=5.1, 1.8 Hz, 1H)), 8.27 (ddd, J=7.3, 4.2, 2.4 Hz, 1H), 7.49 (dd, J=7.8, 5.1 Hz, 1H); EIMS m/z 241 ([M+H])$^+$.

Example 55

Preparation of 4-(methylthio)-5-nitro-2-(pyridin-3-yl)thiazole

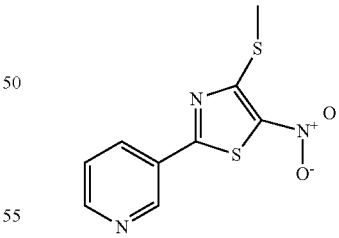

To a solution of 4-chloro-5-nitro-2-(pyridin-3-yl)thiazole (500 mg, 2.07 mmol) in 1,4-dioxane (2 mL) was added in one portion solid sodium thiomethoxide (145 mg, 2.07 mmol). The orange-red mixture was stirred at room temperature for 3 hours. The mixture was diluted with ethyl acetate and rinsed with brine, dried over MgSO$_4$ and concentrated in vacuo to give a yellow solid. This solid was purified by silica gel chromatography (ethyl acetate/hexanes) to give 4-(methylthio)-5-nitro-2-(pyridin-3-yl)thiazole (358 mg, 68%): $^1$H NMR (300 MHz, CDCl$_3$) δ 9.21 (d, J=5.4 Hz, 1H), 8.79 (dd, J=4.8, 1.8 Hz, 1H), 8.24 (dt, J=7.8, 2.1 Hz, 1H), 7.46 (ddd, J=8.1, 4.8, 0.9 Hz, 1H), 2.81 (s, 3H); EIMS m/z 253.

Example 56

Preparation of 3-(methylthio)-N-(4-(methylthio)-2-(pyridin-3-yl)thiazol-5-yl)propanamide (Compound 589)

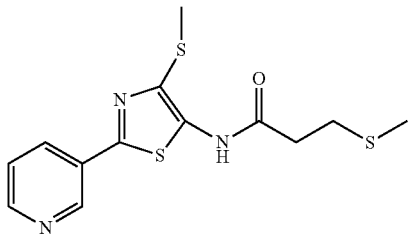 [SMILES: CSCCC(=O)Nc1sc(-c2cccnc2)nc1SC]

To a nitrogen-purged solution of 4-(methylthio)-5-nitro-2-(pyridin-3-yl)thiazole (253 mg, 1 mmol) in ethyl acetate (50 mL) in a Parr bottle were added glacial acetic acid (601 mg, 10 mmol), followed by Pd on carbon (35 mg, 10% (w)). Hydrogen was added and the mixture was shaken in a Parr shaker for 2 hours and filtered through a bed of Celite®. The filtrate was concentrated under vacuum to give 4-(methylthio)-2-(pyridin-3-yl)thiazol-5-amine as a pale yellow solid, which was placed under high vacuum to remove residual acetic acid. This crude was found to be 95% pure by GC-MS. The crude 4-(methylthio)-2-(pyridin-3-yl)thiazol-5-amine was used without further purification to prepare 3-(methylthio)-N-(4-(methylthio)-2-(pyridin-3-yl)thiazol-5-yl) propanamide. To a solution of 4-(methylthio)-2-(pyridin-3-yl)thiazol-5-amine (100 mg, 0.45 mmol) in methylene chloride (2 mL) were added dimethylaminopyridine (137 mg, 1.12 mmol) followed by 3-(methylthio)propanoyl chloride (68 mg, 0.49 mmol). The mixture was stirred at room temperature for 30 min. The mixture was diluted with dichloromethane (10 mL) and water (5 mL). The organic phase was separated, rinsed with brine, dried over $MgSO_4$ and concentrated in vacuo to give a yellow solid. This solid was purified by silica gel chromatography (methylene chloride-methanol) to give 3-(methylthio)-N-(4-(methylthio)-2-(pyridin-3-yl) thiazol-5-yl)propanamide as a yellow solid (32 mg, 22%): mp 72-74° C., $^1$H NMR (300 MHz, DMSO-$d_6$) δ 10.90 (s, 1H), 9.08 (m, 1H), 8.64 (d, J=4.8 Hz, 1H), 8.32 (d, J=9.0 Hz, 1H), 7.57 (dd, J=5.1 Hz, 8.4 Hz, 1H), 3.25 (s, 3H), 2.85 (m, 2H), 2.73 (m, 2H), 2.07 (s, 3H); ESIMS m/z 326.1 (M+1), 324.1 (M−1).

Example 57

Preparation of 1-(2-methyl-pentanoyl)-piperidine-3-carboxylic acid [2-(5-fluoro-pyridin-3-yl)-4-methyl-thiazol-5-yl]-methyl-amide (Compound 582)

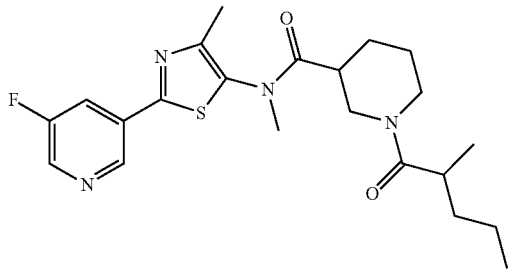 [SMILES: CCCC(C)C(=O)N1CCCC(C(=O)N(C)c2sc(-c3cncc(F)c3)nc2C)C1]

A solution of N-(2-(5-fluoropyridin-3-yl)-4-methylthiazol-5-yl)-N-methylpiperidine-3-carboxamide (250 mg, 0.75 mmol), DMAP (91 mg, 0.75 mmol), potassium carbonate (310 mg, 2.243 mmol), and 2-methylpentanoyl chloride (201 mg, 1.495 mmol) in DCE (10 mL) was heated at 80° C. for 6 h. The cooled contents were diluted with water:dichloromethane (1:1, 20 mL) and the organic layer was collected and concentrated. The residue was purified via reversed phase chromatography (0 to 100% acetonitrile/water) to furnish the title compound as a clear oil (207 mg, 64%): $^1$H NMR (400 MHz, CDCl$_3$) δ 8.89 (s, 1H), 8.54 (d, J=2.2 Hz, 1H), 7.96 (dt, J=9.0, 2.2 Hz, 1H), 4.63-4.59 (m, 1H), 3.92-3.78 (m, 1H), 3.42 (s, 3H), 2.66-2.48 (m, 4H), 2.38 (s, 3H), 1.89-1.73 (m, 2H), 1.71-1.68 (m, 2H), 1.38-1.17 (m, 4H), 1.08-1.01 (m, 3H), 0.97-0.86 (m, 3H); ESIMS m/z 433 (M+1).

Example 58

Preparation of (4-chloro-2-pyridin-3-yl-thiazol-5-yl)-ethyl-carbamic acid tert-butyl ester (Compound 304)

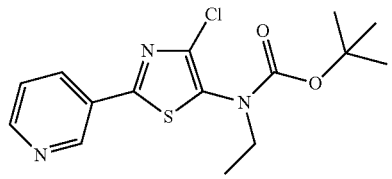 [SMILES: CCN(C(=O)OC(C)(C)C)c1sc(-c2cccnc2)nc1Cl]

To a suspension of 3-pyridine boronic acid (1.5 g, 12.2 mmol) in toluene (50 mL) was added absolute ethanol (25 mL) followed by a 2.0 M solution of $K_2CO_3$ (12.5 mL). To this mixture was added (2-bromo-4-chloro-thiazol-5-yl)-ethyl-carbamic acid tert-butyl ester (4.2 g, 12.2 mmol) followed by tetrakis(triphenylphosphine)palladium(0) (708 mg, 0.61 mmol). The reaction mixture was heated to 100° C. for 16 h. The mixture was cooled and diluted with ethyl acetate. The organic layer was washed with saturated aqueous NaHCO$_3$, dried over Na$_2$SO$_4$, filtered and concentrated. The organic layer was purified by silica gel chromatography (0 to 100% ethyl acetate/hexanes) to afford a red oil (3.3 g, 79%): $^1$H NMR (300 MHz, CDCl$_3$) δ 9.09 (d, J=1.9 Hz, 1H), 8.68 (dd, J=4.8, 1.6 Hz, 1H), 8.19 (dd, J=5.9, 4.2 Hz, 1H), 7.39 (dd, J=7.6, 5.2 Hz, 1H), 3.68 (q, J=7.2 Hz, 2H), 1.45 (s, 9H), 1.22 (t, J=7.0 Hz, 3H); ESIMS m/z 340 (M+1).

Example 59

Preparation of (2-bromo-4-chloro-thiazol-5-yl)-methyl-carbamic acid tert-butyl

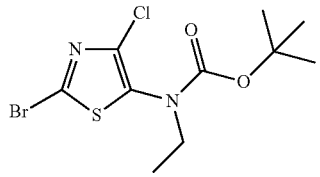 [SMILES: CCN(C(=O)OC(C)(C)C)c1sc(Br)nc1Cl]

To a solution of (2-bromo-thiazol-5-yl)-ethyl-carbamic acid tert-butyl ester (4.0 g, 13 mmol) in acetonitrile (75 mL) was added N-chlorosuccinimide (3.48 g, 26 mmol) in one portion and the reaction mixture was stirred for 16 h. The reaction mixture was concentrated and the crude product was purified by silica gel chromatography (0 to 100% ethyl acetate/hexanes) to give the desired product as a grey solid (4.2 g, 95%): IR (KBr) 1738 cm$^{-1}$; $^1$H NMR (300 MHz, CDCl$_3$) δ 3.61 (q, J=7.1 Hz, 2H), 1.43 (s, 9H), 1.16 (t, J=7.1 Hz, 3H).

Example 60

Preparation of 2,4-dichloro-thiazole-5-carbonyl-azide

To a solution of 2,4-dichloro-thiazole-5-carboxylic acid (1.98 g, 10 mmol) in toluene (50 mL) was added Et$_3$N (1.01 g, 10 mmol) followed by diphenyl phosphoryl azide (2.75 g, 10 mmol). The reaction mixture was stirred at room temperature for 20 h. The reaction mixture was concentrated in vacuo and purified by silica gel chromatography (0 to 100% ethyl acetate/hexanes) to afford product as a brown solid (1.82 g, 82%): $^{13}$C NMR (75 MHz, CDCl$_3$) δ 163.33, 156.83, 143.94, 124.02.

Example 61

Preparation of (2,4-dichloro-thiazol-5-yl)-carbamic acid tert-butyl ester

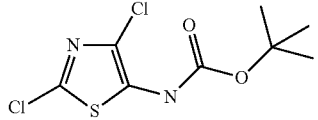

To a 250 mL round bottom flask filled with N$_2$ was added 2,4-dichloro-thiazole-5-carbonyl-azide (1.82 g, 12.1 mmol) and toluene (55 mL). The solution was heated to reflux for 2 h before tert-butyl alcohol (1.21 g mL, 16.3 mmol) was added. The reaction mixture was then refluxed for 1.5 h, cooled and concentrated in vacuo. Purification by silica gel chromatography (0 to 100% ethyl acetate/hexanes) gave product as a white solid (2.06 g, 94%): mp 111-112° C.; $^1$H NMR (300 MHz, CDCl$_3$) δ 6.96 (s, 1H), 1.54 (s, 9H).

Example 62

Preparation of (2,4-dichloro-thiazol-5-yl)-(3-methylsulfanyl-propionyl)-carbamic acid tert-butyl ester

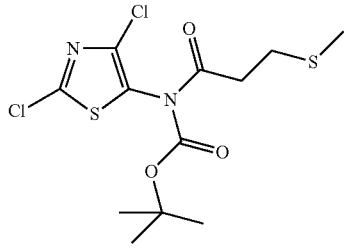 [SMILES: CSCCC(=O)N(C(=O)OC(C)(C)C)c1sc(Cl)nc1Cl]

To a solution of (2,4-dichloro-thiazol-5-yl)-carbamic acid tert-butyl ester (1.0 g, 3.7 mmol) in dichloroethane (20 mL) stirring at room temperature was added triethylamine (935 mg, 9.25 mmol), followed by dropwise addition of methylsulfanyl-propionyl chloride (776 mg, 5.6 mmol) and the mixture was stirred for 5 min before DMAP (45 mg, 0.37 mmol) was added. The mixture was stirred at 75° C. for 4 h. The reaction mixture was cooled, quenched with H$_2$O (30 mL). The organic layer was separated and the aqueous layer extracted with dichloromethane (20 mL). The combined organic layer was dried over Na$_2$SO$_4$ and purified by silica gel chromatography (0 to 100% ethyl acetate/hexanes) to give product as a colorless oil (1.11 g, 81%): $^1$H NMR (300 MHz, CDCl$_3$) δ 3.32 (t, J=7.3 Hz, 2H), 2.83 (t, J=7.3 Hz, 2H), 2.16 (s, 3H), 1.46 (s, 9H); ESIMS m/z 371.2 (M+1).

Example 63

Preparation of N-(2,4-dichloro-thiazol-5-yl)-3-methylsulfanyl-propionamide

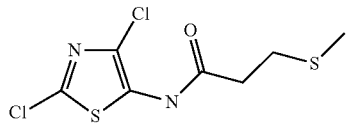

To a solution of (2,4-dichloro-thiazol-5-yl)-(3-methylsulfanyl-propionyl)-carbamic acid tert-butyl ester (1.10 g, 2.97 mmol) in DCM (10 mL) was added trifluoroacetic acid (3.4 g, 2.2 mL, 30 mmol). The solution was stirred at room temperature for 15 minutes, before it was quenched slowly with saturated NaHCO$_3$ solution. The organic layer was separated and the aqueous layer was extracted with 20 mL DCM. The combined organic layer was dried over Na$_2$SO$_4$ and purified by silica gel chromatography (0 to 100% ethyl acetate/hexanes) to give product as a white solid (612 mg, 76%): $^1$H NMR (300 MHz, CDCl$_3$) δ 8.79 (s, 1H), 2.90 (t, J=7.2 Hz, 2H), 2.79 (t, J=7.2 Hz, 2H), 2.29 (s, 3H); ESIMS m/z 271.0 (M+1).

Example 64

Preparation of N-(2,4-dichloro-thiazol-5-yl)-N-methyl-3-methylsulfanyl-propionamide

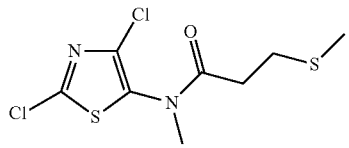

To a solution of N-(2,4-dichloro-thiazol-5-yl)-3-methylsulfanyl-propionamide (596 mg, 2.2 mmol) in DMF (11 mL) stirring at 25° C. was added K$_2$CO$_3$ (365 mg, 2.64 mmol) and iodomethane (375 mg, 1.2 mmol), the solution was stirred at 25° C. for 20 h. The solution was diluted with 50 mL H$_2$O and extracted with ethyl acetate (3×20 mL). The combined organic extracts were washed with H$_2$O (3×20 mL), dried over Na$_2$SO$_4$, filtered and concentrated to dryness under reduced pressure. The crude product was purified by silica gel chromatography (0 to 100% ethyl acetate/hexanes) to give the desired product as a clear oil (273 mg, 44%): $^1$H NMR (300

MHz, CDCl₃) δ 3.23 (s, 3H), 2.79 (t, J=7.2 Hz, 2H), 2.52 (t, J=7.2 Hz, 2H), 2.09 (s, 3H); ESIMS m/z 285.1 (M+1).

Example 65

Preparation of N-[4-chloro-2-(6-fluoro-pyridin-3-yl)-thiazol-5-yl]-N-methyl-3-methylsulfanyl-propionamide (Compound 453)

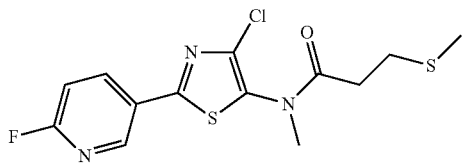 [SMILES: CSCCC(=O)N(C)c1sc(-c2ccc(F)nc2)nc1Cl]

To a solution of N-(2,4-dichloro-thiazol-5-yl)-N-methyl-3-methylsulfanyl-propionamide (273 mg, 0.96 mmol) in toluene (4 mL) was added 6-fluoropyridine-3-boronic acid (162 mg, 1.15 mmol) and Pd(PPh₃)₄ (56 mg, 0.048 mmol), followed by 1 mL 2M K₂CO₃ solution and 2 mL EtOH. The solution was deoxygenated by three vacuum-flush cycles under nitrogen and heated in 110° C. oil bath for 8 hours. H₂O (10 mL) was added and the aqueous layer was extracted with ethyl acetate (2×10 mL). The combined organic layer was dried over Na₂SO₄, concentrated in vacuo and purified by silica gel chromatography (0 to 100% ethyl acetate/hexanes) to afford product as a colorless oil (131 mg, 75%): ¹H NMR (300 MHz, CDCl₃) δ 8.74 (d, J=2.1 Hz, 1H), 8.48-8.21 (m, 1H), 7.09 (dd, J=8.6, 2.9 Hz, 1H), 3.29 (s, 3H), 2.82 (t, J=7.3 Hz, 2H), 2.57 (t, J=7.3 Hz, 2H), 2.09 (s, 3H); IR (KBr) 1685; ESIMS m/z 346.2 (M+1).

Example 66

Preparation of (4-chloro-2-pyridin-3-yl-thiazol-5-yl)-methyl-carbamic acid tert-butyl ester (Compound 228)

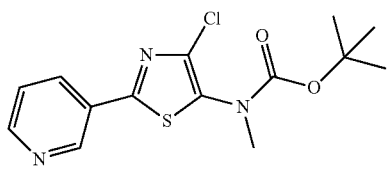 [SMILES: CN(C(=O)OC(C)(C)C)c1sc(-c2cccnc2)nc1Cl]

To a solution of methyl-(2-pyridin-3-yl-thiazol-5-yl)-carbamic acid tert-butyl ester (3.0 g, 10.29 mmol) in acetonitrile (60 mL) was added N-chlorosuccinimide (2.75 g, 20.58 mmol) in one portion and the reaction mixture was stirred at 45° C. for 16 h. The reaction mixture was concentrated and the crude product was purified by silica gel chromatography (0 to 100% ethyl acetate/hexanes) to give the desired product as a yellow solid (2.10 g, 62%): mp 119-122° C.; IR (KBr) 1718 cm⁻¹; ¹H NMR (300 MHz, CDCl₃) δ 9.08 (s, 1H), 8.67 (d, J=4.2 Hz, 1H), 8.22-8.16 (m, 1H), 7.39 (dd, J=7.9, 5.0 Hz, 1H), 3.26 (s, 3H), 1.46 (s, 9H); ESIMS m/z 326 (M+1).

Example 67

Preparation of (4-chloro-2-pyridin-3-yl-thiazol-5-yl)-methyl-amine

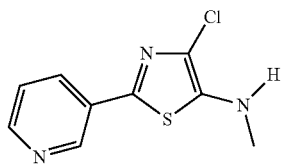

To a solution of (4-chloro-2-pyridin-3-yl-thiazol-5-yl)-methyl-carbamic acid tert-butyl ester (0.072 g, 0.22 mmol) in dichloromethane (1 mL) was added thiophenol (34 µL, 0.33 mmol) followed by trifluoroacetic acid (1 mL). The reaction was stirred for 30 minutes at ambient temperature. The reaction was quenched with saturated aqueous NaHCO₃ and the mixture was extracted with dichloromethane. The organic layer was dried over Na₂SO₄, filtered and concentrated. The crude product was purified by silica gel chromatography (0 to 100% ethyl acetate/hexanes) to afford a bright yellow solid (0.048 g, 98%): mp 79° C.; IR (KBr) 1540 cm⁻¹; ¹H NMR (400 MHz, CDCl₃) δ 8.97 (d, J=2.1 Hz, 1H), 8.55 (dd, J=4.8, J=1.5 Hz, 1H), 8.08 (ddd, J=8.1, 2.0, 2.0 Hz, 1H), 7.32 (dd, J=8.1, 4.8 Hz, 1H), 4.07 (br m, 1H), 3.03 (d, J=5.3 Hz, 3H); ESIMS m/z 226 (M+1).

Example 68

Preparation of N-(4-chloro-2-pyridin-3-yl-thiazol-5-yl)-N-methyl-3-methylsulfanyl-propionamide (Compound 66)

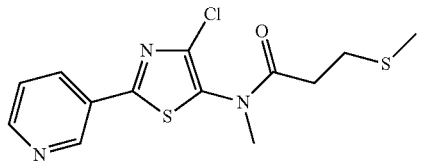 [SMILES: CSCCC(=O)N(C)c1sc(-c2cccnc2)nc1Cl]

To a solution of (4-chloro-2-pyridin-3-yl-thiazol-5-yl)-methylamine (49 mg, 0.21 mmol) in dichloroethane (2 mL) was added N,N-dimethylaminopyridine (39 mg, 0.32 mmol) followed by 3-methylsulfanyl-propionyl chloride (45 mg, 0.32 mmol). The reaction mixture was stirred at ambient temperature for 16 hours. The reaction was diluted with saturated aqueous NaHCO₃ and the mixture was extracted with dichloromethane. The organic layer was dried over Na₂SO₄, filtered and concentrated. The crude product was purified by silica gel chromatography (0 to 100% ethyl acetate/hexanes) to afford a pale yellow gum (52 mg, 73%): IR (KBr) 1682 cm⁻¹; ¹H NMR (300 MHz, CDCl₃) δ 9.11 (s, 1H), 8.73 (d, J=3.4 Hz, 1H), 8.28-8.14 (m, 1H), 7.43 (dd, J=8.2, 5.0 Hz, 1H), 3.28 (s, 3H), 2.81 (t, J=7.2 Hz, 2H), 2.56 (t, J=7.2 Hz, 2H), 2.08 (s, 3H); ESIMS m/z 328 (M+1).

Example 69

Preparation of N-(4-chloro-2-pyridin-3-yl-thiazol-5-yl)-2,N-dimethyl-3-methylsulfanyl-propionamide (Compound 227)

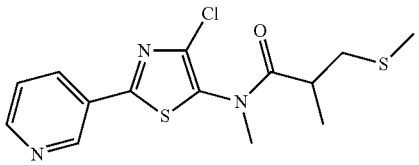 [SMILES: CSCC(C)C(=O)N(C)c1sc(-c2cccnc2)nc1Cl]

To a solution of (4-chloro-2-pyridin-3-yl-thiazol-5-yl)-methylamine (200 mg, 0.88 mmol) in dichloroethane (2 mL) was added pyridine (83 mg, 1.05 mmol), N,N-dimethylaminopyridine (54 mg, 0.44 mmol) followed by 2-methyl-3-methylsulfanyl-propionyl chloride (160 mg, 1.05 mmol). The reaction mixture was stirred at ambient temperature for 16 hours. The reaction was diluted with water and the mixture was extracted with dichloromethane. The organic layer was dried over Na$_2$SO$_4$, filtered and concentrated. The crude product was purified by silica gel chromatography (0 to 100% ethyl acetate/hexanes) to afford a light yellow solid (250 mg, 84%): mp 70-73° C.; $^1$H NMR (300 MHz, CDCl$_3$) δ 9.14 (s, 1H), 8.75 (d, J=3.8 Hz, 1H), 8.28-8.15 (m, 1H), 7.45 (dd, J=8.0, 4.9 Hz, 1H), 3.32 (s, 3H), 2.99-2.72 (m, 2H), 2.50 (d, J=7.5 Hz, 1H), 2.06 (d, J=2.5 Hz, 3H), 1.31-1.14 (m, 3H); ESIMS m/z 342 (M+1).

Example 70

Preparation of (4-chloro-2-pyridin-3-yl-thiazol-5-yl)-ethyl-carbamic acid tert-butyl ester (Compound 304)

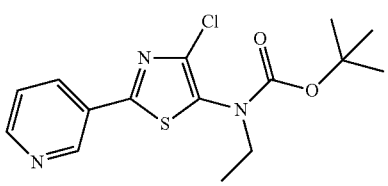 [SMILES: CCN(C(=O)OC(C)(C)C)c1sc(-c2cccnc2)nc1Cl]

To a solution of ethyl-(2-pyridin-3-yl-thiazol-5-yl)-carbamic acid tert-butyl ester (3.0 g, 9.82 mmol) in acetonitrile (58 mL) was added N-chlorosuccinimide (2.62 g, 19.64 mmol) in one portion and the reaction mixture was stirred at 45° C. for 16 h. The reaction mixture was concentrated and the crude product was purified by silica gel chromatography (0 to 100% ethyl acetate/hexanes) to afford a red oil (2.24 g, 67%): $^1$H NMR (300 MHz, CDCl$_3$) δ 9.09 (d, J=1.9 Hz, 1H), 8.68 (dd, J=4.8, 1.6 Hz, 1H), 8.19 (dd, J=5.9, 4.2 Hz, 1H), 7.39 (dd, J=7.6, 5.2 Hz, 1H), 3.68 (q, J=7.2 Hz, 2H), 1.45 (s, 9H), 1.22 (t, J=7.0 Hz, 3H); ESIMS m/z 340 (M+1).

Example 71

Preparation of (4-chloro-2-pyridin-3-yl-thiazol-5-yl)-ethyl-amine hydrochloride

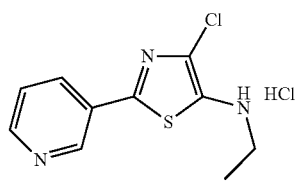

Into a 1 L three-necked flask fitted with a J-KEM type-T temperature probe, overhead stirrer, and nitrogen inlet was added (4-chloro-2-pyridin-3-yl-thiazol-5-yl)-ethyl-carbamic acid tert-butyl ester (63.5 g, 187 mmol) and 1,4-dioxane (125 mL). To the solution was added 4 M HCl/dioxane (100 mL, 400 mmol). The mixture exothermed from 31° C. to 49° C. over 10 seconds and slowly turned from an auburn solution to a green-black solution. After 10 minutes the reaction had cooled back to 25° C. After 30 min a green-yellow precipitate began to form in the reaction mixture. The reaction conversion was 31% after 10 min, 32% after 1.5 hours and 67% after 16 hours. Additional 4M HCl/dioxane (75 mL, 300 mmol) was added (note: no exotherm this time) and the reaction stirred at 23° C. for 1.5 hours (no change in reaction progress by HPLC analysis). The reaction was heated to 40° C. for 4 hours which led to complete conversion. The reaction was allowed to cool to 25° C. and ether (200 mL) was added. The green-yellow suspension was stirred for 30 min and the solid collected by vacuum filtration and washed with ether (2×50 mL). This gave a green-yellow filter cake which was allowed to stand in the air for 16 hours. This gave 67.99 g (131%) of a green-yellow wet cake that assayed to >99% purity by HPLC at 254 nm. The sample was placed into a vacuum oven (55° C., 74 mmHg vacuum, 4 hours). This gave 53.96 g (quantitative yield) of a green solid: mp 180-182 C; $^1$H NMR (400 MHz, DMSO-d$_6$) δ 9.08 (d, J=2.1 Hz, 1H), 8.75 (dd, J=5.5, 0.9 Hz, 1H), 8.66 (ddd, J=8.3, 2.2, 1.3 Hz, 1H), 7.97 (ddd, J=8.3, 5.5, 0.6 Hz, 1H), 3.21 (q, J=7.1 Hz, 2H), 2.51 (dt, J=3.7, 1.8 Hz, 1H), 1.24 (dd, J=9.2, 5.1 Hz, 3H); ESIMS m/z 240 (M+1).

Example 72

Preparation of N-(4-chloro-2-pyridin-3-yl-thiazol-5-yl)-N-ethyl-3-methylsulfanyl-propionamide (Compound 313)

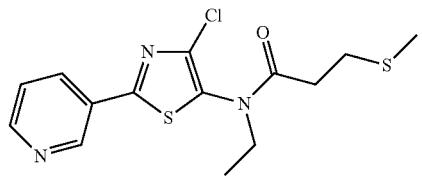 [SMILES: CCN(C(=O)CCSC)c1sc(-c2cccnc2)nc1Cl]

To a solution of (4-chloro-2-pyridin-3-yl-thiazol-5-yl)-ethylamine hydrochloride (275 mg, 1.0 mmol) in dichloroethane (2 mL) was added N,N-dimethylaminopyridine (305 mg, 2.5 mmol) followed by 3-methylsulfanyl-propionyl chloride (180 mg, 1.3 mmol). The reaction mixture was stirred at ambient temperature for 16 hours. The reaction was diluted with saturated aqueous NaHCO$_3$ and the mixture was extracted with dichloromethane. The organic layer was dried over Na$_2$SO$_4$, filtered and concentrated. The crude product was purified by silica gel chromatography (0 to 100% ethyl acetate/hexanes) to afford a yellow oil (298 mg, 87%): IR (KBr) 1680 cm$^{-1}$; $^1$H NMR (300 MHz, CDCl$_3$) δ 9.11 (s, 1H), 8.73 (d, J=3.4 Hz, 1H), 8.28-8.14 (m, 1H), 7.43 (dd, J=8.2, 5.0 Hz, 1H), 3.77 (br s, 2H), 2.81 (t, J=7.2 Hz, 2H), 2.56 (t, J=7.2 Hz, 2H), 2.08 (s, 3H), 1.21 (t, J=7.2 Hz, 3H); ESIMS m/z 342 (M+1).

Example 73

Preparation of N-(4-chloro-2-pyridin-3-yl-thiazol-5-yl)-N-ethyl-2-methyl-3-methylsulfanyl-propionamide (Compound 316)

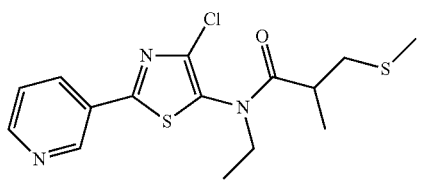 [SMILES: CCN(C(=O)C(C)CSC)c1sc(-c2cccnc2)nc1Cl]

Into a 500-mL three-necked flask fitted with a J-KEM type-T temperature probe, overhead stirrer, reflux condensor, and nitrogen inlet was added (4-chloro-2-pyridin-3-yl-thiazol-5-yl)-ethyl-amine hydrochloride (20.0 g, 72.4 mmol green solid) and dichloromethane (150 mL). To this suspension was added pyridine (14.32 g, 181 mmol, 2.5 eq) (portionwise over 1 min to form a dark green-black solution. To this solution was added DMAP (4.4 g, 36 mmol) followed by 2-methyl-3-methylthiopropanoyl chloride (16.5 g, 108.6 mmol), which was added portionwise over 1 minute. The reaction exotherm went from 20° C. to 31° C. during the addition of the acid chloride. The reaction was heated to 35° C. for 10 hours then cooled to 25° C. for 14 h. To the dark brown reaction mixture was added dichloromethane (200 mL) and the solution was transferred to a 500 mL separatory funnel. The solution was washed with water (100 mL) and the layers were separated. The brown aqueous layers was extracted with dichloromethane (50 mL) and the dark brown dichloromethane extracts combined, washed with brine (100 mL), dried (MgSO$_4$), filtered and rotary evaporated. This gave 30.49 g (74% pure by HPLC at 254 nm) of a crude black oil. The crude product was purified by silica gel chromatography (0 to 100% ethyl acetate/hexanes) to afford a beige solid (23.2 g, 89%): mp 79-81° C.; $^1$H NMR (300 MHz, CDCl$_3$) δ 9.11 (d, J=1.7 Hz, 1H), 8.71 (d, J=4.8 Hz, 1H), 8.27-8.13 (m, 1H), 7.42 (dd, J=8.0, 4.9 Hz, 1H), 3.90 (bs, 1H), 3.69 (bs, 1H), 2.80 (bs, 2H), 2.47 (bs, 1H), 2.02 (s, 3H), 1.21 (q, J=7.3 Hz, 6H); ESIMS m/z 356 (M+1).

Example 74

Preparation of 3-(4-Chloro-thiazole-2-yl)pyridine

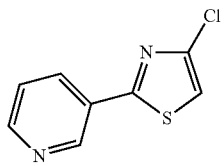 [SMILES: Clc1csc(-c2cccnc2)n1]

To a suspension of pyridin-3-ylboronic acid (3.87 g, 31.5 mmol) in toluene (120 mL) was added 2,4-dichlorothiazole (4.62 g, 30 mmol) followed by ethanol (60 mL) and a 2.0 M solution of K$_2$CO$_3$ (30.0 mL, 60.0 mmol). The solution was degassed by applying vacuum and then purging with nitrogen (3 times). To the reaction mixture was added tetrakis(triphenylphosphine)palladium (0) (1.733 g, 1.500 mmol) and the flask was heated at 95° C. under nitrogen for 16 hours. The aqueous layer was removed and the organic layer was concentrated. The crude product was purified via silica gel chromatography (0-100% ethyl acetate/hexanes) to afford the title compound as a brown solid (4.6 g, 74%): mp 84-86° C.; IR (KBr) 3092 cm$^{-1}$; $^1$H NMR (400 MHz, CDCl$_3$) δ 9.16-9.13 (m, 1H), 8.69 (dd, J=4.8, 1.6 Hz, 1H), 8.23 (ddd, J=8.0, 2.2, 1.7 Hz, 1H), 7.40 (ddd, J=8.0, 4.8, 0.8 Hz, 1H), 7.16 (s, 1H).

Example 75

Preparation of 2,2-dimethyl-3-(methylthio)propanoic acid

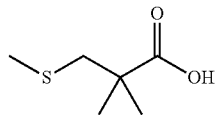

Example 75 can be prepared as demonstrated in the literature (reference Musker, W. K.; et al. *J. Org. Chem.* 1996, 51, 1026-1029). Sodium methanethiolate (1.0 g, 14 mmol, 2.0 equiv) was added to a stirred solution of 3-chloro-2,2-dimethylpropanoic acid (1.0 g, 7.2 mmol, 1.0 equiv) in N,N-dimethylformamide (3.7 mL) at 0° C. The resulting brown suspension was allowed to warm to 23° C. and stirred for 24 h. The reaction mixture was diluted with a saturated solution of sodium bicarbonate (300 mL) and washed with diethyl ether (3×75 mL). The aqueous layer was acidified to pH≈1 with concentrated hydrochloric acid and extracted with diethyl ether (3×75 mL). The combined organic layers were dried (sodium sulfate), gravity filtered, and concentrated to afford a colorless oil (1.2 g, 99% crude yield). $^1$H NMR (300 MHz, CDCl$_3$) δ 2.76 (s, 2H), 2.16 (s, 3H), 1.30 (s, 6H).

Example 76

Preparation of 3-methyl-3-methylsulfanyl-butyric acid

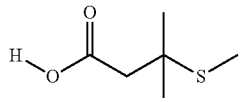

Example 76 was made using the procedures disclosed in *J. Chem Soc Perkin* 1, 1992, 10, 1215-21).

Example 77

Preparation of 3-methylsulfanyl-butyric acid

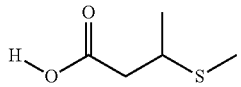

Example 77 was made using the procedures disclosed in *Synthetic Comm.*, 1985, 15 (7), 623-32.

Example 78

Preparation of tetrahydro-thiophene-3-carboxylic acid

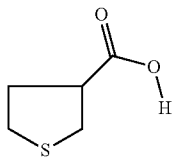

Example 78 was made using the procedures disclosed in *Heterocycles*, 2007, 74, 397-409.

Example 79

Preparation of 2-methyl-3-methylsulfanyl-butyric acid

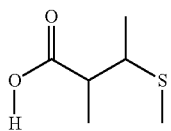

Example 79 was made using the procedures disclosed in *J. Chem Soc Perkin* 1, 1992, 10, 1215-21.

Example 80

Preparation of (1S,2S)-2-(methylthio)cyclopropanecarboxylic acid

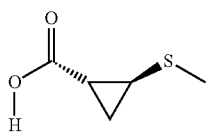

Example 80 was made using the procedures disclosed in *Synthetic Comm.*, 2003, 33 (5); 801-807.

The following compounds were made in accordance with Schemes I through XXI above.

The following compounds were made in accordance with the procedures shown in Scheme I steps a, b, e, i and j followed by Scheme VII above: 138, 174.

The following compounds were made in accordance with the procedures shown in Scheme I steps a, b, e, i and j above: 120.

Compound 476 was prepared according to Scheme XVIII.

Compound 502 was prepared from Compound 481 according to the Scheme IX (step c) and the Scheme V (Step a), respectively.

Compound 494 was prepared from Compound 481 according to Scheme IX (step c) and Scheme VIII (step a), respectively.

Compound 503 was prepared from Compound 277 according to the Scheme VIII (steps b and c), Scheme IX (step a, c) and Scheme III (steps f) and Scheme V (step a), respectively.

Compound 451 was prepared as disclosed in Scheme VII from compound 421.

Compound 459 was prepared as disclosed in Scheme VII from compound 451.

The following compound was made in accordance with the procedures shown in Scheme I steps c, e, and h followed by Scheme XIV steps a and b: 472.

The following compounds were made in accordance with the procedures shown in Scheme I steps c, e, and h followed by Scheme XIV step a: 449, 386, 398, 450, 511, 512.

The following compounds were made in accordance with the procedures shown in Scheme I steps c, e, i, j, and k, Scheme XVI step a, and Scheme VIII step b then a, respectively: 583, 584, and 586.

The following compound was made in accordance with the procedures shown in Scheme I steps c, e, i, j, and k followed by Scheme XVI step a: 580.

The following compound was made in accordance with the procedures shown in Scheme I steps c, e, i, j, and k, Scheme XVI step a, and Scheme VIII step b, respectively: 581.

The following compound was made in accordance with the procedures shown in Scheme I steps c, e, i, j, and k, Scheme XVI step a, Scheme VIII step b, and Scheme XIV step a, respectively: 585.

The following compound was made in accordance with the procedures shown in Scheme I steps c, e, i, j, and k, Scheme XVI step a, Scheme VIII step b, and Scheme II step d, respectively: 587.

The following compound was made in accordance with the procedures shown in Scheme II steps a, b, c: 309.

Compounds 473, 500, 508, 509, 513, 515, 551 were made in accordance with Schemes III (step b, c) and Scheme IV.

Compounds 469, 470, 474, 475, 501, 510, 514, 558 were made in accordance with Schemes III (step b, c), Scheme IV and Scheme VII.

Compounds 527, 528, 529, 540, 541, 542, 543, 544, 545, 547, 548, 550, 554, 555, 556, 557, 561, 562, 563, 564, 570, 571, 574, 575, 576, 577, 578, 579 were made in accordance with Schemes III (step b, c, d, e, f) and Scheme XVI.

Compound 549 was made in accordance with Schemes III (step b, c, d, e, j), Scheme XVI and Scheme VII (step a).

Compounds 139-142, 252 were made in accordance with Schemes I and V.

Compounds 143-148 were made in accordance with Schemes I, V, and VII.

Compounds 133-136 were made in accordance with Schemes II and V.

Compounds 251 and 265 were made in accordance with Scheme III.

Compound 296 was made in accordance with Schemes III and V.

Compound 317 was made in accordance with Schemes III and X.

Compound 318 was made in accordance with Schemes III and IX.

Compounds 149-151, 160, 241, 243-245, and 267 were made in accordance with Scheme III.

Compounds 193, 209-210, 221-224, 226, 231, 233, 236, 237, 240, 253, 254, 255, 262-264, 266, 274, 275, 278, 279, 298, 299, 305, 308, 525, 530-532, 535, 539 and 546 were made in accordance with Schemes III and V.

Compounds 137, 153-155, 158-159, 161, 169-170, 172, 175, 176, 196, 197, 204-205 and 207 were made in accordance with Schemes III and VIII.

Compounds 452 was made in accordance with Schemes III and IX.

Compounds 297, 352, 422 and 478 were made in accordance with Schemes III and X.

Compounds 186, 187, 194, 206, 208, 232, 268, 276, 280-283, 290-295, 310-312, 326, 327, 329, 330-347, 350, 351, 355, 365, 533, 534, 536 and 573 were made in accordance with Schemes III and XVI.

Compounds 152, 162, 173, 183-185, 188, 189, 195 and 200 were made in accordance with Schemes III, IV and V.

Compounds 225, 229, 230, 234, 235, 238, 239, 246, 247, 249, 250, 256-261, 269-273, 288, 289, 306, 307, 314, 315, 348, 349, 559 and 560 were made in accordance with Schemes III, V and VII.

Compound 211 was made in accordance with Schemes III, V and VIII.

Compound 328 was made in accordance with Schemes III, IX and XVI.

Compounds 303, 366 and 423 were made in accordance with Schemes III (step a-c), Scheme X (step a-d) and Scheme II (step d).

Compound 364 was made in accordance with Schemes III (step a-c), Scheme X (step a-d) and Scheme VIII (step a and b).

Compounds 384, 385, 424, 425, 441 and 456 were made in accordance with Schemes III (step a-c), Scheme X (step a-d), Scheme II (step d and e) and Scheme V.

Compounds 354, 457, 458, 480, 498, 499 and 505 were made in accordance with Schemes III (step a-e), Scheme IX (step a), Scheme III (step f) and Scheme V.

Compounds 504, 506, 507 and 526 were made in accordance with Schemes III (step a-e), Scheme IX (step a), Scheme III (step f), Scheme V and Scheme VII.

Compounds 392, 393, 427, 454 and 455 were made in accordance with Schemes III (step a-c), Scheme X (step a-d), Scheme II (step d and e), Scheme V and Scheme VII.

Compound 477 and 496 were made in accordance with Schemes III (step a-e), Scheme V.

Compounds 356, 426, and 460-468 were prepared according to Scheme II (steps c-e) and Scheme XVI.

Compounds 357, 518, 567 and 568 were prepared according to Scheme II (steps c and d).

Compounds 358-362, 367-374, 381, 382, 383, 387-390, 394, 396, 397, 420-421 and 428-440 were prepared according to Scheme XVI.

Compounds 167 and 168 were prepared in accordance with Schemes III, V and XI.

Compound 165 was made according to Scheme III.

Compounds 166, 190, 300 and 446-448 were prepared in accordance with Schemes III and V.

Compounds 178, 179, 181, 182, 191, 192, 198 and 199 were prepared in accordance with Schemes III and VI.

Compounds 212-220, 248, 319, 324, 405, 409, 411, 413, 401, 415, 442-445, 487, 516, 517, 538, 552, 553, 566, 569, 588 were prepared in accordance with Schemes III and XVI.

Compounds 284, 301, 302, 375-378, 379, 380, 482-486, 491-493 were prepared according to Scheme II.

Compounds 285, 287 520-524, 537, 565 were prepared in accordance with Schemes III, XVI and VII.

Compound 286 was prepared according to Schemes II and V.

Compounds 320-323, 400, 402-404, 407, 410 and 412 were prepared in accordance with Schemes II and XVI.

Compound 395 was prepared in accordance with Schemes XII and XVI.

Compounds 399, 406, 408, 414, 416-418 were prepared in accordance with Schemes II, III and XVI.

Compound 489 was prepared in accordance with Schemes III, XVI and VIII.

Compounds 201 and 202 were prepared in accordance with Scheme II.

Compound 177 was prepared in accordance with Schemes III and VI.

Compound 325 was prepared in accordance with Schemes II and VI.

Compound 488 was prepared in accordance with Schemes III and XVI.

Compound 490 was prepared in accordance with Schemes III, XVI, and VIII.

Insecticidal Testing

The compounds were tested against cotton aphid, green peach aphid, and sweet potato whitefly using procedures described in the following examples and reported in Table 2.

In each case of Table 2, the rating scale is as follows at 200 ppm.

| % Control (or Mortality) | Rating |
| --- | --- |
| 80-100 | A |
| Less than 80 | B |
| Not tested | C |

Example 81

Insecticidal Test for Green Peach Aphid (*Myzus persicae*) in Foliar Spray Assay Cabbage seedlings grown in 3-inch pots, with 2-3 small (3-5 cm) true leaves, were used as test substrate. The seedlings were infested with 20-50 green peach aphids (wingless adult and nymph) one day prior to chemical application. Four pots with individual seedlings were used for each treatment. Compounds (2 mg) were dissolved in 2 mL of acetone/methanol (1:1) solvent, forming stock solutions of 1000 ppm. The stock solutions were diluted 5× with 0.025% Tween 20 in $H_2O$ to obtain a test solution at 200 ppm. A hand-held Devilbiss sprayer was used for spraying a solution to both sides of cabbage leaves until runoff. Reference plants (solvent check) were sprayed with the diluent only. Treated plants were held in a holding room for three days at approximately 25° C. and 40% relative humidity (RH) prior to grading. Evaluation was conducted by counting the number of live aphids per plant under a microscope. Insecticidal activity was measured by using Abbott's correction formula are presented in Table 2: (See col. "MYZUPE").

$$\text{Corrected \% Control} = 100*(X-Y)/X$$

where X=No. of live aphids on solvent check plants
Y=No. of live aphids on treated plants

Example 82

Insecticidal Test for Cotton Aphid (*Aphis gossypii*) in Foliar Spray Assay

Squash or cotton seedlings with fully expanded cotyledon leaves were trimmed to one cotyledon per plant and infested with cotton aphid (wingless adult and nymph) one day prior to chemical application. Each plant was examined before chemical application to ensure uniform infestation (ca. 30-70 aphids per plant). Compounds (2 mg) were dissolved in 2 mL of acetone/methanol (1:1) solvent, forming stock solutions of 1000 ppm. The stock solutions were diluted 5× with 0.025% Tween 20 in $H_2O$ to obtain a solution at 200 ppm. A hand-held Devilbiss aspirator type sprayer was used to apply the spray solutions until runoff to both sides of the squash cotyledon leaves. Four plants (4 replications) were used for each concentration of each compound. Reference plants (solvent check) were sprayed with the diluent only. Treated plants were held in a holding room for three days at approximately 25° C. and 40% RH before the number of live aphids on each plant was recorded. Insecticidal activity was measured by Corrected % Control using Abbott's correction formula and presented in Table 2 (see col. "APHIGO"):

Corrected % Control=100*(X−Y)/X where X=No. of live aphids on solvent check plants
Y=No. of live aphids on treated plants

Example 83

Insecticidal Test for Sweetpotato Whitefly-Crawler (*Bemisia tabaci*) in Foliar Spray Assay Cotton plants grown in 3-inch pots, with 1 small (3-5 cm) true leaf, were used as test substrate. The plants were placed in a room with whitefly adults. Adults were allowed to deposit eggs for 2-3 days. After a 2-3 day egg-laying period, plants were taken from the adult whitefly room. Adults were blown off leaves using a hand-held Devilbiss sprayer (23 psi). Plants with egg infestation (100-300 eggs per plant) were placed in a holding room for 5-6 days at 82° F. and 50% RH for egg hatch and crawler stage to develop. Four cotton plants were used for each treatment. Compounds (2 mg) were dissolved in 1 mL of acetone solvent, forming stock solutions of 2000 ppm. The stock solutions were diluted 10× with 0.025% Tween 20 in $H_2O$ to obtain a test solution at 200 ppm. A hand-held Devilbiss sprayer was used for spraying a solution to both sides of cotton leaf until runoff. Reference plants (solvent check) were sprayed with the diluent only. Treated plants were held in a holding room for 8-9 days at approximately 82° F. and 50% RH prior to grading. Evaluation was conducted by counting the number of live nymphs per plant under a microscope. Insecticidal activity was measured by using Abbott's correction formula and presented in Table 2 (see col. "BEMITA"):

Corrected % Control=100*(X−Y)/X where X=No. of live nymphs on solvent check plants
Y=No. of live nymphs on treated plants Pesticidally Acceptable Acid Addition Salts, Salt Derivatives, Solvates, Ester Derivatives, Polymorphs, Isotopes and Radionuclides Molecules of Formula I may be formulated into pesticidally acceptable acid addition salts. By way of a non-limiting example, an amine function can form salts with hydrochloric, hydrobromic, sulfuric, phosphoric, acetic, benzoic, citric, malonic, salicylic, malic, fumaric, oxalic, succinic, tartaric, lactic, gluconic, ascorbic, maleic, aspartic, benzenesulfonic, methanesulfonic, ethanesulfonic, hydroxymethanesulfonic, and hydroxyethanesulfonic acids. Additionally, by way of a non-limiting example, an acid function can form salts including those derived from alkali or alkaline earth metals and those derived from ammonia and amines. Examples of preferred cations include sodium, potassium, magnesium, and ammonium cations.

Molecules of Formula I may be formulated into salt derivatives. By way of a non-limiting example, a salt derivative can be prepared by contacting a free base with a sufficient amount of the desired acid to produce a salt. A free base may be regenerated by treating the salt with a suitable dilute aqueous base solution such as dilute aqueous sodium hydroxide (NaOH), potassium carbonate, ammonia, and sodium bicarbonate. As an example, in many cases, a pesticide, such as 2,4-D, is made more water-soluble by converting it to its dimethylamine salt.

Molecules of Formula I may be formulated into stable complexes with a solvent, such that the complex remains intact after the non-complexed solvent is removed. These complexes are often referred to as "solvates." However, it is particularly desirable to form stable hydrates with water as the solvent.

Molecules of Formula I may be made as various crystal polymorphs. Polymorphism is important in the development of agrochemicals since different crystal polymorphs or structures of the same molecule can have vastly different physical properties and biological performances.

Molecules of Formula I may be made with different isotopes. Of particular importance are molecules having $^2H$ (also known as deuterium) in place of $^1H$.

Molecules of Formula I may be made with different radionuclides. Of particular importance are molecules having $^{14}C$.

Stereoisomers

Molecules of Formula I may exist as one or more stereoisomers. Thus, certain molecules can be produced as racemic mixtures. It will be appreciated by those skilled in the art that one stereoisomer may be more active than the other stereoisomers. Individual stereoisomers may be obtained by known selective synthetic procedures, by conventional synthetic procedures using resolved starting materials, or by conventional resolution procedures.

Insecticides

Molecules of Formula I may also be used in combination (such as, in a compositional mixture, or a simultaneous or sequential application) with one or more of the following insecticides—1,2-dichloropropane, abamectin, acephate, acetamiprid, acethion, acetoprole, acrinathrin, acrylonitrile, alanycarb, aldicarb, aldoxycarb, aldrin, allethrin, allosamidin, allyxycarb, alpha-cypermethrin, alpha-ecdysone, alpha-endosulfan, amidithion, aminocarb, amiton, amiton oxalate, amitraz, anabasine, athidathion, azadirachtin, azamethiphos, azinphos-ethyl, azinphos-methyl, azothoate, barium hexafluorosilicate, barthrin, bendiocarb, benfuracarb, bensultap, beta-cyfluthrin, beta-cypermethrin, bifenthrin, bioallethrin, bioethanomethrin, biopermethrin, bistrifluoron, borax, boric acid, bromfenvinfos, bromocyclen, bromo-DDT, bromophos, bromophos-ethyl, bufencarb, buprofezin, butacarb, butathiofos, butocarboxim, butonate, butoxycarboxim, cadusafos, calcium arsenate, calcium polysulfide, camphechlor, carbanolate, carbaryl, carbofuran, carbon disulfide, carbon tetrachloride, carbophenothion, carbosulfan, cartap, cartap hydrochloride, chlorantraniliprole, chlorbicyclen, chlordane, chlordecone, chlordimeform, chlordimeform hydrochloride, chlorethoxyfos, chlorfenapyr, chlorfenvinphos, chlorfluazuron, chlormephos, chloroform, chloropicrin, chlorphoxim, chlorprazophos, chlorpyrifos, chlorpyrifos-methyl, chlorthiophos, chromafenozide, cinerin I, cinerin II, cinerins, cismethrin, cloethocarb, closantel, clothianidin, copper acetoarsenite, copper arsenate, copper naphthenate, copper oleate, coumaphos, coumithoate, crotamiton, crotoxyphos, crufomate, cryolite, cyanofenphos, cyanophos, cyanthoate, cyantraniliprole, cyclethrin, cycloprothrin, cyfluthrin, cyhalothrin, cypermethrin, cyphenothrin, cyromazine, cythioate, DDT, decarbofuran, deltamethrin, demephion, demephion-O, demephion-S, demeton, demeton-methyl, demeton-O, demeton-O-methyl, demeton-S, demeton-S-methyl, demeton-S-methylsulphon, diafenthiuron, dialifos, diatomaceous earth, diazinon, dicapthon, dichlofenthion, dichlorvos, dicresyl, dicrotophos, dicyclanil, dieldrin, diflubenzuron, dilor, dimefluthrin, dimefox, dimetan, dimethoate, dimethrin, dimethylvinphos, dimetilan, dinex, dinex-diclexine, dinoprop, dinosam, dinotefuran, diofenolan, dioxabenzofos, dioxacarb, dioxathion, disulfoton, dithicrofos, d-limonene, DNOC, DNOC-ammonium, DNOC-potassium, DNOC-sodium, doramectin, ecdysterone, emamectin, emamectin benzoate, EMPC, empenthrin, endosulfan, endothion, endrin, EPN, epofenonane, eprinomectin, esdepalléthrine, esfenvalerate, etaphos, ethiofencarb, ethion, ethiprole, ethoate-methyl, ethoprophos, ethyl formate, ethyl-DDD, ethylene dibromide, ethylene dichloride, ethylene oxide, etofenprox, etrimfos, EXD, famphur, fenamiphos, fenazaflor, fenchlorphos, fenethacarb, fenfluthrin, fenitrothion, fenobucarb, fenoxacrim, fenoxycarb, fenpirithrin, fenpropathrin, fensulfothion, fenthion, fenthion-ethyl, fenvalerate, fipronil, flonicamid, flubendiamide (additionally resolved isomers thereof), flucofuron, flucycloxuron, flucythrinate, flufenerim, flufenoxuron, flufenprox, fluvalinate, fonofos, formetanate, formetanate hydrochloride, formothion, formparanate, formparanate hydrochloride, fosmethilan, fospirate, fosthietan, fufenozide, furathiocarb, furethrin, gamma-cyhalothrin, gamma-HCH, halfenprox, halofenozide, HCH, HEOD, heptachlor, heptenophos, heterophos, hexaflumuron, HHDN, hydramethylnon, hydrogen cyanide, hydroprene, hyquincarb, imidacloprid, imiprothrin, indoxacarb, iodomethane, IPSP, isazofos, isobenzan, isocarbophos, isodrin, isofenphos, isofenphos-methyl, isoprocarb, isoprothiolane, isothioate, isoxathion, ivermectin, jasmolin I, jasmolin II, jodfenphos, juvenile hormone I, juvenile hormone II, juvenile hormone III, kelevan, kinoprene, lambda-cyhalothrin, lead arsenate, lepimectin, leptophos, lindane, lirimfos, lufenuron, lythidathion, malathion, malonoben, mazidox, mecarbam, mecarphon, menazon, meperfluthrin, mephosfolan, mercurous chloride, mesulfenfos, metaflumizone, methacrifos, methamidophos, methidathion, methiocarb, methocrotophos, methomyl, methoprene, methothrin, methoxychlor, methoxyfenozide, methyl bromide, methyl isothiocyanate, methylchloroform, methylene chloride, metofluthrin, metolcarb, metoxadiazone, mevinphos, mexacarbate, milbemectin, milbemycin oxime, mipafox, mirex, molosultap, monocrotophos, monomehypo, monosultap, morphothion, moxidectin, naftalofos, naled, naphthalene, nicotine, nifluridide, nitenpyram, nithiazine, nitrilacarb, novaluron, noviflumuron, omethoate, oxamyl, oxydemeton-methyl, oxydeprofos, oxydisulfoton, para-dichlorobenzene, parathion, parathion-methyl, penfluron, pentachlorophenol, permethrin, phenkapton, phenothrin, phenthoate, phorate, phosalone, phosfolan, phosmet, phosnichlor, phosphamidon, phosphine, phoxim, phoxim-methyl, pirimetaphos, pirimicarb, pirimiphos-ethyl, pirimiphos-methyl, potassium arsenite, potassium thiocyanate, pp'-DDT, prallethrin, precocene I, precocene II, precocene III, primidophos, profenofos, profluralin, profluthrin, promacyl, promecarb, propaphos, propetamphos, propoxur, prothidathion, prothiofos, prothoate, protrifenbute, pymetrozine, pyraclofos, pyrafluprole, pyrazophos, pyresmethrin, pyrethrin I, pyrethrin II, pyrethrins, pyridaben, pyridalyl, pyridaphenthion, pyrifluquinazon, pyrimidifen, pyrimitate, pyriprole, pyriproxyfen, quassia, quinalphos, quinalphos-methyl, quinothion, rafoxanide, resmethrin, rotenone, ryania, sabadilla, schradan, selamectin, silafluofen, silica gel, sodium arsenite, sodium fluoride, sodium hexafluorosilicate, sodium thiocyanate, sophamide, spinetoram, spinosad, spiromesifen, spirotetramat, sulcofuron, sulcofuron-sodium, sulfluramid, sulfotep, sulfoxaflor, sulfuryl fluoride, sulprofos, tau-fluvalinate, tazimcarb, TDE, tebufenozide, tebufenpyrad, tebupirimfos, teflubenzuron, tefluthrin, temephos, TEPP, terallethrin, terbufos, tetrachloroethane, tetrachlorvinphos, tetramethrin, tetramethylfluthrin, theta-cypermethrin, thiacloprid, thiamethoxam, thicrofos, thiocarboxime, thiocyclam, thiocyclam oxalate, thiodicarb, thiofanox, thiometon, thiosultap, thiosultap-disodium, thiosultap-monosodium, thuringiensin, tolfenpyrad, tralomethrin, transfluthrin, transpermethrin, triarathene, triazamate, triazophos, trichlorfon, trichlormetaphos-3, trichloronat, trifenofos, triflumuron, trimethacarb, triprene, vamidothion, vaniliprole, XMC, xylylcarb, zeta-cypermethrin, zolaprofos (collectively these commonly named insecticides are defined as the "Insecticide Group").

Acaricides

Molecules of Formula I may also be used in combination (such as, in a compositional mixture, or a simultaneous or sequential application) with one or more of the following acaricides—acequinocyl, amidoflumet, arsenous oxide, azobenzene, azocyclotin, benomyl, benoxafos, benzoximate, benzyl benzoate, bifenazate, binapacryl, bromopropylate, chinomethionat, chlorbenside, chlorfenethol, chlorfenson, chlorfensulphide, chlorobenzilate, chloromebuform, chloromethiuron, chloropropylate, clofentezine, cyenopyrafen, cyflumetofen, cyhexatin, dichlofluanid, dicofol, dienochlor, diflovidazin, dinobuton, dinocap, dinocap-4, dinocap-6, dinocton, dinopenton, dinosulfon, dinoterbon, diphenyl sulfone, disulfuram, dofenapyn, etoxazole, fenazaquin, fenbutatin oxide, fenothiocarb, fenpyroximate, fenson, fentrifanil, fluacrypyrim, fluazuron, flubenzimine, fluenetil, flumethrin, fluorbenside, hexythiazox, mesulfen, MNAF, nikkomycins, proclonol, propargite, quintiofos, spirodiclofen, sulfuram, sulfur, tetradifon, tetranactin, tetrasul, and thioquinox (collectively these commonly named acaricides are defined as the "Acaricide Group").

Nematicides

Molecules of Formula I may also be used in combination (such as, in a compositional mixture, or a simultaneous or sequential application) with one or more of the following nematicides—1,3-dichloropropene, benclothiaz, dazomet, dazomet-sodium, DBCP, DCIP, diamidafos, fluensulfone, fosthiazate, furfural, imicyafos, isamidofos, isazofos, metam, metam-ammonium, metam-potassium, metam-sodium, phosphocarb, and thionazin (collectively these commonly named nematicides are defined as the "Nematicide Group")

Fungicides

Molecules of Formula I may also be used in combination (such as, in a compositional mixture, or a simultaneous or sequential application) with one or more of the following fungicides—(3-ethoxypropyl)mercury bromide, 2-methoxyethylmercury chloride, 2-phenylphenol, 8-hydroxyquinoline sulfate, 8-phenylmercurioxyquinoline, acibenzolar, acibenzolar-S-methyl, acypetacs, acypetacs-copper, acypetacs-zinc, aldimorph, allyl alcohol, ametoctradin, amisulbrom, ampropylfos, anilazine, aureofungin, azaconazole, azithiram, azoxystrobin, barium polysulfide, benalaxyl, benalaxyl-M, benodanil, benomyl, benquinox, bentaluron, benthiavalicarb, benthiavalicarb-isopropyl, benzalkonium chloride, benzamacril, benzamacril-isobutyl, benzamorf, benzohydroxamic acid, bethoxazin, binapacryl, biphenyl, bitertanol, bithionol, bixafen, blasticidin-S, Bordeaux mixture, boscalid, bromuconazole, bupirimate, Burgundy mixture, buthiobate, butylamine, calcium polysulfide, captafol, captan, carbamorph, carbendazim, carboxin, carpropamid, carvone, Cheshunt mixture, chinomethionat, chlobenthiazone, chloraniformethan, chloranil, chlorfenazole, chlorodinitronaphthalene, chloroneb, chloropicrin, chlorothalonil, chlorquinox, chlozolinate, climbazole, clotrimazole, copper acetate, copper carbonate, basic, copper hydroxide, copper naphthenate, copper oleate, copper oxychloride, copper silicate, copper sulfate, copper zinc chromate, cresol, cufraneb, cuprobam, cuprous oxide, cyazofamid, cyclafuramid, cycloheximide, cyflufenamid, cymoxanil, cypendazole, cyproconazole, cyprodinil, dazomet, dazomet-sodium, DBCP, debacarp, decafentin, dehydroacetic acid, dichlofluanid, dichlone, dichlorophen, dichlozoline, diclobutrazol, diclocymet, diclomezine, diclomezine-sodium, dicloran, diethofencarb, diethyl pyrocarbonate, difenoconazole, diflumetorim, dimethirimol, dimethomorph, dimoxystrobin, diniconazole, diniconazole-M, dinobuton, dinocap, dinocap-4, dinocap-6, dinocton, dinopenton, dinosulfon, dinoterbon, diphenylamine, dipyrithione, disulfuram, ditalimfos, dithianon, DNOC, DNOC-ammonium, DNOC-potassium, DNOC-sodium, dodemorph, dodemorph acetate, dodemorph benzoate, dodicin, dodicin-sodium, dodine, drazoxolon, edifenphos, epoxiconazole, etaconazole, etem, ethaboxam, ethirimol, ethoxyquin, ethylmercury 2,3-dihydroxypropyl mercaptide, ethylmercury acetate, ethylmercury bromide, ethylmercury chloride, ethylmercury phosphate, etridiazole, famoxadone, fenamidone, fenaminosulf, fenapanil, fenarimol, fenbuconazole, fenfuram, fenhexamid, fenitropan, fenoxanil, fenpiclonil, fenpropidin, fenpropimorph, fentin, fentin chloride, fentin hydroxide, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, formaldehyde, fosetyl, fosetyl-aluminium, fuberidazole, furalaxyl, furametpyr, furcarbanil, furconazole, furconazole-cis, furfural, furmecyclox, furophanate, glyodin, griseofulvin, guazatine, halacrinate, hexachlorobenzene, hexachlorobutadiene, hexaconazole, hexylthiofos, hydrargaphen, hymexazol, imazalil, imazalil nitrate, imazalil sulfate, imibenconazole, iminoctadine, iminoctadine triacetate, iminoctadine trialbesilate, iodomethane, ipconazole, iprobenfos, iprodione, iprovalicarb, isoprothiolane, isopyrazam, isotianil, isovaledione, kasugamycin, kresoxim-methyl, mancopper, mancozeb, mandipropamid, maneb, mebenil, mecarbinzid, mepanipyrim, mepronil, meptyldinocap, mercuric chloride, mercuric oxide, mercurous chloride, metalaxyl, metalaxyl-M, metam, metam-ammonium, metam-potassium, metam-sodium, metazoxolon, metconazole, methasulfocarb, methfuroxam, methyl bromide, methyl isothiocyanate, methylmercury benzoate, methylmercury dicyandiamide, methylmercury pentachlorophenoxide, metiram, metominostrobin, metrafenone, metsulfovax, milneb, myclobutanil, myclozolin, N-(ethylmercury)-p-toluenesulphonanilide, nabam, natamycin, nitrostyrene, nitrothalisopropyl, nuarimol, OCH, octhilinone, ofurace, orysastrobin, oxadixyl, oxine-copper, oxpoconazole, oxpoconazole fumarate, oxycarboxin, pefurazoate, penconazole, pencycuron, penflufen, pentachlorophenol, penthiopyrad, phenylmercuriurea, phenylmercury acetate, phenylmercury chloride, phenylmercury derivative of pyrocatechol, phenylmercury nitrate, phenylmercury salicylate, phosdiphen, phthalide, picoxystrobin, piperalin, polycarbamate, polyoxins, polyoxorim, polyoxorim-zinc, potassium azide, potassium polysulfide, potassium thiocyanate, probenazole, prochloraz, procymidone, propamocarb, propamocarb hydrochloride, propiconazole, propineb, proquinazid, prothiocarb, prothiocarb hydrochloride, prothioconazole, pyracarbolid, pyraclostrobin, pyraclostrobin, pyrametostrobin, pyraoxystrobin, pyrazophos, pyribencarb, pyridinitril, pyrifenox, pyrimethanil, pyriofenone, pyroquilon, pyroxychlor, pyroxyfur, quinacetol, quinacetol sulfate, quinazamid, quinconazole, quinoxyfen, quintozene, rabenzazole, salicylanilide, sedaxane, silthiofam, simeconazole, sodium azide, sodium orthophenylphenoxide, sodium pentachlorophenoxide, sodium polysulfide, spiroxamine, streptomycin, sulfur, sultropen, TCMTB, tebuconazole, tebufloquin, tecloftalam, tecnazene, tecoram, tetraconazole, thiabendazole, thiadifluor, thicyofen, thifluzamide, thiochlorfenphim, thiomersal, thiophanate, thiophanate-methyl, thioquinox, thiram, tiadinil, tioxymid, tolclofos-methyl, tolylfluanid, tolylmercury acetate, triadimefon, triadimenol, triamiphos, triarimol, triazbutil, triazoxide, tributyltin oxide, trichlamide, tricyclazole, tridemorph, trifloxystrobin, triflumizole, triforine, triticonazole, uniconazole, uniconazole-P, validamycin, valifenalate, vinclozolin, zarilamid, zinc naphthenate, zineb, ziram, zoxamide (collectively these commonly named fungicides are defined as the "Fungicide Group").

Herbicides

Molecules of Formula I may also be used in combination (such as, in a compositional mixture, or a simultaneous or sequential application) with one or more of the following herbicides—2,3,6-TBA, 2,3,6-TBA-dimethylammonium, 2,3,6-TBA-sodium, 2,4,5-T, 2,4,5-T-2-butoxypropyl, 2,4,5-T-2-ethylhexyl, 2,4,5-T-3-butoxypropyl, 2,4,5-TB, 2,4,5-T-butomethyl, 2,4,5-T-butotyl, 2,4,5-T-butyl, 2,4,5-T-isobutyl, 2,4,5-T-isoctyl, 2,4,5-T-isopropyl, 2,4,5-T-methyl, 2,4,5-T-pentyl, 2,4,5-T-sodium, 2,4,5-T-triethylammonium, 2,4,5-T-trolamine, 2,4-D, 2,4-D-2-butoxypropyl, 2,4-D-2-ethylhexyl, 2,4-D-3-butoxypropyl, 2,4-D-ammonium, 2,4-DB, 2,4-DB-butyl, 2,4-DB-dimethylammonium, 2,4-DB-isoctyl, 2,4-DB-potassium, 2,4-DB-sodium, 2,4-D-butotyl, 2,4-D-butyl, 2,4-D-diethylammonium, 2,4-D-dimethylammonium, 2,4-D-diolamine, 2,4-D-dodecylammonium, 2,4-DEB, 2,4-DEP, 2,4-D-ethyl, 2,4-D-heptylammonium, 2,4-D-isobutyl, 2,4-D-isoctyl, 2,4-D-isopropyl, 2,4-D-isopropylammonium, 2,4-D-lithium, 2,4-D-meptyl, 2,4-D-methyl, 2,4-D-octyl, 2,4-D-pentyl, 2,4-D-potassium, 2,4-D-propyl, 2,4-D-sodium, 2,4-D-tefuryl, 2,4-D-tetradecylammonium, 2,4-D-triethylammonium, 2,4-D-tris(2-hydroxypropyl)ammonium, 2,4-D-trolamine, 3,4-DA, 3,4-DB, 3,4-DP, 4-CPA, 4-CPB, 4-CPP, acetochlor, acifluorfen, acifluorfen-methyl, acifluorfen-sodium, aclonifen, acrolein, alachlor, allidochlor, alloxydim, alloxydim-sodium, allyl alcohol, alorac, ametridione, ametryn, amibuzin, amicarbazone, amidosulfuron, aminocyclopyrachlor, aminocyclopyrachlor-methyl, aminocyclopyrachlor-potassium, aminopyralid, aminopyralid-potassium, aminopyralid-tris(2-hydroxypropyl)ammonium, amiprofos-methyl, amitrole, ammonium sulfamate, anilofos, anisuron, asulam, asulam-potassium, asulam-sodium, atraton, atrazine, azafenidin, azimsulfuron, aziprotryne, barban, BCPC, beflubutamid, benazolin, benazolin-dimethylammonium, benazolin-ethyl, benazolin-potassium, bencarbazone, benfluralin, benfuresate, bensulfuron, bensulfuron-methyl, bensulide, bentazone, bentazone-sodium, benzadox, benzadox-ammonium, benzfendizone, benzipram, benzobicyclon, benzofenap, benzofluor, benzoylprop, benzoylprop-ethyl, benzthiazuron, bicyclopyrone, bifenox, bilanafos, bilanafos-sodium, bispyribac, bispyribac-sodium, borax, bromacil, bromacil-lithium, bromacil-sodium, bromobonil, bromobutide, bromofenoxim, bromoxynil, bromoxynil butyrate, bromoxynil heptanoate, bromoxynil octanoate, bromoxynil-potassium, brompyrazon, butachlor, butafenacil, butamifos, butenachlor, buthidazole, buthiuron, butralin, butroxydim, buturon, butylate, cacodylic acid, cafenstrole, calcium chlorate, calcium cyanamide, cambendichlor, carbasulam, carbetamide, carboxazole, carfentrazone, carfentrazone-ethyl, CDEA, CEPC, chlomethoxyfen, chloramben, chloramben-ammonium, chloramben-diolamine, chloramben-methyl, chloramben-methylammonium, chloramben-sodium, chloranocryl, chlorazifop, chlorazifop-propargyl, chlorazine, chlorbromuron, chlorbufam, chloreturon, chlorfenac, chlorfenac-sodium, chlorfenprop, chlorfenprop-methyl, chlorflurazole, chlorflurenol, chlorflurenol-methyl, chloridazon, chlorimuron, chlorimuron-ethyl, chlornitrofen, chloropon, chlorotoluron, chloroxuron, chloroxynil, chlorprocarb, chlorpropham, chlorsulfuron, chlorthal, chlorthal-dimethyl, chlorthal-monomethyl, chlorthiamid, cinidon-ethyl, cinmethylin, cinosulfuron, cisanilide, clethodim, cliodinate, clodinafop, clodinafop-propargyl, clofop, clofop-isobutyl, clomazone, clomeprop, cloprop, cloproxydim, clopyralid, clopyralid-methyl, clopyralid-olamine, clopyralid-potassium, clopyralid-tris(2-hydroxypropyl)ammonium, cloransulam, cloransulam-methyl, CMA, copper sulfate, CPMF, CPPC, credazine, cresol, cumyluron, cyanamide, cyanatryn, cyanazine, cycloate, cyclosulfamuron, cycloxydim, cycluron, cyhalofop, cyhalofop-butyl, cyperquat, cyperquat chloride, cyprazine, cyprazole, cypromid, daimuron, dalapon, dalapon-calcium, dalapon-magnesium, dalapon-sodium, dazomet, dazomet-sodium, delachlor, desmedipham, desmetryn, di-allate, dicamba, dicamba-dimethylammonium, dicamba-diolamine, dicamba-isopropylammonium, dicamba-methyl, dicamba-olamine, dicamba-potassium, dicamba-sodium, dicamba-trolamine, dichlobenil, dichloralurea, dichlormate, dichlorprop, dichlorprop-2-ethylhexyl, dichlorprop-butotyl, dichlorprop-dimethylammonium, dichlorprop-ethylammonium, dichlorprop-isoctyl, dichlorprop-methyl, dichlorprop-P, dichlorprop-P-dimethylammonium, dichlorprop-potassium, dichlorprop-sodium, diclofop, diclofop-methyl, diclosulam, diethamquat, diethamquat dichloride, diethatyl, diethatyl-ethyl, difenopenten, difenopenten-ethyl, difenoxuron, difenzoquat, difenzoquat metilsulfate, diflufenican, diflufenzopyr, diflufenzopyr-sodium, dimefuron, dimepiperate, dimethachlor, dimethametryn, dimethenamid, dimethenamid-P, dimexano, dimidazon, dinitramine, dinofenate, dinoprop, dinosam, dinoseb, dinoseb acetate, dinoseb-ammonium, dinoseb-diolamine, dinoseb-sodium, dinoseb-trolamine, dinoterb, dinoterb acetate, diphacinone-sodium, diphenamid, dipropetryn, diquat, diquat dibromide, disul, disul-sodium, dithiopyr, diuron, DMPA, DNOC, DNOC-ammonium, DNOC-potassium, DNOC-sodium, DSMA, EBEP, eglinazine, eglinazine-ethyl, endothal, endothal-diammonium, endothal-dipotassium, endothal-disodium, epronaz, EPTC, erbon, esprocarb, ethalfluralin, ethametsulfuron, ethametsulfuron-methyl, ethidimuron, ethiolate, ethofumesate, ethoxyfen, ethoxyfen-ethyl, ethoxysulfuron, etinofen, etnipromid, etobenzanid, EXD, fenasulam, fenoprop, fenoprop-3-butoxypropyl, fenoprop-butomethyl, fenoprop-butotyl, fenoprop-butyl, fenoprop-isoctyl, fenoprop-methyl, fenoprop-potassium, fenoxaprop, fenoxaprop-ethyl, fenoxaprop-P, fenoxaprop-P-ethyl, fenoxasulfone, fenteracol, fenthiaprop, fenthiaprop-ethyl, fentrazamide, fenuron, fenuron TCA, ferrous sulfate, flamprop, flamprop-isopropyl, flamprop-M, flamprop-methyl, flamprop-M-isopropyl, flamprop-M-methyl, flazasulfuron, florasulam, fluazifop, fluazifop-butyl, fluazifop-methyl, fluazifop-P, fluazifop-P-butyl, fluazolate, flucarbazone, flucarbazone-sodium, flucetosulfuron, fluchloralin, flufenacet, flufenican, flufenpyr, flufenpyr-ethyl, flumetsulam, flumezin, flumiclorac, flumiclorac-pentyl, flumioxazin, flumipropyn, fluometuron, fluorodifen, fluoroglycofen, fluoroglycofen-ethyl, fluoromidine, fluoronitrofen, fluothiuron, flupoxam, flupropacil, flupropanate, flupropanate-sodium, flupyrsulfuron, flupyrsulfuron-methyl-sodium, fluridone, fluorochloridone, fluoroxypyr, fluoroxypyr-butomethyl, fluoroxypyr-meptyl, flurtamone, fluthiacet, fluthiacet-methyl, fomesafen, fomesafen-sodium, foramsulfuron, fosamine, fosamine-ammonium, furyloxyfen, glufosinate, glufosinate-ammonium, glufosinate-P, glufosinate-P-ammonium, glufosinate-P-sodium, glyphosate, glyphosate-diammonium, glyphosate-dimethylammonium, glyphosate-isopropylammonium, glyphosate-monoammonium, glyphosate-potassium, glyphosate-sesquisodium, glyphosate-trimesium, halosafen, halosulfuron, halosulfuron-methyl, haloxydine, haloxyfop, haloxyfop-etotyl, haloxyfop-methyl, haloxyfop-P, haloxyfop-P-etotyl, haloxyfop-P-methyl, haloxyfop-sodium, hexachloroacetone, hexaflurate, hexazinone, imazamethabenz, imazamethabenz-methyl, imazamox, imazamox-ammonium, imazapic, imazapic-ammonium, imazapyr, imazapyr-isopropylammonium, imazaquin, imazaquin-ammonium, imazaquin-methyl, imazaquin-sodium, imazethapyr, imazethapyr-ammonium, imazosulfuron, indanofan, indaziflam, iodobonil, iodomethane, iodosulfuron, iodosulfuron-methyl-sodium, ioxynil, ioxynil octanoate, ioxynil-lithium, ioxynil-sodium, ipazine, ipfencarbazone, iprymidam, isocarbamid, isocil, isomethiozin, isonoruron, isopolinate, isopropalin, isoproturon, isouron, isoxaben, isoxachlortole, isoxaflutole, isoxapyrifop, karbutilate, ketospiradox, lactofen, lenacil, linuron, MAA, MAMA, MCPA, MCPA-2-ethylhexyl, MCPA-butotyl, MCPA-butyl, MCPA-dimethylammonium, MCPA-diolamine, MCPA-ethyl, MCPA-isobutyl, MCPA-isoctyl, MCPA-isopropyl, MCPA-methyl, MCPA-olamine, MCPA-potassium, MCPA-sodium, MCPA-thioethyl, MCPA-trolamine, MCPB, MCPB-ethyl, MCPB-methyl, MCPB-sodium, mecoprop, mecoprop-2-ethylhexyl, mecoprop-dimethylammonium, mecoprop-diolamine, mecoprop-ethadyl, mecoprop-isoctyl, mecoprop-methyl, mecoprop-P, mecoprop-P-dimethylammonium, mecoprop-P-isobutyl, mecoprop-potassium, mecoprop-P-potassium, mecoprop-sodium, mecoprop-trolamine, medinoterb, medinoterb acetate, mefenacet, mefluidide, mefluidide-diolamine, mefluidide-potassium, mesoprazine, mesosulfuron, mesosulfuron-methyl, mesotrione, metam, metam-ammonium, metamifop, metamitron, metam-potassium, metam-sodium, metazachlor, metazosulfuron, metflurazon, methabenzthiazuron, methalpropalin, methazole, methiobencarb, methiozolin, methiuron, methometon, methoprotryne, methyl bromide, methyl isothiocyanate, methyldymron, metobenzuron, metolachlor, metosulam, metoxuron, metribuzin, metsulfuron, metsulfuron-methyl, molinate, monalide, monisouron, monochloroacetic acid, monolinuron, monuron, monuron TCA, morfamquat, morfamquat dichloride, MSMA, naproanilide, napropamide, naptalam, naptalam-sodium, neburon, nicosulfuron, nipyraclofen, nitralin, nitrofen, nitrofluorfen, norflurazon, noruron, OCH, orbencarb, ortho-dichlorobenzene, orthosulfamuron, oryzalin, oxadiargyl, oxadiazon, oxapyrazon, oxapyrazon-dimolamine, oxapyrazon-sodium, oxasulfuron, oxaziclomefone, oxyfluorfen, parafluoron, paraquat, paraquat dichloride, paraquat dimetilsulfate, pebulate, pelargonic acid, pendimethalin, penoxsulam, pentachlorophenol, pentanochlor, pentoxazone, perfluidone, pethoxamid, phenisopham, phenmedipham, phenmedipham-ethyl, phenobenzuron, phenylmercury acetate, picloram, picloram-2-ethylhexyl, picloram-isoctyl, picloram-methyl, picloramolamine, picloram-potassium, picloram-triethylammonium, picloram-tris(2-hydroxypropyl)ammonium, picolinafen, pinoxaden, piperophos, potassium arsenite, potassium azide, potassium cyanate, pretilachlor, primisulfuron, primisulfuron-methyl, procyazine, prodiamine, profluazol, profluralin, profoxydim, proglinazine, proglinazine-ethyl, prometon, prometryn, propachlor, propanil, propaquizafop, propazine, propham, propisochlor, propoxycarbazone, propoxycarbazone-sodium, propyrisulfuron, propyzamide, prosulfalin, prosulfocarb, prosulfuron, proxan, proxan-sodium, prynachlor, pydanon, pyraclonil, pyraflufen, pyraflufen-ethyl, pyrasulfotole, pyrazolynate, pyrazosulfuron, pyrazosulfuron-ethyl, pyrazoxyfen, pyribenzoxim, pyributicarb, pyriclor, pyridafol, pyridate, pyriftalid, pyriminobac, pyriminobac-methyl, pyrimisulfan, pyrithiobac, pyrithiobac-sodium, pyroxasulfone, pyroxsulam, quinclorac, quinmerac, quinoclamine, quinonamid, quizalofop, quizalofop-ethyl, quizalofop-P, quizalofop-P-ethyl, quizalofop-P-tefuryl, rhodethanil, rimsulfuron, saflufenacil, sebuthylazine, secbumeton, sethoxydim, siduron, simazine, simeton, simetryn, SMA, S-metolachlor, sodium arsenite, sodium azide, sodium chlorate, sulcotrione, sulfallate, sulfentrazone, sulfometuron, sulfometuron-methyl, sulfosulfuron, sulfuric acid, sulglycapin, swep, TCA, TCA-ammonium, TCA-calcium, TCA-ethadyl, TCA-magnesium, TCA-sodium, tebutam, tebuthiuron, tefuryltrione, tembotrione, tepraloxydim, terbacil, terbucarb, terbuchlor, terbumeton, terbuthylazine, terbutryn, tetrafluoron, thenylchlor, thiazafluoron, thiazopyr, thidiazimin, thidiazuron, thiencarbazone, thiencarbazone-methyl, thifensulfuron, thifensulfuron-methyl, thiobencarb, tiocarbazil, tioclorim, topramezone, tralkoxydim, tri-allate, triasulfuron, triaziflam, tribenuron, tribenuron-methyl, tricamba, triclopyr, triclopyrbutotyl, triclopyr-ethyl, triclopyr-triethylammonium, tridiphane, trietazine, trifloxysulfuron, trifloxysulfuron-sodium, trifluralin, triflusulfuron, triflusulfuron-methyl, trifop, trifopmethyl, trifopsime, trihydroxytriazine, trimeturon, tripropindan, tritac, tritosulfuron, vernolate, xylachlor, (collectively these commonly named herbicides are defined as the "Herbicide Group").

Biopesticides

Molecules of Formula I may also be used in combination (such as in a compositional mixture, or a simultaneous or sequential application) with one or more biopesticides. The term "biopesticide" is used for microbial biological pest control agents that are applied in a similar manner to chemical pesticides. Commonly these are bacterial, but there are also examples of fungal control agents, including *Trichoderma* spp. and *Ampelomyces quisqualis* (a control agent for grape powdery mildew). *Bacillus subtilis* are used to control plant pathogens. Weeds and rodents have also been controlled with microbial agents. One well-known insecticide example is *Bacillus thuringiensis*, a bacterial disease of Lepidoptera, Coleoptera, and Diptera. Because it has little effect on other organisms, it is considered more environmentally friendly than synthetic pesticides. Biological insecticides include products based on:

1. entomopathogenic fungi (e.g. *Metarhizium anisopliae*);
2. entomopathogenic nematodes (e.g. *Steinernema feltiae*); and
3. entomopathogenic viruses (e.g. *Cydia pomonella* granulovirus).

Other examples of entomopathogenic organisms include, but are not limited to, baculoviruses, bacteria and other prokaryotic organisms, fungi, protozoa and Microsproridia. Biologically derived insecticides include, but not limited to, rotenone, veratridine, as well as microbial toxins; insect tolerant or resistant plant varieties; and organisms modified by recombinant DNA technology to either produce insecticides or to convey an insect resistant property to the genetically modified organism. In one embodiment, the molecules of Formula I may be used with one or more biopesticides in the area of seed treatments and soil amendments. *The Manual of Biocontrol Agents* gives a review of the available biological insecticide (and other biology-based control) products. Copping L. G. (ed.) (2004). *The Manual of Biocontrol Agents* (formerly the *Biopesticide Manual*) 3rd Edition. British Crop Production Council (BCPC), Farnham, Surrey UK.

Other Active Compounds

Molecules of Formula I may also be used in combination (such as in a compositional mixture, or a simultaneous or sequential application) with one or more of the following:

1. 3-(4-chloro-2,6-dimethylphenyl)-4-hydroxy-8-oxa-1-azaspiro[4,5]dec-3-en-2-one;
2. 3-(4'-chloro-2,4-dimethyl[1,1'-biphenyl]-3-yl)-4-hydroxy-8-oxa-1-azaspiro[4,5]dec-3-en-2-one;
3. 4-[[(6-chloro-3-pyridinyl)methyl]methylamino]-2(5H)-furanone;
4. 4-[[(6-chloro-3-pyridinyl)methyl]cyclopropylamino]-2(5H)-furanone;
5. 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
6. 2-cyano-N-ethyl-4-fluoro-3-methoxy-benenesulfonamide;
7. 2-cyano-N-ethyl-3-methoxy-benzenesulfonamide;
8. 2-cyano-3-difluoromethoxy-N-ethyl-4-fluoro-benzenesulfonamide;
9. 2-cyano-3-fluoromethoxy-N-ethyl-benzenesulfonamide;
10. 2-cyano-6-fluoro-3-methoxy-N,N-dimethyl-benzenesulfonamide;
11. 2-cyano-N-ethyl-6-fluoro-3-methoxy-N-methyl-benzenesulfonamide;
12. 2-cyano-3-difluoromethoxy-N,N-dimethylbenzenesulfon-amide;
13. 3-(difluoromethyl)-N-[2-(3,3-dimethylbutyl)phenyl]-1-methyl-1H-pyrazole-4-carboxamide;
14. N-ethyl-2,2-dimethylpropionamide-2-(2,6-dichloro-α,α,α-trifluoro-p-tolyl)hydrazone;
15. N-ethyl-2,2-dichloro-1-methylcyclopropane-carboxamide-2-(2,6-dichloro-α,α,α-trifluoro-p-tolyl)hydrazone nicotine;
16. O-{(E-)-[2-(4-chloro-phenyl)-2-cyano-1-(2-trifluoromethylphenyl)-vinyl]}S-methyl thiocarbonate;
17. (E)-N1-[(2-chloro-1,3-thiazol-5-ylmethyl)]-N2-cyano-N1-methylacetamidine;
18. 1-(6-chloropyridin-3-ylmethyl)-7-methyl-8-nitro-1,2,3,5,6,7-hexahydro-imidazo[1,2-a]pyridin-5-ol;
19. 4-[4-chlorophenyl-(2-butylidine-hydrazono)methyl)]phenyl mesylate; and
20. N-Ethyl-2,2-dichloro-1-methylcyclopropanecarboxamide-2-(2,6-dichloro-alpha,alpha,alpha-trifluoro-p-tolyl)hydrazone.

Molecules of Formula I may also be used in combination (such as in a compositional mixture, or a simultaneous or sequential application) with one or more compounds in the following groups: algicides, antifeedants, avicides, bactericides, bird repellents, chemosterilants, herbicide safeners, insect attractants, insect repellents, mammal repellents, mating disrupters, molluscicides, plant activators, plant growth regulators, rodenticides, and/or virucides (collectively these commonly named groups are defined as the "AI Group"). It should be noted that compounds falling within the AI Group, Insecticide Group, Fungicide Group, Herbicide Group, Acaricide Group, or Nematicide Group might be in more than one group, because of multiple activities the compound has. For more information consult the "COMPENDIUM OF PESTICIDE COMMON NAMES" located at http://www.alanwood.net/pesticides/index.html. Also consult "THE PESTICIDE MANUAL" 14th Edition, edited by C D S Tomlin, copyright 2006 by British Crop Production Council, or its prior or more recent editions.

Synergistic Mixtures and Synergists

Molecules of Formula I may be used with the compounds in the Insecticide Group to form synergistic mixtures where the mode of action of such compounds compared to the mode of action of the molecules of Formula I are the same, similar, or different. Examples of modes of action include, but are not limited to: acetylcholinesterase inhibitor; sodium channel modulator; chitin biosynthesis inhibitor; GABA-gated chloride channel antagonist; GABA and glutamate-gated chloride channel agonist; acetylcholine receptor agonist; MET I inhibitor; Mg-stimulated ATPase inhibitor; nicotinic acetylcholine receptor; Midgut membrane disrupter; oxidative phosphorylation disrupter, and ryanodine receptor (RyRs). Additionally, molecules of Formula I may be used with compounds in the Fungicide Group, Acaricide Group, Herbicide Group, or Nematicide Group to form synergistic mixtures. Furthermore, molecules of Formula I may be used with other active compounds, such as the compounds under the heading "OTHER ACTIVE COMPOUNDS", algicides, avicides, bactericides, molluscicides, rodenticides, virucides, herbicide safeners, adjuvants, and/or surfactants to form synergistic mixtures. Generally, weight ratios of the molecules of Formula I in a synergistic mixture with another compound are from about 10:1 to about 1:10, preferably from about 5:1 to about 1:5, and more preferably from about 3:1, and even more preferably about 1:1. Additionally, the following compounds are known as synergists and may be used with the molecules disclosed in Formula I: piperonyl butoxide, piprotal, propyl isome, sesamex, sesamolin, sulfoxide, and tribufos (collectively these synergists are defined as the "Synergists Group").

Formulations

A pesticide is rarely suitable for application in its pure form. It is usually necessary to add other substances so that the pesticide can be used at the required concentration and in an appropriate form, permitting ease of application, handling, transportation, storage, and maximum pesticide activity. Thus, pesticides are formulated into, for example, baits, concentrated emulsions, dusts, emulsifiable concentrates, fumigants, gels, granules, microencapsulations, seed treatments, suspension concentrates, suspoemulsions, tablets, water soluble liquids, water dispersible granules or dry flowables, wettable powders, and ultra low volume solutions. For further information on formulation types see "Catalogue of Pesticide Formulation Types and International Coding System" Technical Monograph n°2, 5th Edition by CropLife International (2002).

Pesticides are applied most often as aqueous suspensions or emulsions prepared from concentrated formulations of such pesticides. Such water-soluble, water-suspendable, or emulsifiable formulations are either solids, usually known as wettable powders, or water dispersible granules, or liquids usually known as emulsifiable concentrates, or aqueous suspensions. Wettable powders, which may be compacted to form water dispersible granules, comprise an intimate mixture of the pesticide, a carrier, and surfactants. The concentration of the pesticide is usually from about 10% to about 90% by weight. The carrier is usually chosen from among the attapulgite clays, the montmorillonite clays, the diatomaceous earths, or the purified silicates. Effective surfactants, comprising from about 0.5% to about 10% of the wettable powder, are found among sulfonated lignins, condensed naphthalenesulfonates, naphthalenesulfonates, alkylbenzenesulfonates, alkyl sulfates, and non-ionic surfactants such as ethylene oxide adducts of alkyl phenols.

Emulsifiable concentrates of pesticides comprise a convenient concentration of a pesticide, such as from about 50 to about 500 grams per liter of liquid dissolved in a carrier that is either a water miscible solvent or a mixture of water-immiscible organic solvent and emulsifiers. Useful organic solvents include aromatics, especially xylenes and petroleum fractions, especially the high-boiling naphthalenic and olefinic portions of petroleum such as heavy aromatic naphtha. Other organic solvents may also be used, such as the terpenic solvents including rosin derivatives, aliphatic ketones such as cyclohexanone, and complex alcohols such as 2-ethoxyethanol. Suitable emulsifiers for emulsifiable concentrates are chosen from conventional anionic and non-ionic surfactants.

Aqueous suspensions comprise suspensions of water-insoluble pesticides dispersed in an aqueous carrier at a concentration in the range from about 5% to about 50% by weight. Suspensions are prepared by finely grinding the pesticide and vigorously mixing it into a carrier comprised of water and surfactants. Ingredients, such as inorganic salts and synthetic or natural gums may also be added, to increase the density and viscosity of the aqueous carrier. It is often most effective to grind and mix the pesticide at the same time by preparing the aqueous mixture and homogenizing it in an implement such as a sand mill, ball mill, or piston-type homogenizer.

Pesticides may also be applied as granular compositions that are particularly useful for applications to the soil. Granular compositions usually contain from about 0.5% to about 10% by weight of the pesticide, dispersed in a carrier that comprises clay or a similar substance. Such compositions are usually prepared by dissolving the pesticide in a suitable solvent and applying it to a granular carrier which has been pre-formed to the appropriate particle size, in the range of from about 0.5 to about 3 mm. Such compositions may also be formulated by making a dough or paste of the carrier and compound and crushing and drying to obtain the desired granular particle size.

Dusts containing a pesticide are prepared by intimately mixing the pesticide in powdered form with a suitable dusty agricultural carrier, such as kaolin clay, ground volcanic rock, and the like. Dusts can suitably contain from about 1% to about 10% of the pesticide. They can be applied as a seed dressing or as a foliage application with a dust blower machine.

It is equally practical to apply a pesticide in the form of a solution in an appropriate organic solvent, usually petroleum oil, such as the spray oils, which are widely used in agricultural chemistry.

Pesticides can also be applied in the form of an aerosol composition. In such compositions the pesticide is dissolved or dispersed in a carrier, which is a pressure-generating propellant mixture. The aerosol composition is packaged in a container from which the mixture is dispensed through an atomizing valve.

Pesticide baits are formed when the pesticide is mixed with food or an attractant or both. When the pests eat the bait they also consume the pesticide. Baits may take the form of granules, gels, flowable powders, liquids, or solids. They can be used in pest harborages.

Fumigants are pesticides that have a relatively high vapor pressure and hence can exist as a gas in sufficient concentrations to kill pests in soil or enclosed spaces. The toxicity of the fumigant is proportional to its concentration and the exposure time. They are characterized by a good capacity for diffusion and act by penetrating the pest's respiratory system or being absorbed through the pest's cuticle. Fumigants are applied to control stored product pests under gas proof sheets, in gas sealed rooms or buildings or in special chambers.

Pesticides can be microencapsulated by suspending the pesticide particles or droplets in plastic polymers of various types. By altering the chemistry of the polymer or by changing factors in the processing, microcapsules can be formed of various sizes, solubility, wall thicknesses, and degrees of penetrability. These factors govern the speed with which the active ingredient within is released, which in turn, affects the residual performance, speed of action, and odor of the product.

Oil solution concentrates are made by dissolving pesticide in a solvent that will hold the pesticide in solution. Oil solutions of a pesticide usually provide faster knockdown and kill of pests than other formulations due to the solvents themselves having pesticidal action and the dissolution of the waxy covering of the integument increasing the speed of uptake of the pesticide. Other advantages of oil solutions include better storage stability, better penetration of crevices, and better adhesion to greasy surfaces.

Another embodiment is an oil-in-water emulsion, wherein the emulsion comprises oily globules which are each provided with a lamellar liquid crystal coating and are dispersed in an aqueous phase, wherein each oily globule comprises at least one compound which is agriculturally active, and is individually coated with a monolamellar or oligolamellar layer comprising: (1) at least one non-ionic lipophilic surface-active agent, (2) at least one non-ionic hydrophilic surface-active agent and (3) at least one ionic surface-active agent, wherein the globules having a mean particle diameter of less than 800 nanometers. Further information on the embodiment is disclosed in U.S. patent publication 20070027034 published Feb. 1, 2007, having patent application Ser. No. 11/495,228. For ease of use, this embodiment will be referred to as "OIWE".

For further information consult "Insect Pest Management" 2nd Edition by D. Dent, copyright CAB International (2000). Additionally, for more detailed information consult "Handbook of Pest Control—The Behavior, Life History, and Control of Household Pests" by Arnold Mallis, 9th Edition, copyright 2004 by GIE Media Inc.

Other Formulation Components

Generally, when the molecules disclosed in Formula I are used in a formulation, such formulation can also contain other components. These components include, but are not limited to, (this is a non-exhaustive and non-mutually exclusive list) wetters, spreaders, stickers, penetrants, buffers, sequestering agents, drift reduction agents, compatibility agents, antifoam agents, cleaning agents, and emulsifiers. A few components are described forthwith.

A wetting agent is a substance that when added to a liquid increases the spreading or penetration power of the liquid by reducing the interfacial tension between the liquid and the surface on which it is spreading. Wetting agents are used for two main functions in agrochemical formulations: during processing and manufacture to increase the rate of wetting of powders in water to make concentrates for soluble liquids or suspension concentrates; and during mixing of a product with water in a spray tank to reduce the wetting time of wettable powders and to improve the penetration of water into water-dispersible granules. Examples of wetting agents used in wettable powder, suspension concentrate, and water-dispersible granule formulations are: sodium lauryl sulfate; sodium dioctyl sulfosuccinate; alkyl phenol ethoxylates; and aliphatic alcohol ethoxylates.

A dispersing agent is a substance which adsorbs onto the surface of particles and helps to preserve the state of dispersion of the particles and prevents them from reaggregating. Dispersing agents are added to agrochemical formulations to facilitate dispersion and suspension during manufacture, and to ensure the particles redisperse into water in a spray tank. They are widely used in wettable powders, suspension concentrates and water-dispersible granules. Surfactants that are used as dispersing agents have the ability to adsorb strongly onto a particle surface and provide a charged or steric barrier to reaggregation of particles. The most commonly used surfactants are anionic, non-ionic, or mixtures of the two types. For wettable powder formulations, the most common dispersing agents are sodium lignosulfonates. For suspension concentrates, very good adsorption and stabilization are obtained using polyelectrolytes, such as sodium naphthalene sulfonate formaldehyde condensates. Tristyrylphenol ethoxylate phosphate esters are also used. Non-ionics such as alkylarylethylene oxide condensates and EO-PO block copolymers are sometimes combined with anionics as dispersing agents for suspension concentrates. In recent years, new types of very high molecular weight polymeric surfactants have been developed as dispersing agents. These have very long hydrophobic 'backbones' and a large number of ethylene oxide chains forming the 'teeth' of a 'comb' surfactant. These high molecular weight polymers can give very good long-term stability to suspension concentrates because the hydrophobic backbones have many anchoring points onto the particle surfaces. Examples of dispersing agents used in agrochemical formulations are: sodium lignosulfonates; sodium naphthalene sulfonate formaldehyde condensates; tristyrylphenol ethoxylate phosphate esters; aliphatic alcohol ethoxylates; alkyl ethoxylates; EO-PO block copolymers; and graft copolymers.

An emulsifying agent is a substance which stabilizes a suspension of droplets of one liquid phase in another liquid phase. Without the emulsifying agent the two liquids would separate into two immiscible liquid phases. The most commonly used emulsifier blends contain alkylphenol or aliphatic alcohol with twelve or more ethylene oxide units and the oil-soluble calcium salt of dodecylbenzenesulfonic acid. A range of hydrophile-lipophile balance ("HLB") values from 8 to 18 will normally provide good stable emulsions. Emulsion stability can sometimes be improved by the addition of a small amount of an EO-PO block copolymer surfactant.

A solubilizing agent is a surfactant which will form micelles in water at concentrations above the critical micelle concentration. The micelles are then able to dissolve or solubilize water-insoluble materials inside the hydrophobic part of the micelle. The types of surfactants usually used for solubilization are non-ionics, sorbitan monooleates, sorbitan monooleate ethoxylates, and methyl oleate esters.

Surfactants are sometimes used, either alone or with other additives such as mineral or vegetable oils as adjuvants to spray-tank mixes to improve the biological performance of the pesticide on the target. The types of surfactants used for bioenhancement depend generally on the nature and mode of action of the pesticide. However, they are often non-ionics such as: alkyl ethoxylates; linear aliphatic alcohol ethoxylates; aliphatic amine ethoxylates.

A carrier or diluent in an agricultural formulation is a material added to the pesticide to give a product of the required strength. Carriers are usually materials with high absorptive capacities, while diluents are usually materials with low absorptive capacities. Carriers and diluents are used in the formulation of dusts, wettable powders, granules and water-dispersible granules.

Organic solvents are used mainly in the formulation of emulsifiable concentrates, oil-in-water emulsions, suspoemulsions, and ultra low volume formulations, and to a lesser extent, granular formulations. Sometimes mixtures of solvents are used. The first main groups of solvents are aliphatic paraffinic oils such as kerosene or refined paraffins. The second main group (and the most common) comprises the aromatic solvents such as xylene and higher molecular weight fractions of C9 and C10 aromatic solvents. Chlorinated hydrocarbons are useful as cosolvents to prevent crystallization of pesticides when the formulation is emulsified into water. Alcohols are sometimes used as cosolvents to increase solvent power. Other solvents may include vegetable oils, seed oils, and esters of vegetable and seed oils.

Thickeners or gelling agents are used mainly in the formulation of suspension concentrates, emulsions and suspoemulsions to modify the rheology or flow properties of the liquid and to prevent separation and settling of the dispersed particles or droplets. Thickening, gelling, and anti-settling agents generally fall into two categories, namely water-insoluble particulates and water-soluble polymers. It is possible to produce suspension concentrate formulations using clays and silicas. Examples of these types of materials, include, but are not limited to, montmorillonite, bentonite, magnesium aluminum silicate, and attapulgite. Water-soluble polysaccharides have been used as thickening-gelling agents for many years. The types of polysaccharides most commonly used are natural extracts of seeds and seaweeds or are synthetic derivatives of cellulose. Examples of these types of materials include, but are not limited to, guar gum; locust bean gum; carrageenam; alginates; methyl cellulose; sodium carboxymethyl cellulose (SCMC); hydroxyethyl cellulose (HEC). Other types of anti-settling agents are based on modified starches, polyacrylates, polyvinyl alcohol and polyethylene oxide. Another good anti-settling agent is xanthan gum.

Microorganisms can cause spoilage of formulated products. Therefore preservation agents are used to eliminate or reduce their effect. Examples of such agents include, but are not limited to: propionic acid and its sodium salt; sorbic acid and its sodium or potassium salts; benzoic acid and its sodium salt; p-hydroxybenzoic acid sodium salt; methyl p-hydroxybenzoate; and 1,2-benzisothiazolin-3-one (BIT).

The presence of surfactants often causes water-based formulations to foam during mixing operations in production and in application through a spray tank. In order to reduce the tendency to foam, anti-foam agents are often added either during the production stage or before filling into bottles. Generally, there are two types of anti-foam agents, namely silicones and non-silicones. Silicones are usually aqueous emulsions of dimethyl polysiloxane, while the non-silicone anti-foam agents are water-insoluble oils, such as octanol and nonanol, or silica. In both cases, the function of the anti-foam agent is to displace the surfactant from the air-water interface.

"Green" agents (e.g., adjuvants, surfactants, solvents) can reduce the overall environmental footprint of crop protection formulations. Green agents are biodegradable and generally derived from natural and/or sustainable sources, e.g. plant and animal sources. Specific examples are: vegetable oils, seed oils, and esters thereof, also alkoxylated alkyl polyglucosides.

For further information, see "Chemistry and Technology of Agrochemical Formulations" edited by D. A. Knowles, copyright 1998 by Kluwer Academic Publishers. Also see "Insecticides in Agriculture and Environment—Retrospects and Prospects" by A. S. Perry, I. Yamamoto, I. Ishaaya, and R. Perry, copyright 1998 by Springer-Verlag.

Pests

In general, the molecules of Formula I may be used to control pests e.g. beetles, earwigs, cockroaches, flies. aphids, scales, whiteflies, leafhoppers, ants, wasps, termites, moths, butterflies, lice, grasshoppers, locusts, crickets, fleas, thrips, bristletails, mites, ticks, nematodes, and symphylans.

In another embodiment, the molecules of Formula I may be used to control pests in the Phyla Nematoda and/or Arthropoda.

In another embodiment, the molecules of Formula I may be used to control pests in the Subphyla Chelicerata, Myriapoda, and/or Hexapoda.

In another embodiment, the molecules of Formula I may be used to control pests in the Classes of Arachnida, Symphyla, and/or Insecta.

In another embodiment, the molecules of Formula I may be used to control pests of the Order Anoplura. A non-exhaustive list of particular genera includes, but is not limited to, *Haematopinus* spp., *Hoplopleura* spp., *Linognathus* spp., *Pediculus* spp., and *Polyplax* spp. A non-exhaustive list of particular species includes, but is not limited to, *Haematopinus asini, Haematopinus suis, Linognathus setosus, Linognathus ovillus, Pediculus humanus capitis, Pediculus humanus humanus*, and *Pthirus pubis*.

In another embodiment, the molecules of Formula I may be used to control pests in the Order Coleoptera. A non-exhaustive list of particular genera includes, but is not limited to, *Acanthoscelides* spp., *Agriotes* spp., *Anthonomus* spp., *Apion* spp., *Apogonia* spp., *Aulacophora* spp., *Bruchus* spp., *Cerosterna* spp., *Cerotoma* spp., *Ceutorhynchus* spp., *Chaetocnema* spp., *Colaspis* spp., *Ctenicera* spp., *Curculio* spp., *Cyclocephala* spp., *Diabrotica* spp., *Hypera* spp., *Ips* spp., *Lyctus* spp., *Megascelis* spp., *Meligethes* spp., *Otiorhynchus* spp., *Pantomorus* spp., *Phyllophaga* spp., *Phyllotreta* spp., *Rhizotrogus* spp., *Rhynchites* spp., *Rhynchophorus* spp., *Scolytus* spp., *Sphenophorus* spp., *Sitophilus* spp., and *Tribolium* spp. A non-exhaustive list of particular species includes, but is not limited to, *Acanthoscelides obtectus, Agrilus planipennis, Anoplophora glabripennis, Anthonomus grandis, Ataenius spretulus, Atomaria linearis, Bothynoderes punctiventris, Bruchus pisorum, Callosobruchus maculatus, Carpophilus hemipterus, Cassida vittata, Cerotoma trifurcata, Ceutorhynchus assimilis, Ceutorhynchus napi, Conoderus scalaris, Conoderus stigmosus, Conotrachelus nenuphar, Cotinis nitida, Crioceris asparagi, Cryptolestes ferrugineus, Cryptolestes pusillus, Cryptolestes turcicus, Cylindrocopturus adspersus, Deporaus marginatus, Dermestes lardarius, Dermestes maculatus, Epilachna varivestis, Faustinus cubae, Hylobius pales, Hypera postica, Hypothenemus hampei, Lasioderma serricorne, Leptinotarsa decemlineata, Liogenys fuscus, Liogenys suturalis, Lissorhoptrus oryzophilus, Maecolaspis joliveti, Melanotus communis, Meligethes aeneus, Melolontha melolontha, Oberea brevis, Oberea linearis, Oryctes rhinoceros, Oryzaephilus mercator, Oryzaephilus surinamensis, Oulema melanopus, Oulema oryzae, Phyllophaga cuyabana, Popillia japonica, Prostephanus truncatus, Rhyzopertha dominica, Sitona lineatus, Sitophilus granarius, Sitophilus oryzae, Sitophilus zeamais, Stegobium paniceum, Tribolium castaneum, Tribolium confusum, Trogoderma variabile*, and *Zabrus tenebrioides*.

In another embodiment, the molecules of Formula I may be used to control pests of the Order Dermaptera.

In another embodiment, the molecules of Formula I may be used to control pests of the Order Blattaria. A non-exhaustive list of particular species includes, but is not limited to, *Blattella germanica, Blatta orientalis, Parcoblatta pennsylvanica, Periplaneta americana, Periplaneta australasiae, Periplaneta brunnea, Periplaneta fuliginosa, Pycnoscelus surinamensis*, and *Supella longipalpa*.

In another embodiment, the molecules of Formula I may be used to control pests of the Order Diptera. A non-exhaustive list of particular genera includes, but is not limited to, *Aedes* spp., *Agromyza* spp., *Anastrepha* spp., *Anopheles* spp., *Bactrocera* spp., *Ceratitis* spp., *Chrysops* spp., *Cochliomyia* spp., *Contarinia* spp., *Culex* spp., *Dasineura* spp., *Delia* spp., *Drosophila* spp., *Fannia* spp., *Hylemyia* spp., *Liriomyza* spp., *Musca* spp., *Phorbia* spp., *Tabanus* spp., and *Tipula* spp. A non-exhaustive list of particular species includes, but is not limited to, *Agromyza frontella, Anastrepha suspensa, Anastrepha ludens, Anastrepha obliqa, Bactrocera cucurbitae, Bactrocera dorsalis, Bactrocera invadens, Bactrocera zonata, Ceratitis capitata, Dasineura brassicae, Delia platura, Fannia canicularis, Fannia scalaris, Gasterophilus intestinalis, Gracillia perseae, Haematobia irritans, Hypoderma lineatum, Liriomyza brassicae, Melophagus ovinus, Musca autumnalis, Musca domestica, Oestrus ovis, Oscinella frit, Pegomya betae, Psila rosae, Rhagoletis cerasi, Rhagoletis pomonella, Rhagoletis mendax, Sitodiplosis mosellana*, and *Stomoxys calcitrans*.

In another embodiment, the molecules of Formula I may be used to control pests of the Order Hemiptera. A non-exhaustive list of particular genera includes, but is not limited to, *Adelges* spp., *Aulacaspis* spp., *Aphrophora* spp., *Aphis* spp., *Bemisia* spp., *Ceroplastes* spp., *Chionaspis* spp., *Chrysomphalus* spp., *Coccus* spp., *Empoasca* spp., *Lepidosaphes* spp., *Lagynotomus* spp., *Lygus* spp., *Macrosiphum* spp., *Nephotettix* spp., *Nezara* spp., *Philaenus* spp., *Phytocoris* spp., *Piezodorus* spp., *Planococcus* spp., *Pseudococcus* spp., *Rhopalosiphum* spp., *Saissetia* spp., *Therioaphis* spp., *Toumeyella* spp., *Toxoptera* spp., *Trialeurodes* spp., *Triatoma* spp. and *Unaspis* spp. A non-exhaustive list of particular species includes, but is not limited to, *Acrosternum hilare, Acyrthosiphon pisum, Aleyrodes proletella, Aleurodicus dispersus, Aleurothrixus floccosus, Amrasca biguttula biguttula, Aonidiella aurantii, Aphis gossypii, Aphis glycines, Aphis pomi, Aulacorthum solani, Bemisia argentifolii, Bemisia tabaci, Blissus leucopterus, Brachycorynella asparagi, Brevennia rehi, Brevicoryne brassicae, Calocoris norvegicus, Ceroplastes rubens, Cimex hemipterus, Cimex lectularius, Dagbertus fasciatus, Dichelops furcatus, Diuraphis noxia, Diaphorina citri, Dysaphis plantaginea, Dysdercus suturellus, Edessa meditabunda, Eriosoma lanigerum, Eurygaster maura, Euschistus heros, Euschistus servus, Helopeltis antonii, Helopeltis theivora, Icerya purchasi, Idioscopus nitidulus, Laodelphax striatellus, Leptocorisa oratorius, Leptocorisa varicornis, Lygus hesperus, Maconellicoccus hirsutus, Macrosiphum euphorbiae, Macrosiphum granarium, Macrosiphum rosae, Macrosteles quadrilineatus, Mahanarva frimbiolata, Metopolophium dirhodum, Mictis longicornis, Myzus persicae, Nephotettix cinctipes, Neurocolpus longirostris, Nezara viridula, Nilaparvata lugens, Parlatoria pergandii, Parlatoria ziziphi, Peregrinus maidis, Phylloxera vitifoliae, Physokermes piceae, Phytocoris californicus, Phytocoris relativus, Piezodorus guildinii, Poecilocapsus lineatus, Psallus vaccinicola, Pseudacysta perseae, Pseudococcus brevipes, Quadraspidiotus perniciosus, Rhopalosiphum maidis, Rhopalosiphum padi, Saissetia oleae, Scaptocoris castanea, Schizaphis graminum, Sitobion avenae, Sogatella furcifera, Trialeurodes vaporariorum, Trialeurodes abutiloneus, Unaspis yanonensis*, and *Zulia entrerriana*.

In another embodiment, the molecules of Formula I may be used to control pests of the Order Hymenoptera. A non-exhaustive list of particular genera includes, but is not limited to, *Acromyrmex* spp., *Atta* spp., *Camponotus* spp., *Diprion* spp., *Formica* spp., *Monomorium* spp., *Neodiprion* spp., *Pogonomyrmex* spp., *Polistes* spp., *Solenopsis* spp., *Vespula* spp., and *Xylocopa* spp. A non-exhaustive list of particular species includes, but is not limited to, *Athalia rosae, Atta texana, Iridomyrmex humilis, Monomorium minimum, Monomorium pharaonis, Solenopsis invicta, Solenopsis geminata, Solenopsis molesta, Solenopsis richtery, Solenopsis xyloni*, and *Tapinoma sessile*.

In another embodiment, the molecules of Formula I may be used to control pests of the Order Isoptera. A non-exhaustive list of particular genera includes, but is not limited to, *Coptotermes* spp., *Cornitermes* spp., *Cryptotermes* spp., *Heterotermes* spp., *Kalotermes* spp., *Incisbermes* spp., *Macrotermes* spp., *Marginitermes* spp., *Microcerotermes* spp., *Procornitermes* spp., *Reticulitermes* spp., *Schedorhinotermes* spp., and *Zootermopsis* spp. A non-exhaustive list of particular species includes, but is not limited to, *Coptotermes curvignathus, Coptotermes frenchi, Coptotermes formosanus, Heterotermes aureus, Microtermes obesi, Reticulitermes banyulensis, Reticulitermes grassei, Reticulitermes flavipes, Reticulitermes hageni, Reticulitermes hesperus, Reticulitermes santonensis, Reticulitermes speratus, Reticulitermes tibialis*, and *Reticulitermes virginicus*.

In another embodiment, the molecules of Formula I may be used to control pests of the Order Lepidoptera. A non-exhaustive list of particular genera includes, but is not limited to, *Adoxophyes* spp., *Agrotis* spp., *Argyrotaenia* spp., *Cacoecia* spp., *Caloptilia* spp., *Chilo* spp., *Chrysodeixis* spp., *Colias* spp., *Crambus* spp., *Diaphania* spp., *Diatraea* spp., *Earias* spp., *Ephestia* spp., *Epimecis* spp., *Feltia* spp., *Gortyna* spp., *Helicoverpa* spp., *Heliothis* spp., *Indarbela* spp., *Lithocolletis* spp., *Loxagrotis* spp., *Malacosoma* spp., *Peridroma* spp., *Phyllonorycter* spp., *Pseudaletia* spp., *Sesamia* spp., *Spodoptera* spp., *Synanthedon* spp., and *Yponomeuta* spp. A non-exhaustive list of particular species includes, but is not limited to, *Achaea janata, Adoxophyes orana, Agrotis ipsilon, Alabama argillacea, Amorbia cuneana, Amyelois transitella, Anacamptodes defectaria, Anarsia lineatella, Anomis sabulifera, Anticarsia gemmatalis, Archips argyrospila, Archips rosana, Argyrotaenia citrana, Autographa gamma, Bonagota cranaodes, Borbo cinnara, Bucculatrix thurberiella, Capua reticulana, Carposina niponensis, Chlumetia transversa, Choristoneura rosaceana, Cnaphalocrocis medinalis, Conopomorpha cramerella, Cossus cossus, Cydia caryana, Cydia funebrana, Cydia molesta, Cydia nigricana, Cydia pomonella, Darna diducta, Diatraea saccharalis, Diatraea grandiosella, Earias insulana, Earias vittella, Ecdytolopha aurantianum, Elasmopalpus lignosellus, Ephestia cautella, Ephestia elutella, Ephestia kuehniella, Epinotia aporema, Epiphyas postvittana, Erionota thrax, Eupoecilia ambiguella, Euxoa auxiliaris, Grapholita molesta, Hedylepta indicata, Helicoverpa armigera, Helicoverpa zea, Heliothis virescens, Hellula undalis, Keiferia lycopersicella, Leucinodes orbonalis, Leucoptera coffeella, Leucoptera malifoliella, Lobesia botrana, Loxagrotis albicosta, Lymantria dispar, Lyonetia clerkella, Mahasena corbetti, Mamestra brassicae, Maruca testulalis, Metisa plana, Mythimna unipuncta, Neoleucinodes elegantalis, Nymphula depunctalis, Operophtera brumata, Ostrinia nubilalis, Oxydia vesulia, Pandemis cerasana, Pandemis heparana, Papilio demodocus, Pectino-*

*phora gossypiella, Peridroma saucia, Perileucoptera coffeella, Phthorimaea operculella, Phyllocnistis citrella, Pieris rapae, Plathypena scabra, Plodia interpunctella, Plutella xylostella, Polychrosis viteana, Prays endocarpa, Prays oleae, Pseudaletia unipuncta, Pseudoplusia includens, Rachiplusia nu, Scirpophaga incertulas, Sesamia inferens, Sesamia nonagrioides, Setora nitens, Sitotroga cerealella, Sparganothis pilleriana, Spodoptera exigua, Spodoptera frugiperda, Spodoptera eridania, Thecla basilides, Tineola bisselliella, Trichoplusia ni, Tuta absoluta, Zeuzera coffeae,* and *Zeuzera pyrina.*

In another embodiment, the molecules of Formula I may be used to control pests of the Order Mallophaga. A non-exhaustive list of particular genera includes, but is not limited to, *Anaticola* spp., *Bovicola* spp., *Chelopistes* spp., *Goniodes* spp., *Menacanthus* spp., and *Trichodectes* spp. A non-exhaustive list of particular species includes, but is not limited to, *Bovicola bovis, Bovicola caprae, Bovicola ovis, Chelopistes meleagridis, Goniodes dissimilis, Goniodes gigas, Menacanthus stramineus, Menopon gallinae,* and *Trichodectes canis.*

In another embodiment, the molecules of Formula I may be used to control pests of the Order Orthoptera. A non-exhaustive list of particular genera includes, but is not limited to, *Melanoplus* spp., and *Pterophylla* spp. A non-exhaustive list of particular species includes, but is not limited to, *Anabrus simplex, Gryllotalpa africana, Gryllotalpa australis, Gryllotalpa brachyptera, Gryllotalpa hexadactyla, Locusta migratoria, Microcentrum retinerve, Schistocerca gregaria,* and *Scudderia furcata.*

In another embodiment, the molecules of Formula I may be used to control pests of the Order Siphonaptera. A non-exhaustive list of particular species includes, but is not limited to, *Ceratophyllus gallinae, Ceratophyllus niger, Ctenocephalides canis, Ctenocephalides felis,* and *Pulex irritans.*

In another embodiment, the molecules of Formula I may be used to control pests of the Order Thysanoptera. A non-exhaustive list of particular genera includes, but is not limited to, *Caliothrips* spp., *Frankliniella* spp., *Scirtothrips* spp., and *Thrips* spp. A non-exhaustive list of particular sp. includes, but is not limited to, *Frankliniella fusca, Frankliniella occidentalis, Frankliniella schultzei, Frankliniella williamsi, Heliothrips haemorrhoidalis, Rhipiphorothrips cruentatus, Scirtothrips citri, Scirtothrips dorsalis,* and *Taeniothrips rhopalantennalis, Thrips hawaiiensis, Thrips nigropilosus, Thrips orientalis, Thrips tabaci.*

In another embodiment, the molecules of Formula I may be used to control pests of the Order Thysanura. A non-exhaustive list of particular genera includes, but is not limited to, *Lepisma* spp. and *Thermobia* spp.

In another embodiment, the molecules of Formula I may be used to control pests of the Order Acarina. A non-exhaustive list of particular genera includes, but is not limited to, *Acarus* spp., *Aculops* spp., *Boophilus* spp., *Demodex* spp., *Dermacentor* spp., *Epitrimerus* spp., *Eriophyes* spp., *Ixodes* spp., *Oligonychus* spp., *Panonychus* spp., *Rhizoglyphus* spp., and *Tetranychus* spp. A non-exhaustive list of particular species includes, but is not limited to, *Acarapis woodi, Acarus siro, Aceria mangiferae, Aculops lycopersici, Aculus pelekassi, Aculus schlechtendali, Amblyomma americanum, Brevipalpus obovatus, Brevipalpus phoenicis, Dermacentor variabilis, Dermatophagoides pteronyssinus, Eotetranychus carpini, Notoedres cati, Oligonychus coffeae, Oligonychus ilicis, Panonychus citri, Panonychus ulmi, Phyllocoptruta oleivora, Polyphagotarsonemus latus, Rhipicephalus sanguineus, Sarcoptes scabiei, Tegolophus perseaflorae, Tetranychus urticae,* and *Varroa destructor.*

In another embodiment, the molecules of Formula I may be used to control pest of the Order Symphyla. A non-exhaustive list of particular sp. includes, but is not limited to, *Scutigerella immaculata.*

In another embodiment, the molecules of Formula I may be used to control pests of the Phylum Nematoda. A non-exhaustive list of particular genera includes, but is not limited to, *Aphelenchoides* spp., *Belonolaimus* spp., *Criconemella* spp., *Ditylenchus* spp., *Heterodera* spp., *Hirschmanniella* spp., *Hoplolaimus* spp., *Meloidogyne* spp., *Pratylenchus* spp., and *Radopholus* spp. A non-exhaustive list of particular sp. includes, but is not limited to, *Dirofilaria immitis, Heterodera zeae, Meloidogyne incognita, Meloidogyne javanica, Onchocerca volvulus, Radopholus similis,* and *Rotylenchulus reniformis.*

For additional information consult "HANDBOOK OF PEST CONTROL—THE BEHAVIOR, LIFE HISTORY, AND CONTROL OF HOUSEHOLD PESTS" by Arnold Mallis, 9th Edition, copyright 2004 by GIE Media Inc.

Applications

Molecules of Formula I are generally used in amounts from about 0.01 grams per hectare to about 5000 grams per hectare to provide control. Amounts from about 0.1 grams per hectare to about 500 grams per hectare are generally preferred, and amounts from about 1 gram per hectare to about 50 grams per hectare are generally more preferred. The area to which a molecule of Formula I is applied can be any area inhabited (or maybe inhabited, or traversed by) a pest, for example: where crops, trees, fruits, cereals, fodder species, vines, turf and ornamental plants, are growing; where domesticated animals are residing; the interior or exterior surfaces of buildings (such as places where grains are stored), the materials of construction used in building (such as impregnated wood), and the soil around buildings. Particular crop areas to use a molecule of Formula I include areas where apples, corn, sunflowers, cotton, soybeans, canola, wheat, rice, sorghum, barley, oats, potatoes, oranges, alfalfa, lettuce, strawberries, tomatoes, peppers, crucifers, pears, tobacco, almonds, sugar beets, beans and other valuable crops are growing or the seeds thereof are going to be planted. It is also advantageous to use aluminum sulfate with a molecule of Formula I when growing various plants.

Controlling pests generally means that pest populations, pest activity, or both, are reduced in an area. This can come about when: pest populations are repulsed from an area; when pests are incapacitated in or around an area; or pests are exterminated, in whole, or in part, in or around an area. Of course, a combination of these results can occur. Generally, pest populations, activity, or both are desirably reduced more than fifty percent, preferably more than 90 percent. Generally, the area is not in or on a human; consequently, the locus is generally a non-human area.

The molecules of Formula I may be used in mixtures, applied simultaneously or sequentially, alone or with other compounds to enhance plant vigor (e.g. to grow a better root system, to better withstand stressful growing conditions). Such other compounds are, for example, compounds that modulate plant ethylene receptors, most notably 1-methylcyclopropene (also know as 1-MCP).

The molecules of Formula I can be applied to the foliar and fruiting portions of plants to control pests. The molecules will either come in direct contact with the pest, or the pest will consume the pesticide when eating leaf, fruit mass, or extracting sap, that contains the pesticide. The molecules of Formula I can also be applied to the soil, and when applied in this manner, root and stem feeding pests can be controlled. The roots can absorb a molecule taking it up into the foliar portions of the plant to control above ground chewing and sap feeding pests.

Generally, with baits, the baits are placed in the ground where, for example, termites can come into contact with, and/or be attracted to, the bait. Baits can also be applied to a surface of a building, (horizontal, vertical, or slant surface) where, for example, ants, termites, cockroaches, and flies, can come into contact with, and/or be attracted to, the bait. Baits can comprise a molecule of Formula I.

The molecules of Formula I can be encapsulated inside, or placed on the surface of a capsule. The size of the capsules can range from nanometer size (about 100-900 nanometers in diameter) to micrometer size (about 10-900 microns in diameter).

Because of the unique ability of the eggs of some pests to resist certain pesticides, repeated applications of the molecules of Formula I may be desirable to control newly emerged larvae.

Systemic movement of pesticides in plants may be utilized to control pests on one portion of the plant by applying (for example by spraying an area) the molecules of Formula I to a different portion of the plant. For example, control of foliar-feeding insects can be achieved by drip irrigation or furrow application, by treating the soil with for example pre- or post-planting soil drench, or by treating the seeds of a plant before planting.

Seed treatment can be applied to all types of seeds, including those from which plants genetically modified to express specialized traits will germinate. Representative examples include those expressing proteins toxic to invertebrate pests, such as *Bacillus thuringiensis* or other insecticidal toxins, those expressing herbicide resistance, such as "Roundup Ready" seed, or those with "stacked" foreign genes expressing insecticidal toxins, herbicide resistance, nutrition-enhancement, drought resistance, or any other beneficial traits. Furthermore, such seed treatments with the molecules of Formula I may further enhance the ability of a plant to better withstand stressful growing conditions. This results in a healthier, more vigorous plant, which can lead to higher yields at harvest time. Generally, about 1 gram of the molecules of Formula I to about 500 grams per 100,000 seeds is expected to provide good benefits, amounts from about 10 grams to about 100 grams per 100,000 seeds is expected to provide better benefits, and amounts from about 25 grams to about 75 grams per 100,000 seeds is expected to provide even better benefits.

It should be readily apparent that the molecules of Formula I may be used on, in, or around plants genetically modified to express specialized traits, such as *Bacillus thuringiensis* or other insecticidal toxins, or those expressing herbicide resistance, or those with "stacked" foreign genes expressing insecticidal toxins, herbicide resistance, nutrition-enhancement, or any other beneficial traits.

The molecules of Formula I may be used for controlling endoparasites and ectoparasites in the veterinary medicine sector or in the field of non-human animal keeping. The molecules of Formula I are applied, such as by oral administration in the form of, for example, tablets, capsules, drinks, granules, by dermal application in the form of, for example, dipping, spraying, pouring on, spotting on, and dusting, and by parenteral administration in the form of, for example, an injection.

The molecules of Formula I may also be employed advantageously in livestock keeping, for example, horses, cattle, sheep, pigs, chickens, and geese. They may also be employed advantageously in pets such as, horses, dogs, and cats. Particular pests to control would be fleas and ticks that are bothersome to such animals. Suitable formulations are administered orally to the animals with the drinking water or feed. The dosages and formulations that are suitable depend on the species.

The molecules of Formula I may also be employed in therapeutic methods for human health care. Such methods include, but are limited to, oral administration in the form of, for example, tablets, capsules, drinks, granules, and by dermal application.

Before a pesticide can be used or sold commercially, such pesticide undergoes lengthy evaluation processes by various governmental authorities (local, regional, state, national, and international). Voluminous data requirements are specified by regulatory authorities and must be addressed through data generation and submission by the product registrant or by a third party on the product registrant's behalf, often using a computer with a connection to the World Wide Web. These governmental authorities then review such data and if a determination of safety is concluded, provide the potential user or seller with product registration approval. Thereafter, in that locality where the product registration is granted and supported, such user or seller may use or sell such pesticide.

The headings in this document are for convenience only and must not be used to interpret any portion hereof.

TABLE 1

| Compound Number | Appearance | mp (° C.) | IR | MS (ESIMS m/z) | MOLECULAR STRUCTURE |
| --- | --- | --- | --- | --- | --- |
| 22 | pale yellow solid | 162-163 | | 234.0 (M + 1) | 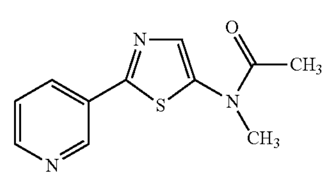 [SMILES: CC(=O)N(C)c1cnc(-c2cccnc2)s1] |

TABLE 1-continued

| Compound Number | Appearance | mp (° C.) | IR | MS (ESIMS m/z) | MOLECULAR STRUCTURE |
|---|---|---|---|---|---|
| 23 | pale yellow solid | 102-105 | | 276.2 (M + 1) | 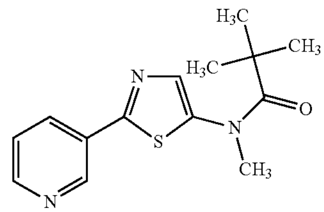 [SMILES: CN(C(=O)C(C)(C)C)c1cnc(-c2cccnc2)s1] |
| 24 | pale yellow solid | 113-114 | | 262.2 (M + 1) | 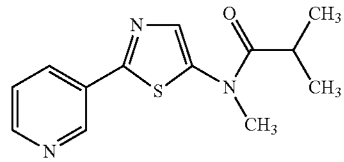 [SMILES: CC(C)C(=O)N(C)c1cnc(-c2cccnc2)s1] |
| 25 | pale yellow solid | 126-128 | | 302.0 (M + 1) | 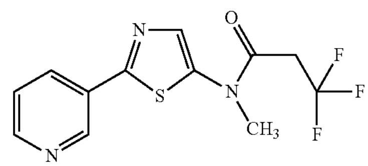 [SMILES: CN(C(=O)CC(F)(F)F)c1cnc(-c2cccnc2)s1] |
| 26 | pale yellow solid | 173-175 | | 297.0 (M + 1) | 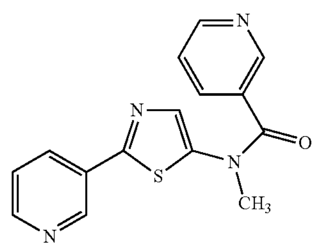 [SMILES: CN(C(=O)c1cccnc1)c1cnc(-c2cccnc2)s1] |
| 27 | pale yellow solid | 127-129 | | 306.2 (M + 1) | 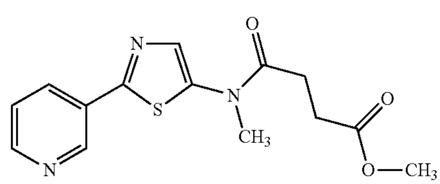 [SMILES: COC(=O)CCC(=O)N(C)c1cnc(-c2cccnc2)s1] |
| 28 | light yellow solid | 98-100 | | 307.9 (M + 1) | 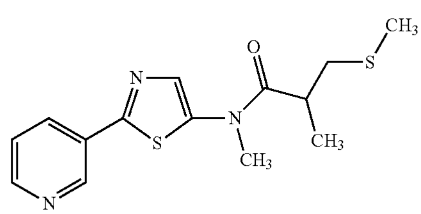 [SMILES: CSCC(C)C(=O)N(C)c1cnc(-c2cccnc2)s1] |
| 29 | white solid | 92-94 | | 322.2 (M + 1) | 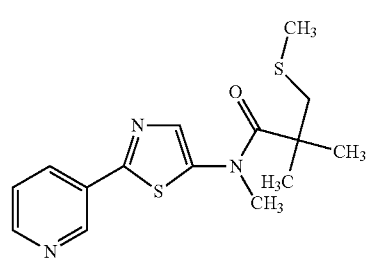 [SMILES: CSCC(C)(C)C(=O)N(C)c1cnc(-c2cccnc2)s1] |

TABLE 1-continued
| Compound Number | Appearance | mp (° C.) | IR | MS (ESIMS m/z) | MOLECULAR STRUCTURE |
|---|---|---|---|---|---|
| 30 | white solid | 111-114 | | 312.1 (M + 1) | 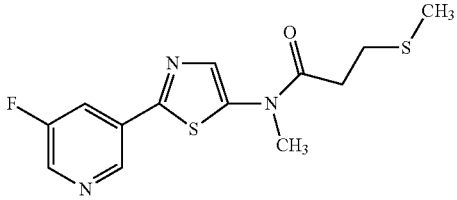 [SMILES: CSCCC(=O)N(C)c1cnc(-c2cncc(F)c2)s1] |
| 31 | orange solid | 75-77 | | 326.1 (M + 1) | 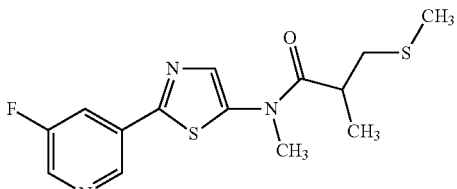 |
| 32 | white solid | 156-158 | | 279.9 (M + 1) | 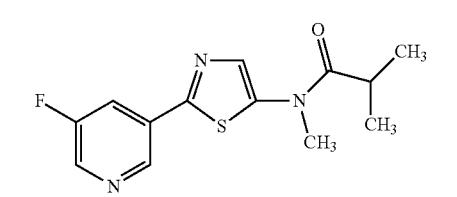 [SMILES: CC(C)C(=O)N(C)c1cnc(-c2cncc(F)c2)s1] |
| 33 | tan solid | 153-155 | | 293.8 (M + 1) | 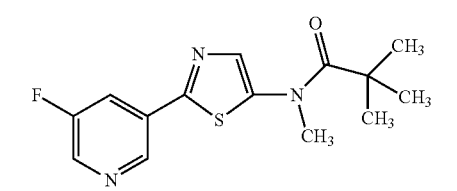 [SMILES: CN(C(=O)C(C)(C)C)c1cnc(-c2cncc(F)c2)s1] |
| 34 | white solid | 83-88 | | 336.2 (M + 1) | 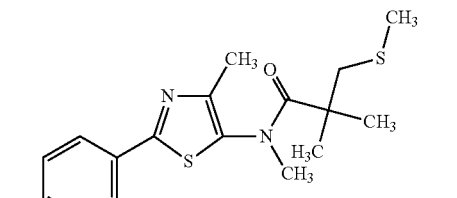 |
| 35 | clear oil | | 2918, 1674, 1553 | 308.2 (M + 1) | 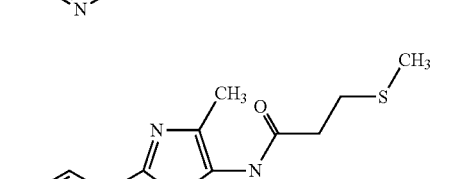 |
| 36 | light yellow oil | | 2973, 2917, 1675, 1554 | 322.2 (M + 1) | 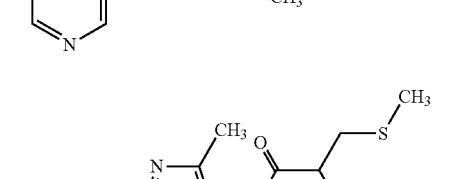 |

TABLE 1-continued

| Compound Number | Appearance | mp (° C.) | IR | MS (ESIMS m/z) | MOLECULAR STRUCTURE |
|---|---|---|---|---|---|
| 37 | clear orange oil | | 2917, 2934, 1676, 1554 | 275.9 (M + 1) | 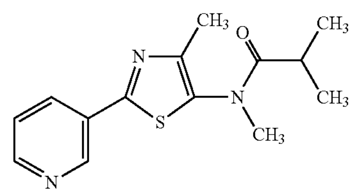 [SMILES: Cc1nc(-c2cccnc2)sc1N(C)C(=O)C(C)C] |
| 38 | colorless oil | | 1679 | 326.2 (M + 1) | 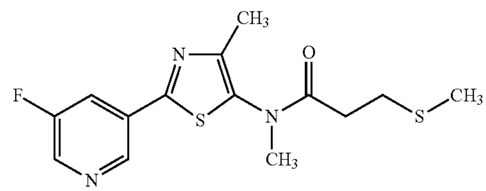 [SMILES: CSCCC(=O)N(C)c1sc(-c2cncc(F)c2)nc1C] |
| 39 | colorless oil | | 1663 | 354.3 (M + 1) | 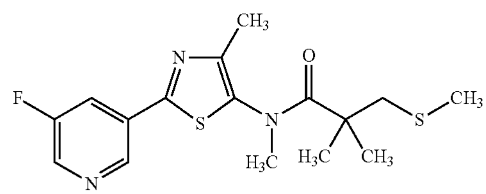 [SMILES: CSCC(C)(C)C(=O)N(C)c1sc(-c2cncc(F)c2)nc1C] |
| 40 | yellow oil | | 1676 | 340.2 (M + 1) | 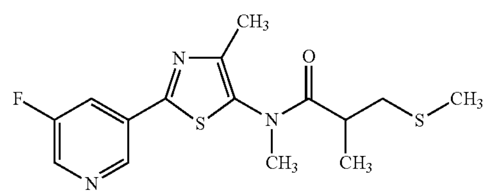 [SMILES: CSCC(C)C(=O)N(C)c1sc(-c2cncc(F)c2)nc1C] |
| 41 | yellow solid | 123 | | 294.2 (M + 1) | 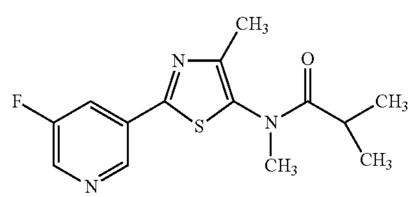 [SMILES: Cc1nc(-c2cncc(F)c2)sc1N(C)C(=O)C(C)C] |
| 42 | yellow oil | | 1697 | 336.2 (M + 1) | 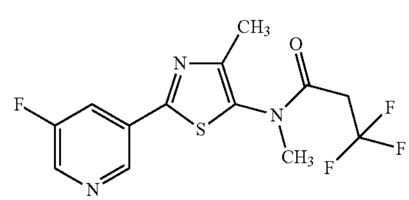 [SMILES: Cc1nc(-c2cncc(F)c2)sc1N(C)C(=O)CC(F)(F)F] |
| 43 | yellow oil | | 1686 | 362 (M + 1) | 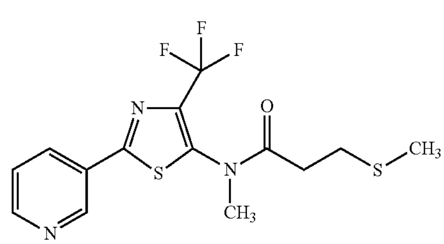 [SMILES: CSCCC(=O)N(C)c1sc(-c2cccnc2)nc1C(F)(F)F] |

TABLE 1-continued

| Compound Number | Appearance | mp (° C.) | IR | MS (ESIMS m/z) | MOLECULAR STRUCTURE |
|---|---|---|---|---|---|
| 44 | yellow oil | | 1688 | 376 (M + 1) | 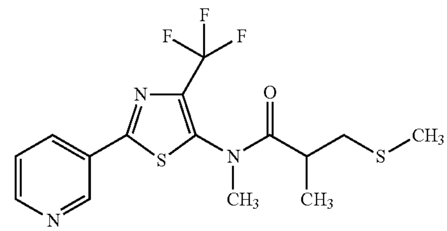 [SMILES: CSCC(C)C(=O)N(C)c1sc(-c2cccnc2)nc1C(F)(F)F] |
| 45 | clear colorless oil | | 1663 | 390.4 (M + 1) | 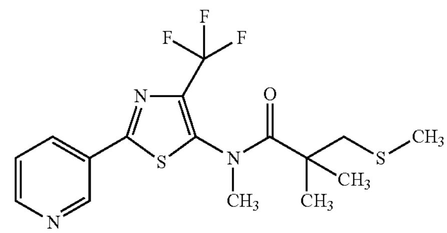 [SMILES: CSCC(C)(C)C(=O)N(C)c1sc(-c2cccnc2)nc1C(F)(F)F] |
| 46 | clear yellow oil | | 1694 | 332.3 (M + 3) | 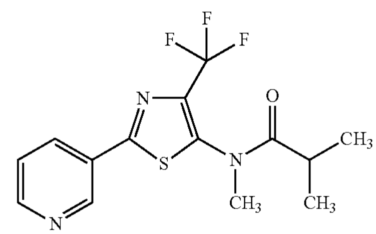 [SMILES: CC(C)C(=O)N(C)c1sc(-c2cccnc2)nc1C(F)(F)F] |
| 47 | yellow gum | | 1678 | 324.4 (M + 3) | 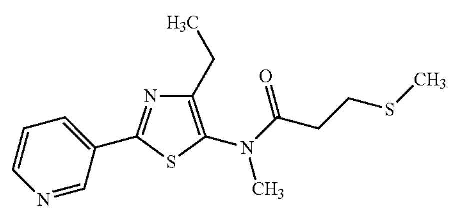 [SMILES: CCc1nc(-c2cccnc2)sc1N(C)C(=O)CCSC] |
| 48 | yellow gum | | | 291.59 (M + 2) | 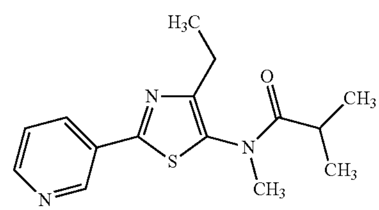 [SMILES: CCc1nc(-c2cccnc2)sc1N(C)C(=O)C(C)C] |
| 49 | yellow gum | | 1656, 1684 | 352.3 (M + 2) | 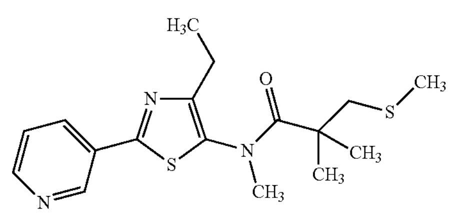 [SMILES: CCc1nc(-c2cccnc2)sc1N(C)C(=O)C(C)(C)CSC] |
| 50 | yellow gum | | 1676 | 336.0 (M + 1) | 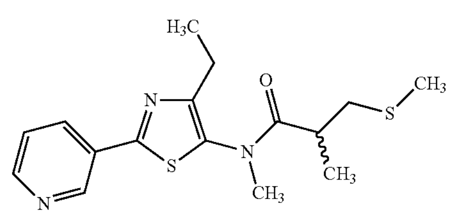 [SMILES: CCc1nc(-c2cccnc2)sc1N(C)C(=O)C(C)CSC] |

TABLE 1-continued

| Compound Number | Appearance | mp (° C.) | IR | MS (ESIMS m/z) | MOLECULAR STRUCTURE |
|---|---|---|---|---|---|
| 51 | yellow oil | | 1679 | 310.5 (M + 2) | 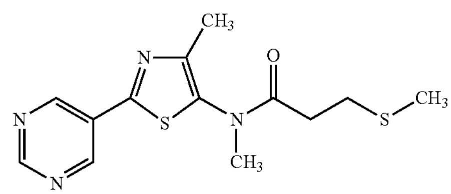 [SMILES: CSCCC(=O)N(C)c1sc(-c2cncnc2)nc1C] |
| 52 | yellow-orange oil | | 1676 | 324.5 (M + 2) | 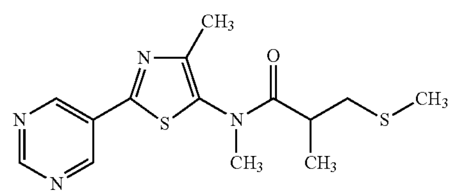 [SMILES: CSCC(C)C(=O)N(C)c1sc(-c2cncnc2)nc1C] |
| 53 | yellow solid | 123-125 | | 338.6 (M + 2) | 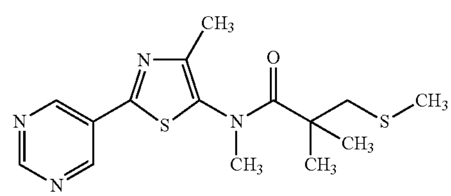 [SMILES: CSCC(C)(C)C(=O)N(C)c1sc(-c2cncnc2)nc1C] |
| 54 | white solid | 108-109 | | 378.5 (M + 2) | 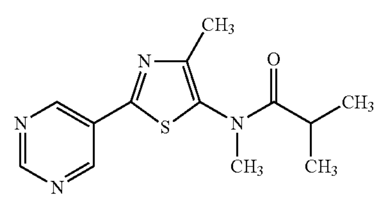 [SMILES: Cc1nc(-c2cncnc2)sc1N(C)C(=O)C(C)C] |
| 55 | yellow solid | 136-139 | 1668, 1573 | 291.9 (M − 1) | 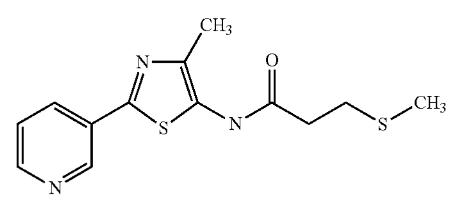 [SMILES: CSCCC(=O)Nc1sc(-c2cccnc2)nc1C] |
| 56 | orange solid | 132-136 | | 308.2 (M + 1) | 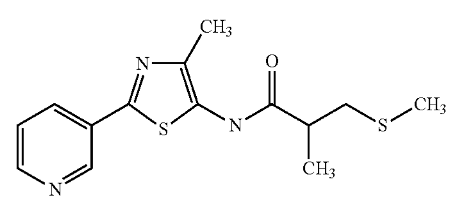 [SMILES: CSCC(C)C(=O)Nc1sc(-c2cccnc2)nc1C] |
| 57 | orange oil | | 1671, 1560 | 322.2 (M + 1) | 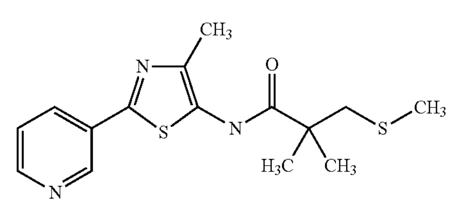 [SMILES: CSCC(C)(C)C(=O)Nc1sc(-c2cccnc2)nc1C] |

TABLE 1-continued
| Compound Number | Appearance | mp (° C.) | IR | MS (ESIMS m/z) | MOLECULAR STRUCTURE |
|---|---|---|---|---|---|
| 58 | yellow solid | 159-162 | | 261.9 (M + 1) | 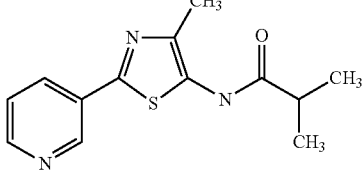 |
| 59 | beige gum | | 1686, 1715 | 338.4 (M + 3) | 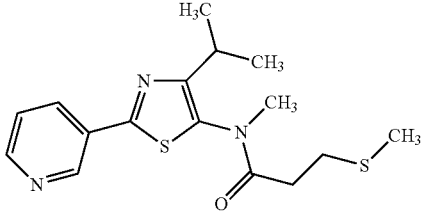 [SMILES: CSCCC(=O)N(C)c1sc(-c2cccnc2)nc1C(C)C] |
| 60 | yellow gum | | 1674 | 350.3 (M + 1) | 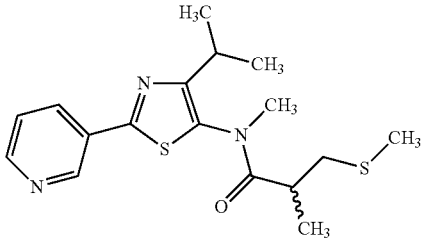 [SMILES: CSCC(C)C(=O)N(C)c1sc(-c2cccnc2)nc1C(C)C] |
| 61 | orange gum | | 1675 | 384.3 (M + 1) | 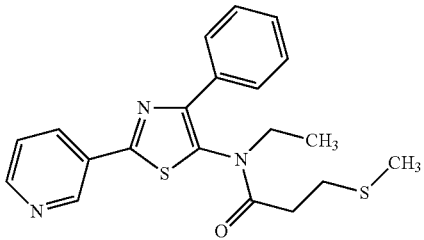 [SMILES: CCN(C(=O)CCSC)c1sc(-c2cccnc2)nc1-c1ccccc1] |
| 62 | brown gum | | 1672 | 397.13 (M+) | 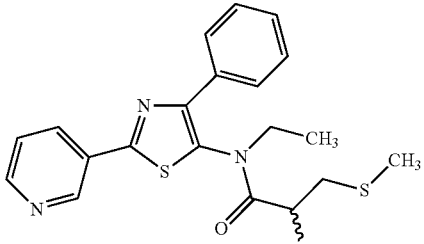 |
| 63 | gold gum | | 1713, 1676 | 353.66 (M + 2) | 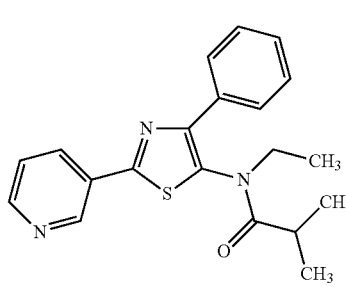 |

TABLE 1-continued

| Compound Number | Appearance | mp (° C.) | IR | MS (ESIMS m/z) | MOLECULAR STRUCTURE |
|---|---|---|---|---|---|
| 64 | yellow solid | 86-88 | 1711 | 265.98 (M − 1) | 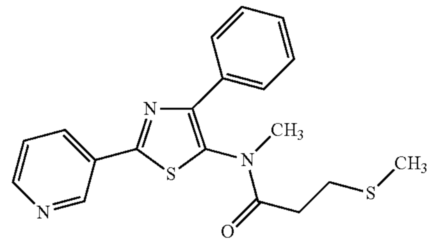 [SMILES: CSCCC(=O)N(C)c1sc(-c2cccnc2)nc1-c1ccccc1] |
| 65 | yellow green gum | | 1677 | 369.1 (M+) | 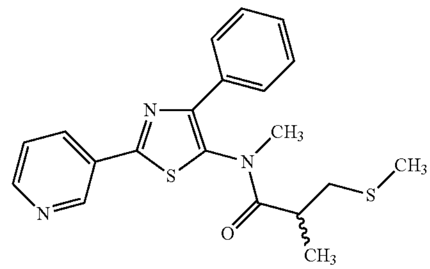 [SMILES: CSCC(C)C(=O)N(C)c1sc(-c2cccnc2)nc1-c1ccccc1] |
| 66 | beige gum | | 1682 | 320.29 (M + 1) | 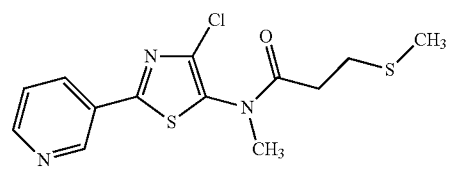 [SMILES: CSCCC(=O)N(C)c1sc(-c2cccnc2)nc1Cl] |
| 67 | brown gum | | 1674 | 383.11 (M+) | 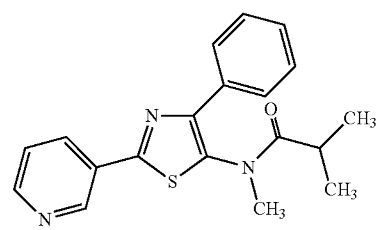 [SMILES: CC(C)C(=O)N(C)c1sc(-c2cccnc2)nc1-c1ccccc1] |
| 68 | light brown solid | 104-108 | 1623 | 356.1 (M + 1) | 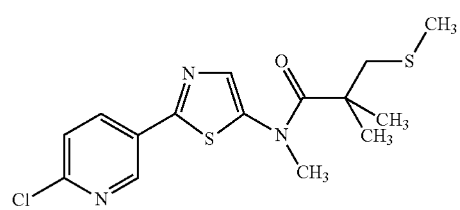 [SMILES: CSCC(C)(C)C(=O)N(C)c1cnc(-c2ccc(Cl)nc2)s1] |
| 69 | light yellow solid | 155-159 | 1643 | 296.1 (M + 1) | 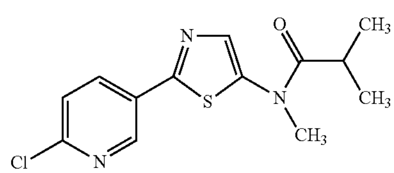 [SMILES: CC(C)C(=O)N(C)c1cnc(-c2ccc(Cl)nc2)s1] |
| 70 | beige solid | 160-164 | | 328.1 (M + 1) | 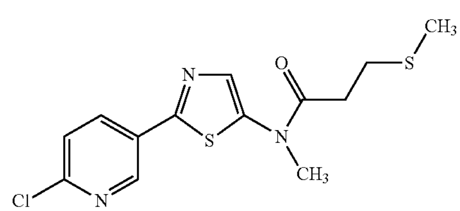 [SMILES: CSCCC(=O)N(C)c1cnc(-c2ccc(Cl)nc2)s1] |

TABLE 1-continued

| Compound Number | Appearance | mp (° C.) | IR | MS (ESIMS m/z) | MOLECULAR STRUCTURE |
|---|---|---|---|---|---|
| 71 | white solid | 182-186 | | 280.1 (M + 1) | 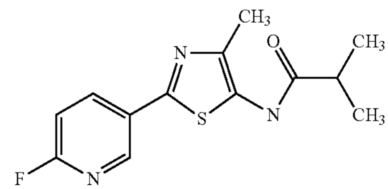 [SMILES: Cc1nc(-c2ccc(F)nc2)sc1NC(=O)C(C)C] |
| 79 | tan solid | 135-140 | | 324.1 (M + 1) | 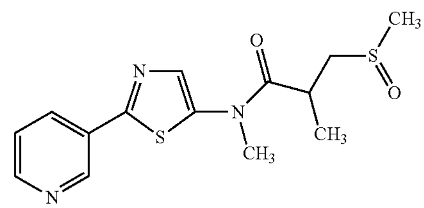 [SMILES: CC(CS(C)=O)C(=O)N(C)c1cnc(-c2cccnc2)s1] |
| 80 | white solid | 118-122 | | 338.1 (M + 1) | 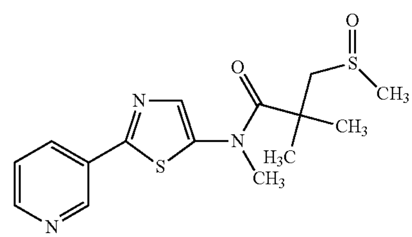 [SMILES: CN(C(=O)C(C)(C)CS(C)=O)c1cnc(-c2cccnc2)s1] |
| 81 | dark green solid | 68-70 | | 342.1 (M + 1) | 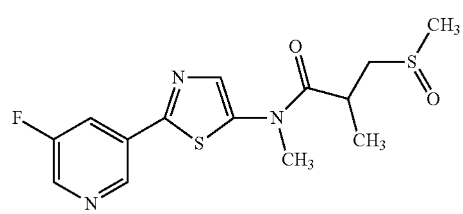 [SMILES: CC(CS(C)=O)C(=O)N(C)c1cnc(-c2cncc(F)c2)s1] |
| 82 | yellow solid | 202-203 | | 343.1 (M + 1) | 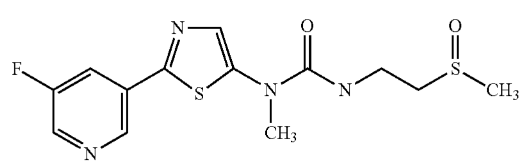 [SMILES: CN(C(=O)NCCS(C)=O)c1cnc(-c2cncc(F)c2)s1] |
| 83 | yellow solid | 95-99 | | 351.1 (M + 1) | 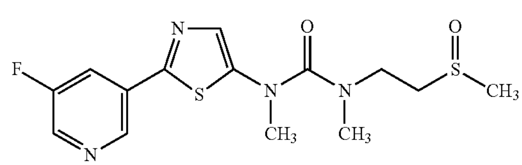 [SMILES: CN(CCS(C)=O)C(=O)N(C)c1cnc(-c2cncc(F)c2)s1] |
| 84 | white solid | 153-155 | | 344.1 (M + 1) | 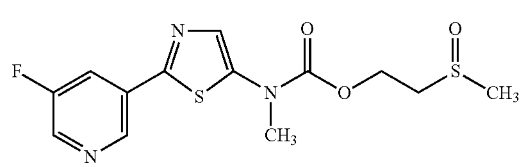 [SMILES: CN(C(=O)OCCS(C)=O)c1cnc(-c2cncc(F)c2)s1] |

| Compound Number | Appearance | mp (° C.) | IR | MS (ESIMS m/z) | MOLECULAR STRUCTURE |
|---|---|---|---|---|---|
| 85 | yellow solid | 155-159 | | 356.2 (M + 1) | 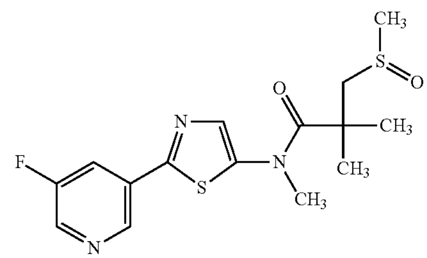 [SMILES: CN(C(=O)C(C)(C)CS(C)=O)c1cnc(-c2cncc(F)c2)s1] |
| 86 | colorless oil | | 1677 | 355.8 (M + 1) | 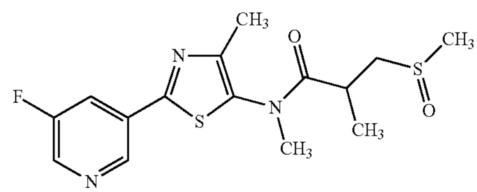 [SMILES: Cc1nc(-c2cncc(F)c2)sc1N(C)C(=O)C(C)CS(C)=O] |
| 87 | yellow oil | | 1674 | 338.2 (M + 1) | 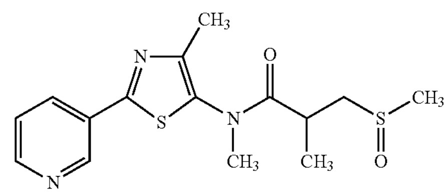 [SMILES: Cc1nc(-c2cccnc2)sc1N(C)C(=O)C(C)CS(C)=O] |
| 88 | yellow oil | | 1684 | 378.2 (M + 1) | 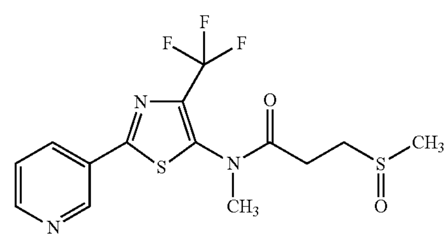 [SMILES: CN(C(=O)CCS(C)=O)c1sc(-c2cccnc2)nc1C(F)(F)F] |
| 89 | yellow oil | | 1682 | 392.3 (M + 1) | 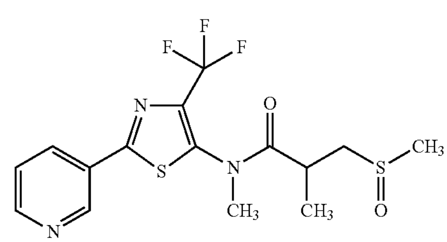 [SMILES: CC(CS(C)=O)C(=O)N(C)c1sc(-c2cccnc2)nc1C(F)(F)F] |
| 90 | white oil | | 1674 | 324.2 (M + 1) | 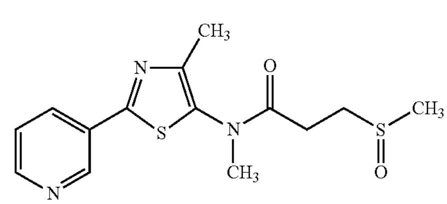 [SMILES: Cc1nc(-c2cccnc2)sc1N(C)C(=O)CCS(C)=O] |
| 91 | yellow syrup | | 1675 | 342.2 (M + 1) | 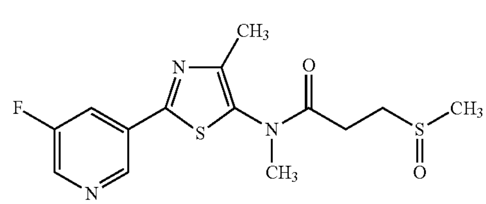 [SMILES: Cc1nc(-c2cncc(F)c2)sc1N(C)C(=O)CCS(C)=O] |

TABLE 1-continued
| Compound Number | Appearance | mp (° C.) | IR | MS (ESIMS m/z) | MOLECULAR STRUCTURE |
|---|---|---|---|---|---|
| 92 | white solid | 160-163 | | 323.9 (M + 1) | 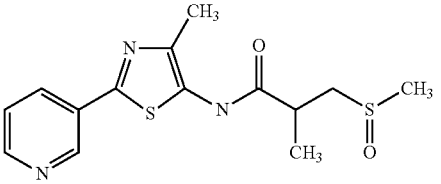 [SMILES: Cc1nc(-c2cccnc2)sc1NC(=O)C(C)CS(C)=O] |
| 93 | yellow solid | 171-173 | | 307.8 (M + 1) | 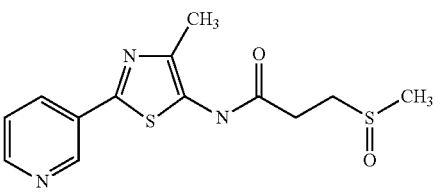 [SMILES: Cc1nc(-c2cccnc2)sc1NC(=O)CCS(C)=O] |
| 94 | yellow foam | 55-60 | | 338.5 (M + 1) | 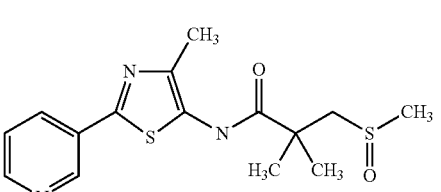 |
| 96 | colorless oil | | 1676 | 360.3 (M + 1) | 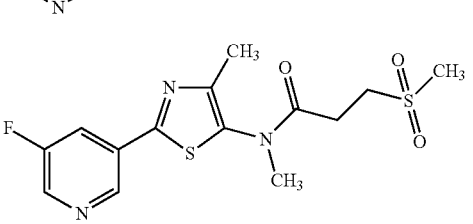 |
| 97 | milky white oil | | 1648 | 368.3 (M + 1) | 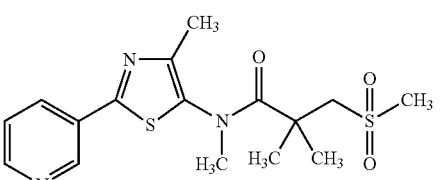 |
| 98 | white solid | 105-109 | | 372.2 (M + 1) | 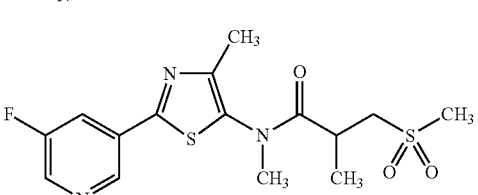 |
| 99 | white solid | 175-180 | | 340.2 (M + 1) | 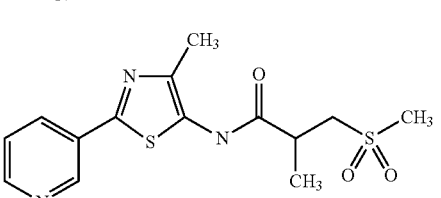 |
| 100 | white solid | 222-224 | | 326.1 (M + 1) | 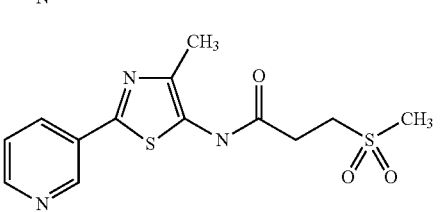 |

TABLE 1-continued

| Compound Number | Appearance | mp (° C.) | IR | MS (ESIMS m/z) | MOLECULAR STRUCTURE |
|---|---|---|---|---|---|
| 101 | yellow solid | 134-136 | | 354.4 (M + 1) | 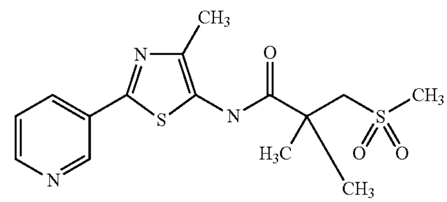 [SMILES: Cc1nc(-c2cccnc2)sc1NC(=O)C(C)(C)CS(C)(=O)=O] |
| 120 | Thick beige gum | | 1720 | 332.0 (M + 3) | 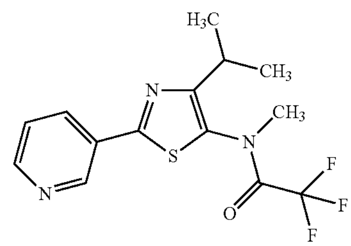 [SMILES: CC(C)c1nc(-c2cccnc2)sc1N(C)C(=O)C(F)(F)F] |
| 133 | white solid | 131-133 | | 346.1 (M − 1) | 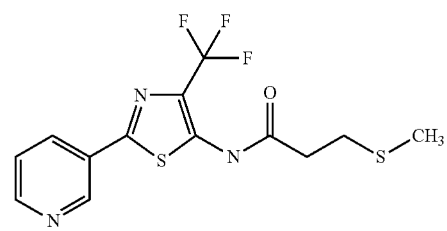 [SMILES: CSCCC(=O)Nc1sc(-c2cccnc2)nc1C(F)(F)F] |
| 134 | orange oil | | 1556 | 360.1 (M − 1) | 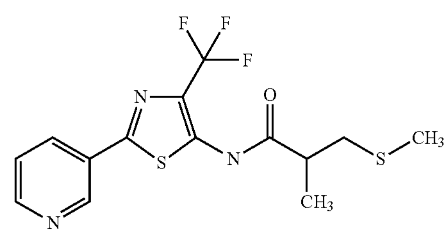 [SMILES: CSCC(C)C(=O)Nc1sc(-c2cccnc2)nc1C(F)(F)F] |
| 135 | orange oil | | 1555 | 374.2 (M − 1) | 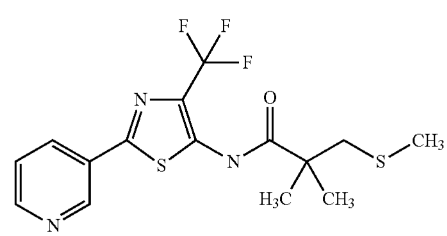 [SMILES: CSCC(C)(C)C(=O)Nc1sc(-c2cccnc2)nc1C(F)(F)F] |
| 136 | white solid | 130-131 | | 314.2 (M − 1) | 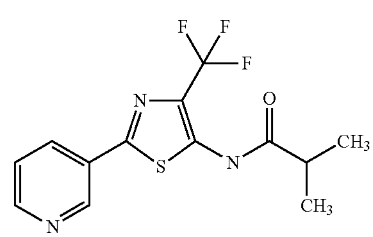 [SMILES: CC(C)C(=O)Nc1sc(-c2cccnc2)nc1C(F)(F)F] |

TABLE 1-continued

| Compound Number | Appearance | mp (° C.) | IR | MS (ESIMS m/z) | MOLECULAR STRUCTURE |
|---|---|---|---|---|---|
| 137 | viscous yellow oil | | 3258, 2971, 2918, 1710 | 338.2 (M + 1) | (5-methoxypyridin-3-yl)-4-methylthiazol-5-yl amide with 2-methyl-3-(methylthio)propanamide |
| 138 | Yellow gum | | 1674 | 349.51 (M + 2) | 2-(pyridin-3-yl)-4-methylthiazol-5-yl, N-methyl amide with 2-methyl-3-(allylthio)propanamide |
| 139 | orange oil | | 1558 | 340.5 (M + 1) | 2-(5-fluoropyridin-3-yl)-4-methylthiazol-5-yl amide with 2,2-dimethyl-3-(methylthio)propanamide |
| 140 | yellow solid | 155-159 | | 280.4 (M + 1) | 2-(5-fluoropyridin-3-yl)-4-methylthiazol-5-yl amide with isobutyramide |
| 141 | orange-yellow solid | 110-113 | | 323.9 (M − 1) | 2-(5-fluoropyridin-3-yl)-4-methylthiazol-5-yl amide with 2-methyl-3-(methylthio)propanamide |
| 142 | white solid | 126-130 | | 309.9 (M − 1) | 2-(5-fluoropyridin-3-yl)-4-methylthiazol-5-yl amide with 3-(methylthio)propanamide |
| 143 | white solid | 160-163 | | 353.9 (M − 1) | 2-(5-fluoropyridin-3-yl)-4-methylthiazol-5-yl amide with 2,2-dimethyl-3-(methylsulfinyl)propanamide |
| 144 | white solid | 157-167 | | 369.9 (M − 1) | 2-(5-fluoropyridin-3-yl)-4-methylthiazol-5-yl amide with 2,2-dimethyl-3-(methylsulfonyl)propanamide |

TABLE 1-continued
| Compound Number | Appearance | mp (° C.) | IR | MS (ESIMS m/z) | MOLECULAR STRUCTURE |
|---|---|---|---|---|---|
| 145 | white solid | 194-198 | | 342.1 (M + 1) | 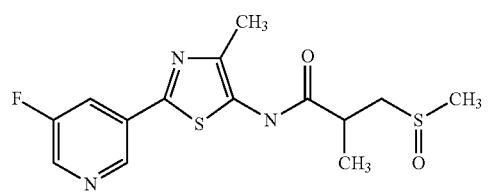 [SMILES: Cc1nc(-c2cncc(F)c2)sc1NC(=O)C(C)CS(C)=O] |
| 146 | white solid | 187-189 | | 358.1 (M + 1) | 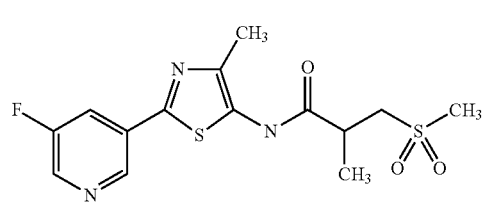 [SMILES: Cc1nc(-c2cncc(F)c2)sc1NC(=O)C(C)CS(C)(=O)=O] |
| 147 | white solid | 181-184 | | 325.9 (M − 1) | 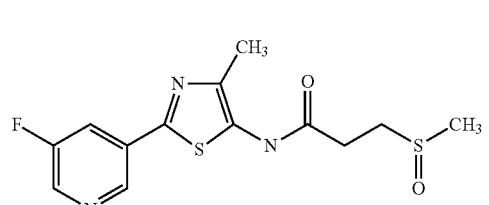 |
| 148 | white solid | 230-232 | | 341.9 (M − 1) | 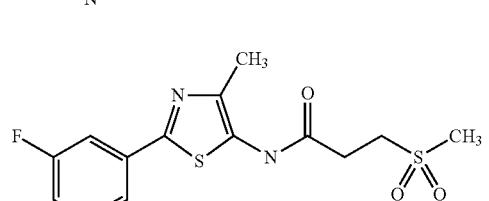 |
| 149 | light yellow solid | 154-157 | | 326.2 (M + 1) | 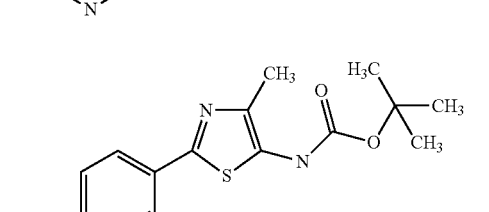 |
| 150 | dark yellow solid | 135-138 | | 304.2 (M − 1) | 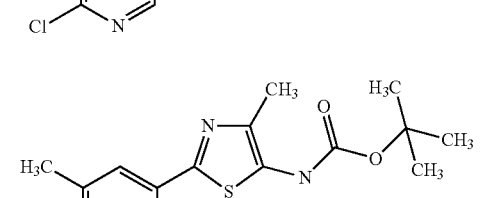 |
| 151 | orange solid | 171-174 | | 317.2 (M + 1) | 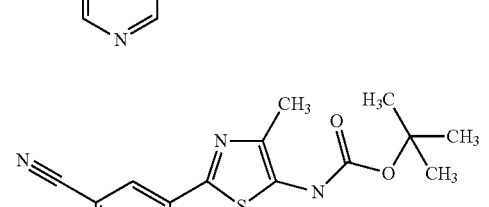 |

TABLE 1-continued

| Compound Number | Appearance | mp (° C.) | IR | MS (ESIMS m/z) | MOLECULAR STRUCTURE |
|---|---|---|---|---|---|
| 152 | yellow gum | | 1713 | 456.1 (M + 1) | 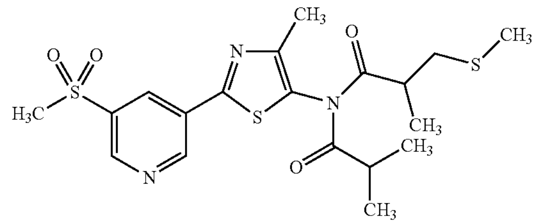 |
| 153 | light yellow solid | 82-85 | | 442.1 (M + 1) | 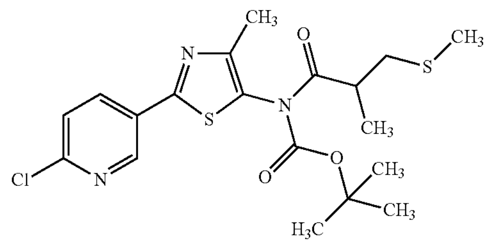 [SMILES: CSCC(C)C(=O)N(C(=O)OC(C)(C)C)c1sc(-c2ccc(Cl)nc2)nc1C] |
| 154 | yellow oil | | 1744, 1714 | 426.2 (M + 1) | 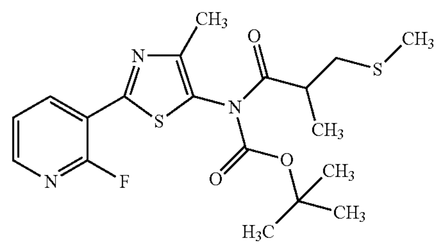 [SMILES: CSCC(C)C(=O)N(C(=O)OC(C)(C)C)c1sc(-c2cccnc2F)nc1C] |
| 155 | yellow oil | | 1743, 1725 | 480.2 (M + 1) | 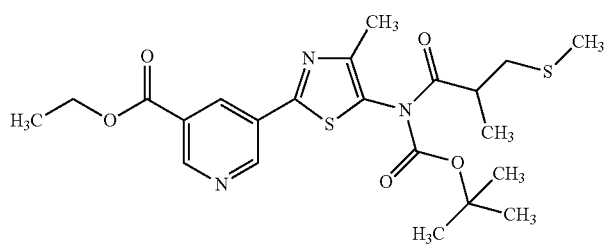 [SMILES: CCOC(=O)c1cncc(-c2nc(C)c(N(C(=O)OC(C)(C)C)C(=O)C(C)CSC)s2)c1] |
| 156 | orange oil | | 1743, 1713 | 422.2 (M + 1) | 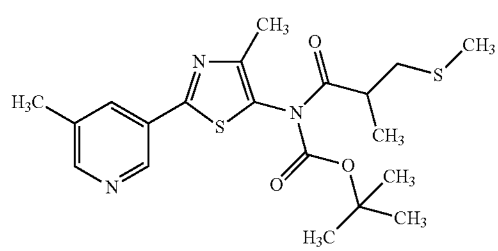 |
| 157 | orange gum | | 1744, 1711 | 486.2 (M + 1) | 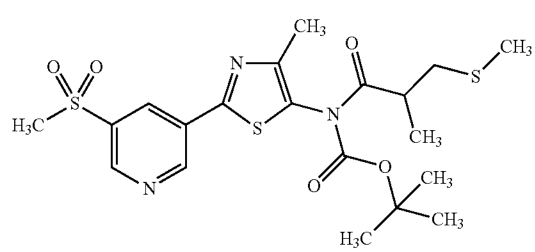 |

TABLE 1-continued

| Compound Number | Appearance | mp (° C.) | IR | MS (ESIMS m/z) | MOLECULAR STRUCTURE |
|---|---|---|---|---|---|
| 158 | white solid | 125-128 | | 433.2 (M + 1) | 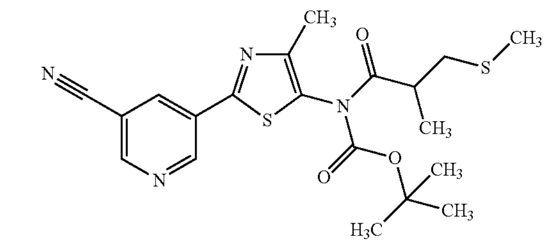 [SMILES: CSCC(C)C(=O)N(C(=O)OC(C)(C)C)c1sc(-c2cncc(C#N)c2)nc1C] |
| 159 | off-white solid | 143-146 | | 325.8 (M + 1) | 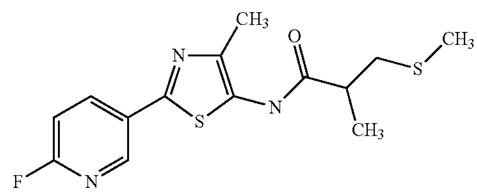 [SMILES: CSCC(C)C(=O)Nc1sc(-c2ccc(F)nc2)nc1C] |
| 160 | orange solid | 124-128 | | 364.5 (M + 1) | 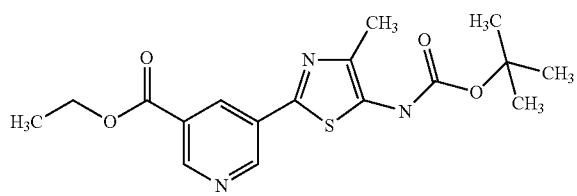 [SMILES: CCOC(=O)c1cncc(-c2nc(C)c(NC(=O)OC(C)(C)C)s2)c1] |
| 161 | white solid | 168-172 | | 387.1 (M + 1) | 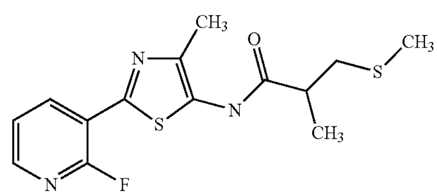 [SMILES: CSCC(C)C(=O)Nc1sc(-c2cccnc2F)nc1C] |
| 162 | light yellow oil | | 1722 | 350.2 (M + 1) | 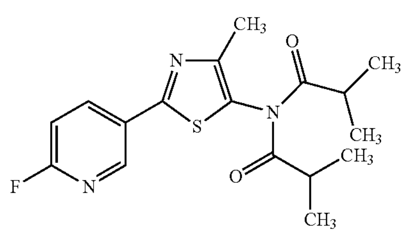 [SMILES: Cc1nc(-c2ccc(F)nc2)sc1N(C(=O)C(C)C)C(=O)C(C)C] |
| 163 | light yellow solid | 75-81 | | 365.93 (M + 1) | 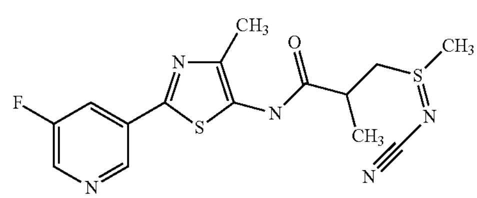 [SMILES: Cc1nc(-c2cncc(F)c2)sc1NC(=O)C(C)C/S(C)=N\C#N] |
| 164 | light yellow solid | | | | 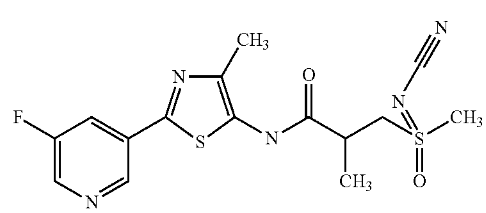 [SMILES: Cc1nc(-c2cncc(F)c2)sc1NC(=O)C(C)CS(C)(=O)=NC#N] |

TABLE 1-continued

| Compound Number | Appearance | mp (°C.) | IR | MS (ESIMS m/z) | MOLECULAR STRUCTURE |
|---|---|---|---|---|---|
| 165 | white semisolid | | 1714.54 | 324.43 (M + 1) | 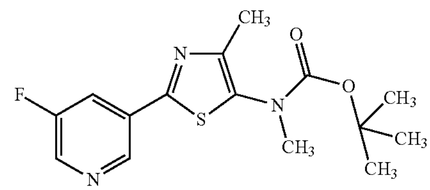 [SMILES: Cc1nc(-c2cncc(F)c2)sc1N(C)C(=O)OC(C)(C)C] |
| 166 | yellow oil | | 1671.41 | 432.5 (M + 1) | 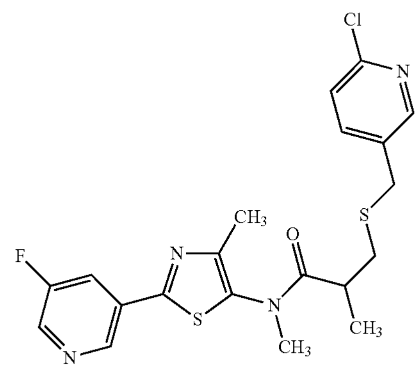 [SMILES: Cc1nc(-c2cncc(F)c2)sc1N(C)C(=O)C(C)CSCc1ccc(Cl)nc1] |
| 167 | clear oil | | | 508.36 (M + 1) | 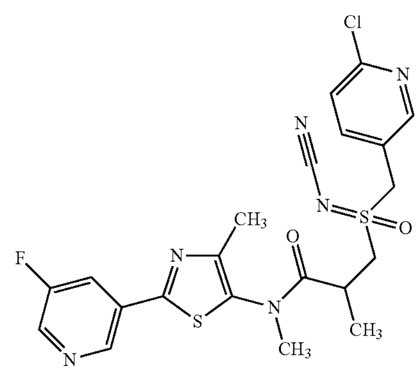 [SMILES: Cc1nc(-c2cncc(F)c2)sc1N(C)C(=O)C(C)CS(=O)(Cc1ccc(Cl)nc1)=NC#N] |
| 168 | clear oil | | | 397.4 (M + 2) | 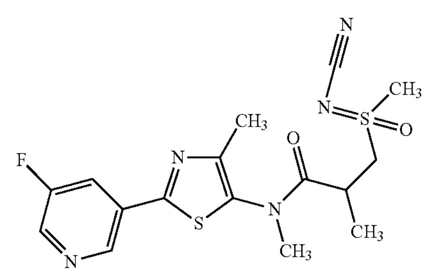 [SMILES: Cc1nc(-c2cncc(F)c2)sc1N(C)C(=O)C(C)CS(C)(=O)=NC#N] |
| 169 | light yellow solid | 142-146 | | 342.1 (M + 1) | 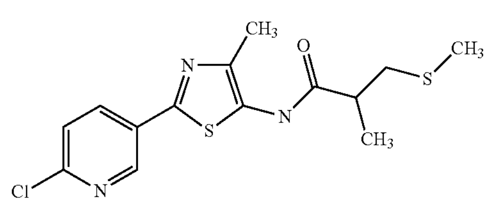 [SMILES: CSCC(C)C(=O)Nc1sc(-c2ccc(Cl)nc2)nc1C] |

TABLE 1-continued

| Compound Number | Appearance | mp (° C.) | IR | MS (ESIMS m/z) | MOLECULAR STRUCTURE |
|---|---|---|---|---|---|
| 170 | dark orange gum | | 3214, 2979, 2919, 1712 | 379.9 (M + 1) | 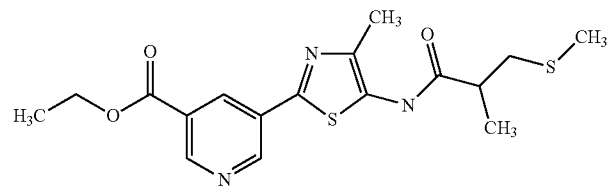 [SMILES: CCOC(=O)c1cncc(-c2nc(C)c(NC(=O)C(C)CSC)s2)c1] |
| 171 | yellow gum | | 2973, 2920 | 322.5 (M + 1) | 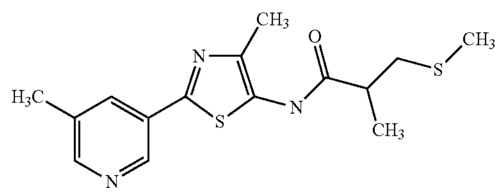 |
| 172 | yellow solid | 127-131 | | 333.1 (M + 1) | 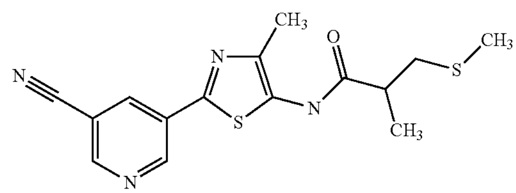 [SMILES: CSCC(C)C(=O)Nc1sc(-c2cncc(C#N)c2)nc1C] |
| 173 | dark orange oil | | 1715 | 424.2 (M + 1) | 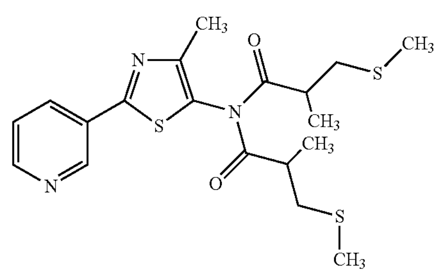 [SMILES: CSCC(C)C(=O)N(C(=O)C(C)CSC)c1sc(-c2cccnc2)nc1C] |
| 174 | Yellow gum | | 1681 | 343.74 (M − 2) | 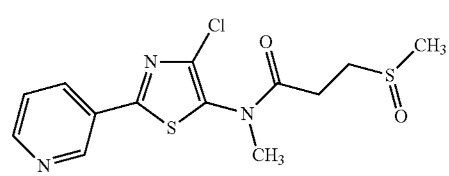 [SMILES: CN(C(=O)CCS(C)=O)c1sc(-c2cccnc2)nc1Cl] |
| 175 | beige solid | 136-140 | | 322.5 (M + 1) | 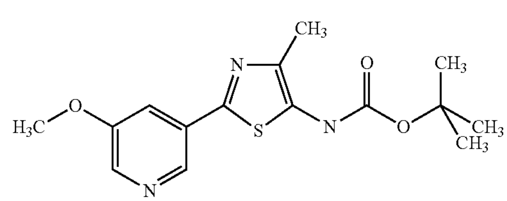 [SMILES: COc1cncc(-c2nc(C)c(NC(=O)OC(C)(C)C)s2)c1] |
| 176 | dark yellow oil | | 1743, 1713 | 438.5 (M + 1) | 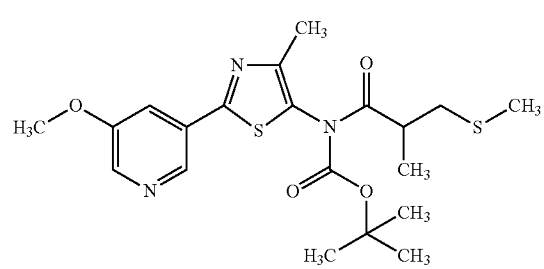 |

TABLE 1-continued

| Compound Number | Appearance | mp (° C.) | IR | MS (ESIMS m/z) | MOLECULAR STRUCTURE |
|---|---|---|---|---|---|
| 177 | yellow solid | 115-119 | | 324.5 (M + 2) | 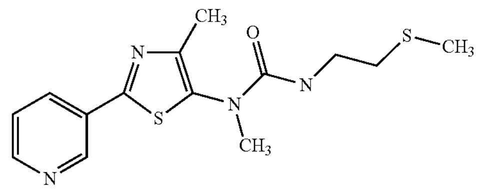 [SMILES: CSCCNC(=O)N(C)c1sc(-c2cccnc2)nc1C] |
| 178 | tan solid | 145-146 | | 324.5 (M + 1) | 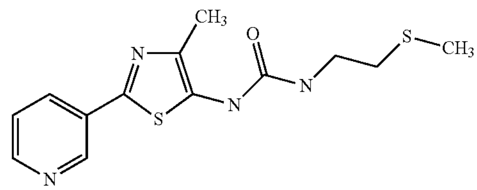 [SMILES: CSCCNC(=O)Nc1sc(-c2cccnc2)nc1C] |
| 179 | yellow oil | | 1648.92 | 309.4 (M + 1) | 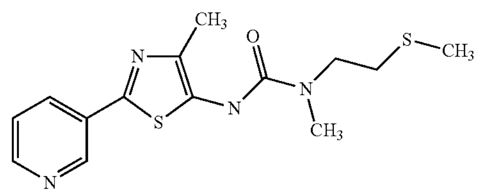 [SMILES: CSCCN(C)C(=O)Nc1sc(-c2cccnc2)nc1C] |
| 180 | yellow semisolid | | 2972, 2918 | 324.12 (M + 1) | 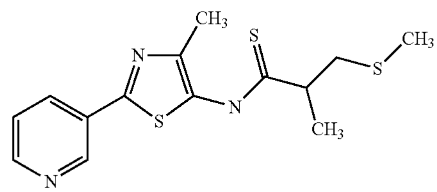 [SMILES: CSCC(C)C(=S)Nc1sc(-c2cccnc2)nc1C] |
| 181 | white solid | 123-126 | | 311.89 (M + 2) | 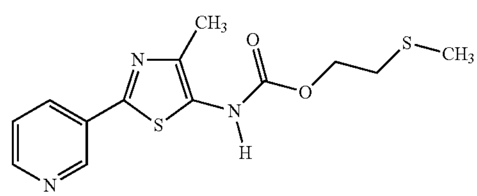 [SMILES: CSCCOC(=O)Nc1sc(-c2cccnc2)nc1C] |
| 182 | light yellow semisolid | | 1711.82 | 437.8 (M + 1) | AND Enantiomer |
| 183 | dark orange oil | | 1720 | 377.9 (M + 1) | 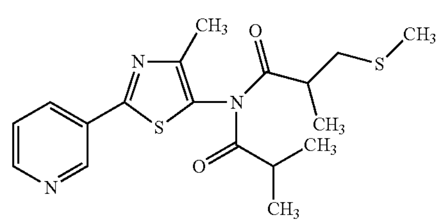 [SMILES: CSCC(C)C(=O)N(C(=O)C(C)C)c1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 184 | orange oil | | 1712 | 350.5 (M + 1) | 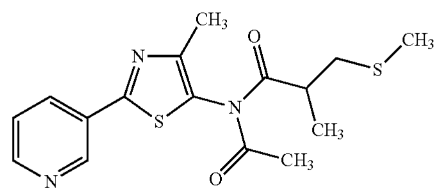 [SMILES: CSCC(C)C(=O)N(C(C)=O)c1sc(-c2cccnc2)nc1C] |
| 185 | yellow oil | | 1721 | 414.1 (M + 1) | 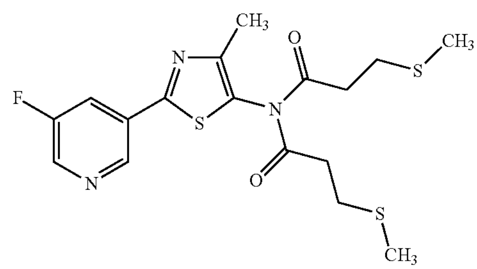 [SMILES: CSCCC(=O)N(C(=O)CCSC)c1sc(-c2cncc(F)c2)nc1C] |
| 186 | light yellow solid | 180-182 | | 235.1 (M + 1) | 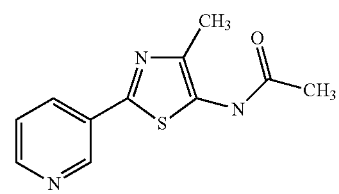 [SMILES: CC(=O)Nc1sc(-c2cccnc2)nc1C] |
| 187 | light yellow solid | 166-169 | | 362.9 (M + 1) | 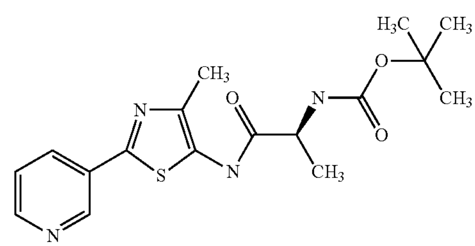 [SMILES: Cc1nc(-c2cccnc2)sc1NC(=O)[C@H](C)NC(=O)OC(C)(C)C] |
| 188 | light yellow oil | | 1713 | 442.1 (M + 1) | 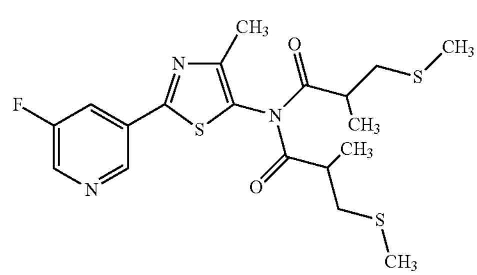 [SMILES: CSCC(C)C(=O)N(C(=O)C(C)CSC)c1sc(-c2cncc(F)c2)nc1C] |
| 189 | orange oil | | 1723 | 423.2 (M + 1) | 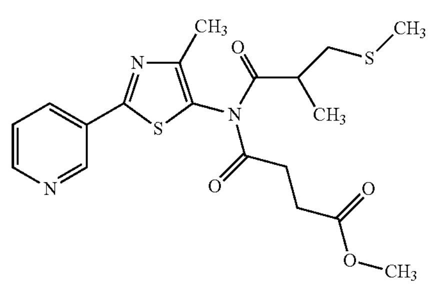 [SMILES: COC(=O)CCC(=O)N(C(=O)C(C)CSC)c1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 190 | yellow oil | | | 451.4 (M + 1) | 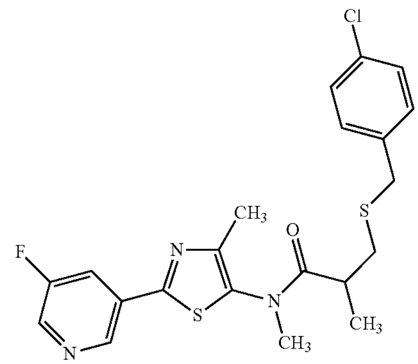 |
| 191 | yellow solid | 140-143 | | 347.9 (M + 1) | 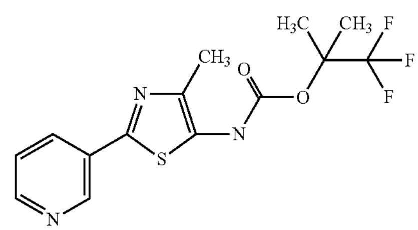 [SMILES: Cc1nc(-c2cccnc2)sc1NC(=O)OC(C)(C)C(F)(F)F] |
| 192 | yellow oil | | 1712.68 | 321.4 (M + 1) | 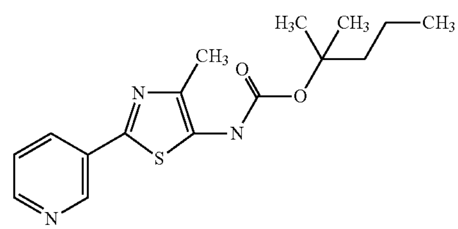 [SMILES: CCCC(C)(C)OC(=O)Nc1sc(-c2cccnc2)nc1C] |
| 193 | yellow solid | 127-130 | | 249.1 (M + 1) | 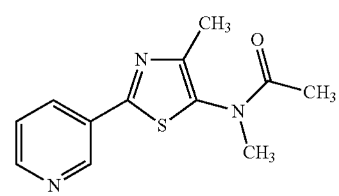 [SMILES: CC(=O)N(C)c1sc(-c2cccnc2)nc1C] |
| 194 | semi-solid orange | | 1708, 1679 | 377.1 (M + 1) | 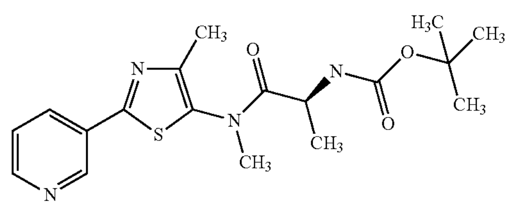 [SMILES: Cc1nc(-c2cccnc2)sc1N(C)C(=O)[C@H](C)NC(=O)OC(C)(C)C] |
| 195 | light orange oil | | 1707 | 439.2 (M + 1) | 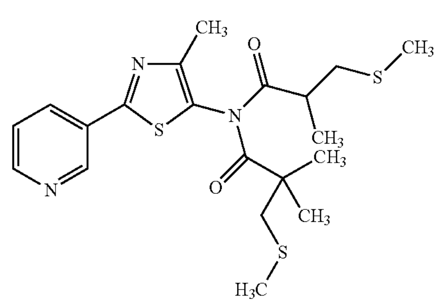 [SMILES: CSCC(C)C(=O)N(C(=O)C(C)(C)CSC)c1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 196 | light orange oil | | 1684 | 351.9 (M + 1) | 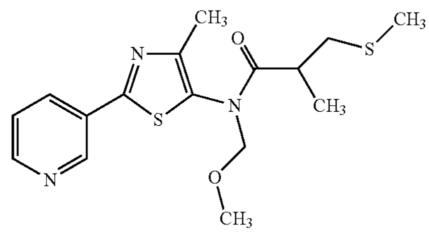 [SMILES: COCN(C(=O)C(C)CSC)c1sc(-c2cccnc2)nc1C] |
| 197 | light yellow solid | 151-153 | | 306.5 (M + 1) | 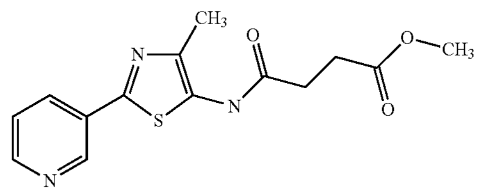 [SMILES: COC(=O)CCC(=O)Nc1sc(-c2cccnc2)nc1C] |
| 198 | yellow oil | | 1711.53 | 331.99 (M + 1) | 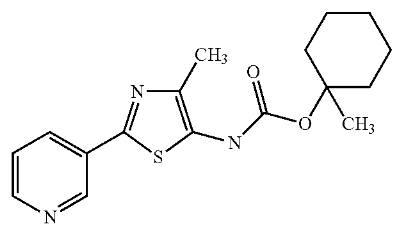 [SMILES: Cc1nc(-c2cccnc2)sc1NC(=O)OC1(C)CCCCC1] |
| 199 | yellow solid | 120-123 | | 322.5 (M + 1) | 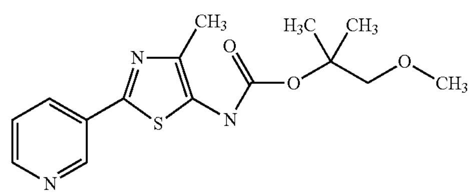 [SMILES: COCC(C)(C)OC(=O)Nc1sc(-c2cccnc2)nc1C] |
| 200 | yellow oil | | 1719 | 396.2 (M + 1) | 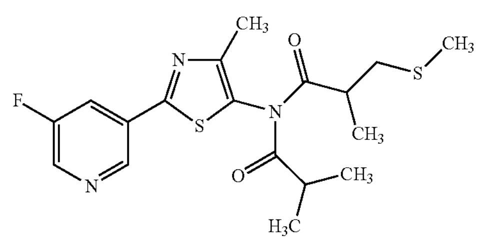 [SMILES: CSCC(C)C(=O)N(C(=O)C(C)C)c1sc(-c2cncc(F)c2)nc1C] |
| 201 | white solid | 137-139 | | 324.1 (M − 1) | 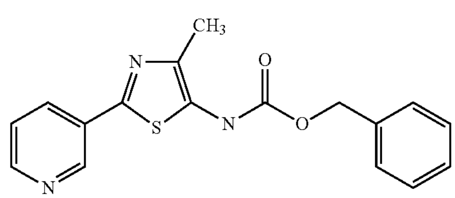 [SMILES: Cc1nc(-c2cccnc2)sc1NC(=O)OCc1ccccc1] |
| 202 | white solid | 159-160 | | 248.1 (M − 1) | 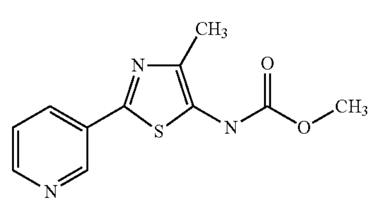 [SMILES: COC(=O)Nc1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 203 | light yellow oil | | 1721, 1694 | 442.1 (M + 1) | 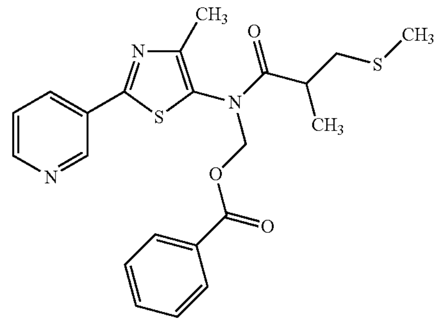 [SMILES: CSCC(C)C(=O)N(COC(=O)c1ccccc1)c1sc(-c2cccnc2)nc1C] |
| 204 | orange oil | | 1710 | 362.0 (M + 1) | 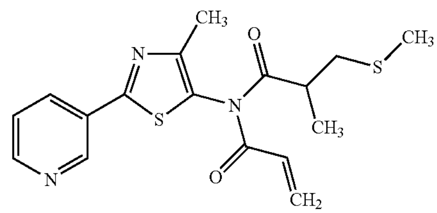 [SMILES: C=CC(=O)N(C(=O)C(C)CSC)c1sc(-c2cccnc2)nc1C] |
| 205 | beige solid | 68-70 | | 346.5 (M + 1) | 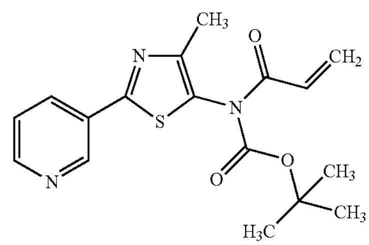 [SMILES: C=CC(=O)N(C(=O)OC(C)(C)C)c1sc(-c2cccnc2)nc1C] |
| 206 | yellow oil | | 1671 | 320.1 (M + 1) | 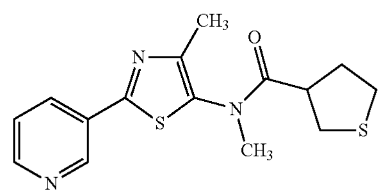 [SMILES: Cc1nc(-c2cccnc2)sc1N(C)C(=O)C1CCSC1] |
| 207 | yellow oil | | 1740, 1694 | 409.2 (M + 1) | 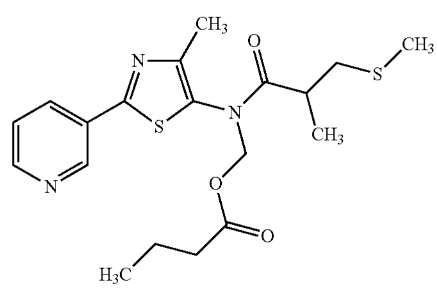 [SMILES: CCCC(=O)OCN(C(=O)C(C)CSC)c1sc(-c2cccnc2)nc1C] |
| 208 | yellow solid | 165-167 | | 247.1 (M + 1) | 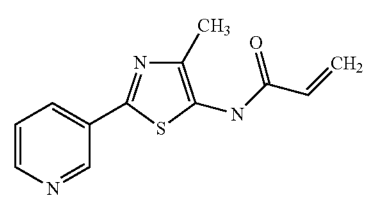 [SMILES: C=CC(=O)Nc1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 209 | yellow solid | 144-147 | | 296.1 (M + 1) | 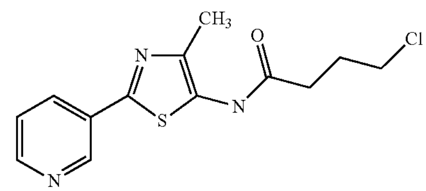 [SMILES: Cc1nc(-c2cccnc2)sc1NC(=O)CCCCl] |
| 210 | yellow oil | | 1671 | 336.2 (M + 1) | 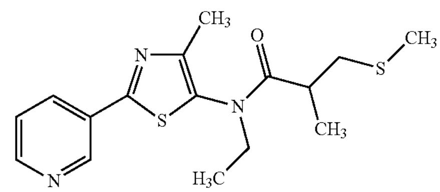 [SMILES: CCN(C(=O)C(C)CSC)c1sc(-c2cccnc2)nc1C] |
| 211 | orange semi-solid | | 1695 | 259.9 (M + 1) | 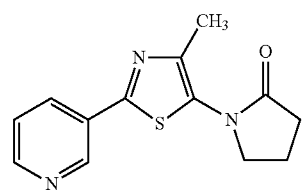 [SMILES: Cc1nc(-c2cccnc2)sc1N1CCCC1=O] |
| 212 | white solid | 73-80 | | 354.2 (M + 1) | 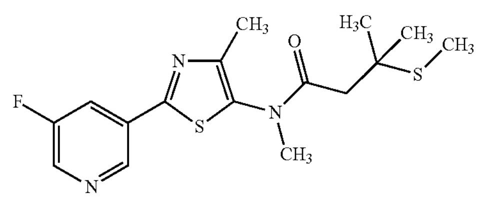 |
| 213 | yellow oil | | 1670.97 | 340.2 (M + 1) | 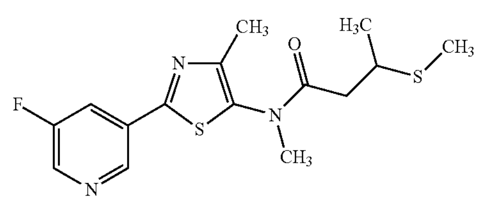 [SMILES: CSC(C)CC(=O)N(C)c1sc(-c2cncc(F)c2)nc1C] |
| 214 | yellow semi solid | | 1661.6 | 338.1 | 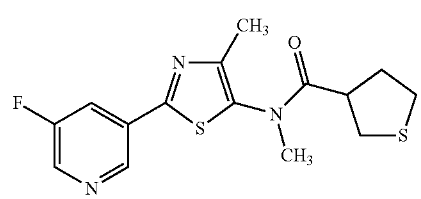 [SMILES: Cc1nc(-c2cncc(F)c2)sc1N(C)C(=O)C1CCSC1] |
| 215 | yellow oil | | 1673.26 | 354.2 (M + 1) | 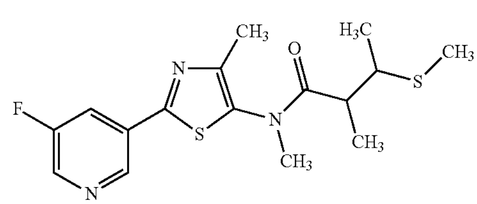 |

TABLE 1-continued

| Compound Number | Appearance | mp (° C.) | IR | MS (ESIMS m/z) | MOLECULAR STRUCTURE |
|---|---|---|---|---|---|
| 216 | white solid | 88-90 | | 338.1 (M + 1) | 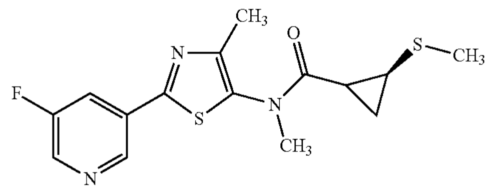 [SMILES: CS[C@H]1CC1C(=O)N(C)c1sc(-c2cncc(F)c2)nc1C] |
| 217 | off white solid | 123-126 | | 340.2 (M + 1) | 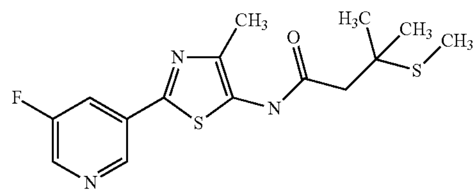 [SMILES: CSC(C)(C)CC(=O)Nc1sc(-c2cncc(F)c2)nc1C] |
| 218 | off white solid | 130-133 | | 326.1 (M + 1) | 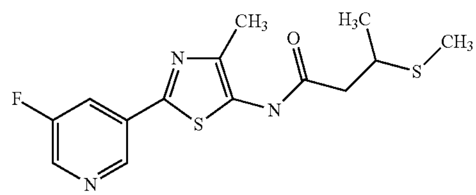 [SMILES: CSC(C)CC(=O)Nc1sc(-c2cncc(F)c2)nc1C] |
| 219 | yellow solid | 209-213 | | 324.1 (M + 1) | 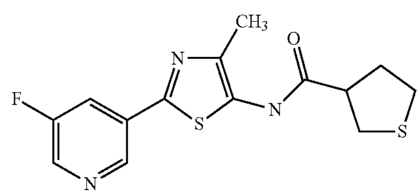 [SMILES: Cc1nc(-c2cncc(F)c2)sc1NC(=O)C1CCSC1] |
| 220 | dark yellow solid | 206-212 | | 324.1 (M + 1) | 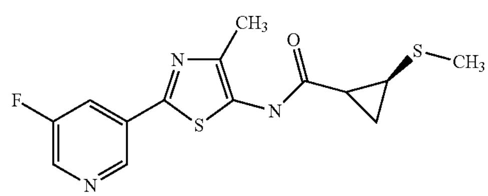 [SMILES: CS[C@H]1CC1C(=O)Nc1sc(-c2cncc(F)c2)nc1C] |
| 221 | yellow oil | | 1671 | 398.2 (M + 1) | 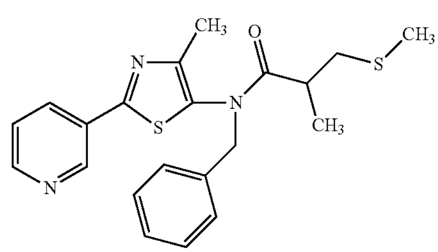 [SMILES: CSCC(C)C(=O)N(Cc1ccccc1)c1sc(-c2cccnc2)nc1C] |
| 222 | yellow oil | | 1699 | 350.2 (M + 1) | 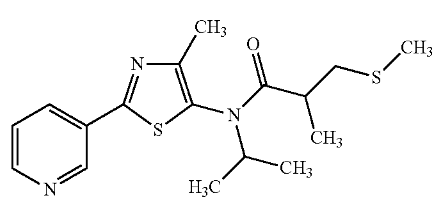 [SMILES: CSCC(C)C(=O)N(c1sc(-c2cccnc2)nc1C)C(C)C] |

TABLE 1-continued

| Compound Number | Appearance | mp (° C.) | IR | MS (ESIMS m/z) | MOLECULAR STRUCTURE |
|---|---|---|---|---|---|
| 223 | thick yellow gum | | 1672 | 364.2 (M + 1) | 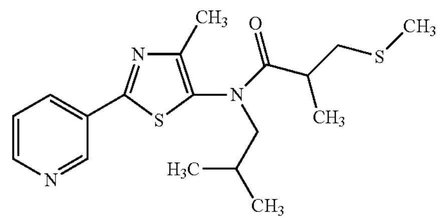 [SMILES: CSCC(C)C(=O)N(CC(C)C)c1sc(-c2cccnc2)nc1C] |
| 224 | yellow oil | | 3039, 2975, 2938, 1635 | 334.1 (M + 1) | 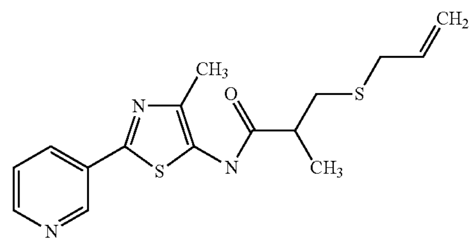 [SMILES: C=CCSCC(C)C(=O)Nc1sc(-c2cccnc2)nc1C] |
| 225 | pale yellow solid | 147-149 | | 349.9 (M + 1) | 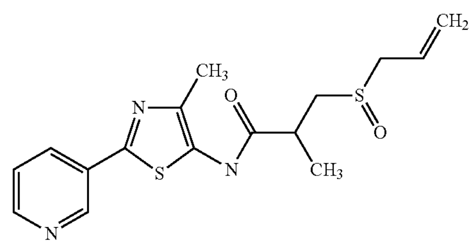 [SMILES: C=CCS(=O)CC(C)C(=O)Nc1sc(-c2cccnc2)nc1C] |
| 226 | orange solid | 76-79 | | 352.2 (M + 1) | 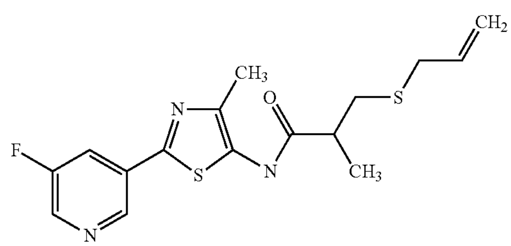 [SMILES: C=CCSCC(C)C(=O)Nc1sc(-c2cncc(F)c2)nc1C] |
| 227 | yellow oil | | 1681 | 342.2 (M + 1) | 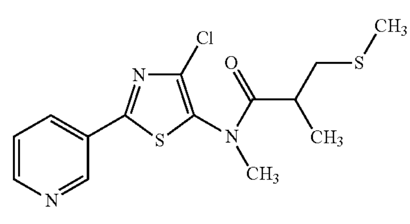 [SMILES: CSCC(C)C(=O)N(C)c1sc(-c2cccnc2)nc1Cl] |
| 228 | yellow solid | 119-122 | | 326.2 (M + 1) | 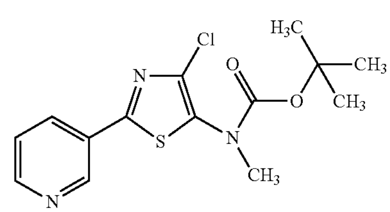 [SMILES: CN(C(=O)OC(C)(C)C)c1sc(-c2cccnc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 229 | yellow solid | 170-174 | | 368.2 (M + 1) | 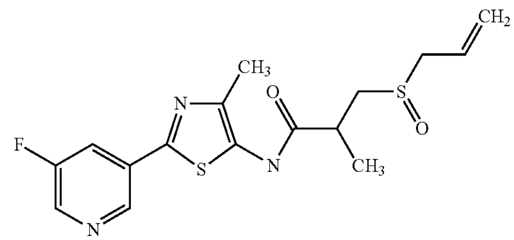 [SMILES: C=CCS(=O)CC(C)C(=O)Nc1sc(-c2cncc(F)c2)nc1C] |
| 230 | clear gum | | 1678 | 358.2 (M + 1) | 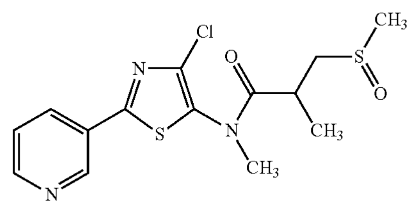 [SMILES: CC(CS(C)=O)C(=O)N(C)c1sc(-c2cccnc2)nc1Cl] |
| 231 | clear oil | | 1686 | 296.2 (M + 1) | 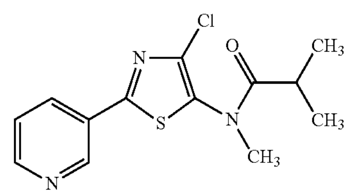 [SMILES: CC(C)C(=O)N(C)c1sc(-c2cccnc2)nc1Cl] |
| 232 | pale yellow oil | | 1746, 1679 | 334.3 (M + 1) | 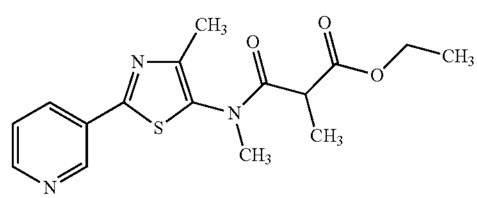 [SMILES: CCOC(=O)C(C)C(=O)N(C)c1sc(-c2cccnc2)nc1C] |
| 233 | pale yellow oil | | 1676 | 290.2 (M + 1) | 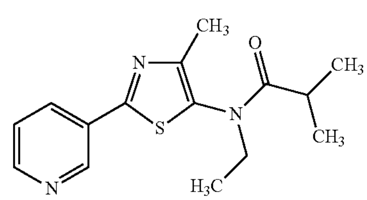 |
| 234 | clear oil | | 1660 | 352.2 (M + 1) | 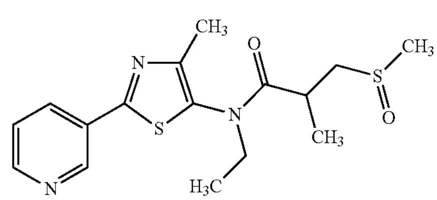 |
| 235 | pale yellow oil | | 1668 | 368.3 (M + 1) | 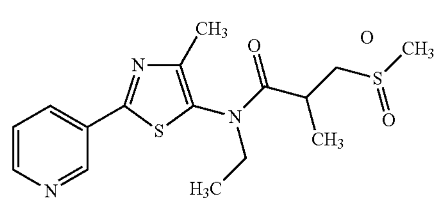 [SMILES: CCN(C(=O)C(C)CS(C)=O)c1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 236 | pale yellow oil | | 1675 | 322.2 (M + 1) | 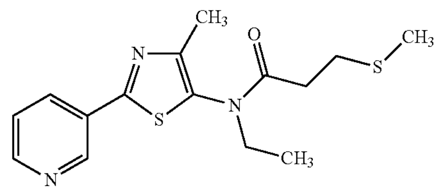 [SMILES: CCN(C(=O)CCSC)c1sc(-c2cccnc2)nc1C] |
| 237 | dark red oil | | 1650 | 350.3 (M + 1) | 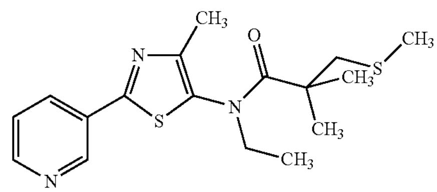 [SMILES: CCN(C(=O)C(C)(C)CSC)c1sc(-c2cccnc2)nc1C] |
| 238 | white solid | 89-92 | 1672 | 338.3 (M + 1) | 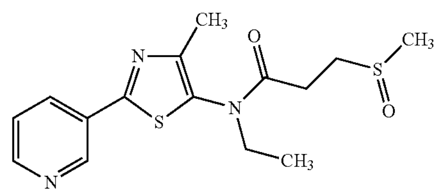 [SMILES: CCN(C(=O)CCS(C)=O)c1sc(-c2cccnc2)nc1C] |
| 239 | clear oil | | 1674 | 354.2 (M + 1) | 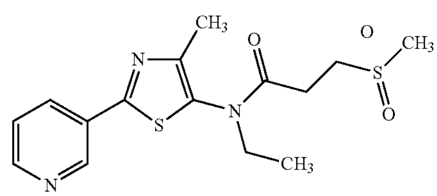 |
| 240 | dark red oil | | 1675 | 354.3 (M + 1) | 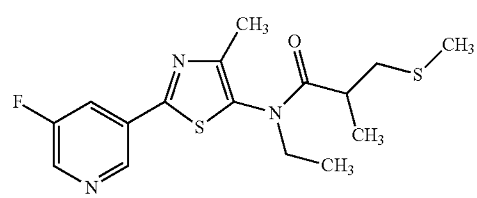 [SMILES: CCN(C(=O)C(C)CSC)c1sc(-c2cncc(F)c2)nc1C] |
| 241 | tan solid | 104-107 | | 326.1 (M + 1) | 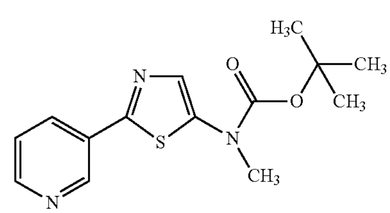 [SMILES: CN(C(=O)OC(C)(C)C)c1cnc(-c2cccnc2)s1] |
| 242 | white solid | 88-91 | | 372.1 (M + 2) | 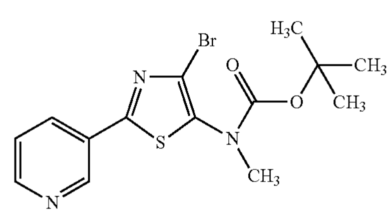 |

TABLE 1-continued

| Compound Number | Appearance | mp (° C.) | IR | MS (ESIMS m/z) | MOLECULAR STRUCTURE |
|---|---|---|---|---|---|
| 243 | yellow solid | 148-151 | 1682 | 310.2 (M + 1) | 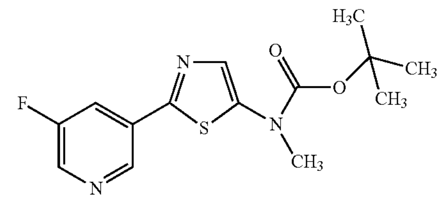 [SMILES: CN(C(=O)OC(C)(C)C)c1cnc(-c2cncc(F)c2)s1] |
| 244 | beige solid | 124-126 | | 397.9 (M + 1) | 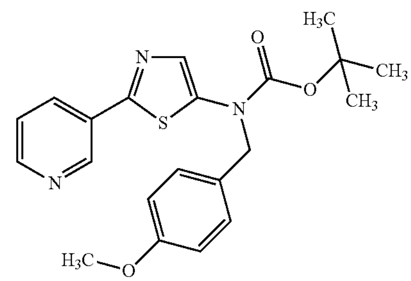 [SMILES: COc1ccc(CN(C(=O)OC(C)(C)C)c2cnc(-c3cccnc3)s2)cc1] |
| 245 | light pink solid | 89-92 | | 323.8 (M + 1) | 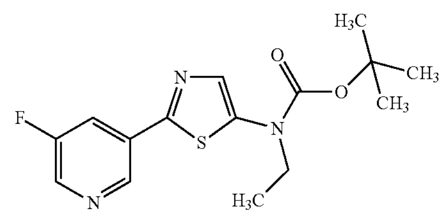 [SMILES: CCN(C(=O)OC(C)(C)C)c1cnc(-c2cncc(F)c2)s1] |
| 246 | clear viscous oil | | 1684 | 362.5 (M + 1) | 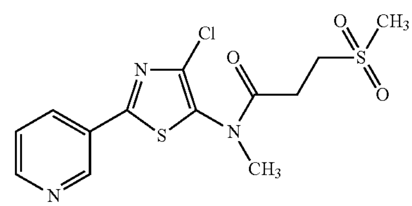 [SMILES: CN(C(=O)CCS(C)(=O)=O)c1sc(-c2cccnc2)nc1Cl] |
| 247 | light yellow oil | | 1680 | 377.3 (M + 1) | 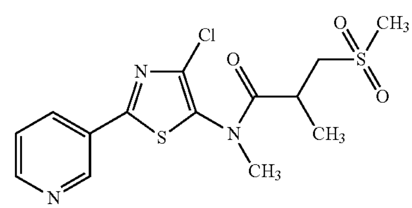 [SMILES: CC(CS(C)(=O)=O)C(=O)N(C)c1sc(-c2cccnc2)nc1Cl] |
| 248 | dark oil | | 1684.18 | 342.1 (M + 1) | 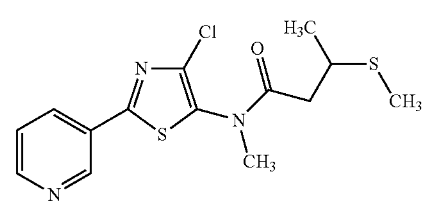 [SMILES: CSC(C)CC(=O)N(C)c1sc(-c2cccnc2)nc1Cl] |
| 249 | clear oil | | 1641 | 387.9 (M + 1) | 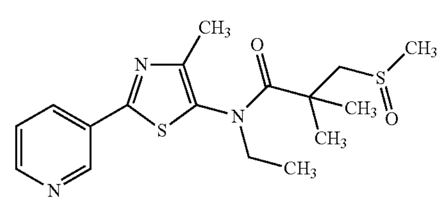 [SMILES: CCN(C(=O)C(C)(C)CS(C)=O)c1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 250 | clear oil | | 1646 | 382.9 (M + 1) | 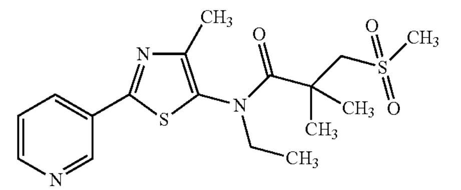 [SMILES: CCN(C(=O)C(C)(C)CS(C)(=O)=O)c1sc(-c2cccnc2)nc1C] |
| 251 | white solid | 74-76 | | 386.2 (M + 2) | 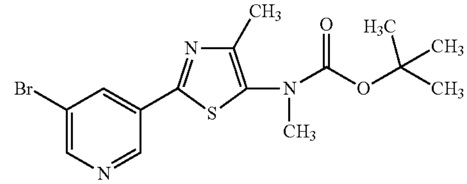 [SMILES: Cc1nc(-c2cncc(Br)c2)sc1N(C)C(=O)OC(C)(C)C] |
| 252 | clear oil | | 1715 | 320.3 (M + 1) | 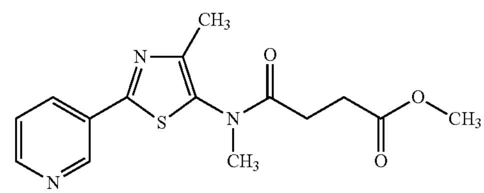 [SMILES: COC(=O)CCC(=O)N(C)c1sc(-c2cccnc2)nc1C] |
| 253 | orange solid | | 1678 | 308.6 (M + 1) | 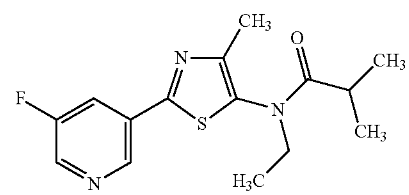 [SMILES: CCN(C(=O)C(C)C)c1sc(-c2cncc(F)c2)nc1C] |
| 254 | light red oil | | 1675 | 341.6 (M + 1) | 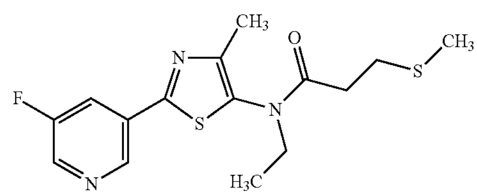 [SMILES: CCN(C(=O)CCSC)c1sc(-c2cncc(F)c2)nc1C] |
| 255 | red oil | | 1653 | 368.6 (M + 1) | 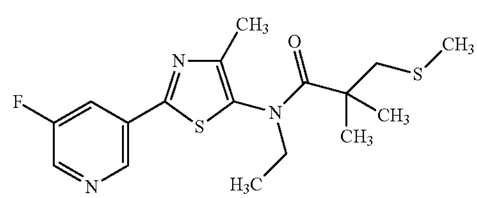 [SMILES: CCN(C(=O)C(C)(C)CSC)c1sc(-c2cncc(F)c2)nc1C] |
| 256 | pale yellow oil | | 1673 | 356.2 (M + 1) | 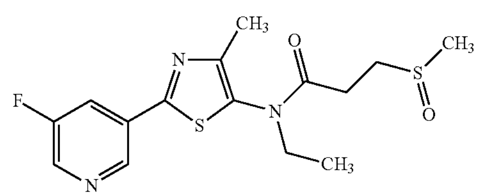 [SMILES: CCN(C(=O)CCS(C)=O)c1sc(-c2cncc(F)c2)nc1C] |
| 257 | pale yellow oil | | 1675 | 372.2 (M + 1) | 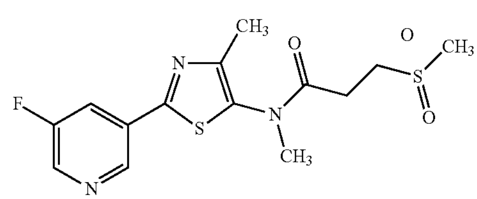 |

TABLE 1-continued
| Compound Number | Appearance | mp (° C.) | IR | MS (ESIMS m/z) | MOLECULAR STRUCTURE |
|---|---|---|---|---|---|
| 258 | yellow oil | | 1670 | 370.2 (M + 1) | 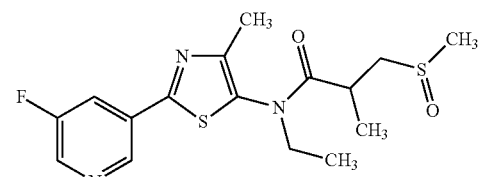 |
| 259 | clear solid | 148.7-156.9 | 1676 | 386.2 (M + 1) | 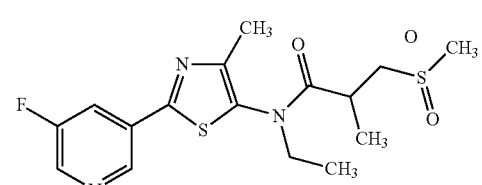 |
| 260 | light yellow oil | | 1645 | 384.2 (M + 1) | 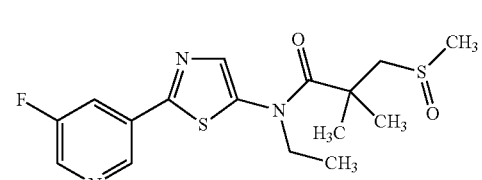 |
| 261 | clear oil | | 1648 | 400.2 (M + 1) | 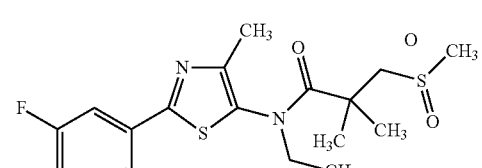 |
| 262 | yellow oil | | 1684 | 360.2 (M + 1) | 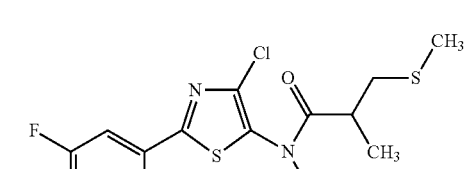 |
| 263 | light yellow solid | 123-125 | | 314.2 (M + 1) | 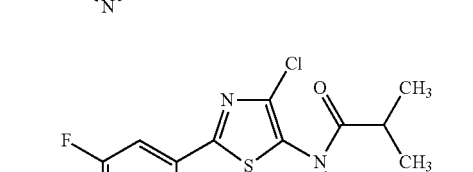 |
| 264 | light yellow solid | 103-106 | | 356.2 (M + 1) | 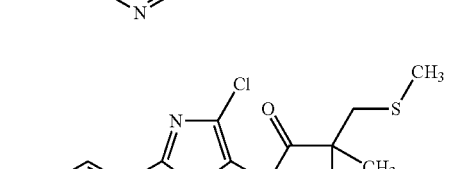 |

TABLE 1-continued

| Compound Number | Appearance | mp (° C.) | IR | MS (ESIMS m/z) | MOLECULAR STRUCTURE |
|---|---|---|---|---|---|
| 265 | pink solid | 98-99 | | 398.3 (M + 1) | 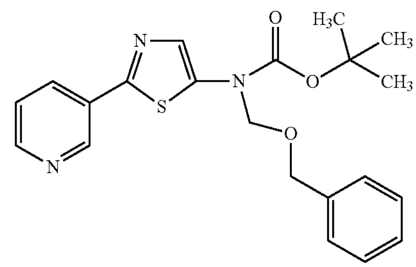 [SMILES: CC(C)(C)OC(=O)N(COCc1ccccc1)c1cnc(-c2cccnc2)s1] |
| 266 | yellow oil | | 1698 | 346.2 (M + 1) | 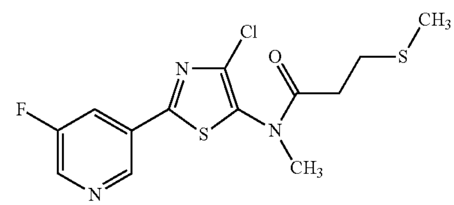 [SMILES: CSCCC(=O)N(C)c1sc(-c2cncc(F)c2)nc1Cl] |
| 267 | dark red oil | | 1718 | 358.2 (M + 1) | 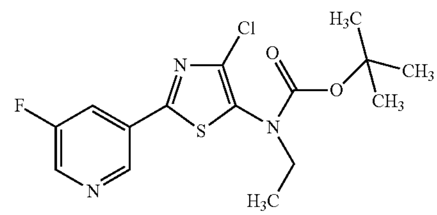 [SMILES: CCN(C(=O)OC(C)(C)C)c1sc(-c2cncc(F)c2)nc1Cl] |
| 268 | yellow solid | 151-155 | | 352.2 (M + 1) | 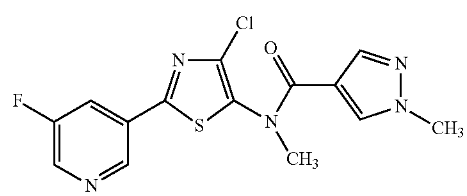 [SMILES: CN(C(=O)c1cnn(C)c1)c1sc(-c2cncc(F)c2)nc1Cl] |
| 269 | clear gum | | 1653 | 372.2 (M + 1) | 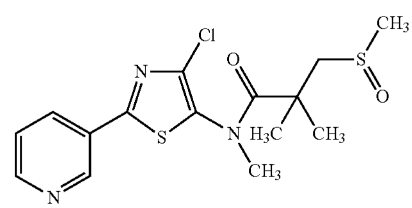 [SMILES: CN(C(=O)C(C)(C)CS(C)=O)c1sc(-c2cccnc2)nc1Cl] |
| 270 | light yellow gum | | 1680 | 376.2 (M + 1) | 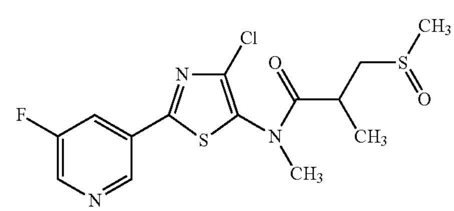 [SMILES: CC(CS(C)=O)C(=O)N(C)c1sc(-c2cncc(F)c2)nc1Cl] |
| 271 | white solid | 151-154 | 1686 | 392.2 (M + 1) | 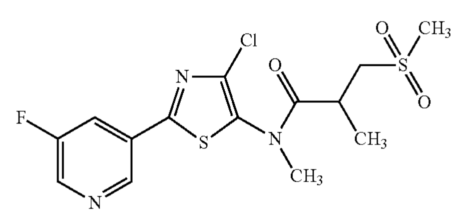 [SMILES: CC(CS(C)(=O)=O)C(=O)N(C)c1sc(-c2cncc(F)c2)nc1Cl] |

TABLE 1-continued

| Compound Number | Appearance | mp (° C.) | IR | MS (ESIMS m/z) | MOLECULAR STRUCTURE |
|---|---|---|---|---|---|
| 372 | beige solid | 123-126 | | 362.2 (M + 1) | 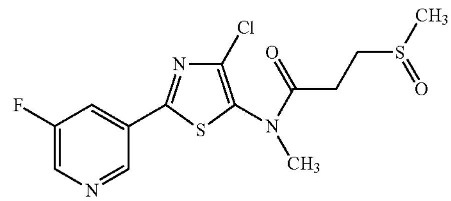 [SMILES: CN(C(=O)CCS(C)=O)c1sc(-c2cncc(F)c2)nc1Cl] |
| 273 | yellow gum | | 1684 | 378.1 (M + 1) | 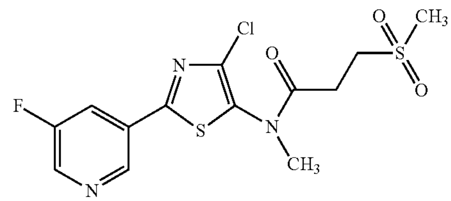 [SMILES: CN(C(=O)CCS(C)(=O)=O)c1sc(-c2cncc(F)c2)nc1Cl] |
| 274 | red oil | | 1684 | 360.2 (M + 1) | 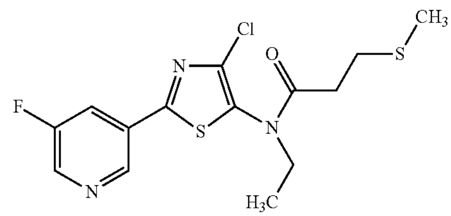 [SMILES: CCN(C(=O)CCSC)c1sc(-c2cncc(F)c2)nc1Cl] |
| 275 | red oil | | 1685 | 328.2 (M + 1) | 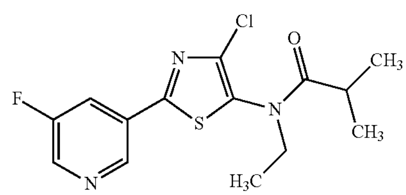 [SMILES: CCN(C(=O)C(C)C)c1sc(-c2cncc(F)c2)nc1Cl] |
| 276 | orange oil | | 1713, 1692 | 363.3 (M + 1) | 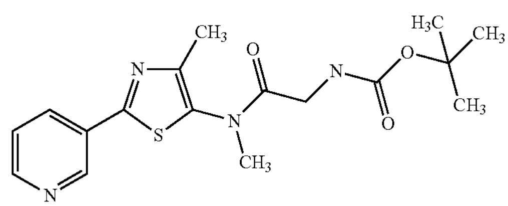 [SMILES: Cc1nc(-c2cccnc2)sc1N(C)C(=O)CNC(=O)OC(C)(C)C] |
| 277 | off white solid | 94-96 | | 396.3 (M + 1) | 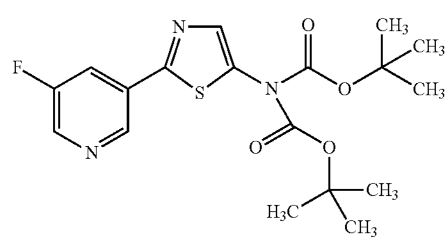 [SMILES: CC(C)(C)OC(=O)N(C(=O)OC(C)(C)C)c1cnc(-c2cncc(F)c2)s1] |
| 278 | red oil | | 1660 | 388.2 (M + 1) | 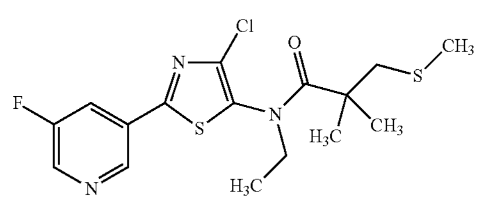 [SMILES: CCN(C(=O)C(C)(C)CSC)c1sc(-c2cncc(F)c2)nc1Cl] |

TABLE 1-continued

| Compound Number | Appearance | mp (° C.) | IR | MS (ESIMS m/z) | MOLECULAR STRUCTURE |
|---|---|---|---|---|---|
| 279 | orange oil | | 1681 | 374.2 (M + 1) | 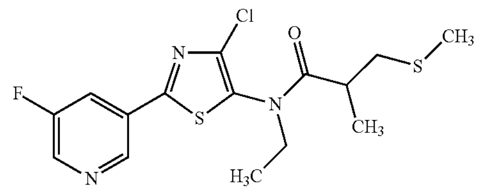 |
| 280 | clear gum | | 1709, 1672 | 453.4 (M + 1) | 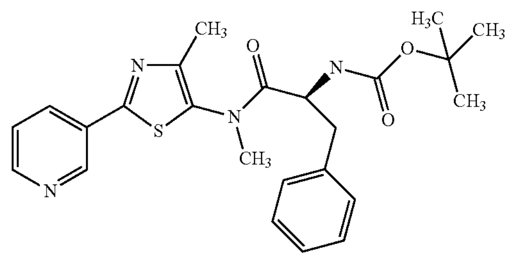 [SMILES: Cc1nc(-c2cccnc2)sc1N(C)C(=O)[C@H](Cc1ccccc1)NC(=O)OC(C)(C)C] |
| 281 | yellow oil | | 1710, 1678 | 437.3 (M + 1) | 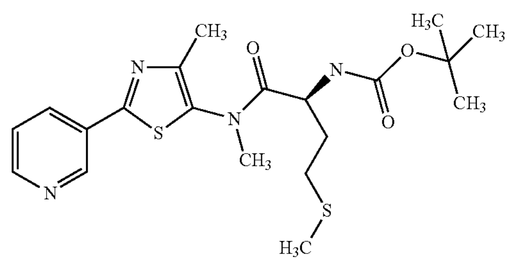 [SMILES: CSCC[C@H](NC(=O)OC(C)(C)C)C(=O)N(C)c1sc(-c2cccnc2)nc1C] |
| 282 | yellow gum | | | 377.3 (M + 1) | 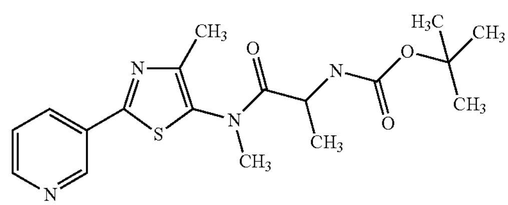 [SMILES: Cc1nc(-c2cccnc2)sc1N(C)C(=O)C(C)NC(=O)OC(C)(C)C] |
| 283 | pale yellow oil | | 1710, 1677 | | 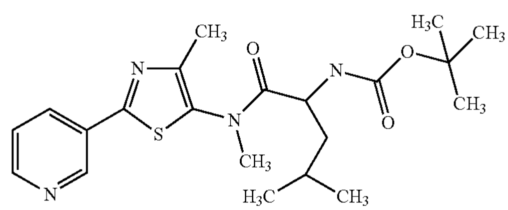 [SMILES: Cc1nc(-c2cccnc2)sc1N(C)C(=O)C(CC(C)C)NC(=O)OC(C)(C)C] |
| 284 | yellow oil | | 1729.59 | 334.3 (M + 1) | 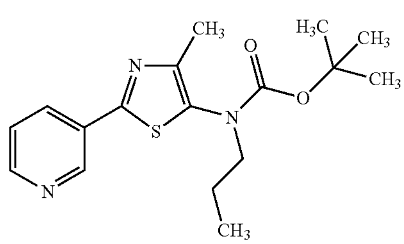 [SMILES: CCCN(C(=O)OC(C)(C)C)c1sc(-c2cccnc2)nc1C] |
| 285 | clear oil | | 1675.42 | 356.2 (M + 1) | 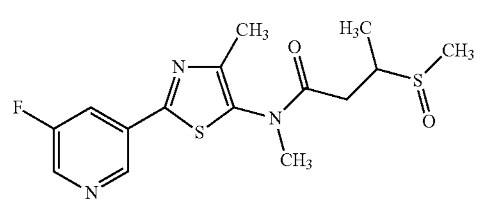 [SMILES: Cc1nc(-c2cncc(F)c2)sc1N(C)C(=O)CC(C)S(C)=O] |

TABLE 1-continued

| Compound Number | Appearance | mp (° C.) | IR | MS (ESIMS m/z) | MOLECULAR STRUCTURE |
|---|---|---|---|---|---|
| 286 | clear oil | | 1674.32 | 350.3 (M + 1) | 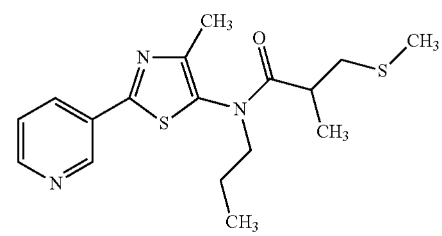 [SMILES: CCCN(C(=O)C(C)CSC)c1sc(-c2cccnc2)nc1C] |
| 287 | clear oil | | 1677.01 | 356.2 (M + 1) | 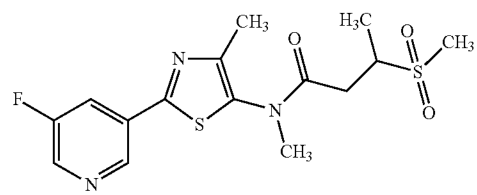 [SMILES: Cc1nc(-c2cncc(F)c2)sc1N(C)C(=O)CC(C)S(C)(=O)=O] |
| 288 | orange gum | | 1682 | 376.2 (M + 1) | 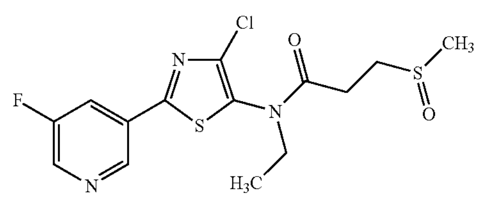 [SMILES: CCN(C(=O)CCS(C)=O)c1sc(-c2cncc(F)c2)nc1Cl] |
| 289 | colorless gum | | 1687 | 390.2 (M + 1) | 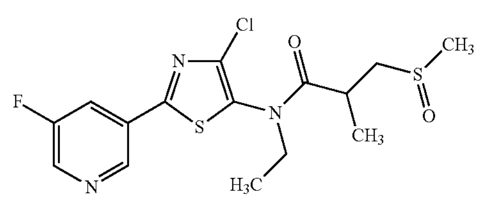 [SMILES: CCN(C(=O)C(C)CS(C)=O)c1sc(-c2cncc(F)c2)nc1Cl] |
| 290 | pale yellow oil | | 1711, 1678 | 499.4 (M + 1) | 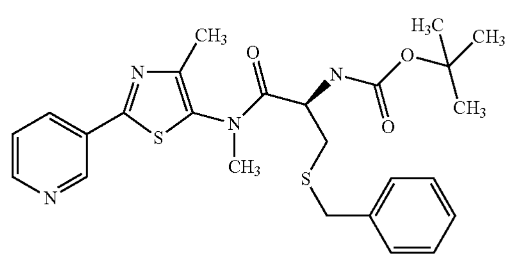 [SMILES: Cc1nc(-c2cccnc2)sc1N(C)C(=O)[C@H](CSCc1ccccc1)NC(=O)OC(C)(C)C] |
| 291 | yellow gum | | 1707, 1675 | 568.5 (M + 1) | 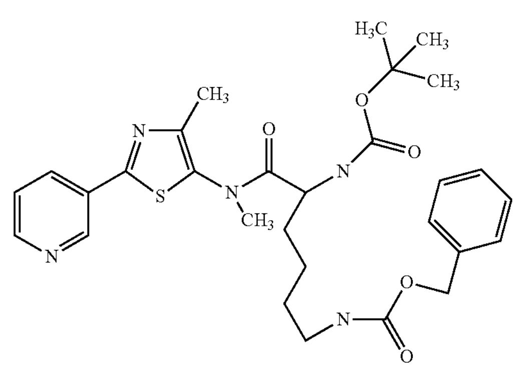 [SMILES: Cc1nc(-c2cccnc2)sc1N(C)C(=O)C(CCCCNC(=O)OCc1ccccc1)NC(=O)OC(C)(C)C] |

TABLE 1-continued

| Compound Number | Appearance | mp (° C.) | IR | MS (ESIMS m/z) | MOLECULAR STRUCTURE |
|---|---|---|---|---|---|
| 292 | yellow oil | | 1695 | 403.3 (M + 1) | 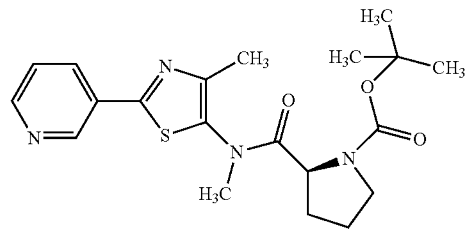 [SMILES: Cc1nc(-c2cccnc2)sc1N(C)C(=O)[C@@H]1CCCN1C(=O)OC(C)(C)C] |
| 293 | red oil | | 1712, 1674 | 497.4 (M + 1) | 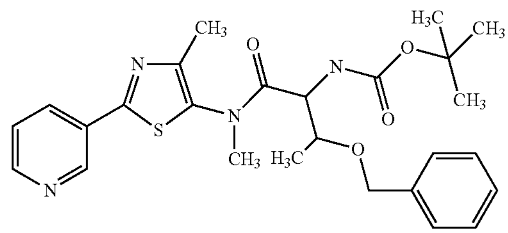 [SMILES: Cc1nc(-c2cccnc2)sc1N(C)C(=O)C(NC(=O)OC(C)(C)C)C(C)OCc1ccccc1] |
| 294 | clear gum | | 1684 | 391.3 (M + 1) | 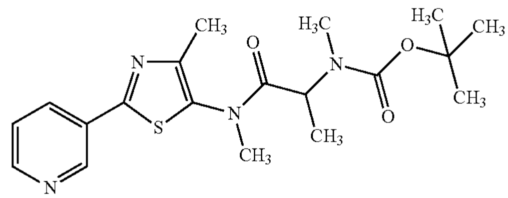 [SMILES: Cc1nc(-c2cccnc2)sc1N(C)C(=O)C(C)N(C)C(=O)OC(C)(C)C] |
| 295 | clear oil | | 1671 | 291.3 (M + 1) | 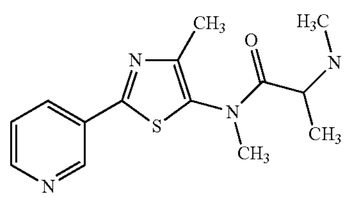 [SMILES: CNC(C)C(=O)N(C)c1sc(-c2cccnc2)nc1C] |
| 296 | yellow solid | 79-81 | | 402.2 (M + 2) | 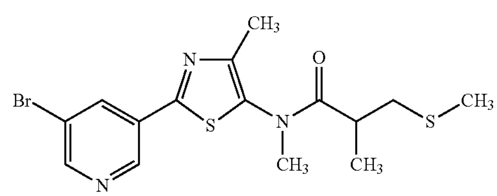 [SMILES: CSCC(C)C(=O)N(C)c1sc(-c2cncc(Br)c2)nc1C] |
| 297 | white solid | 164-166 | | 376.2 (M + 1) | 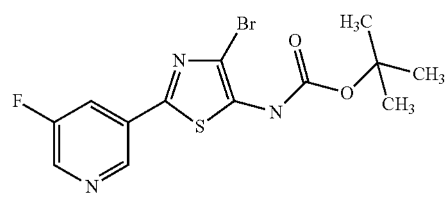 [SMILES: CC(C)(C)OC(=O)Nc1sc(-c2cncc(F)c2)nc1Br] |
| 298 | white solid | 160-163 | | 378.1 (M + 2) | 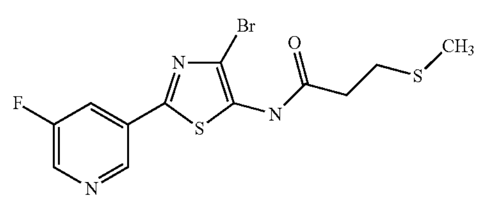 [SMILES: CSCCC(=O)Nc1sc(-c2cncc(F)c2)nc1Br] |

TABLE 1-continued
| Compound Number | Appearance | mp (° C.) | IR | MS (ESIMS m/z) | MOLECULAR STRUCTURE |
|---|---|---|---|---|---|
| 299 | yellow gum | | 3163, 3057, 2919, 1679 | 391.9 (M + 2) | 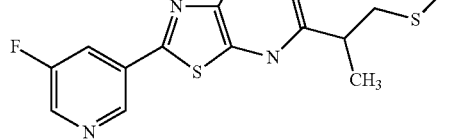 |
| 300 | yellow oil | | | 354.3 (M + 1) | 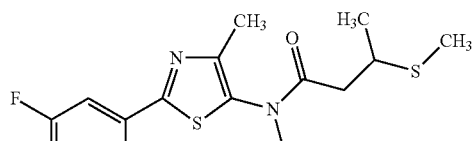 |
| 301 | yellow oil | | 1714.5 | 338.3 (M + 1) | 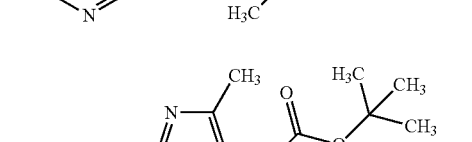 |
| 302 | oil | | 1713.23 | 336.3 (M + 1) | 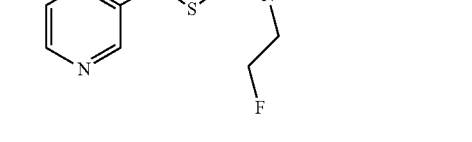 |
| 303 | pale yellow oil | | 1720 | 403.2 (M + 1) | 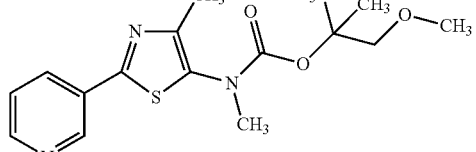 |
| 304 | red oil | | 1718 | 340.3 (M + 1) | 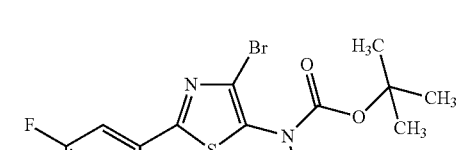 |
| 305 | red oil | | 1679 | 342.2 (M + 1) | 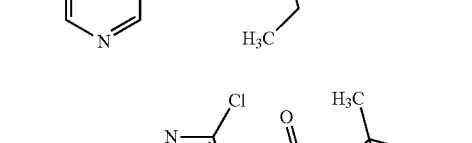 |

TABLE 1-continued

| Compound Number | Appearance | mp (° C.) | IR | MS (ESIMS m/z) | MOLECULAR STRUCTURE |
|---|---|---|---|---|---|
| 306 | white solid | 172-175 | | 408.1 (M + 2) | 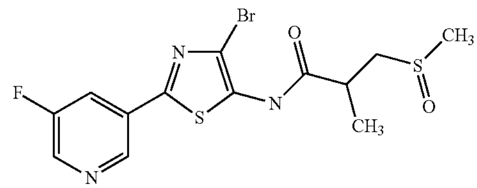 [SMILES: CC(CS(C)=O)C(=O)Nc1sc(-c2cncc(F)c2)nc1Br] |
| 307 | beige solid | 185-188 | | 424 (M + 2) | 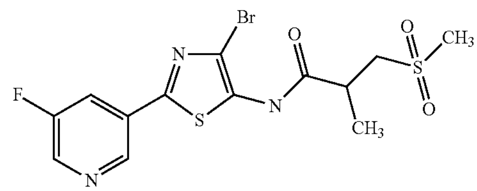 [SMILES: CC(CS(C)(=O)=O)C(=O)Nc1sc(-c2cncc(F)c2)nc1Br] |
| 308 | beige solid | 78-81 | | 326.2 (M + 1) | 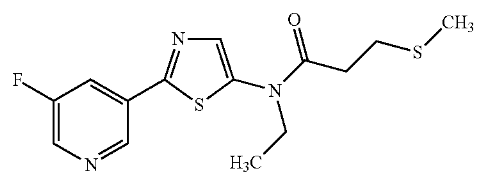 [SMILES: CCN(C(=O)CCSC)c1cnc(-c2cncc(F)c2)s1] |
| 309 | pale yellow crystalline solid | 160-161 | | 310.1 (M + 1) | 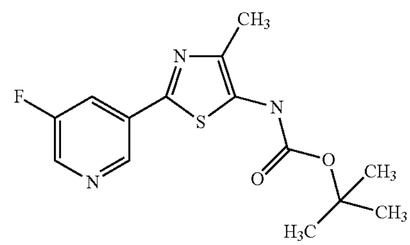 [SMILES: Cc1nc(-c2cncc(F)c2)sc1NC(=O)OC(C)(C)C] |
| 310 | yellow oil | | 1712, 1680 | 484.4 (M + 1) | 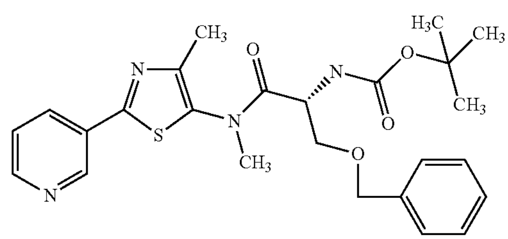 [SMILES: Cc1nc(-c2cccnc2)sc1N(C)C(=O)[C@@H](COCc1ccccc1)NC(=O)OC(C)(C)C] |
| 311 | clear oil | | 1711, 1692 | 405.4 (M + 1) | 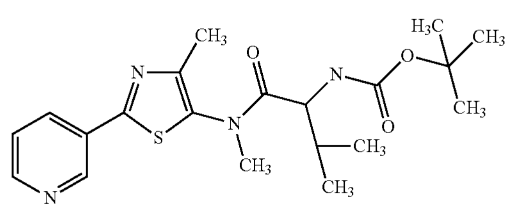 [SMILES: Cc1nc(-c2cccnc2)sc1N(C)C(=O)C(NC(=O)OC(C)(C)C)C(C)C] |
| 312 | pale yellow oil | | 1711, 1679 | 391.4 (M + 1) | 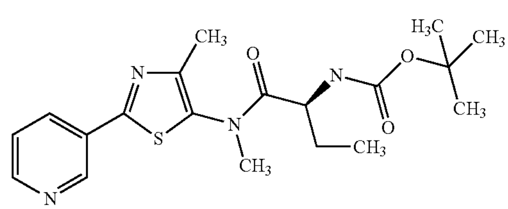 [SMILES: CC[C@H](NC(=O)OC(C)(C)C)C(=O)N(C)c1sc(-c2cccnc2)nc1C] |

TABLE 1-continued
| Compound Number | Appearance | mp (° C.) | IR | MS (ESIMS m/z) | MOLECULAR STRUCTURE |
|---|---|---|---|---|---|
| 313 | red oil | | 1680 | 342.2 (M + 1) | 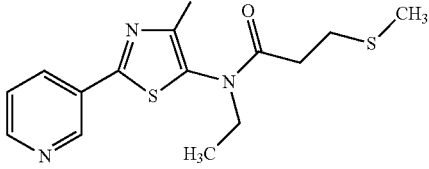 |
| 314 | orange oil | | 1680 | 358.3 (M + 1) | 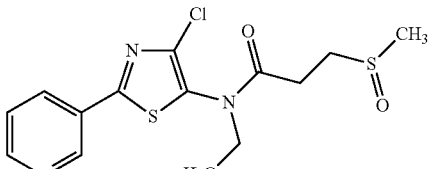 |
| 315 | yellow oil | | 1681 | 374.3 (M + 1) | 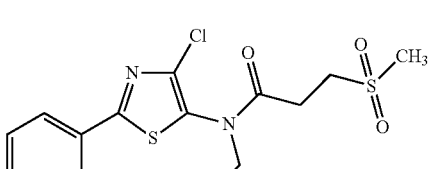 |
| 316 | orange oil | 79-81 | | 356.3 (M + 1) | 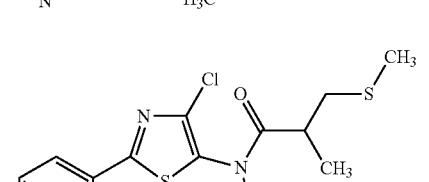 |
| 317 | off white solid | 154-156 | | 476.2 (M + 2) | 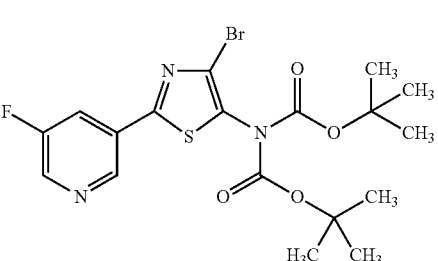 |
| 318 | tan solid | 108-110 | | 290.2 (M + 2) | 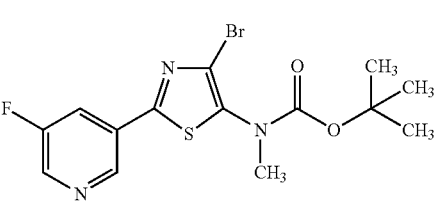 [SMILES: CN(C(=O)OC(C)(C)C)c1sc(-c2cncc(F)c2)nc1Br] |
| 319 | yellow oil | | 1676.65 | 354.3 (M + 1) | 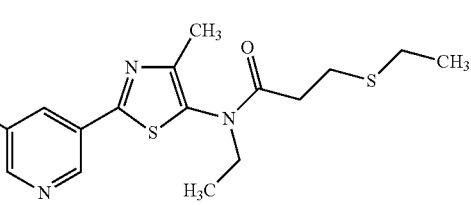 |

TABLE 1-continued

| Compound Number | Appearance | mp (° C.) | IR | MS (ESIMS m/z) | MOLECULAR STRUCTURE |
|---|---|---|---|---|---|
| 320 | brownish oil | | 1673.91 | 398.3 (M + 1) | 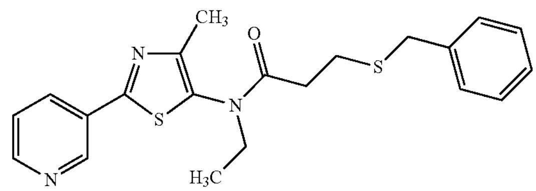 [SMILES: CCN(C(=O)CCSCc1ccccc1)c1sc(-c2cccnc2)nc1C] |
| 321 | brownish oil | | 1674.03 | 384.3 (M + 1) | 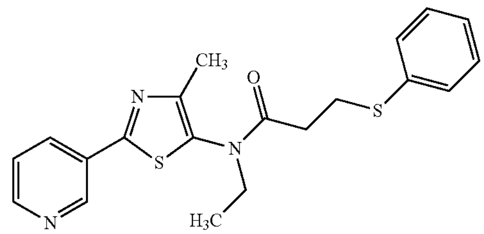 [SMILES: CCN(C(=O)CCSc1ccccc1)c1sc(-c2cccnc2)nc1C] |
| 322 | yellow oil | | 1675.46 | 336.3 (M + 1) | 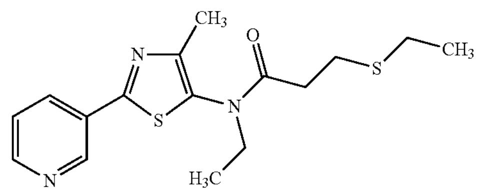 [SMILES: CCSCCC(=O)N(CC)c1sc(-c2cccnc2)nc1C] |
| 323 | yellow oil | | 1676.25 | 350.6 (M + 1) | 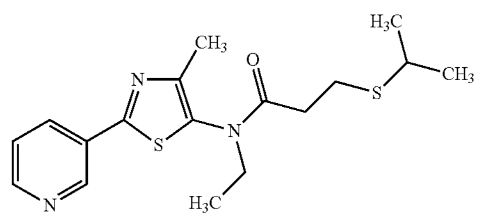 [SMILES: CCN(C(=O)CCSC(C)C)c1sc(-c2cccnc2)nc1C] |
| 324 | brown oil | | 1681.22 | 356.2 (M + 1) | 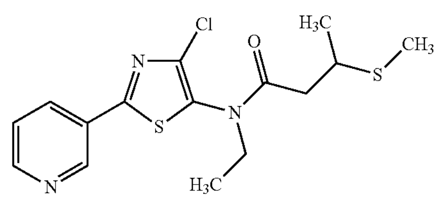 [SMILES: CCN(C(=O)CC(C)SC)c1sc(-c2cccnc2)nc1Cl] |
| 325 | yellow solid | 106-111 | | 308.3 (M + 1) | 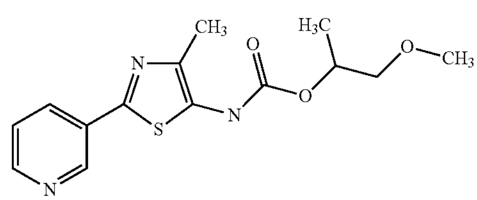 [SMILES: COCC(C)OC(=O)Nc1sc(-c2cccnc2)nc1C] |
| 326 | | | 2979, 2938, 1718, 1670 | 344.2 (M + 1) | 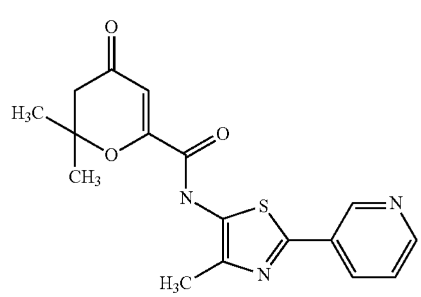 [SMILES: Cc1nc(-c2cccnc2)sc1NC(=O)C1=CC(=O)CC(C)(C)O1] |

TABLE 1-continued

| Compound Number | Appearance | mp (° C.) | IR | MS (ESIMS m/z) | MOLECULAR STRUCTURE |
|---|---|---|---|---|---|
| 327 | | | 1718, 1675 | 358.3 (M + 1) | 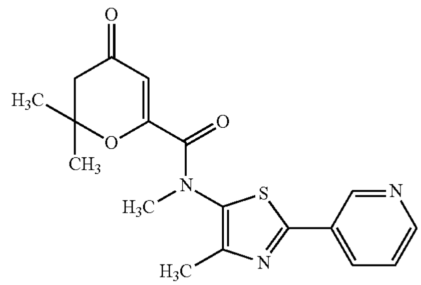 [SMILES: Cc1nc(-c2cccnc2)sc1N(C)C(=O)C1=CC(=O)CC(C)(C)O1] |
| 328 | | | 1678 | 378.2 (M + 1) | 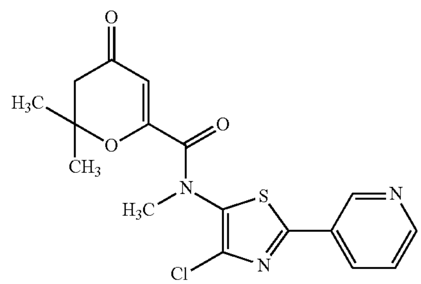 [SMILES: CN(C(=O)C1=CC(=O)CC(C)(C)O1)c1sc(-c2cccnc2)nc1Cl] |
| 329 | | | 3197, 2917, 1665 | 384.2 (M + 1) | 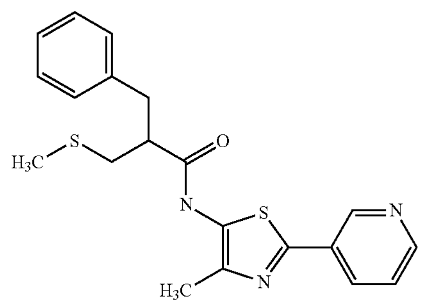 [SMILES: CSCC(Cc1ccccc1)C(=O)Nc1sc(-c2cccnc2)nc1C] |
| 330 | | | 1669 | 398.3 (M + 1) | 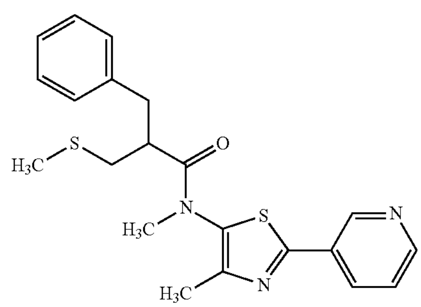 [SMILES: CSCC(Cc1ccccc1)C(=O)N(C)c1sc(-c2cccnc2)nc1C] |
| 331 | | | 1677 | 418.2 (M + 1) | 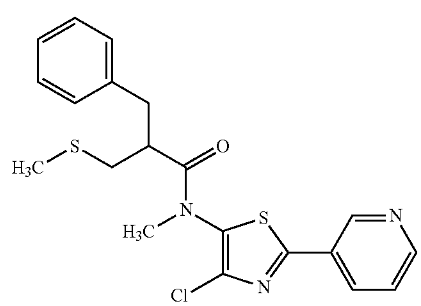 [SMILES: CSCC(Cc1ccccc1)C(=O)N(C)c1sc(-c2cccnc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 332 | | | 3247, 2985, 1697 | 357.3 (M + 1) | 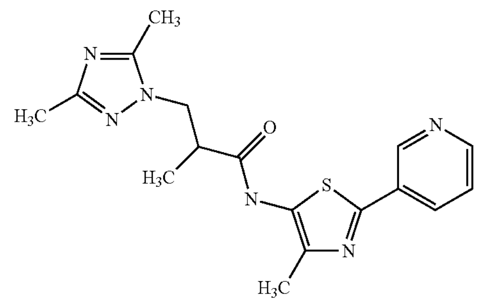 [SMILES: Cc1nc(C)n(CC(C)C(=O)Nc2sc(-c3cccnc3)nc2C)n1] |
| 333 | | | 1678 | 391.2 (M + 1) | 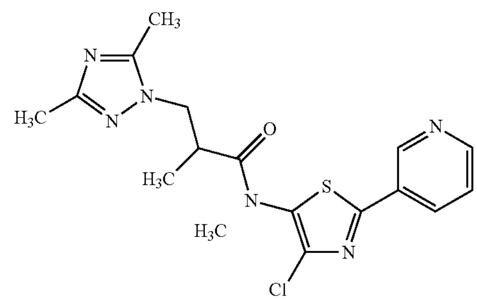 |
| 334 | | | 3448, 1748 | 306.2 (M + 1) | 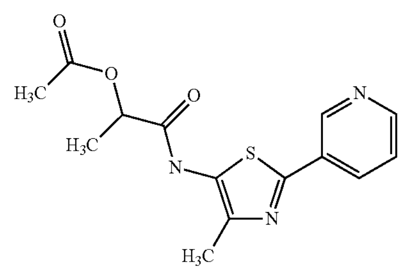 [SMILES: CC(=O)OC(C)C(=O)Nc1sc(-c2cccnc2)nc1C] |
| 335 | | | 1743, 1692 | 320.3 (M + 1) | 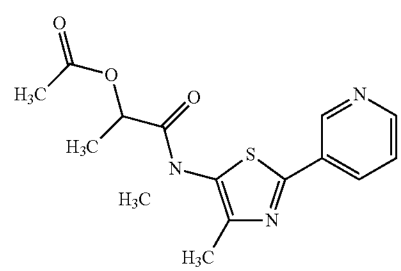 |
| 336 | | | 1742, 1699 | 340.2 (M + 1) | 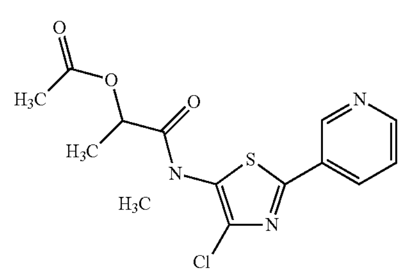 |

TABLE 1-continued
| Compound Number | Appearance | mp (° C.) | IR | MS (ESIMS m/z) | MOLECULAR STRUCTURE |
|---|---|---|---|---|---|
| 337 | | | 3209, 2976, 1682, 1661 | 375.3 (M + 1) | 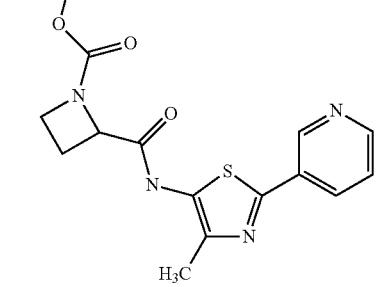 |
| 338 | | | 1701 | 389.3 (M + 1) | 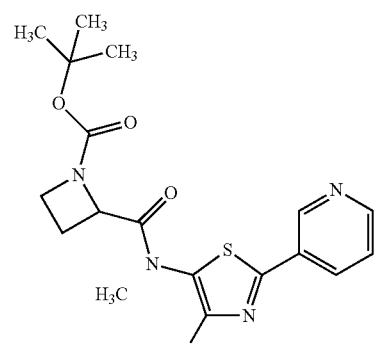 |
| 339 | | | 1669 | 409.2 (M + 1) | 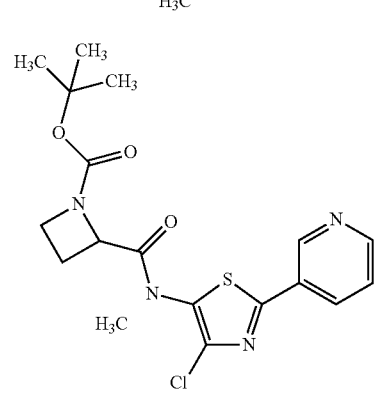 |
| 340 | | | 3346, 1669 | 303.2 (M + 1) | 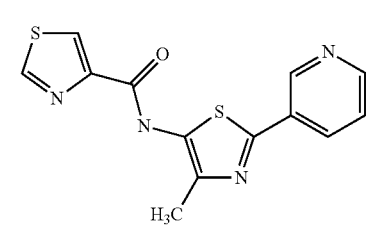 |
| 341 | | | 1658 | 337.1 (M + 1) | 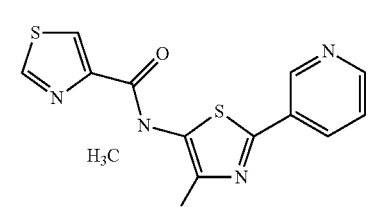 |

TABLE 1-continued

| Compound Number | Appearance | mp (° C.) | IR | MS (ESIMS m/z) | MOLECULAR STRUCTURE |
|---|---|---|---|---|---|
| 342 | | | 3389, 1667 | 287.2 (M + 1) | 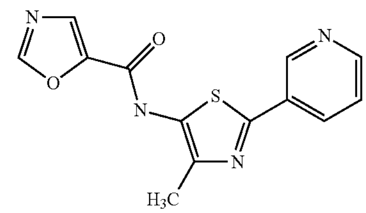 [SMILES: Cc1nc(-c2cccnc2)sc1NC(=O)c1cnco1] |
| 343 | | | 1665 | 301.2 (M + 1) | 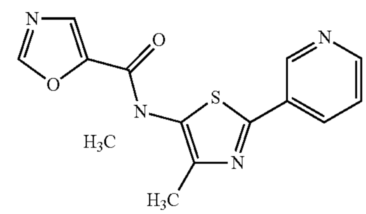 |
| 344 | | | 3167, 2937, 1641 | 303.2 (M + 1) | 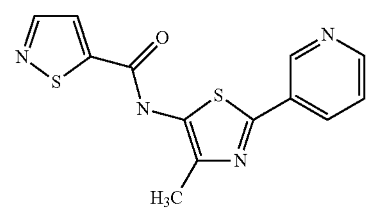 [SMILES: Cc1nc(-c2cccnc2)sc1NC(=O)c1ccns1] |
| 345 | | | 1654 | 317.2 (M + 1) | 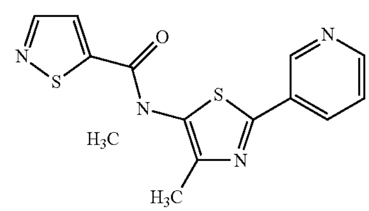 |
| 346 | | | 1659 | 337.1 (M + 1) | 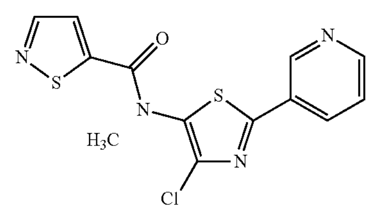 |
| 347 | | | 3173, 2975, 1658, 1637 | 344.2 (M + 1) | 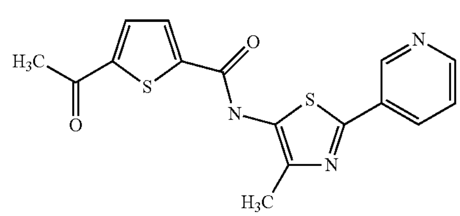 [SMILES: CC(=O)c1ccc(C(=O)Nc2sc(-c3cccnc3)nc2C)s1] |
| 348 | yellow oil | | 1679 | 372.2 (M + 1) | 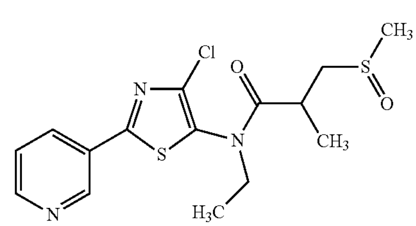 [SMILES: CCN(C(=O)C(C)CS(C)=O)c1sc(-c2cccnc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 349 | white solid | 152-154 | | 388.2 (M + 1) | 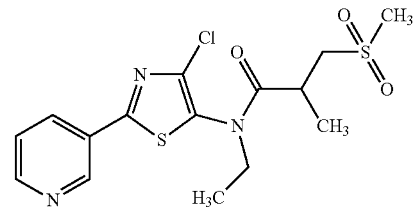 [SMILES: CCN(C(=O)C(C)CS(C)(=O)=O)c1sc(-c2cccnc2)nc1Cl] |
| 350 | yellow oil | | 1668, 1643 | 358.2 (M + 1) | 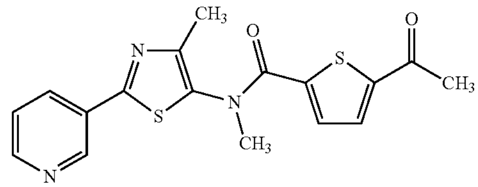 [SMILES: CC(=O)c1ccc(C(=O)N(C)c2sc(-c3cccnc3)nc2C)s1] |
| 351 | pale yellow oil | | 1669, 1640 | 378.2 (M + 1) | 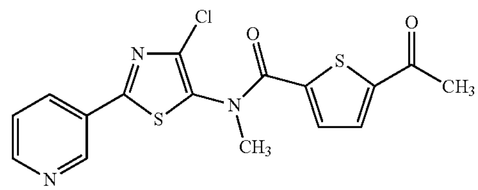 [SMILES: CC(=O)c1ccc(C(=O)N(C)c2sc(-c3cccnc3)nc2Cl)s1] |
| 352 | off white solid | 125-128 | | 430.2 (M + 1) | 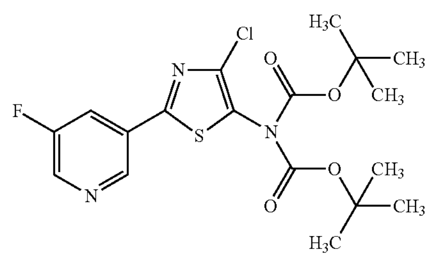 [SMILES: CC(C)(C)OC(=O)N(C(=O)OC(C)(C)C)c1sc(-c2cncc(F)c2)nc1Cl] |
| 353 | pale yellow solid | 188-191 | | 258.1 (M + 1) | 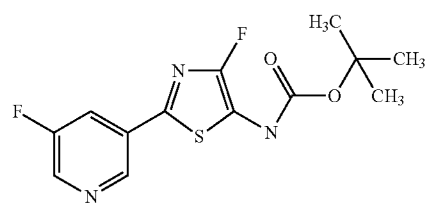 [SMILES: CC(C)(C)OC(=O)Nc1sc(-c2cncc(F)c2)nc1F] |
| 354 | red oil | | 1682 | 406.1 (M + 1) | 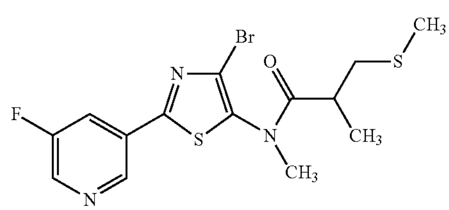 [SMILES: CSCC(C)C(=O)N(C)c1sc(-c2cncc(F)c2)nc1Br] |
| 355 | pale yellow solid | 219-222 | | 300.3 (M + 1) | 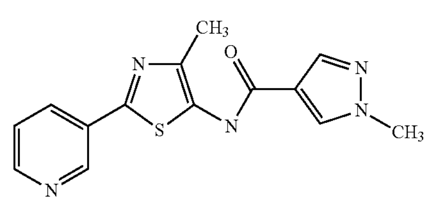 [SMILES: Cc1nc(-c2cccnc2)sc1NC(=O)c1cnn(C)c1] |

TABLE 1-continued

| Compound Number | Appearance | mp (° C.) | IR | MS (ESIMS m/z) | MOLECULAR STRUCTURE |
|---|---|---|---|---|---|
| 356 | white solid | 72-76 | | 333 (M + 2) | 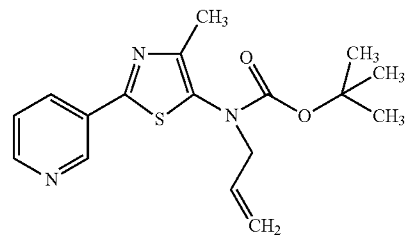 [SMILES: C=CCN(C(=O)OC(C)(C)C)c1sc(-c2cccnc2)nc1C] |
| 357 | tan oil | | | 394 (M + 1) | 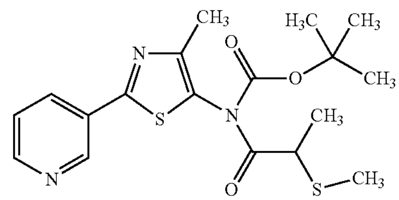 [SMILES: CSC(C)C(=O)N(C(=O)OC(C)(C)C)c1sc(-c2cccnc2)nc1C] |
| 358 | brown oil | | 1673 | 308 (M + 1) | 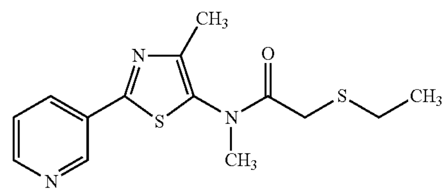 [SMILES: CCSCC(=O)N(C)c1sc(-c2cccnc2)nc1C] |
| 359 | tan solid | 135-138 | 1665 | 294 (M + 1) | 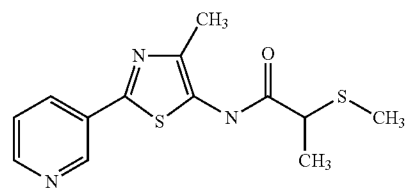 [SMILES: CSC(C)C(=O)Nc1sc(-c2cccnc2)nc1C] |
| 360 | tacky tan solid | | 1673 | 308 (M + 1) | 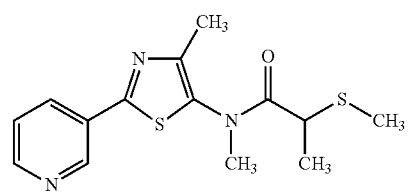 [SMILES: CSC(C)C(=O)N(C)c1sc(-c2cccnc2)nc1C] |
| 361 | tan solid | 97-104 | 1663 | 328 (M + 1) | 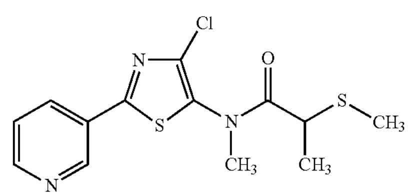 [SMILES: CSC(C)C(=O)N(C)c1sc(-c2cccnc2)nc1Cl] |
| 363 | pale yellow oil | | 1685 | 336.3 (M + 1) | 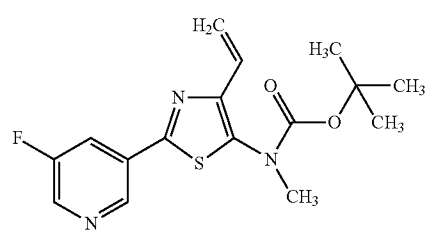 [SMILES: C=Cc1nc(-c2cncc(F)c2)sc1N(C)C(=O)OC(C)(C)C] |

TABLE 1-continued

| Compound Number | Appearance | mp (° C.) | IR | MS (ESIMS m/z) | MOLECULAR STRUCTURE |
|---|---|---|---|---|---|
| 364 | yellow gum | | 3258, 3072, 2977, 2919, 1682 | 346.2 (M + 1) | 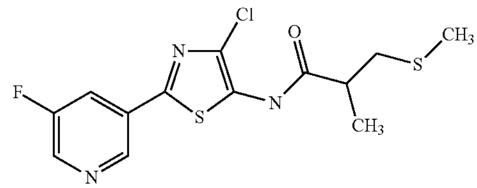 [SMILES: CSCC(C)C(=O)Nc1sc(-c2cncc(F)c2)nc1Cl] |
| 365 | yellow oil | | 1655 | 317.2 (M + 1) | 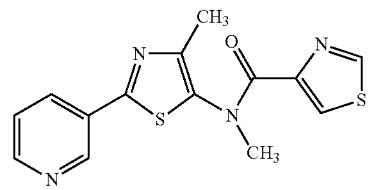 [SMILES: Cc1nc(-c2cccnc2)sc1N(C)C(=O)c1cscn1] |
| 366 | yellow solid | 81-84 | | 328.2 (M + 1) | 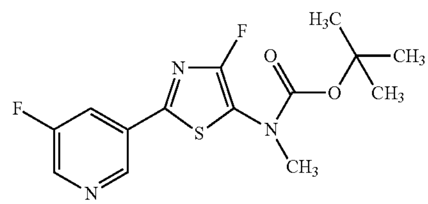 [SMILES: CN(C(=O)OC(C)(C)C)c1sc(-c2cncc(F)c2)nc1F] |
| 367 | yellow oil | | 1672 | 294.4 (M + 1) | 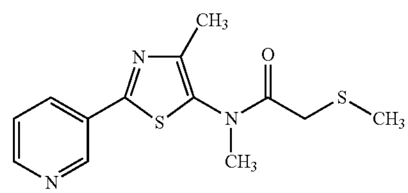 |
| 368 | brown oil | | 1677 | 322 (M + 1) | 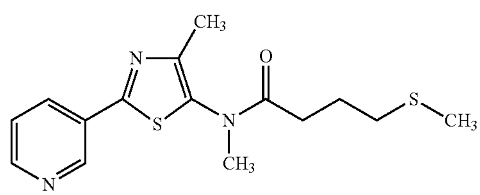 [SMILES: CSCCCC(=O)N(C)c1sc(-c2cccnc2)nc1C] |
| 369 | tan solid | 111-114 | 1661 | 316 (M + 2) | 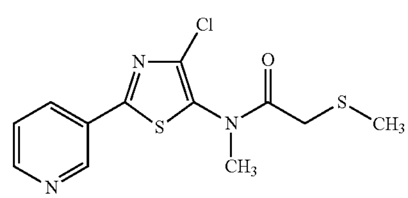 [SMILES: CSCC(=O)N(C)c1sc(-c2cccnc2)nc1Cl] |
| 370 | tan solid | 68-71 | 1667 | 328.2 (M + 1) | 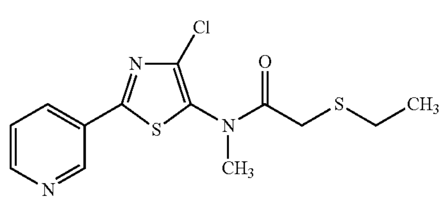 |

TABLE 1-continued

| Compound Number | Appearance | mp (° C.) | IR | MS (ESIMS m/z) | MOLECULAR STRUCTURE |
|---|---|---|---|---|---|
| 371 | brown oil | | 1684 | 344 (M + 2) | 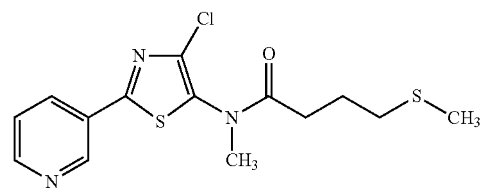 |
| 372 | light yellow solid | 164-167 | 1674 | 282.4 (M + 2) | 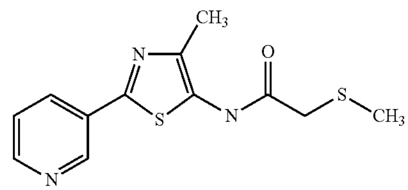 [SMILES: CSCC(=O)Nc1sc(-c2cccnc2)nc1C] |
| 373 | yellow solid | 157-158 | 1668 | 294 (M + 1) | 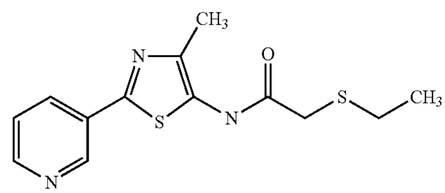 [SMILES: CCSCC(=O)Nc1sc(-c2cccnc2)nc1C] |
| 374 | yellow solid | 110-112 | 1642 | 308 (M + 1) | 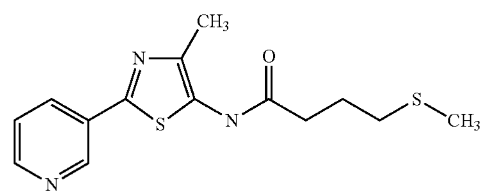 [SMILES: CSCCCC(=O)Nc1sc(-c2cccnc2)nc1C] |
| 375 | yellow solid | 163-167 | | 319.3 (M + 2) | 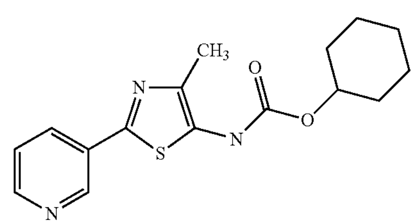 [SMILES: Cc1nc(-c2cccnc2)sc1NC(=O)OC1CCCCC1] |
| 376 | light yellow solid | 88-94 | | 306.3 (M + 1) | 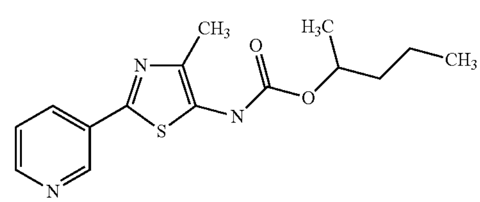 |
| 377 | yellow solid | 108-110 | | 292 (M + 1) | 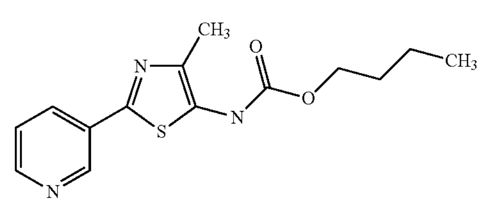 [SMILES: CCCCOC(=O)Nc1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 378 | yellow solid | 133-137 | | 332.3 (M + 1) | 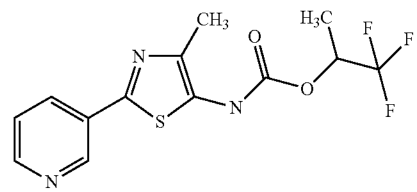 [SMILES: Cc1nc(-c2cccnc2)sc1NC(=O)OC(C)C(F)(F)F] |
| 379 | yellow solid | 131-134 | | 294.2 (M + 1) | 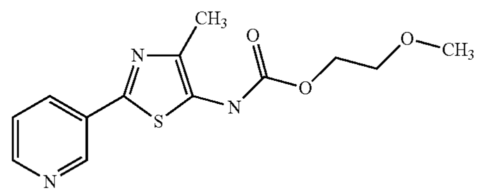 [SMILES: COCCOC(=O)Nc1sc(-c2cccnc2)nc1C] |
| 380 | yellow solid | 170-178 | | 318.2 (M + 1) | 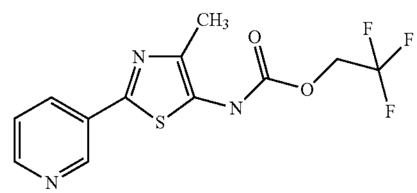 [SMILES: Cc1nc(-c2cccnc2)sc1NC(=O)OCC(F)(F)F] |
| 381 | fluffy yellow solid | 158-159 | | 376.2, 378.2 | 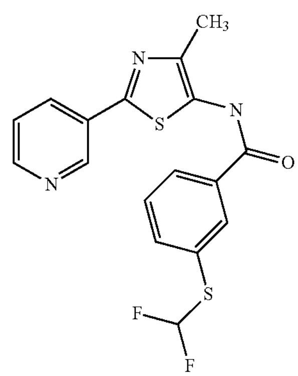 [SMILES: Cc1nc(-c2cccnc2)sc1NC(=O)c1cccc(SC(F)F)c1] |
| 382 | pale yellow oil | | | 412.2 | 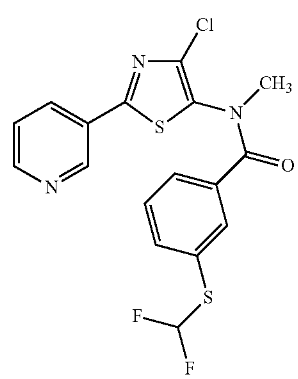 [SMILES: CN(C(=O)c1cccc(SC(F)F)c1)c1sc(-c2cccnc2)nc1Cl] |

TABLE 1-continued
| Compound Number | Appearance | mp (° C.) | IR | MS (ESIMS m/z) | MOLECULAR STRUCTURE |
|---|---|---|---|---|---|
| 383 | rust colored solid | 121-124 | | 349.2 | 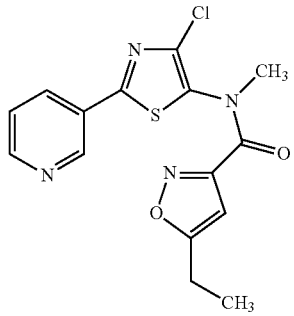 [SMILES: CCc1cc(C(=O)N(C)c2sc(-c3cccnc3)nc2Cl)no1] |
| 384 | orange oil | | 1684 | 331.4 (M + 1) | 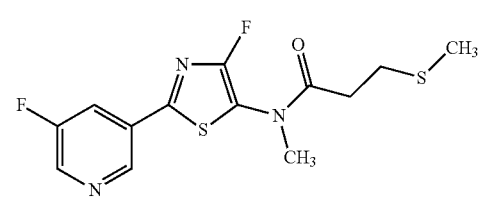 [SMILES: CSCCC(=O)N(C)c1sc(-c2cncc(F)c2)nc1F] |
| 385 | yellow oil | | 1683 | 345.5 (M + 1) | 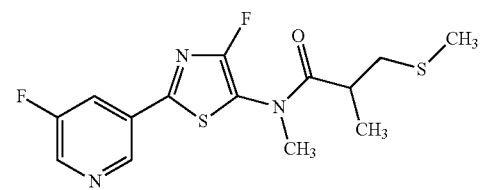 [SMILES: CSCC(C)C(=O)N(C)c1sc(-c2cncc(F)c2)nc1F] |
| 386 | white solid | 163-164 | | 307.3 | 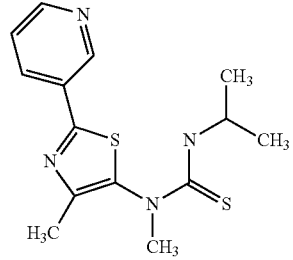 [SMILES: Cc1nc(-c2cccnc2)sc1N(C)C(=S)NC(C)C] |
| 387 | pale yellow solid | 129-130 | | 315.3, 314.3 | 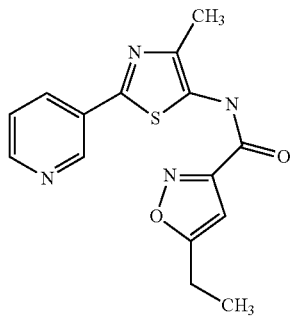 [SMILES: CCc1cc(C(=O)Nc2sc(-c3cccnc3)nc2C)no1] |

TABLE 1-continued

| Compound Number | Appearance | mp (° C.) | IR | MS (ESIMS m/z) | MOLECULAR STRUCTURE |
|---|---|---|---|---|---|
| 388 | pale yellow solid | 190-194 | | 395.4, 393.4 | 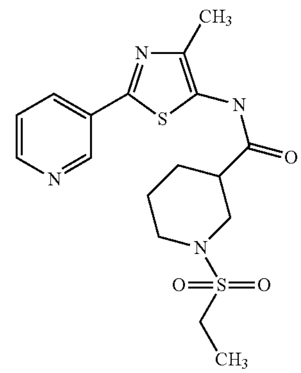 [SMILES: CCS(=O)(=O)N1CCCC(C(=O)Nc2sc(-c3cccnc3)nc2C)C1] |
| 389 | off-white solid | 214-215 | | 435 | 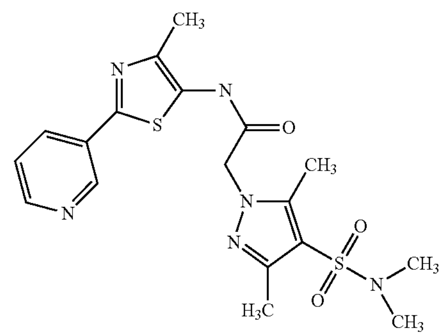 [SMILES: Cc1nc(-c2cccnc2)sc1NC(=O)Cn1nc(C)c(S(=O)(=O)N(C)C)c1C] |
| 390 | off-white solid | 185-186 | | 468.08 | 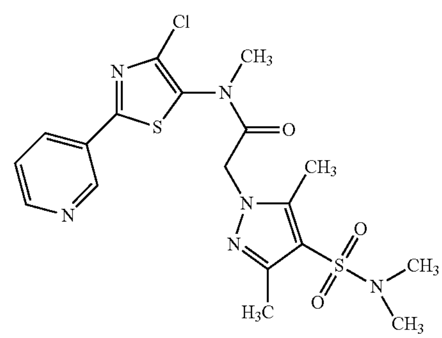 [SMILES: Cc1nn(CC(=O)N(C)c2sc(-c3cccnc3)nc2Cl)c(C)c1S(=O)(=O)N(C)C] |
| 391 | yellow solid | 150-151 | | 290.12 | 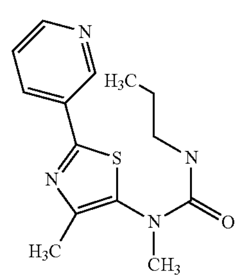 [SMILES: CCCNC(=O)N(C)c1sc(-c2cccnc2)nc1C] |
| 392 | white solid | 113-116 | | 346.1 (M + 1) | 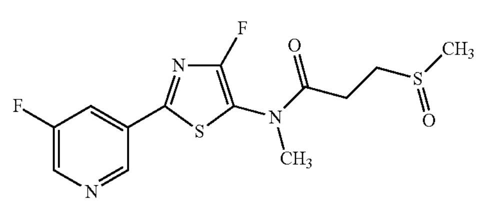 [SMILES: CN(C(=O)CCS(C)=O)c1sc(-c2cncc(F)c2)nc1F] |

TABLE 1-continued

| Compound Number | Appearance | mp (° C.) | IR | MS (ESIMS m/z) | MOLECULAR STRUCTURE |
|---|---|---|---|---|---|
| 393 | pale yellow gum | | 1682 | 381.9 (M + 1) | 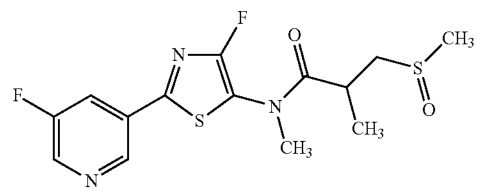 [SMILES: CC(CS(C)=O)C(=O)N(C)c1sc(-c2cncc(F)c2)nc1F] |
| 394 | orange glass | | 1675 | 429.3 | 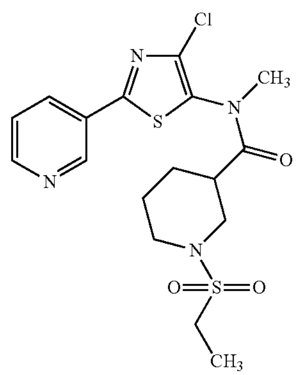 [SMILES: CCS(=O)(=O)N1CCCC(C(=O)N(C)c2sc(-c3cccnc3)nc2Cl)C1] |
| 395 | white solid | 93-101 | | 366.1 (M + 1) | 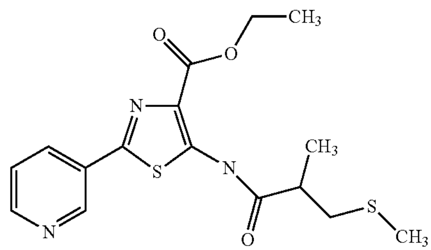 [SMILES: CCOC(=O)c1nc(-c2cccnc2)sc1NC(=O)C(C)CSC] |
| 396 | off-white solid | 97-98 | | 331 | 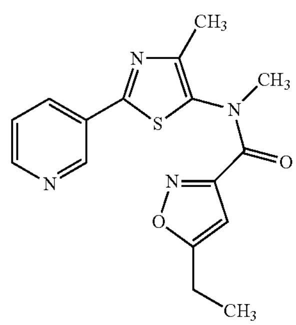 [SMILES: CCc1cc(C(=O)N(C)c2sc(-c3cccnc3)nc2C)no1] |
| 397 | tan oil | | 1663 | 391.06 | 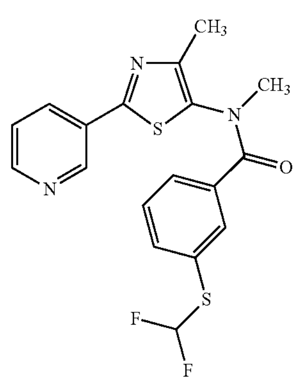 [SMILES: Cc1nc(-c2cccnc2)sc1N(C)C(=O)c1cccc(SC(F)F)c1] |

TABLE 1-continued

| Compound Number | Appearance | mp (° C.) | IR | MS (ESIMS m/z) | MOLECULAR STRUCTURE |
|---|---|---|---|---|---|
| 398 | white solid | 53-54 | | 374.04 | 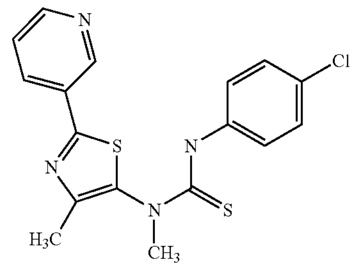 [SMILES: Cc1nc(-c2cccnc2)sc1N(C)C(=S)Nc1ccc(Cl)cc1] |
| 399 | | | 1653.05 | 286.2 (M + 1) | 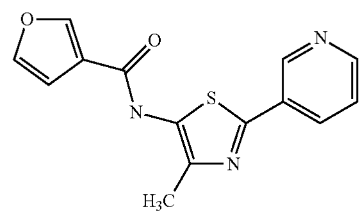 |
| 400 | | | 1658.56 | 300.2 (M + 1) | 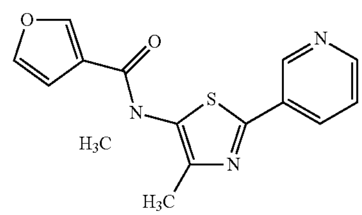 |
| 401 | | | 1668.99 | 320.2 (M + 1) | 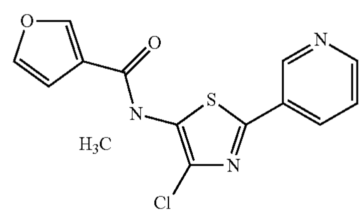 |
| 402 | | | 1657.88 | 372.3 (M + 1) | 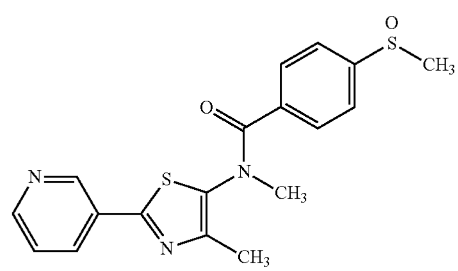 |
| 403 | | | 1664.94 | 392.2 (M + 1) | 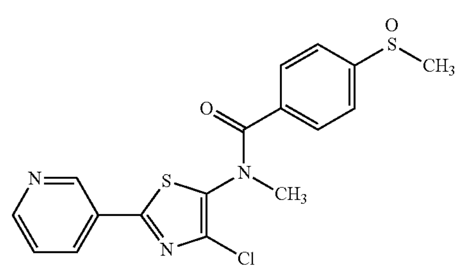 |

TABLE 1-continued

| Compound Number | Appearance | mp (° C.) | IR | MS (ESIMS m/z) | MOLECULAR STRUCTURE |
|---|---|---|---|---|---|
| 404 | | | 1662.35 | 342.3 (M + 1) | 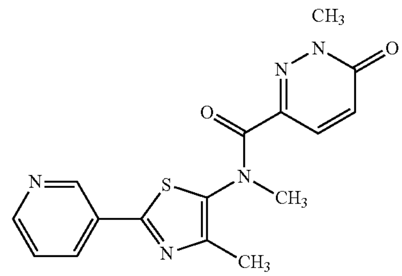 |
| 405 | | | 1673.28 | 362.2 (M + 1) | 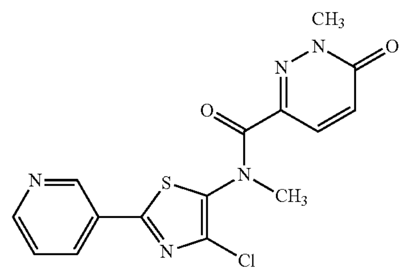 |
| 406 | | | 1665 | 311.3 (M + 1) | 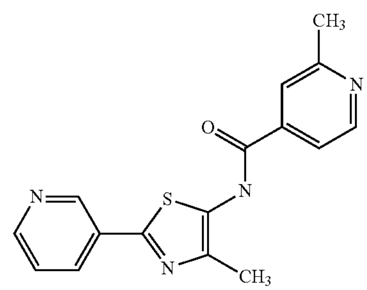 [SMILES: Cc1cc(C(=O)Nc2sc(-c3cccnc3)nc2C)ccn1] |
| 407 | | | 1674 | 345.2 (M + 1) | 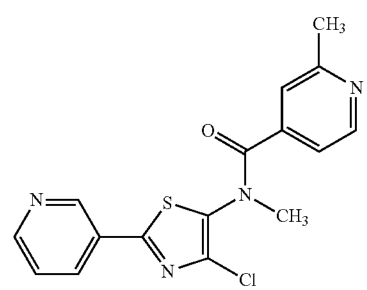 [SMILES: Cc1cc(C(=O)N(C)c2sc(-c3cccnc3)nc2Cl)ccn1] |
| 408 | | | 1660.22 | 346.2 (M + 1) | 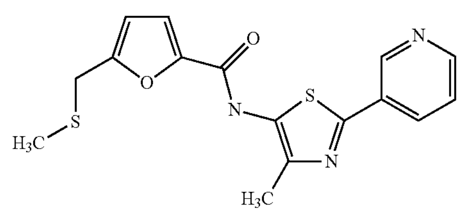 [SMILES: CSCc1ccc(C(=O)Nc2sc(-c3cccnc3)nc2C)o1] |
| 409 | | | 1713.63 | 380.2 (M + 1) | 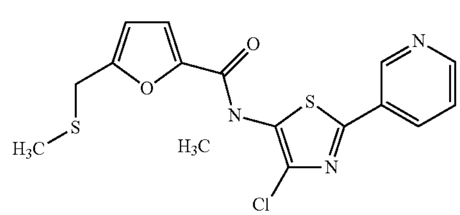 |

TABLE 1-continued

| Compound Number | Appearance | mp (° C.) | IR | MS (ESIMS m/z) | MOLECULAR STRUCTURE |
|---|---|---|---|---|---|
| 410 | | | 1668.86 | 387.3 (M + 1) | 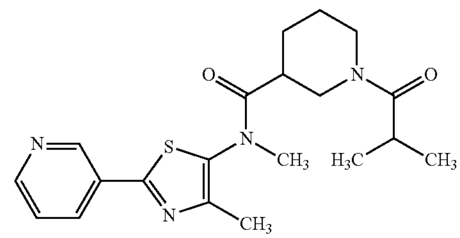 [SMILES: Cc1nc(-c2cccnc2)sc1N(C)C(=O)C1CCCN(C(=O)C(C)C)C1] |
| 411 | | | 1676.13 | 407.3 (M + 1) | 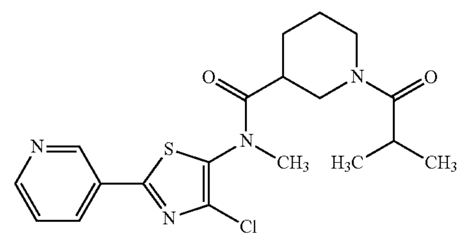 [SMILES: CC(C)C(=O)N1CCCC(C(=O)N(C)c2sc(-c3cccnc3)nc2Cl)C1] |
| 412 | | | 1668.23 | 359.3 (M + 1) | 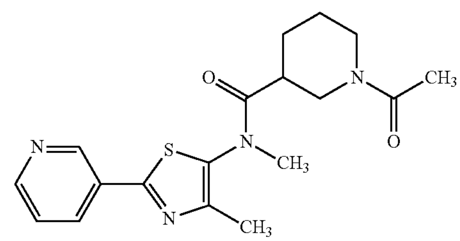 [SMILES: CC(=O)N1CCCC(C(=O)N(C)c2sc(-c3cccnc3)nc2C)C1] |
| 413 | | | 1675.32 | 379.3 (M + 1) | 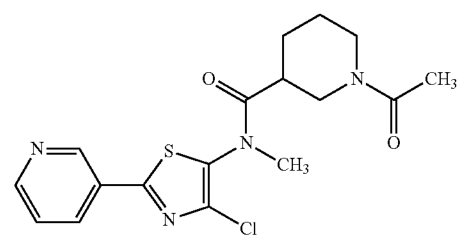 [SMILES: CC(=O)N1CCCC(C(=O)N(C)c2sc(-c3cccnc3)nc2Cl)C1] |
| 414 | | | 1648 | 345.3 (M + 1) | 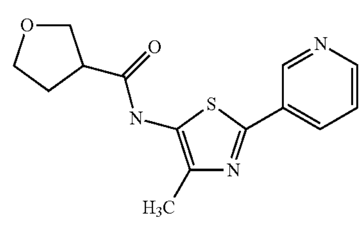 |
| 415 | | | | 324.2 (M + 1) | 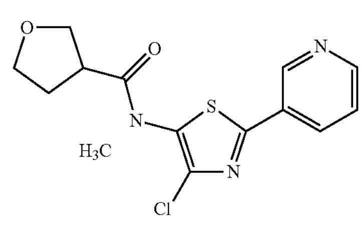 |

TABLE 1-continued

| Compound Number | Appearance | mp (° C.) | IR | MS (ESIMS m/z) | MOLECULAR STRUCTURE |
|---|---|---|---|---|---|
| 416 | | | 1668.03 | 288.3 (M + 1) | 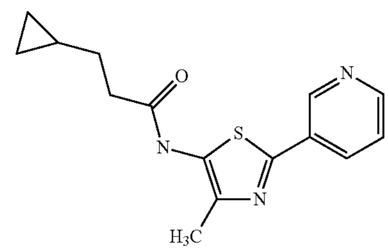 [SMILES: Cc1nc(-c2cccnc2)sc1NC(=O)CCC1CC1] |
| 417 | | | 1672.2 | 274.2 (M + 1) | 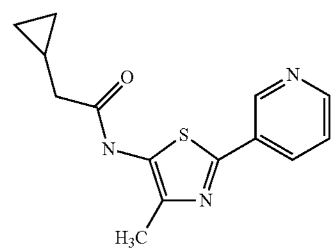 [SMILES: Cc1nc(-c2cccnc2)sc1NC(=O)CC1CC1] |
| 418 | | | 1672.45 | 288.3 (M + 1) | 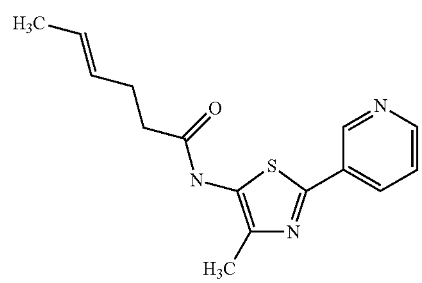 [SMILES: C/C=C/CCC(=O)Nc1sc(-c2cccnc2)nc1C] |
| 420 | tan glass | | 1695 | 451.2 | 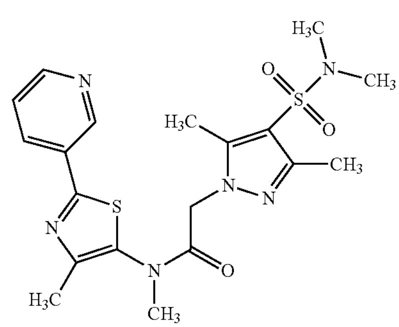 [SMILES: Cc1nc(-c2cccnc2)sc1N(C)C(=O)Cn1nc(C)c(S(=O)(=O)N(C)C)c1C] |
| 421 | off-white solid | 153-154 | | 332, 330 | 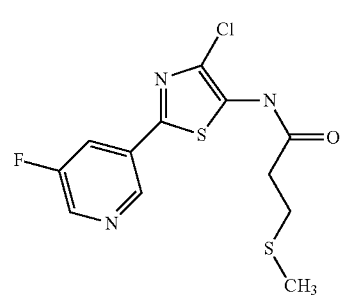 [SMILES: CSCCC(=O)Nc1sc(-c2cncc(F)c2)nc1Cl] |

TABLE 1-continued
| Compound Number | Appearance | mp (° C.) | IR | MS (ESIMS m/z) | MOLECULAR STRUCTURE |
|---|---|---|---|---|---|
| 422 | beige solid | 114-117 | | 378.3 (M + 1) | 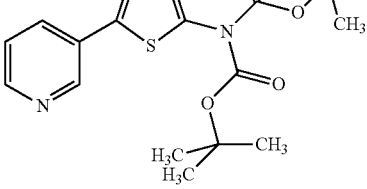 |
| 423 | yellow oil | | 1718 | 342.3 (M + 1) | 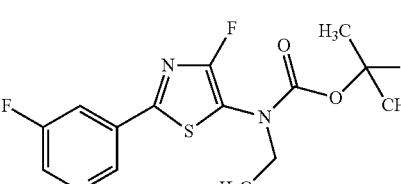 |
| 424 | orange gum | | 1684 | 312.3 (M + 1) | 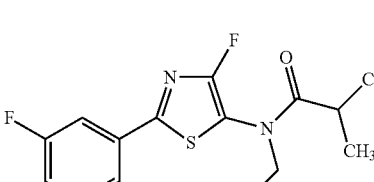 |
| 425 | yellow oil | | 1684 | 344.2 (M + 1) | 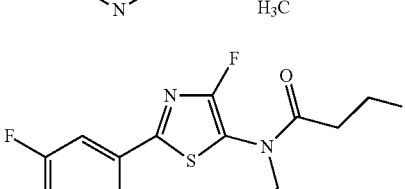 |
| 426 | tan oil | | | 348 (M + 1) | 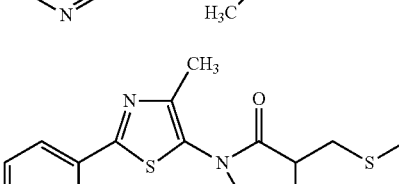 |
| 427 | yellow oil | | 1676 | 360.2 | 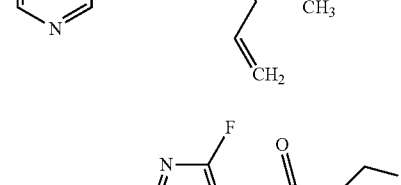 |
| 428 | | | 1708 | 438 (M + 1) | 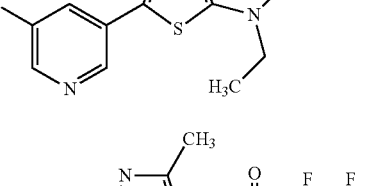 |

TABLE 1-continued

| Compound Number | Appearance | mp (° C.) | IR | MS (ESIMS m/z) | MOLECULAR STRUCTURE |
|---|---|---|---|---|---|
| 429 | | | 1652 | 385 (M + 1) | 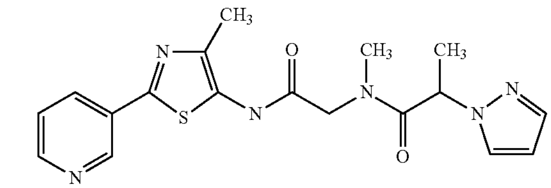 [SMILES: Cc1nc(-c2cccnc2)sc1NC(=O)CN(C)C(=O)C(C)n1cccn1] |
| 430 | | | 1689 | 399 (M + 1) | 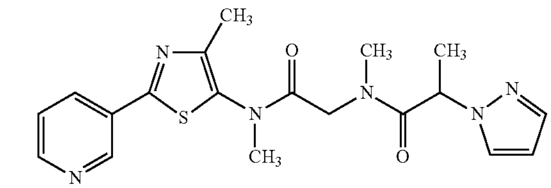 [SMILES: Cc1nc(-c2cccnc2)sc1N(C)C(=O)CN(C)C(=O)C(C)n1cccn1] |
| 431 | | | 1695 | 419 (M + 1) | 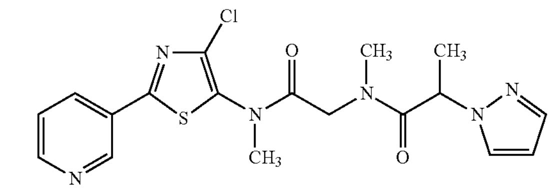 [SMILES: CC(C(=O)N(C)CC(=O)N(C)c1sc(-c2cccnc2)nc1Cl)n1cccn1] |
| 432 | | | 1691 | 311 (M + 1) | 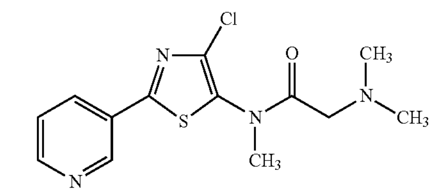 [SMILES: CN(C)CC(=O)N(C)c1sc(-c2cccnc2)nc1Cl] |
| 433 | | | 1686 | 355 (M + 1) | 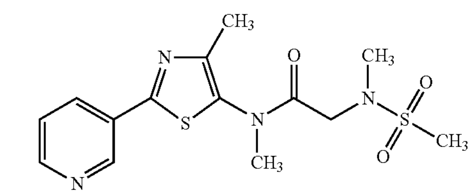 [SMILES: Cc1nc(-c2cccnc2)sc1N(C)C(=O)CN(C)S(C)(=O)=O] |
| 434 | | | 1696 | 375 (M + 1), 377 (M + 3) | 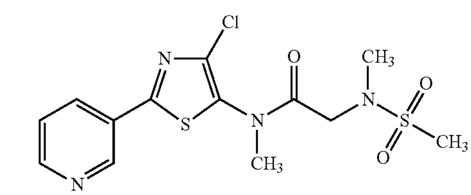 [SMILES: CN(C(=O)CN(C)S(C)(=O)=O)c1sc(-c2cccnc2)nc1Cl] |
| 435 | | | 1683 | 429 (M + 1) | 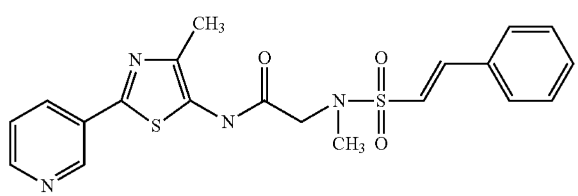 [SMILES: Cc1nc(-c2cccnc2)sc1NC(=O)CN(C)S(=O)(=O)/C=C/c1ccccc1] |
| 436 | | | 1688 | 443 (M + 1) | 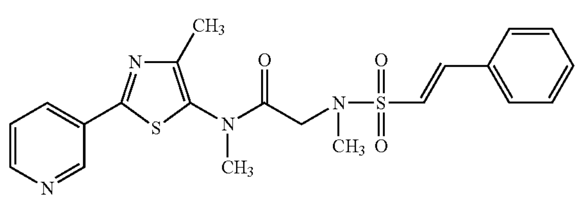 |

TABLE 1-continued

| Compound Number | Appearance | mp (° C.) | IR | MS (ESIMS m/z) | MOLECULAR STRUCTURE |
|---|---|---|---|---|---|
| 437 | | | 1695 | 463 (M + 1) | 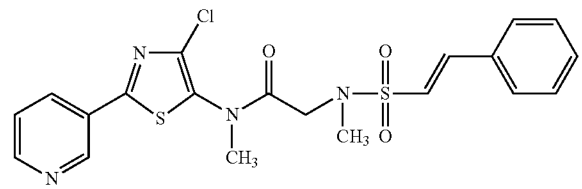 [SMILES: Cc1nc(-c2cccnc2)sc1N(C)C(=O)CN(C)S(=O)(=O)/C=C/c1ccccc1] |
| 438 | | | 1670 | 373 (M + 1) | 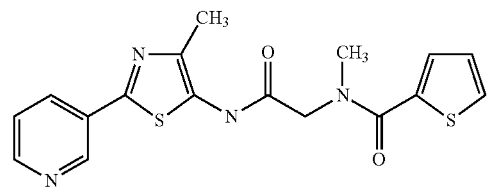 [SMILES: Cc1nc(-c2cccnc2)sc1NC(=O)CN(C)C(=O)c1cccs1] |
| 439 | | | 1702 | 426 (M + 2) | 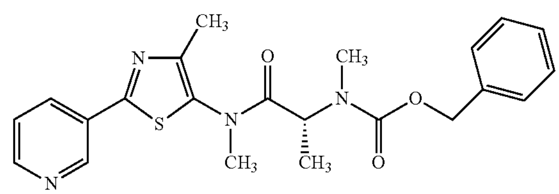 |
| 440 | | | 1692 | 445 (M + 1) | 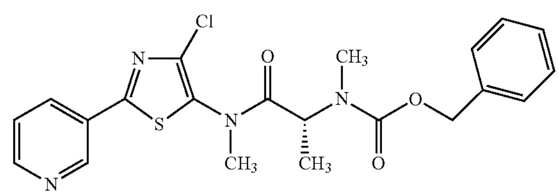 [SMILES: C[C@H](C(=O)N(C)c1sc(-c2cccnc2)nc1Cl)N(C)C(=O)OCc1ccccc1] |
| 441 | orange oil | | 1686 | 392.1 (M + 2) | 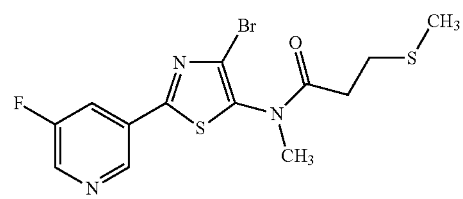 [SMILES: CSCCC(=O)N(C)c1sc(-c2cncc(F)c2)nc1Br] |
| 442 | yellow oil | | 1675.84 | | 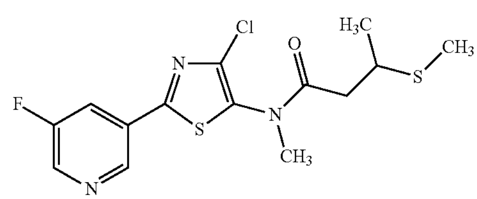 [SMILES: CSC(C)CC(=O)N(C)c1sc(-c2cncc(F)c2)nc1Cl] |
| 443 | white solid | | 1673.55 | 375.84 (M + 2) | 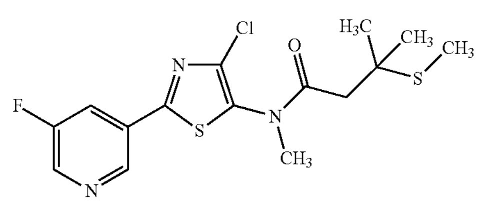 [SMILES: CSC(C)(C)CC(=O)N(C)c1sc(-c2cncc(F)c2)nc1Cl] |

TABLE 1-continued

| Compound Number | Appearance | mp (° C.) | IR | MS (ESIMS m/z) | MOLECULAR STRUCTURE |
|---|---|---|---|---|---|
| 444 | white solid | | 1673.04 | 375.8 (M + 2) | 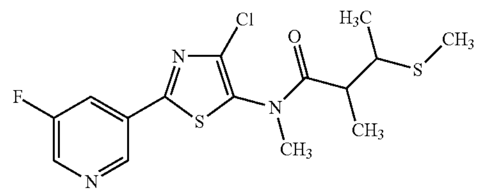 [SMILES: CSC(C)C(C)C(=O)N(C)c1sc(-c2cncc(F)c2)nc1Cl] |
| 445 | orange oil | | 1677.42 | 357.87 (M + 1) | AND Enantiomer |
| 446 | dark oil | | 1683.62 | 375.8 (M + 2) | 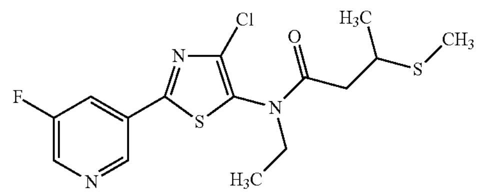 |
| 447 | dark oil | | 1685.07 | 387.9 (M + 1) | 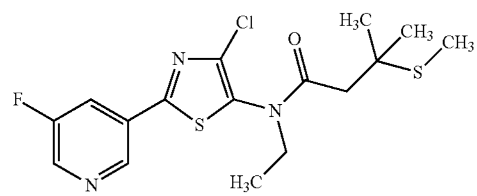 [SMILES: CCN(C(=O)CC(C)(C)SC)c1sc(-c2cncc(F)c2)nc1Cl] |
| 448 | dark oil | | 1675.15 | 372.06 (M + 1) | AND Enantiomer |
| 449 | orange solid | 137-140 | | | 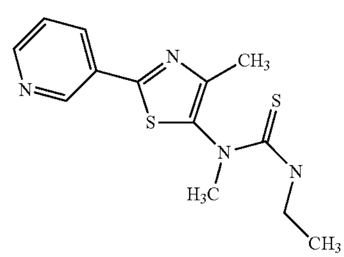 [SMILES: CCNC(=S)N(C)c1sc(-c2cccnc2)nc1C] |
| 450 | brown solid | | | 361.98 | 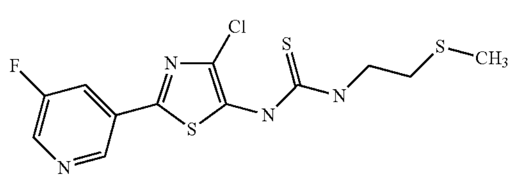 [SMILES: CSCCNC(=S)Nc1sc(-c2cncc(F)c2)nc1Cl] |

TABLE 1-continued
| Compound Number | Appearance | mp (° C.) | IR | MS (ESIMS m/z) | MOLECULAR STRUCTURE |
|---|---|---|---|---|---|
| 451 | fluffy white solid | 184-185 | | 348, 346 | 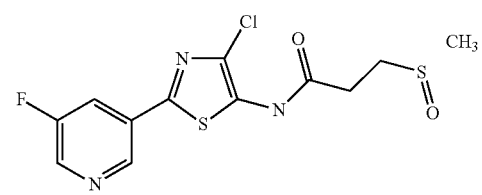 |
| 452 | orange oil | | 1717 | 384.1 (M + 2) | 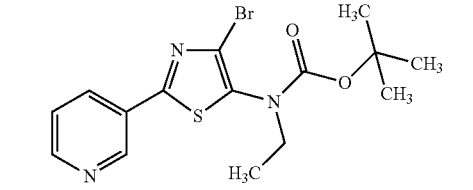 [SMILES: CCN(C(=O)OC(C)(C)C)c1sc(-c2cccnc2)nc1Br] |
| 453 | oil | | 1685 | 346.2 (M + 1) | 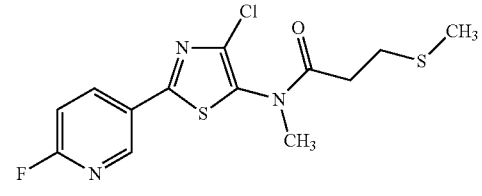 [SMILES: CSCCC(=O)N(C)c1sc(-c2ccc(F)nc2)nc1Cl] |
| 454 | white solid | 170-173 | | 408 (M + 1) | 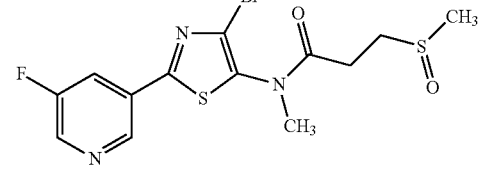 |
| 455 | off-white solid | 198-201 | | 424.1 (M + 1) | 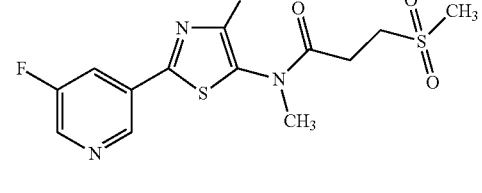 |
| 456 | yellow oil | | 1682 | 358.3 (M + 1) | 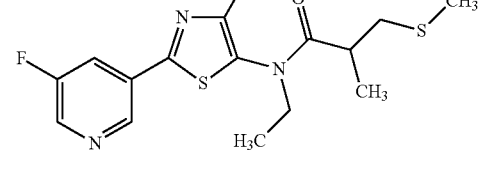 |
| 457 | orange oil | | 1683 | 356.2 (M + 2) | 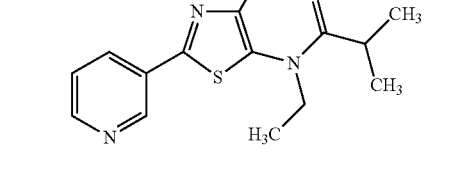 |

TABLE 1-continued

| Compound Number | Appearance | mp (° C.) | IR | MS (ESIMS m/z) | MOLECULAR STRUCTURE |
|---|---|---|---|---|---|
| 458 | yellow oil | | 1683 | 388.2 (M + 2) | 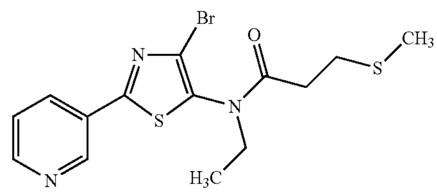 |
| 459 | white solid | 239-240 | | 364, 362 | 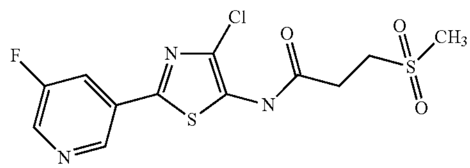 [SMILES: CS(=O)(=O)CCC(=O)Nc1sc(-c2cncc(F)c2)nc1Cl] |
| 460 | tan oil | | 1713 | 350 (M + 1) | 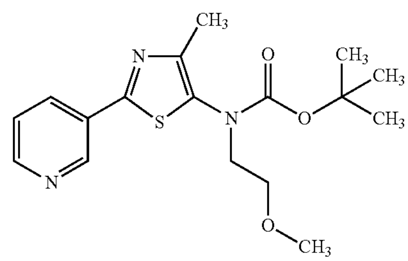 [SMILES: COCCN(C(=O)OC(C)(C)C)c1sc(-c2cccnc2)nc1C] |
| 461 | tan oil | | | 383 (M + 2) | 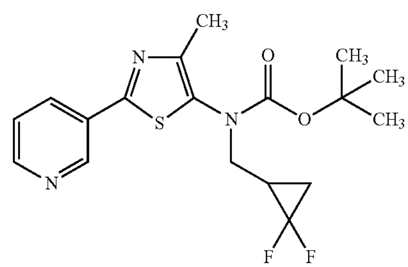 [SMILES: Cc1nc(-c2cccnc2)sc1N(CC1CC1(F)F)C(=O)OC(C)(C)C] |
| 462 | tan oil | | | 347 (M + 2) | 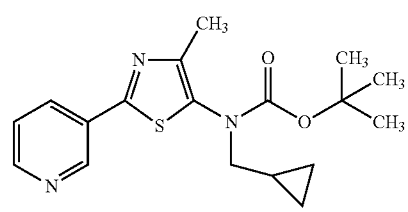 [SMILES: Cc1nc(-c2cccnc2)sc1N(CC1CC1)C(=O)OC(C)(C)C] |
| 463 | tan oil | | | 347 (M + 2) | 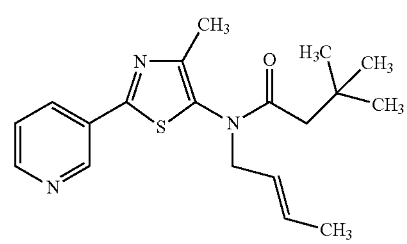 [SMILES: C/C=C/CN(C(=O)CC(C)(C)C)c1sc(-c2cccnc2)nc1C] |

TABLE 1-continued

| Compound Number | Appearance | mp (° C.) | IR | MS (ESIMS m/z) | MOLECULAR STRUCTURE |
| --- | --- | --- | --- | --- | --- |
| 464 | brown oil | | | 406 (M + 1) | 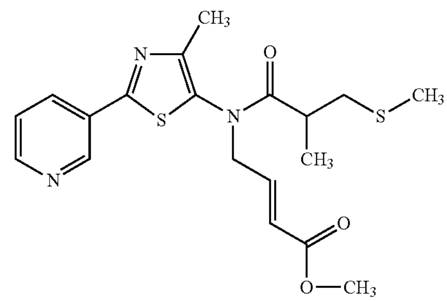 [SMILES: COC(=O)/C=C/CN(C(=O)C(C)CSC)c1sc(-c2cccnc2)nc1C] |
| 465 | tan oil | | | 366 (M + 1) | 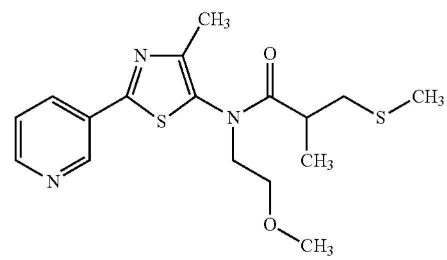 [SMILES: COCCN(C(=O)C(C)CSC)c1sc(-c2cccnc2)nc1C] |
| 466 | light yellow oil | | 1674 | 362 (M + 2) | 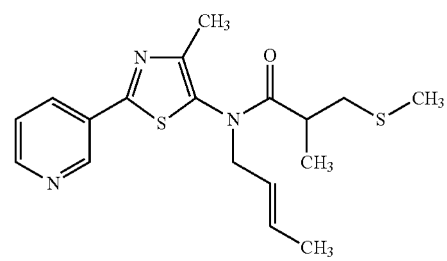 [SMILES: C/C=C/CN(C(=O)C(C)CSC)c1sc(-c2cccnc2)nc1C] |
| 467 | Tan Oil | | 1677 | 400 (M + 2) | 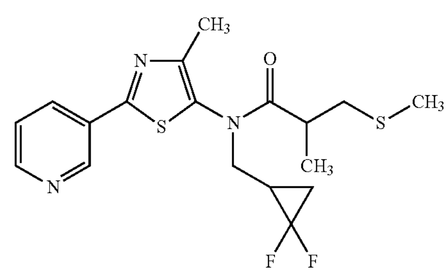 [SMILES: CSCC(C)C(=O)N(CC1CC1(F)F)c1sc(-c2cccnc2)nc1C] |
| 468 | tan oil | | 1674 | 362 (M + 1) | 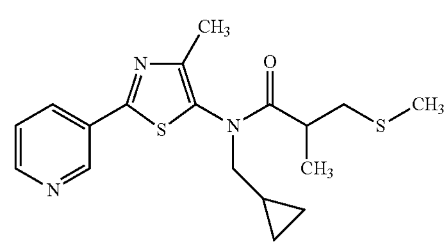 [SMILES: CSCC(C)C(=O)N(CC1CC1)c1sc(-c2cccnc2)nc1C] |
| 469 | light yellow oil | | 1684 | 362.1 (M + 1) | 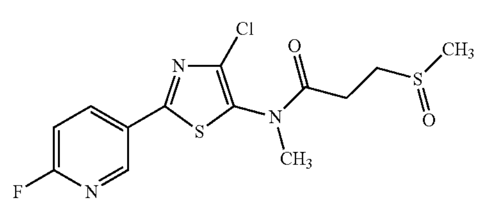 [SMILES: CN(C(=O)CCS(C)=O)c1sc(-c2ccc(F)nc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 470 | white solid | 42-46 | 1672 | 378.1 (M + 1) | 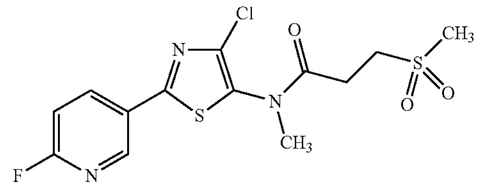 [SMILES: CN(C(=O)CCS(C)(=O)=O)c1sc(-c2ccc(F)nc2)nc1Cl] |
| 471 | clear oil | | | 321.8 (M + 1) | 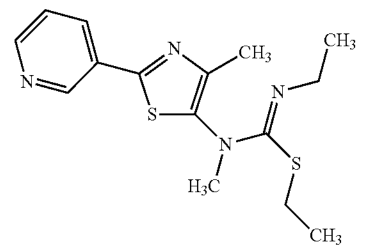 [SMILES: CC/N=C(\SCC)N(C)c1sc(-c2cccnc2)nc1C] |
| 472 | orange oil | | | 349.5 (M + 1) | 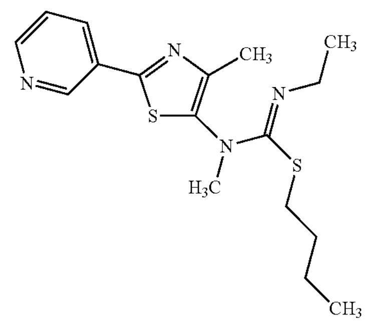 [SMILES: CCCCS/C(=N\CC)N(C)c1sc(-c2cccnc2)nc1C] |
| 473 | yellow oil | | 1683 | 394.2 (M + 1) | 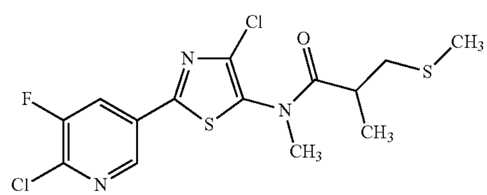 [SMILES: CSCC(C)C(=O)N(C)c1sc(-c2cnc(Cl)c(F)c2)nc1Cl] |
| 474 | light yellow solid | 30-35 | 1682 | 410.1 (M + 1) | 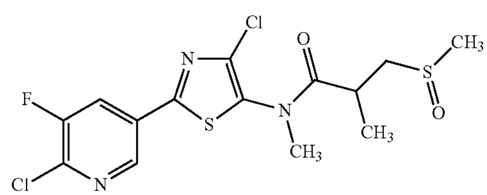 [SMILES: CC(CS(C)=O)C(=O)N(C)c1sc(-c2cnc(Cl)c(F)c2)nc1Cl] |
| 475 | white solid | 55-61 | 1683 | 426 (M + 1) | 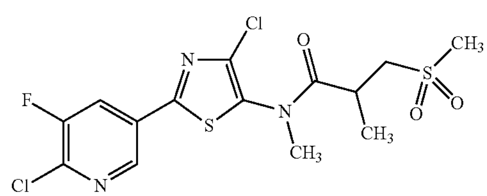 [SMILES: CC(CS(C)(=O)=O)C(=O)N(C)c1sc(-c2cnc(Cl)c(F)c2)nc1Cl] |
| 476 | light yellow solid | 119-120 | 1723.48 | 344.53 (M + 1) | 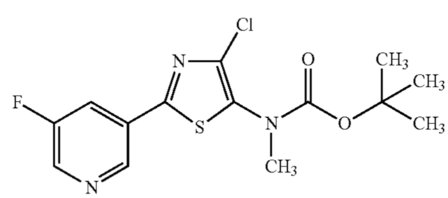 [SMILES: CN(C(=O)OC(C)(C)C)c1sc(-c2cncc(F)c2)nc1Cl] |

TABLE 1-continued

| Compound Number | Appearance | mp (° C.) | IR | MS (ESIMS m/z) | MOLECULAR STRUCTURE |
|---|---|---|---|---|---|
| 477 | brown reddish solid | 65-67 | | 306.1 (M + 1) | 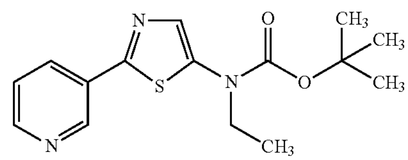 [SMILES: CCN(C(=O)OC(C)(C)C)c1cnc(-c2cccnc2)s1] |
| 478 | dark yellow solid | 184-186 | | 296.2 (M + 1) | 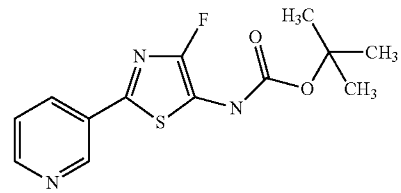 [SMILES: CC(C)(C)OC(=O)Nc1sc(-c2cccnc2)nc1F] |
| 480 | orange oil | | 1682 | 402.1 (M + 2) | 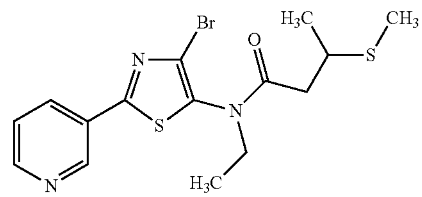 [SMILES: CCN(C(=O)CC(C)SC)c1sc(-c2cccnc2)nc1Br] |
| 481 | dirt yellow solid | 148-149 | | 433.1 (M + 1), 420.2 (M − 1), | 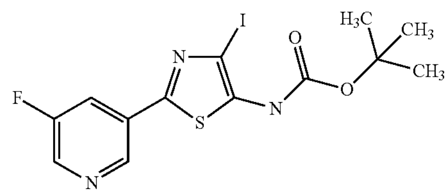 [SMILES: CC(C)(C)OC(=O)Nc1sc(-c2cncc(F)c2)nc1I] |
| 482 | yellow oil | | 1715.43 | 320.3 (M + 1) | 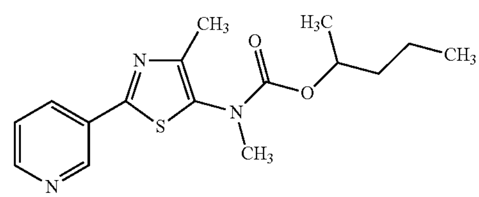 |
| 483 | yellow oil | | 1719.48 | 306.3 (M + 1) | 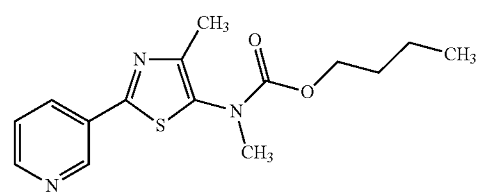 [SMILES: CCCCOC(=O)N(C)c1sc(-c2cccnc2)nc1C] |
| 484 | yellow oil | | 1716.41 | 322.2 (M + 1) | 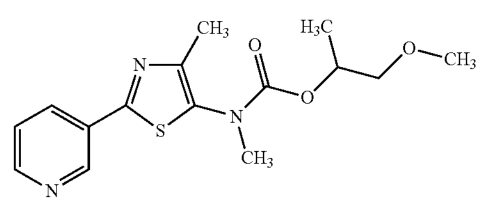 [SMILES: COCC(C)OC(=O)N(C)c1sc(-c2cccnc2)nc1C] |
| 485 | yellow oil | | 1719.95 | 308.2 (M + 1) | 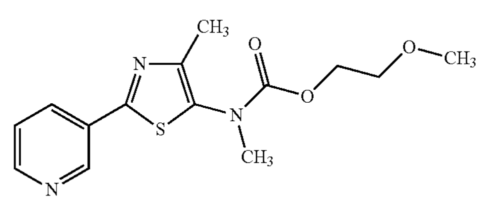 [SMILES: COCCOC(=O)N(C)c1sc(-c2cccnc2)nc1C] |

TABLE 1-continued

| Compound Number | Appearance | mp (° C.) | IR | MS (ESIMS m/z) | MOLECULAR STRUCTURE |
|---|---|---|---|---|---|
| 486 | yellow oil | | 1737.4 | 332.2 (M + 1) | 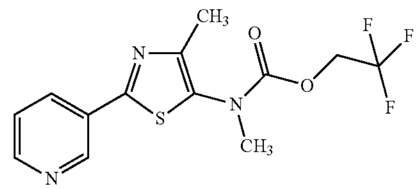 [SMILES: Cc1nc(-c2cccnc2)sc1N(C)C(=O)OCC(F)(F)F] |
| 487 | brown solid | 120-125 | | 328.1 (M + 1) | 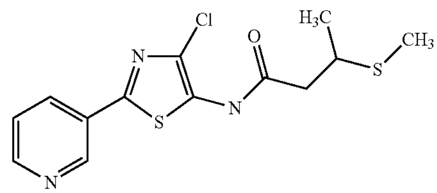 [SMILES: CSC(C)CC(=O)Nc1sc(-c2cccnc2)nc1Cl] |
| 488 | tan solid | 113-115 | | 342.2 (M + 1) | 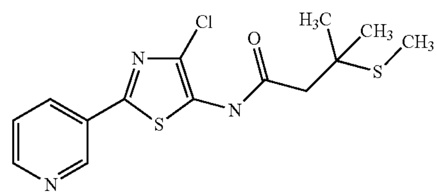 [SMILES: CSC(C)(C)CC(=O)Nc1sc(-c2cccnc2)nc1Cl] |
| 489 | yellow semi solid | | 1678.14 | 356.1 (M + 1) | 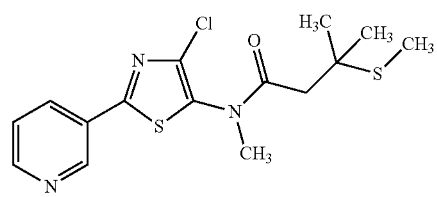 [SMILES: CSC(C)(C)CC(=O)N(C)c1sc(-c2cccnc2)nc1Cl] |
| 490 | yellow oil | | 1683.6 | 370.1 (M + 1) | 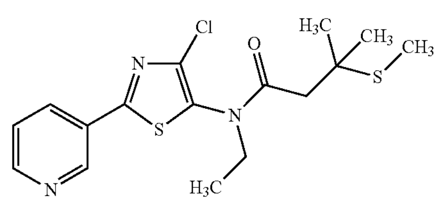 [SMILES: CCN(C(=O)CC(C)(C)SC)c1sc(-c2cccnc2)nc1Cl] |
| 491 | yellow solid | 65-69 | | 334.2 (M + 1) | 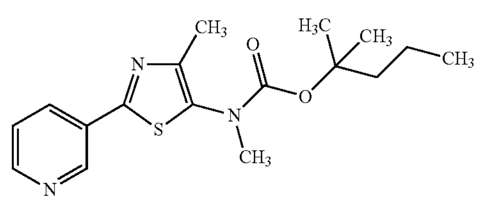 [SMILES: CCCC(C)(C)OC(=O)N(C)c1sc(-c2cccnc2)nc1C] |
| 492 | yellow oil | | 1731.07 | 360.4 (M + 1) | 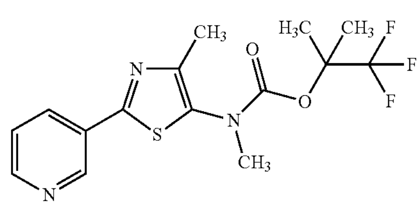 [SMILES: Cc1nc(-c2cccnc2)sc1N(C)C(=O)OC(C)(C)C(F)(F)F] |

TABLE 1-continued

| Compound Number | Appearance | mp (° C.) | IR | MS (ESIMS m/z) | MOLECULAR STRUCTURE |
|---|---|---|---|---|---|
| 493 | yellow oil | | 1715.81 | 346.2 (M + 1) | 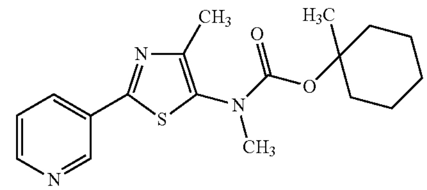 [SMILES: Cc1nc(-c2cccnc2)sc1N(C)C(=O)OC1(C)CCCCC1] |
| 494 | yellow solid | 105-106 | | 423.2 (M + 1), 422.1 (M − 1); | 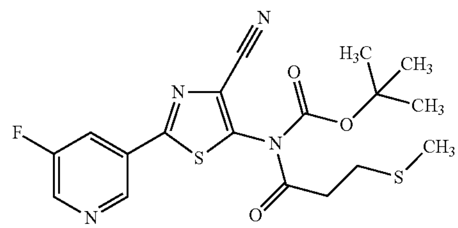 [SMILES: CSCCC(=O)N(C(=O)OC(C)(C)C)c1sc(-c2cncc(F)c2)nc1C#N] |
| 495 | yellow solid | 219-220 | | 323.1 (M + 1) 322.1 (M − 1); | 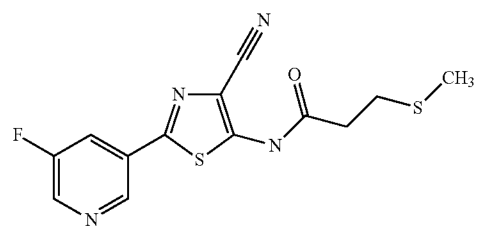 [SMILES: CSCCC(=O)Nc1sc(-c2cncc(F)c2)nc1C#N] |
| 496 | brown oil | | | 444.2 (M + 1) | 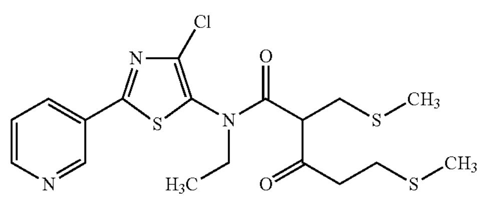 [SMILES: CCN(C(=O)C(CSC)C(=O)CCSC)c1sc(-c2cccnc2)nc1Cl] |
| 497 | yellow solid | 70-71 | | 436.1 (M + 1) | 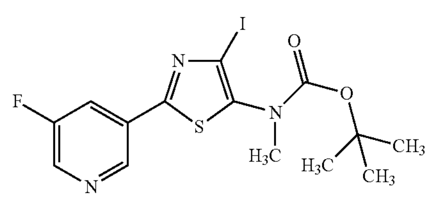 [SMILES: CN(C(=O)OC(C)(C)C)c1sc(-c2cncc(F)c2)nc1I] |
| 498 | orange oil | | 1683 | 374 (M + 2) | 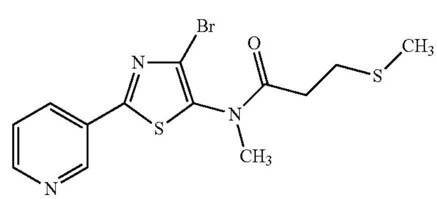 [SMILES: CSCCC(=O)N(C)c1sc(-c2cccnc2)nc1Br] |
| 499 | dark orange oil | | 1684 | 388 (M + 2) | 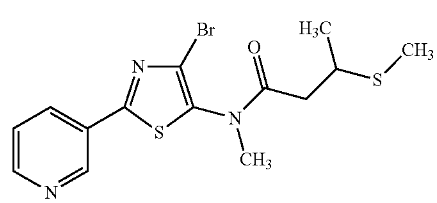 [SMILES: CSC(C)CC(=O)N(C)c1sc(-c2cccnc2)nc1Br] |

TABLE 1-continued

| Compound Number | Appearance | mp (° C.) | IR | MS (ESIMS m/z) | MOLECULAR STRUCTURE |
|---|---|---|---|---|---|
| 500 | light yellow oil | | 1686 | 362.1 (M + 1) | 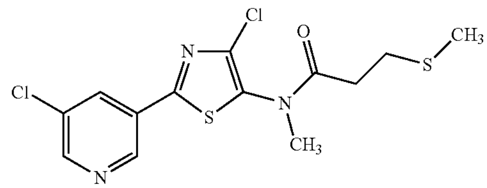 [SMILES: CSCCC(=O)N(C)c1sc(-c2cncc(Cl)c2)nc1Cl] |
| 501 | colorless oil | | 1684 | 378 (M + 1) | 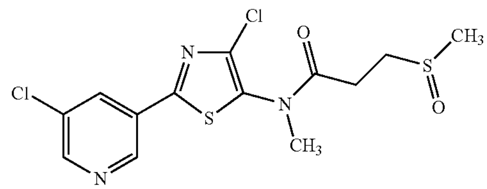 [SMILES: CN(C(=O)CCS(C)=O)c1sc(-c2cncc(Cl)c2)nc1Cl] |
| 502 | yellow solid | 231-232 | | 275.1 (M + 1) 273.1 (M − 1) | 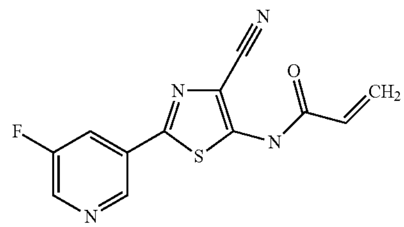 [SMILES: C=CC(=O)Nc1sc(-c2cncc(F)c2)nc1C#N] |
| 503 | yellow solid | 97-98 | | 336.1 (M + 1)+; | 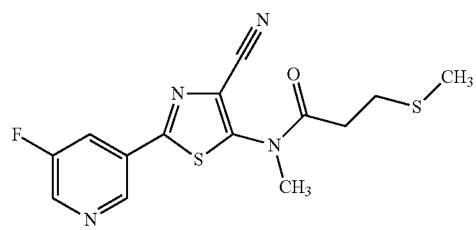 [SMILES: CSCCC(=O)N(C)c1sc(-c2cncc(F)c2)nc1C#N] |
| 504 | yellow foam | | 1681 | 404 (M + 2) | 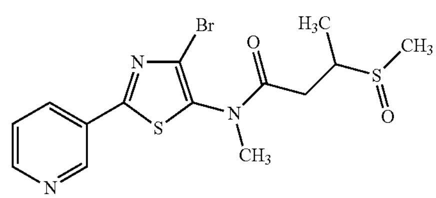 [SMILES: CC(CC(=O)N(C)c1sc(-c2cccnc2)nc1Br)S(C)=O] |
| 505 | red oil | | 1681 | 388 (M + 2) | 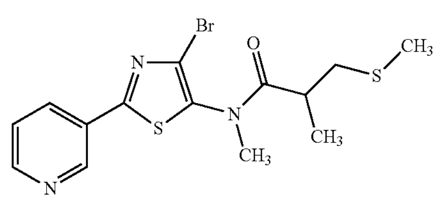 [SMILES: CSCC(C)C(=O)N(C)c1sc(-c2cccnc2)nc1Br] |
| 506 | yellow oil | | 1682 | 390 (M + 2) | 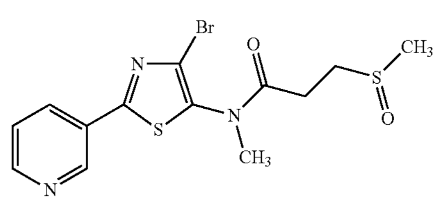 [SMILES: CN(C(=O)CCS(C)=O)c1sc(-c2cccnc2)nc1Br] |

TABLE 1-continued
| Compound Number | Appearance | mp (° C.) | IR | MS (ESIMS m/z) | MOLECULAR STRUCTURE |
|---|---|---|---|---|---|
| 507 | white foam | | 1683 | 406 (M + 2) | 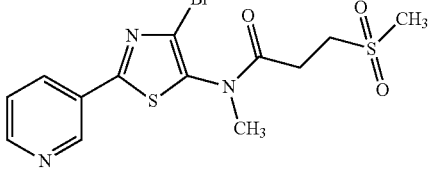 |
| 508 | red oil | | 1684, 2237 | 353.0 (M + 1) | 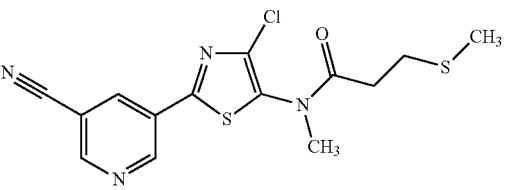 [SMILES: CSCCC(=O)N(C)c1sc(-c2cncc(C#N)c2)nc1Cl] |
| 509 | light yellow oil | | 1674 | 329.1 (M + 1) | 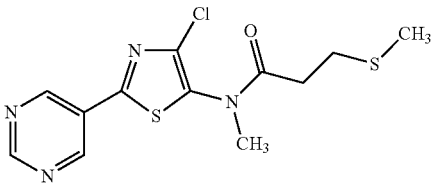 [SMILES: CSCCC(=O)N(C)c1sc(-c2cncnc2)nc1Cl] |
| 510 | white solid | 137-140 | 1684 | 345.1 (M + 1) | 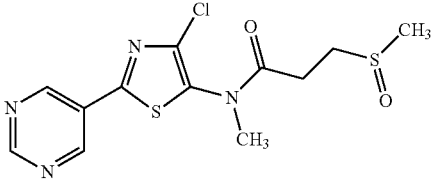 [SMILES: CN(C(=O)CCS(C)=O)c1sc(-c2cncnc2)nc1Cl] |
| 511 | sticky orange-brown solid | | 1513 | 377, 375 | 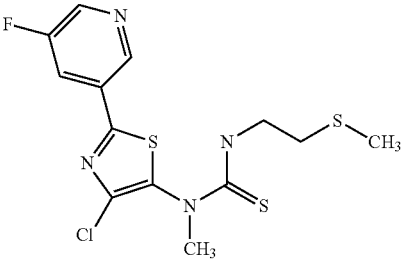 [SMILES: CSCCNC(=S)N(C)c1sc(-c2cncc(F)c2)nc1Cl] |
| 512 | brown oil | | 1521 | 457, 455 | 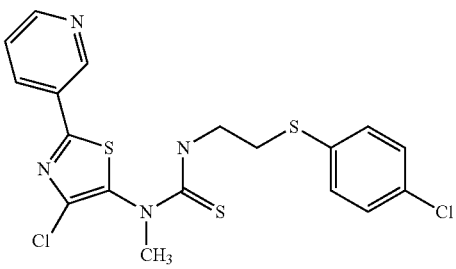 [SMILES: CN(C(=S)NCCSc1ccc(Cl)cc1)c1sc(-c2cccnc2)nc1Cl] |
| 513 | light yellow oil | | 1648 | 358.1 (M + 1) | 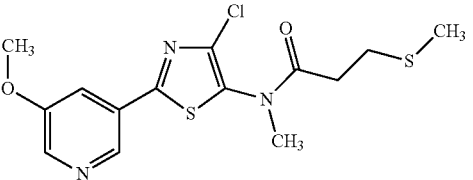 [SMILES: COc1cncc(-c2nc(Cl)c(N(C)C(=O)CCSC)s2)c1] |

TABLE 1-continued

| Compound Number | Appearance | mp (° C.) | IR | MS (ESIMS m/z) | MOLECULAR STRUCTURE |
|---|---|---|---|---|---|
| 514 | white amorphous solid | | 1683 | 374.1 (M + 1) | 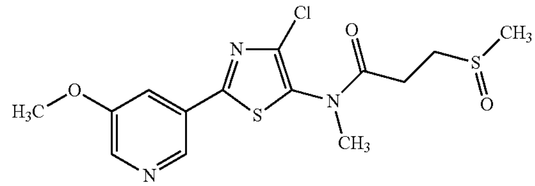 |
| 515 | off-white solid | 74-76 | 1648 | 346.1 (M + 1) | 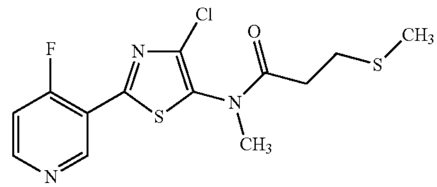 [SMILES: CSCCC(=O)N(C)c1sc(-c2cnccc2F)nc1Cl] |
| 516 | orange oil | | 1682.18 | 356.1 (M + 1) | 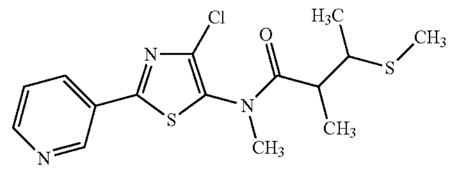 [SMILES: CSC(C)C(C)C(=O)N(C)c1sc(-c2cccnc2)nc1Cl] |
| 517 | yellow oil | | 1681.17 | 340.1 (M + 1) | 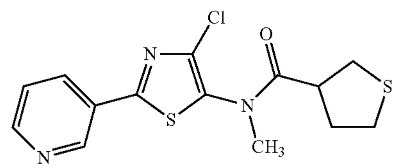 [SMILES: CN(C(=O)C1CCSC1)c1sc(-c2cccnc2)nc1Cl] |
| 518 | tan oil | | 1724 | 377 (M + 2) | 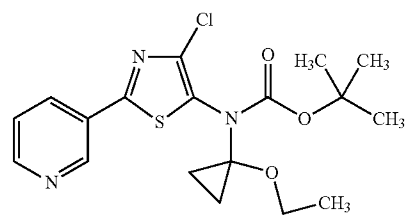 [SMILES: CCOC1(N(C(=O)OC(C)(C)C)c2sc(-c3cccnc3)nc2Cl)CC1] |
| 519 | yellow solid | 117-119 | | 323.4 (M + 1) | 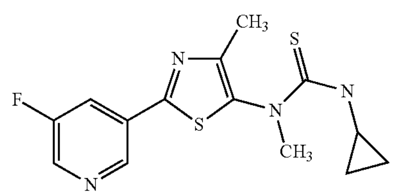 [SMILES: Cc1nc(-c2cncc(F)c2)sc1N(C)C(=S)NC1CC1] |
| 520 | light yellow oil | | 1683.5 | 358.1 (M + 1) | 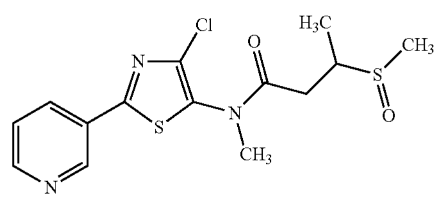 [SMILES: CC(CC(=O)N(C)c1sc(-c2cccnc2)nc1Cl)S(C)=O] |
| 521 | light yellow oil | | 1683.77 | 372.1 (M + 1) | 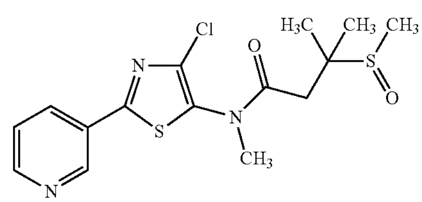 [SMILES: CN(C(=O)CC(C)(C)S(C)=O)c1sc(-c2cccnc2)nc1Cl] |

TABLE 1-continued
| Compound Number | Appearance | mp (° C.) | IR | MS (ESIMS m/z) | MOLECULAR STRUCTURE |
|---|---|---|---|---|---|
| 522 | | | 1679 | 372.1 (M + 1) | 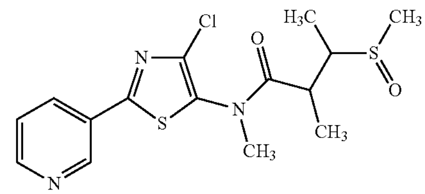 [SMILES: CC(C(=O)N(C)c1sc(-c2cccnc2)nc1Cl)C(C)S(C)=O] |
| 523 | light yellow oil | | 1678.82 | 356.1 (M + 1) | 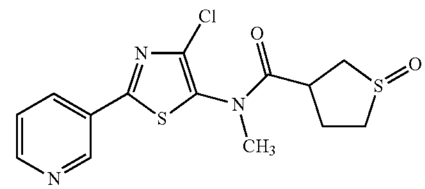 [SMILES: CN(C(=O)C1CCS(=O)C1)c1sc(-c2cccnc2)nc1Cl] |
| 524 | light yellow oil | | 1681.3 | 372.1 (M + 1) | 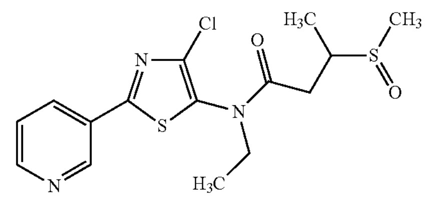 [SMILES: CCN(C(=O)CC(C)S(C)=O)c1sc(-c2cccnc2)nc1Cl] |
| 525 | thick clear oil | | 1682 | 354.1 (M + 1) | 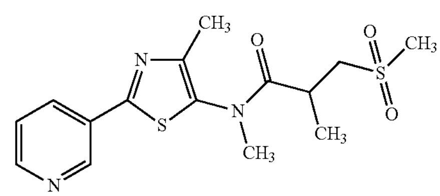 [SMILES: Cc1nc(-c2cccnc2)sc1N(C)C(=O)C(C)CS(C)(=O)=O] |
| 526 | pale yellow solid | 121-125 | 1678 | 388 (M + 1) | 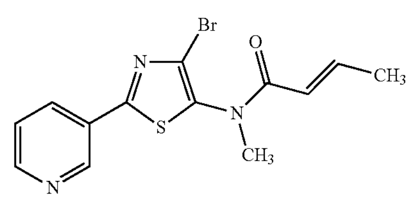 [SMILES: C/C=C/C(=O)N(C)c1sc(-c2cccnc2)nc1Br] |
| 527 | light yellow oil | | 1660 | 350.1 (M + 1) | 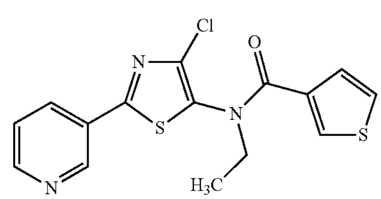 [SMILES: CCN(C(=O)c1ccsc1)c1sc(-c2cccnc2)nc1Cl] |
| 528 | light yellow oil | | 1683 | 364.1 (M + 1) | 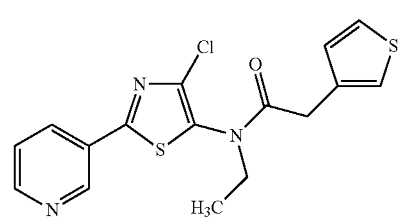 [SMILES: CCN(C(=O)Cc1ccsc1)c1sc(-c2cccnc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 529 | white solid | 82-86 | 1660 | 351.1 (M + 1) | 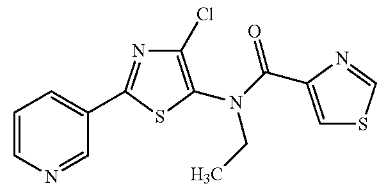 [SMILES: CCN(C(=O)c1cscn1)c1sc(-c2cccnc2)nc1Cl] |
| 530 | yellow oil | | 1686 | 324.1 (M + 1) | 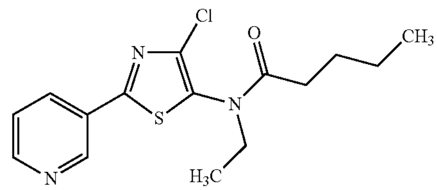 [SMILES: CCCCC(=O)N(CC)c1sc(-c2cccnc2)nc1Cl] |
| 531 | brown oil | | 1684 | 324.1 (M + 1) | 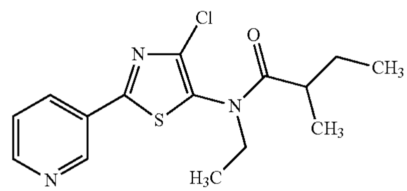 [SMILES: CCC(C)C(=O)N(CC)c1sc(-c2cccnc2)nc1Cl] |
| 533 | orange oil | | 1688 | 282.1 (M + 1) | 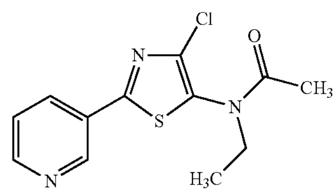 [SMILES: CCN(C(C)=O)c1sc(-c2cccnc2)nc1Cl] |
| 534 | orange oil | | 1671 | 322.1 (M + 1) | 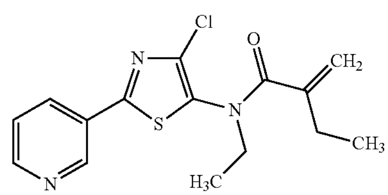 [SMILES: C=C(CC)C(=O)N(CC)c1sc(-c2cccnc2)nc1Cl] |
| 535 | brown oil | | 1675 | 294.1 (M + 1) | 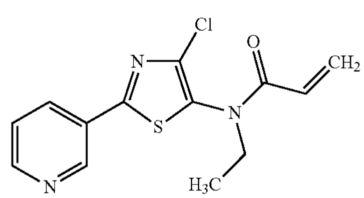 [SMILES: C=CC(=O)N(CC)c1sc(-c2cccnc2)nc1Cl] |
| 536 | yellow solid | 144-146 | | 392 (M + 1) | 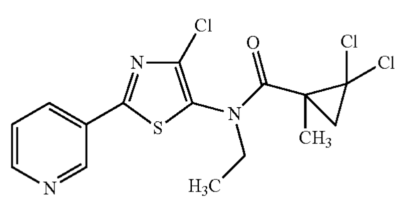 [SMILES: CCN(C(=O)C1(C)CC1(Cl)Cl)c1sc(-c2cccnc2)nc1Cl] |

TABLE 1-continued
| Compound Number | Appearance | mp (° C.) | IR | MS (ESIMS m/z) | MOLECULAR STRUCTURE |
|---|---|---|---|---|---|
| 537 | light yellow oil | | 1679.81 | 386.1 (M + 1) | 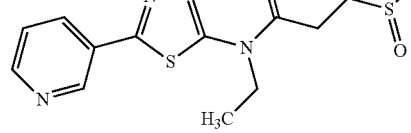 |
| 538 | dark oil | | 1679.94 | 370.1 (M + 1) | 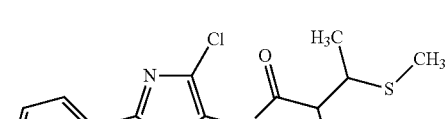 |
| 540 | yellow oil | | 1683 | 406.1 (M + 1) | 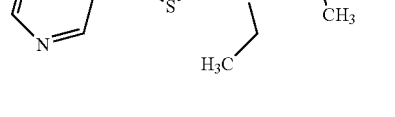 |
| 541 | white solid | 102-105 | 1674 | 405.2 (M + 1) | 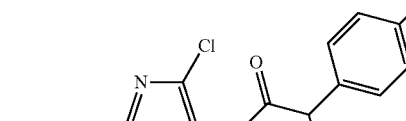 |
| 542 | yellow amorphous solid | | 1668 | 335.1 (M + 1) | 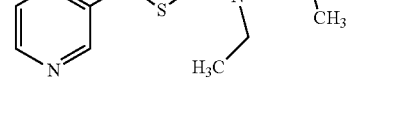 |
| 543 | yellow amorphous solid | | 1669 | 392.1 (M + 1) | 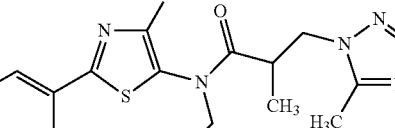 |
| 544 | light yellow oil | | 1675 | 359.1 (M + 1) | 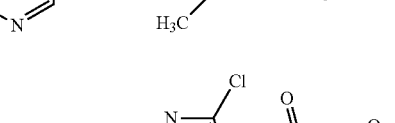 |

TABLE 1-continued

| Compound Number | Appearance | mp (° C.) | IR | MS (ESIMS m/z) | MOLECULAR STRUCTURE |
|---|---|---|---|---|---|
| 545 | light yellow oil | | 1657 | 394.1 (M + 1) | 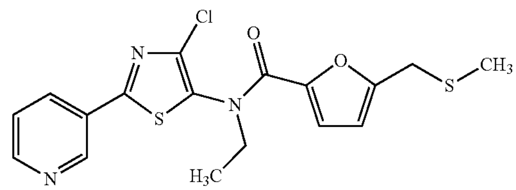 [SMILES: CCN(C(=O)c1ccc(CSC)o1)c1sc(-c2cccnc2)nc1Cl] |
| 546 | brown solid | | 2977 | 326 (M + 1) | 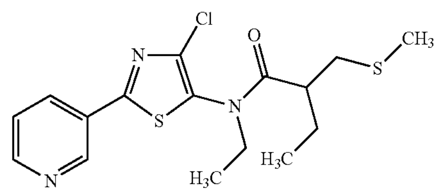 [SMILES: CCC(CSC)C(=O)N(CC)c1sc(-c2cccnc2)nc1Cl] |
| 547 | white solid | 110-111 | 1675 | 415.9 (M + 1) | 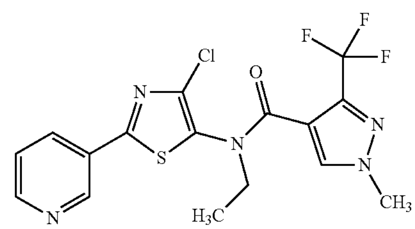 [SMILES: CCN(C(=O)c1cn(C)nc1C(F)(F)F)c1sc(-c2cccnc2)nc1Cl] |
| 548 | light yellow solid | 102-103 | 1674 | 432.8 (M + 1) | 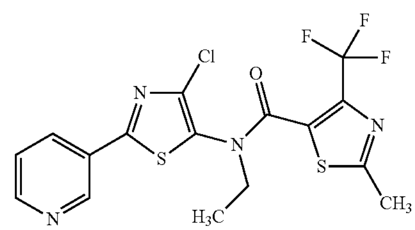 [SMILES: CCN(C(=O)c1sc(C)nc1C(F)(F)F)c1sc(-c2cccnc2)nc1Cl] |
| 549 | colorless oil | | 2925 1650 | 409.9 (M + 1) | 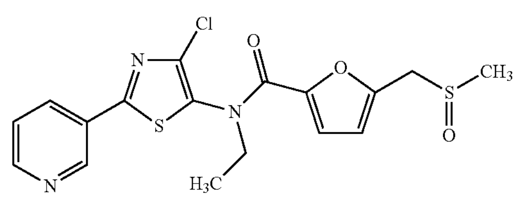 [SMILES: CCN(C(=O)c1ccc(CS(C)=O)o1)c1sc(-c2cccnc2)nc1Cl] |
| 550 | brown oil | | 1681 | 363.9 (M + 1) | 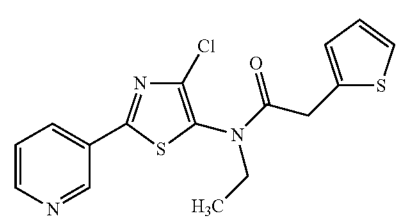 [SMILES: CCN(C(=O)Cc1cccs1)c1sc(-c2cccnc2)nc1Cl] |
| 551 | white solid | 92-94 | 1681 | 375.9 (M + 1) | 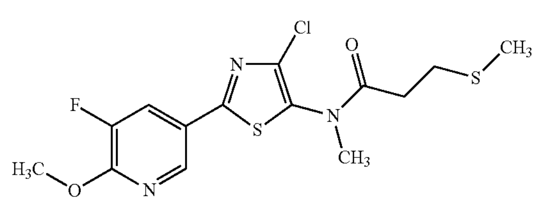 |

TABLE 1-continued
| Compound Number | Appearance | mp (° C.) | IR | MS (ESIMS m/z) | MOLECULAR STRUCTURE |
|---|---|---|---|---|---|
| 552 | yellow oil | | 1675.25 | 431.9 (M + 1) | 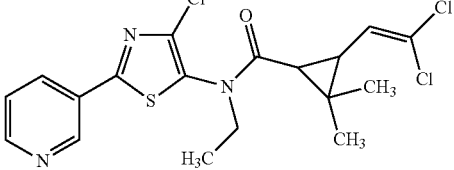 |
| 553 | dark oil | | 1682.96 | 321.9 (M + 1) | 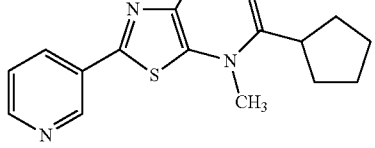 |
| 554 | light yellow oil | | 1645 | 349.8 (M + 1) | 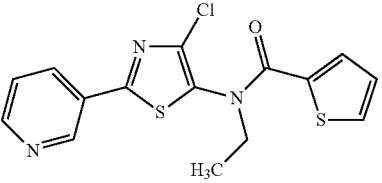 [SMILES: CCN(C(=O)c1cccs1)c1sc(-c2cccnc2)nc1Cl] |
| 555 | light yellow oil | | 1660 | 365.0 (M + 1) | 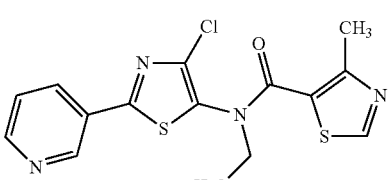 |
| 556 | light yellow oil | | 1668 | 365.9 (M + 1) | 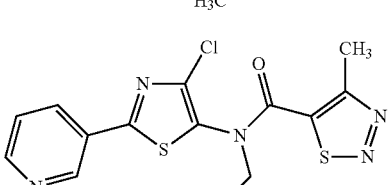 |
| 557 | red oil | | 1683 | 405.9 (M + 1) | 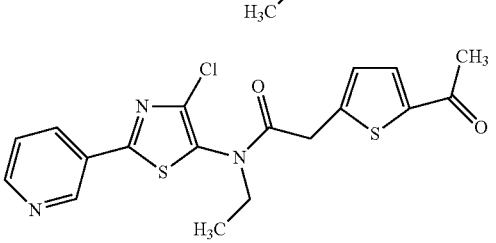 |
| 558 | white solid | 132-135 | 1684 | 391.9 (M + 1) | 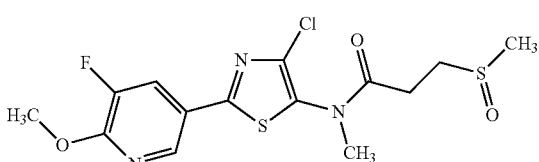 |
| 559 | pale yellow oil | | 1674 | 386 (M + 1) | 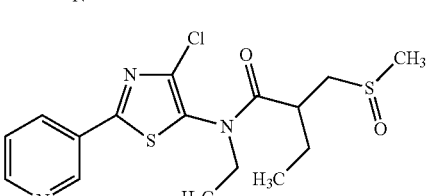 |

TABLE 1-continued

| Compound Number | Appearance | mp (° C.) | IR | MS (ESIMS m/z) | MOLECULAR STRUCTURE |
|---|---|---|---|---|---|
| 560 | pale yellow oil | | 1675 | 402 (M + 1) | 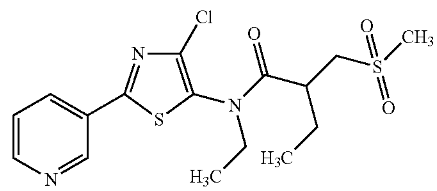 [SMILES: CCC(CS(C)(=O)=O)C(=O)N(CC)c1sc(-c2cccnc2)nc1Cl] |
| 561 | dark brown oil | | 1684 | 392.9 (M + 1) | 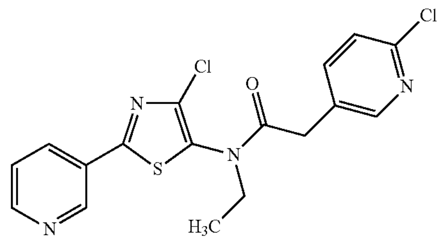 [SMILES: CCN(C(=O)Cc1ccc(Cl)nc1)c1sc(-c2cccnc2)nc1Cl] |
| 562 | dark brown oil | | 2926 1681 | 358.9 (M + 1) | 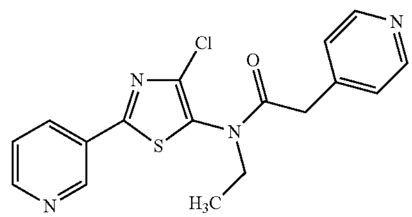 [SMILES: CCN(C(=O)Cc1ccncc1)c1sc(-c2cccnc2)nc1Cl] |
| 563 | light yellow oil | | 1683 | 379.9 (M + 1) | 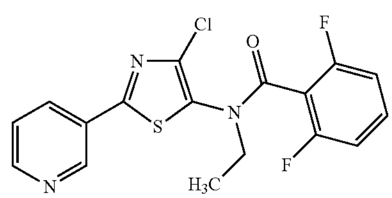 [SMILES: CCN(C(=O)c1c(F)cccc1F)c1sc(-c2cccnc2)nc1Cl] |
| 564 | white solid | 172-174 | 1674 | 413.8 (M + 1) | 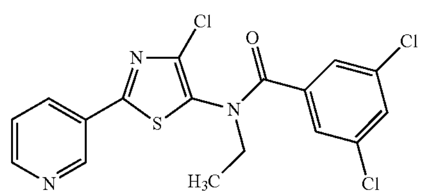 [SMILES: CCN(C(=O)c1cc(Cl)cc(Cl)c1)c1sc(-c2cccnc2)nc1Cl] |
| 565 | yellow oil | | 1673.19 | 388.0 (M + 2) | 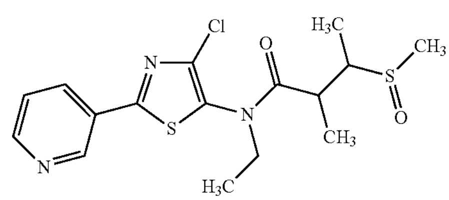 [SMILES: CCN(C(=O)C(C)C(C)S(C)=O)c1sc(-c2cccnc2)nc1Cl] |
| 566 | yellow oil | | 1669.72 | 307.98 (M + 1) | 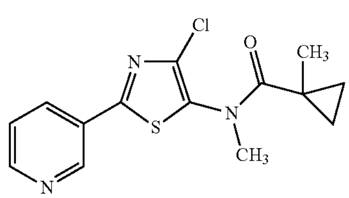 [SMILES: CN(C(=O)C1(C)CC1)c1sc(-c2cccnc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 567 | tan solid | 63-68 | | 367.6 (M + 1) | 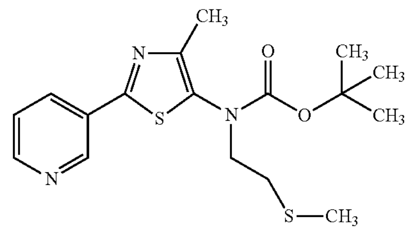 [SMILES: CSCCN(C(=O)OC(C)(C)C)c1sc(-c2cccnc2)nc1C] |
| 568 | clear oil | | | 398 (M + 1) | 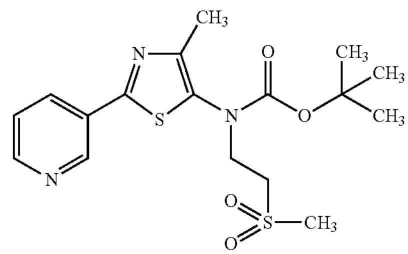 [SMILES: Cc1nc(-c2cccnc2)sc1N(CCS(C)(=O)=O)C(=O)OC(C)(C)C] |
| 569 | dark oil | | 1675.09 | 307.98 (M + 1) | 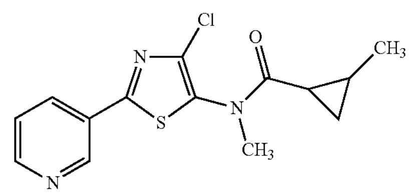 [SMILES: CC1CC1C(=O)N(C)c1sc(-c2cccnc2)nc1Cl] |
| 570 | yellow solid | 118-120 | 1658 | 335.1 (M + 1) | 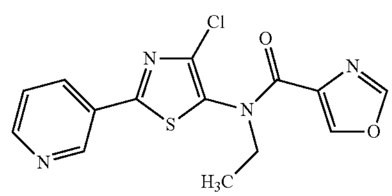 [SMILES: CCN(C(=O)c1cocn1)c1sc(-c2cccnc2)nc1Cl] |
| 571 | colorless oil | | 1669 | 345.1 (M + 1) | 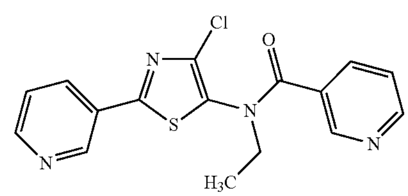 [SMILES: CCN(C(=O)c1cccnc1)c1sc(-c2cccnc2)nc1Cl] |
| 573 | yellow oil | | 1656 | 334.0 (M + 1) | 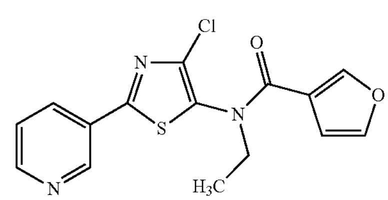 [SMILES: CCN(C(=O)c1ccoc1)c1sc(-c2cccnc2)nc1Cl] |
| 574 | dark brown oil | | 1669 | 345.5 (M + 1) | 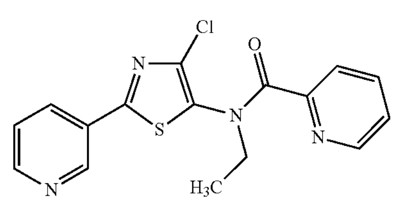 [SMILES: CCN(C(=O)c1ccccn1)c1sc(-c2cccnc2)nc1Cl] |

TABLE 1-continued

| Compound Number | Appearance | mp (° C.) | IR | MS (ESIMS m/z) | MOLECULAR STRUCTURE |
|---|---|---|---|---|---|
| 575 | yellow oil | | 1684 | 394.0 (M + 2) | 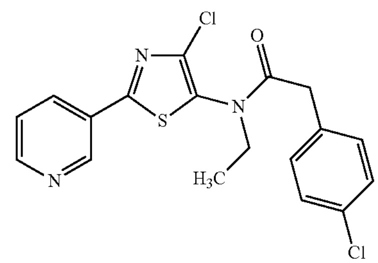 [SMILES: CCN(C(=O)Cc1ccc(Cl)cc1)c1sc(-c2cccnc2)nc1Cl] |
| 576 | yellow oil | | 1658 | 336.0 (M + 2) | 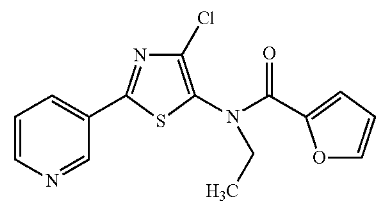 [SMILES: CCN(C(=O)c1ccco1)c1sc(-c2cccnc2)nc1Cl] |
| 577 | white solid | 115-117 | 1672 | 418.0 (M + 2) | 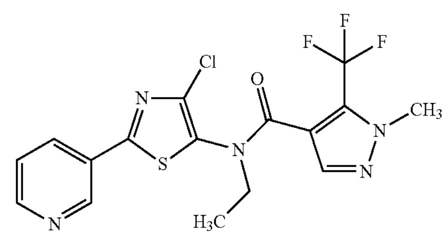 [SMILES: CCN(C(=O)c1cnn(C)c1C(F)(F)F)c1sc(-c2cccnc2)nc1Cl] |
| 578 | yellow oil | | 1659 | 404.1 (M + 1) | 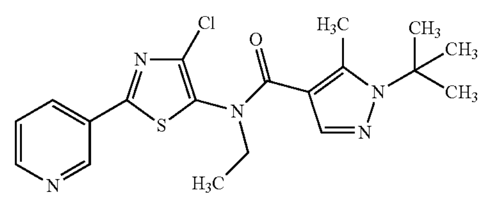 [SMILES: CCN(C(=O)c1cnn(C(C)(C)C)c1C)c1sc(-c2cccnc2)nc1Cl] |
| 579 | yellow solid | 46-49 | 1653 | 425.5 (M + 1) | 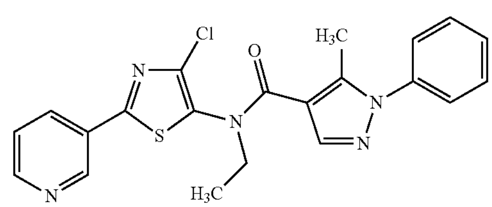 [SMILES: CCN(C(=O)c1cnn(-c2ccccc2)c1C)c1sc(-c2cccnc2)nc1Cl] |
| 580 | yellow solid | 51-60 | | 435.5 (M + 1) | 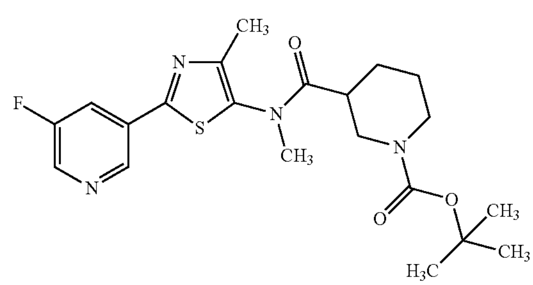 [SMILES: Cc1nc(-c2cncc(F)c2)sc1N(C)C(=O)C1CCCN(C(=O)OC(C)(C)C)C1] |

TABLE 1-continued

| Compound Number | Appearance | mp (° C.) | IR | MS (ESIMS m/z) | MOLECULAR STRUCTURE |
|---|---|---|---|---|---|
| 581 | yellow oil | | | 334.5 (M + 1) | 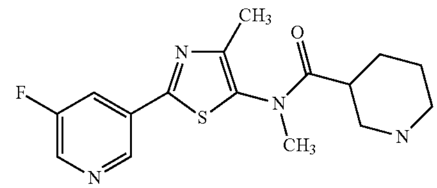 [SMILES: Cc1nc(-c2cncc(F)c2)sc1N(C)C(=O)C1CCCNC1] |
| 582 | clear oil | | | 433.5 (M + 1) | 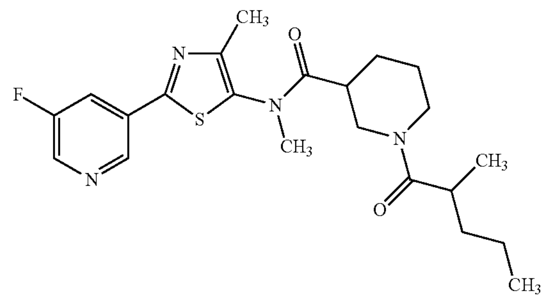 [SMILES: CCCC(C)C(=O)N1CCCC(C(=O)N(C)c2sc(-c3cncc(F)c3)nc2C)C1] |
| 583 | clear oil | | | 407.4 (M + 1) | 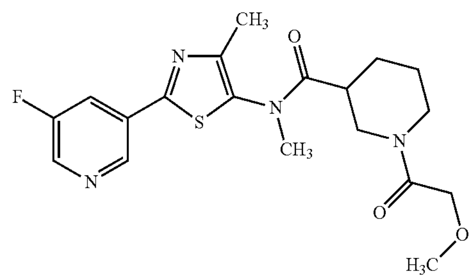 [SMILES: COCC(=O)N1CCCC(C(=O)N(C)c2sc(-c3cncc(F)c3)nc2C)C1] |
| 584 | clear oil | | | 445.4 (M + 1) | 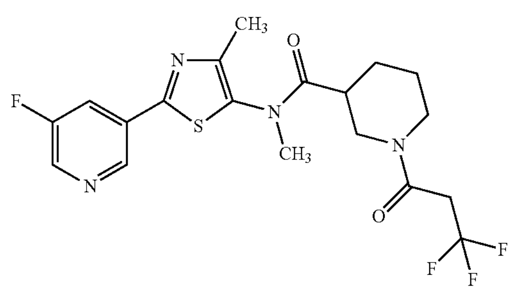 [SMILES: Cc1nc(-c2cncc(F)c2)sc1N(C)C(=O)C1CCCN(C(=O)CC(F)(F)F)C1] |
| 585 | off-white solid | 190-192 | | 434.5 (M + 1) | 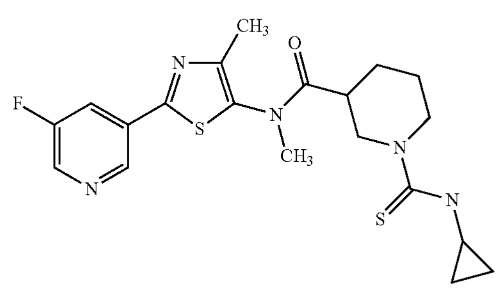 [SMILES: Cc1nc(-c2cncc(F)c2)sc1N(C)C(=O)C1CCCN(C(=S)NC2CC2)C1] |

TABLE 1-continued

| Compound Number | Appearance | mp (° C.) | IR | MS (ESIMS m/z) | MOLECULAR STRUCTURE |
|---|---|---|---|---|---|
| 586 | yellow oil | | | 407.4 (M + 1) | 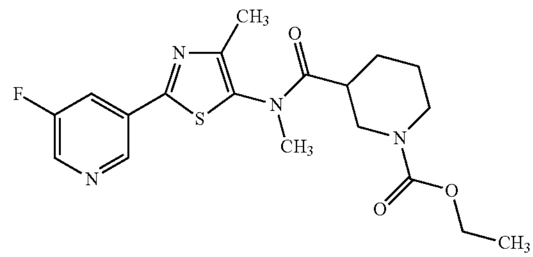 [SMILES: CCOC(=O)N1CCCC(C(=O)N(C)c2sc(-c3cncc(F)c3)nc2C)C1] |
| 587 | orange semi-solid | | | 391.5 (M + 1) | 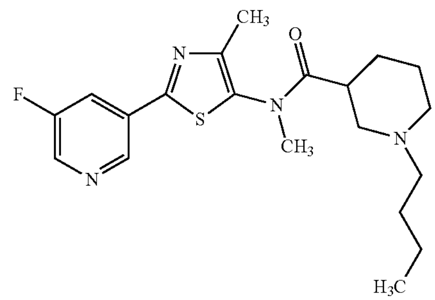 [SMILES: CCCCN1CCCC(C(=O)N(C)c2sc(-c3cncc(F)c3)nc2C)C1] |
| 588 | | | 1681.88 | 328.05 (M + 1) | 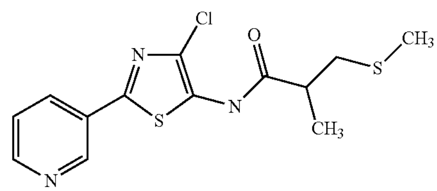 [SMILES: CSCC(C)C(=O)Nc1sc(-c2cccnc2)nc1Cl] |
| 589 | yellow solid | 72-74 | | 326.1 (M + 1), 324.1 (M − 1) | 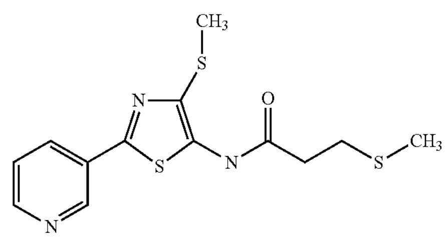 [SMILES: CSCCC(=O)Nc1sc(-c2cccnc2)nc1SC] |

TABLE 2

Biological Results

| Compound Number | MYZUPE 200 ppm | APHIGO 200 ppm | BEMITA 200 ppm |
|---|---|---|---|
| 1 | B | C | A |
| 2 | B | C | B |
| 3 | B | C | B |
| 4 | B | C | B |
| 5 | C | C | C |
| 6 | B | C | B |
| 7 | B | C | B |
| 8 | A | C | C |
| 9 | A | C | A |
| 10 | B | C | A |
| 11 | B | C | C |
| 12 | A | C | A |
| 13 | A | C | A |
| 14 | B | C | A |
| 15 | A | C | A |
| 16 | B | C | A |
| 17 | A | C | A |
| 18 | A | C | A |
| 19 | A | B | B |
| 20 | A | C | A |
| 21 | A | C | A |
| 22 | B | C | B |
| 23 | A | C | B |
| 24 | A | C | A |
| 25 | A | C | B |
| 26 | B | C | B |
| 27 | A | C | B |
| 28 | A | C | A |
| 29 | A | C | A |
| 30 | A | C | B |
| 31 | A | C | A |
| 32 | A | C | A |
| 33 | B | C | A |
| 34 | A | C | A |
| 35 | A | C | A |
| 36 | A | C | A |

TABLE 2-continued

Biological Results

| Compound Number | MYZUPE 200 ppm | APHIGO 200 ppm | BEMITA 200 ppm |
|---|---|---|---|
| 37 | A | C | A |
| 38 | A | C | A |
| 39 | A | C | A |
| 40 | A | C | A |
| 41 | A | C | A |
| 42 | A | C | A |
| 43 | A | C | A |
| 44 | A | C | A |
| 45 | B | C | A |
| 46 | B | C | B |
| 47 | A | C | A |
| 48 | A | C | A |
| 49 | B | C | A |
| 50 | A | C | A |
| 51 | A | C | A |
| 52 | B | C | A |
| 53 | B | C | A |
| 54 | A | C | A |
| 55 | A | C | A |
| 56 | A | C | A |
| 57 | A | C | A |
| 58 | A | C | A |
| 59 | B | C | A |
| 60 | B | C | B |
| 61 | B | C | B |
| 62 | B | C | B |
| 63 | B | C | B |
| 64 | B | C | B |
| 65 | B | C | B |
| 66 | A | C | A |
| 67 | B | C | B |
| 68 | A | C | A |
| 69 | B | C | A |
| 70 | B | C | B |
| 71 | A | C | C |
| 72 | A | C | B |
| 73 | A | C | A |
| 74 | A | C | A |
| 75 | A | C | B |
| 76 | A | C | A |
| 77 | A | C | B |
| 78 | A | C | B |
| 79 | A | C | B |
| 80 | A | C | A |
| 81 | A | C | A |
| 82 | A | C | B |
| 83 | A | C | A |
| 84 | A | C | C |
| 85 | A | C | A |
| 86 | A | C | A |
| 87 | A | C | A |
| 88 | A | C | A |
| 89 | B | C | A |
| 90 | A | C | A |
| 91 | A | C | A |
| 92 | A | C | B |
| 93 | A | C | B |
| 94 | A | C | B |
| 95 | A | C | A |
| 96 | A | C | A |
| 97 | A | C | A |
| 98 | A | C | A |
| 99 | A | C | A |
| 100 | A | C | B |
| 101 | A | C | A |
| 120 | C | C | C |
| 133 | A | C | B |
| 134 | A | C | B |
| 135 | A | C | B |
| 136 | A | C | B |
| 137 | B | C | B |
| 138 | A | C | A |
| 139 | A | C | A |
| 140 | A | C | B |
| 141 | A | C | A |
| 142 | A | C | B |
| 143 | A | C | B |
| 144 | A | C | B |
| 145 | A | C | B |
| 146 | A | C | B |
| 147 | A | C | B |
| 148 | A | C | B |
| 149 | B | C | B |
| 150 | A | C | B |
| 151 | B | C | B |
| 152 | B | C | B |
| 153 | B | C | A |
| 154 | B | C | B |
| 155 | B | C | B |
| 156 | A | C | B |
| 157 | B | C | B |
| 158 | B | C | B |
| 159 | A | C | A |
| 160 | B | C | B |
| 161 | B | C | B |
| 162 | A | C | A |
| 163 | A | C | B |
| 164 | A | C | B |
| 165 | A | C | A |
| 166 | A | C | A |
| 167 | B | C | A |
| 168 | A | C | A |
| 169 | B | C | A |
| 170 | B | C | B |
| 171 | A | C | B |
| 172 | A | C | A |
| 173 | A | C | A |
| 174 | A | C | A |
| 175 | B | C | B |
| 176 | B | C | B |
| 177 | A | C | B |
| 178 | A | C | B |
| 179 | A | C | A |
| 180 | A | C | A |
| 181 | A | C | B |
| 182 | A | C | B |
| 183 | A | C | A |
| 184 | A | C | A |
| 185 | A | C | A |
| 186 | B | C | B |
| 187 | A | C | B |
| 188 | A | C | A |
| 189 | A | C | A |
| 190 | A | C | A |
| 191 | A | C | B |
| 192 | A | C | A |
| 193 | A | C | A |
| 194 | A | C | A |
| 195 | A | C | A |
| 196 | A | C | A |
| 197 | A | C | B |
| 198 | A | C | A |
| 199 | A | C | A |
| 200 | A | C | A |
| 201 | B | C | B |
| 202 | B | C | B |
| 203 | A | C | A |
| 204 | A | C | B |
| 205 | A | C | A |
| 206 | A | C | A |
| 207 | A | C | A |
| 208 | B | C | B |
| 209 | A | C | B |
| 210 | A | A | A |
| 211 | A | C | A |
| 212 | A | C | A |
| 213 | A | C | A |
| 214 | A | C | A |
| 215 | A | C | A |
| 216 | A | C | A |

TABLE 2-continued

Biological Results

| Compound Number | MYZUPE 200 ppm | APHIGO 200 ppm | BEMITA 200 ppm |
|---|---|---|---|
| 217 | A | C | B |
| 218 | A | A | A |
| 219 | A | C | B |
| 220 | A | C | A |
| 221 | A | C | B |
| 222 | A | C | B |
| 223 | A | C | A |
| 224 | A | C | A |
| 225 | A | C | A |
| 226 | A | A | A |
| 227 | A | A | A |
| 228 | A | A | A |
| 229 | A | A | B |
| 230 | A | A | A |
| 231 | A | C | A |
| 232 | B | C | A |
| 233 | A | A | A |
| 234 | A | A | A |
| 235 | A | A | A |
| 236 | A | C | A |
| 237 | A | C | A |
| 238 | A | C | A |
| 239 | A | C | A |
| 240 | A | A | A |
| 241 | A | A | A |
| 242 | A | B | A |
| 243 | A | A | A |
| 244 | B | B | B |
| 245 | A | A | A |
| 246 | A | C | A |
| 247 | A | A | A |
| 248 | A | C | A |
| 249 | A | B | A |
| 250 | A | B | B |
| 251 | B | C | A |
| 252 | A | C | A |
| 253 | A | A | A |
| 254 | A | A | A |
| 255 | A | A | A |
| 256 | A | C | A |
| 257 | A | C | A |
| 258 | A | C | A |
| 259 | A | C | A |
| 260 | A | C | A |
| 261 | A | C | A |
| 262 | A | A | A |
| 263 | A | C | A |
| 264 | A | C | A |
| 265 | A | C | B |
| 266 | A | C | A |
| 267 | A | C | A |
| 268 | A | C | A |
| 269 | A | C | A |
| 270 | A | B | A |
| 271 | A | C | A |
| 272 | A | A | A |
| 273 | A | C | A |
| 274 | A | A | A |
| 275 | A | C | A |
| 276 | A | C | B |
| 277 | A | C | A |
| 278 | A | C | A |
| 279 | A | A | A |
| 280 | B | C | B |
| 281 | B | C | B |
| 282 | A | C | A |
| 283 | B | C | B |
| 284 | A | C | A |
| 285 | A | C | A |
| 286 | A | C | A |
| 287 | A | C | A |
| 288 | A | A | A |
| 289 | A | A | A |
| 290 | B | C | B |
| 291 | B | C | B |
| 292 | B | C | A |
| 293 | A | C | B |
| 294 | B | C | B |
| 295 | B | C | A |
| 296 | A | C | A |
| 297 | B | C | B |
| 298 | A | C | B |
| 299 | A | C | A |
| 300 | A | C | B |
| 301 | A | C | A |
| 302 | B | C | A |
| 303 | B | C | A |
| 304 | A | C | A |
| 305 | A | C | A |
| 306 | A | C | B |
| 307 | A | C | B |
| 308 | A | C | A |
| 309 | B | C | B |
| 310 | B | C | C |
| 311 | A | C | C |
| 312 | A | C | A |
| 313 | A | C | A |
| 314 | A | C | A |
| 315 | A | C | A |
| 316 | A | C | B |
| 317 | A | C | B |
| 318 | A | C | B |
| 319 | A | C | A |
| 320 | A | C | B |
| 321 | A | C | B |
| 322 | A | C | B |
| 323 | A | C | B |
| 324 | A | C | B |
| 325 | A | C | A |
| 326 | B | C | B |
| 327 | B | C | B |
| 328 | B | C | B |
| 329 | B | C | B |
| 330 | B | C | B |
| 331 | B | C | A |
| 332 | A | C | B |
| 333 | A | C | B |
| 334 | A | C | B |
| 335 | A | C | A |
| 336 | A | C | A |
| 337 | B | C | A |
| 338 | C | C | A |
| 339 | B | C | A |
| 340 | A | C | B |
| 341 | B | C | B |
| 342 | B | C | B |
| 343 | A | C | B |
| 344 | B | C | B |
| 345 | A | C | A |
| 346 | B | C | A |
| 347 | B | C | B |
| 348 | A | C | A |
| 349 | A | C | A |
| 350 | B | C | B |
| 351 | B | C | B |
| 352 | A | C | B |
| 353 | B | C | A |
| 354 | A | C | A |
| 355 | A | C | B |
| 356 | A | C | A |
| 357 | A | C | A |
| 358 | A | C | A |
| 359 | A | C | A |
| 360 | A | C | B |
| 361 | A | C | B |
| 363 | B | C | A |
| 364 | A | C | A |
| 365 | A | C | B |
| 366 | A | C | A |
| 367 | A | C | B |

TABLE 2-continued

Biological Results

| Compound Number | MYZUPE 200 ppm | APHIGO 200 ppm | BEMITA 200 ppm |
|---|---|---|---|
| 368 | A | C | A |
| 369 | A | C | A |
| 370 | A | C | A |
| 371 | A | C | A |
| 372 | A | C | A |
| 373 | A | C | A |
| 374 | A | C | A |
| 375 | B | C | B |
| 376 | A | C | A |
| 377 | B | C | A |
| 378 | A | C | A |
| 379 | A | C | B |
| 380 | B | C | B |
| 381 | B | C | B |
| 382 | B | C | B |
| 383 | B | C | A |
| 384 | A | C | A |
| 385 | A | C | B |
| 386 | A | C | A |
| 387 | B | C | A |
| 388 | A | C | A |
| 389 | B | C | B |
| 390 | B | C | A |
| 391 | A | C | A |
| 392 | A | C | A |
| 393 | A | C | A |
| 394 | A | C | A |
| 395 | B | C | B |
| 396 | A | C | A |
| 397 | A | C | A |
| 398 | B | C | A |
| 399 | A | C | A |
| 400 | C | C | C |
| 401 | A | C | A |
| 402 | A | C | A |
| 403 | A | C | B |
| 404 | A | C | B |
| 405 | A | C | B |
| 406 | A | C | B |
| 407 | A | C | B |
| 408 | A | C | A |
| 409 | A | C | A |
| 410 | A | C | A |
| 411 | A | C | A |
| 412 | A | C | A |
| 413 | A | C | B |
| 414 | A | C | A |
| 415 | A | C | A |
| 416 | A | C | A |
| 417 | A | C | A |
| 418 | A | C | A |
| 420 | B | C | A |
| 421 | A | C | B |
| 422 | A | C | B |
| 423 | B | C | A |
| 424 | A | C | A |
| 425 | A | C | A |
| 426 | A | C | A |
| 427 | A | C | A |
| 428 | B | C | B |
| 429 | A | C | B |
| 430 | A | C | B |
| 431 | A | C | B |
| 432 | B | C | B |
| 433 | A | C | A |
| 434 | A | C | A |
| 435 | B | C | B |
| 436 | B | C | B |
| 437 | B | C | B |
| 438 | A | C | B |
| 439 | B | C | B |
| 440 | B | C | B |
| 441 | A | C | A |
| 442 | A | C | A |
| 443 | A | C | A |
| 444 | A | C | A |
| 445 | A | C | A |
| 446 | A | C | A |
| 447 | A | C | A |
| 448 | A | C | A |
| 449 | A | C | A |
| 450 | A | C | A |
| 451 | A | C | B |
| 452 | A | C | A |
| 453 | A | C | A |
| 454 | A | C | A |
| 455 | A | C | A |
| 456 | A | C | B |
| 457 | A | C | A |
| 458 | A | C | A |
| 459 | A | C | B |
| 460 | B | C | B |
| 461 | A | C | B |
| 462 | A | C | B |
| 463 | B | C | B |
| 464 | A | C | B |
| 465 | A | C | B |
| 466 | A | C | B |
| 467 | A | C | B |
| 468 | A | C | B |
| 469 | A | C | B |
| 470 | A | C | B |
| 471 | A | C | B |
| 472 | A | C | B |
| 473 | C | C | B |
| 474 | B | C | B |
| 475 | B | C | B |
| 476 | A | C | B |
| 477 | C | C | C |
| 478 | A | C | B |
| 480 | A | C | A |
| 481 | B | C | B |
| 482 | A | C | A |
| 483 | B | C | A |
| 484 | B | C | A |
| 485 | A | C | A |
| 486 | A | C | B |
| 487 | A | C | A |
| 488 | A | C | A |
| 489 | A | C | A |
| 490 | A | C | B |
| 491 | A | C | A |
| 492 | B | C | A |
| 493 | A | C | A |
| 494 | B | C | B |
| 495 | B | C | B |
| 496 | A | C | B |
| 497 | A | C | A |
| 498 | A | C | A |
| 499 | A | C | B |
| 500 | A | C | A |
| 501 | A | C | A |
| 502 | B | C | B |
| 503 | B | C | B |
| 504 | A | C | A |
| 505 | A | C | A |
| 506 | A | C | B |
| 507 | A | C | A |
| 508 | B | C | A |
| 509 | A | C | A |
| 510 | A | C | A |
| 511 | A | C | B |
| 512 | B | C | A |
| 513 | B | C | B |
| 514 | B | C | B |
| 515 | B | C | B |
| 516 | A | C | B |
| 517 | A | C | B |
| 518 | A | C | B |
| 519 | A | C | B |

TABLE 2-continued

| | Biological Results | | |
|---|---|---|---|
| Compound Number | MYZUPE 200 ppm | APHIGO 200 ppm | BEMITA 200 ppm |
| 520 | A | C | B |
| 521 | A | C | B |
| 522 | A | C | B |
| 523 | A | C | B |
| 524 | A | C | A |
| 525 | C | C | C |
| 526 | A | C | A |
| 527 | B | C | A |
| 528 | B | C | A |
| 529 | A | C | B |
| 530 | A | C | A |
| 531 | A | C | A |
| 533 | A | C | A |
| 534 | B | C | A |
| 535 | B | C | A |
| 536 | B | C | B |
| 537 | A | C | B |
| 538 | A | C | A |
| 540 | A | C | A |
| 541 | A | C | B |
| 542 | A | C | A |
| 543 | A | C | A |
| 544 | A | C | B |
| 545 | A | C | B |
| 546 | A | C | A |
| 547 | A | C | A |
| 548 | A | C | A |
| 549 | A | C | A |
| 550 | B | C | A |
| 551 | B | C | B |
| 552 | A | C | B |
| 553 | B | C | A |
| 554 | B | C | B |
| 555 | A | C | B |
| 556 | A | C | B |
| 557 | B | C | B |
| 558 | B | C | B |
| 559 | A | C | A |
| 560 | A | C | A |
| 561 | A | C | B |
| 562 | A | C | B |
| 563 | A | C | B |
| 564 | B | C | B |
| 565 | A | C | A |
| 566 | A | C | A |
| 567 | A | C | B |
| 568 | B | C | B |
| 569 | A | C | A |
| 570 | A | C | B |
| 571 | A | C | B |
| 573 | B | C | B |
| 574 | A | C | B |
| 575 | A | C | B |
| 576 | A | C | B |
| 577 | A | C | B |
| 578 | A | C | A |
| 579 | A | C | B |
| 580 | B | C | A |
| 581 | B | C | B |
| 582 | A | C | A |
| 583 | A | C | A |
| 584 | B | C | B |
| 585 | A | C | B |
| 586 | A | C | A |
| 587 | A | C | A |
| 588 | A | C | A |
| 589 | B | C | B |

We claim:

1. A molecule having the following formula ("Formula I"), and isotopes and stereoisomers thereof:

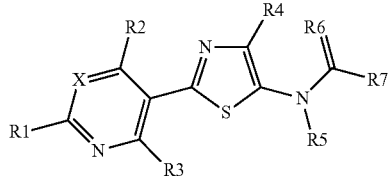

Formula I wherein:
(a) X is N or CR8;
(b) R1 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
   wherein each said R1, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);
(c) R2 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
   wherein each said R2, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, $C_6$-$C_{20}$ aryl, or $C_1$-$C_{20}$ heterocyclyl, (each of which that can be substituted, may optionally be substituted with R9);
(d) R3 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, S(O)$_n$OR9, or R9S(O)$_n$R9,
   wherein each said R3, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, $S(O)_n$OR9, $C_6$-$C_{20}$ aryl, or $C_1$-$C_{20}$ heterocyclyl, (each of which that can be substituted, may optionally be substituted with R9);

(e) R4 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, $S(O)_n$OR9, or R9$S(O)_n$R9, wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, $S(O)_n$OR9, $C_6$-$C_{20}$ aryl, or $C_1$-$C_{20}$ heterocyclyl, (each of which that can be substituted, may optionally be substituted with R9);

(f) R5 is H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, $S(O)_n$OR9, R9$S(O)_n$R9, $C_1$-$C_6$ alkyl $C_6$-$C_{20}$ aryl (wherein the alkyl and aryl can independently be substituted or unsubstituted), C(=X2)R9, C(=X1)X2R9, R9X2C(=X1)R9, R9X2R9, C(=O)($C_1$-$C_6$ alkyl)$S(O)_n$($C_1$-$C_6$ alkyl), C(=O)($C_1$-$C_6$ alkyl)C(=O)O($C_1$-$C_6$ alkyl), ($C_1$-$C_6$ alkyl)OC(=O)($C_1$-$C_6$ alkyl), $C_1$-$C_6$ alkyl-($C_3$-$C_{10}$ cyclohaloalkyl), or ($C_1$-$C_6$ alkenyl)C(=O)O($C_1$-$C_6$ alkyl), or R9X2C(=X1)X2R9;

wherein each said R5, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, or $S(O)_n$OR9;

(g) R6 is O, S, NR9, or NOR9;

(h) R7 is substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, OR9$S(O)_n$R9, C(=X1)R9, C(=X1)OR9, R9C(=X1)OR9, R9X2C(=X1)R9X2R9, C(=X1)N(R9)$_2$, N(R9)$_2$, N(R9)(R9$S(O)_n$R9), N(R9)C(=X1)R9, SR9, $S(O)_n$OR9, R9$S(O)_n$R9, $C_1$-$C_6$alkylOC(=O)$C_1$-$C_6$alkyl, O$C_1$-$C_6$ alkyl $C_1$-$C_{20}$ heterocyclyl, $C_1$-$C_6$alkyl$C_1$-$C_{20}$ heterocyclyl, $C_1$-$C_6$, alkylS(=N—CN)($C_1$-$C_6$alkyl), $C_1$-$C_6$alkylS(O)(=N—CN)($C_1$-$C_6$alkyl), $C_1$-$C_6$alkyl$S(O)_n$($C_1$-$C_6$alkyl$C_1$-$C_{20}$heterocyclyl), $C_1$-$C_6$alkylS(O)(=N—CN)($C_1$-$C_6$ alkyl-$C_1$-$C_{20}$ heterocyclyl), $C_1$-$C_6$alkylNH(C(=O)O$C_1$-$C_6$ alkyl), $C_1$-$C_6$ alkylC(=O)O$C_1$-$C_6$ alkyl, $C_1$-$C_6$alkyl($C_6$-$C_{20}$aryl)NH(C(=O)O$C_1$-$C_6$alkyl), $C_1$-$C_6$alkyl(S—$C_1$-$C_6$ alkyl)NH(C(=O)O$C_1$-$C_6$alkyl), $C_1$-$C_6$alkyl(S—$C_1$-$C_6$alkyl-$C_6$-$C_{20}$aryl)NH(C(=O)O$C_1$-$C_6$alkyl), $C_1$-$C_6$ alkyl(NHC(=O)O$C_1$-$C_6$alkyl$C_6$-$C_{20}$ aryl)NH(C(=O)O$C_1$-$C_6$alkyl), $C_1$-$C_6$alkyl(O$C_1$-$C_6$alkyl$C_6$-$C_{20}$aryl)NH(C(=O)O$C_1$-$C_6$alkyl), $C_1$-$C_6$alkylN($C_1$-$C_6$alkyl)(C(=O)O$C_1$-$C_6$alkyl), $C_1$-$C_6$alkylNH($C_1$-$C_6$alkyl), $C_6$-$C_{20}$ arylS$C_1$-$C_6$haloalkyl, $C_1$-$C_6$alkyl-N($C_1$-$C_6$ alkyl)(C(=O)$C_1$-$C_6$alkyl$C_6$-$C_{20}$aryl), $C_1$-$C_6$alkylN($C_1$-$C_6$alkyl)($C_1$-$C_6$alkyl), $C_1$-$C_6$alkylN($C_1$-$C_6$ alkyl)$(S(O)_n$$C_1$-$C_6$ alkyl), $C_1$-$C_6$ alkylN($C_1$-$C_6$ alkyl)$(S(O)_n$$C_1$-$C_6$ alkenyl$C_6$-$C_{20}$ aryl), $C_1$-$C_6$ alkylN($C_1$-$C_6$alkyl)(C(=O)$C_1$-$C_{20}$ heterocyclyl), $C_1$-$C_6$alkylN($C_1$-$C_6$alkyl)(C(=O)O$C_1$-$C_6$alkyl$C_6$-$C_{20}$aryl), NH($C_1$-$C_6$ alkylS(O)$_n$$C_1$-$C_6$ aryl), $C_1$-$C_6$alkyl($S(O)_n$$C_1$-$C_6$ alkyl)(C(=O)$C_1$-$C_6$alkylS(O)$_n$($C_1$-$C_6$ alkyl), or R9$S(O)_n$(NZ)R9, wherein each said R7, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, $S(O)_n$OR9, $C_6$-$C_{20}$ aryl, or $C_1$-$C_{20}$ heterocyclyl, (each of which that can be substituted, may optionally be substituted with R9), C(=X1)R9, C(=X1)OR9, C(=X1)N(R9)$_2$, =X2, N(R9)$_2$, S(=X2)$_n$R9, R9S(O)$_n$R9, S(O)$_n$N(R9)$_2$;

(i) R8 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, OR9, C(=X1)R9, C(=X1)OR9, C(=X1)N(R9)$_2$, N(R9)$_2$, N(R9)C(=X1)R9, SR9, $S(O)_n$R9, $S(O)_n$OR9, or R9$S(O)_n$R9, wherein each said R8, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, $S(O)_n$OR9, $C_6$-$C_{20}$ aryl, or $C_1$-$C_{20}$ heterocyclyl, (each of which that can be substituted, may optionally be substituted with R9);

(j) R9 (each independently) is H, CN, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, substituted or unsubstituted $C_1$-$C_{20}$ heterocyclyl, $S(O)_n$$C_1$-$C_6$ alkyl, N($C_1$-$C_6$alkyl)$_2$, wherein each said R9, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, O$C_1$-$C_6$ alkyl, O$C_1$-$C_6$ haloalkyl, $S(O)_n$$C_1$-$C_6$alkyl, $S(O)_n$O$C_1$-$C_6$ alkyl, $C_6$-$C_{20}$ aryl, or $C_1$-$C_{20}$ heterocyclyl;

(k) n is 0, 1, or 2;

(l) X1 is (each independently) O or S;

(m) X2 is (each independently) O, S, =NR9, or =NOR9; and (n) Z is CN, $NO_2$, $C_1$-$C_6$ alkyl(R9), C(=X1)N(R9)$_2$.

2. A molecule having the following formula ("Formula I"), and isotopes and steroisomers thereof:

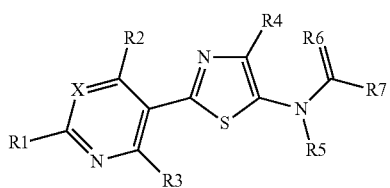

Formula I wherein:
(a) X is N or CR8;
(b) R1 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=XOR9, C(=X1)OR9, C(=X1)N(R9)$_2$, N(R9)$_2$, N(R9)C(=X1)R9, SR9, S(O)$_n$OR9, or R9S(O)$_n$R9,
wherein each said R1, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);
(c) R2 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R2, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);
(d) R3 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, S(O)$_n$OR9, or R9S(O)$_n$R9,
wherein each said R3, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);
(e) R4 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R4, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9);
(f) R5 is H, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, R9S(O)$_n$R9, C(=X2)R9, C(=X1)X2R9, R9X2C(=X1)R9, R9X2R9, or R9X2C(=X1)X2R9;
wherein each said R5, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, or S(O)$_n$OR9;
(g) R6 is O, S, NR9, or NOR9;
(h) R7 is substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, OR9S(O)$_n$R9, C(=X1)R9, C(=X1)OR9, R9C(=X1)OR9, R9X2C(=X1)R9X2R9, C(=X1)N(R9)$_2$, N(R9)$_2$, N(R9)(R9S(O)$_n$R9), N(R9)C(=X1)R9, SR9, S(O)$_n$OR9, R9S(O)$_n$R9, or R9S(O)$_n$(NZ)R9,
wherein each said R7, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, S(O)$_n$OR9, or $C_6$-$C_{20}$ aryl, (each of which that can be substituted, may optionally be substituted with R9)
(i) R8 is H, F, Cl, Br, I, CN, $NO_2$, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, OR9, C(=X1)R9, C(=X1)OR9, C(=X1)N(R9)$_2$, N(R9)$_2$, N(R9)C(=X1)R9, SR9, S(O)$_n$OR9, or R9S(O)$_n$R9,
wherein each said R8, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, OR9, $S(O)_n$OR9, or $C_6$-$C_{20}$ aryl (each of which that can be substituted, may optionally be substituted with R9);

(j) R9 (each independently) is H, CN, substituted or unsubstituted $C_1$-$C_6$ alkyl, substituted or unsubstituted $C_2$-$C_6$ alkenyl, substituted or unsubstituted $C_1$-$C_6$ alkoxy, substituted or unsubstituted $C_2$-$C_6$ alkenyloxy, substituted or unsubstituted $C_3$-$C_{10}$ cycloalkyl, substituted or unsubstituted $C_3$-$C_{10}$ cycloalkenyl, substituted or unsubstituted $C_6$-$C_{20}$ aryl, wherein each said R9, which is substituted, has one or more substituents selected from F, Cl, Br, I, CN, $NO_2$, $C_1$-$C_6$ alkyl, $C_2$-$C_6$ alkenyl, $C_1$-$C_6$ haloalkyl, $C_2$-$C_6$ haloalkenyl, $C_1$-$C_6$ haloalkyloxy, $C_2$-$C_6$ haloalkenyloxy, $C_3$-$C_{10}$ cycloalkyl, $C_3$-$C_{10}$ cycloalkenyl, $C_3$-$C_{10}$ halocycloalkyl, $C_3$-$C_{10}$ halocycloalkenyl, $OC_1$-$C_6$ alkyl, $OC_1$-$C_6$ haloalkyl, $S(O)_nOC_1$-$C_6$ alkyl, $C_6$-$C_{20}$ aryl;

(k) n is 0, 1, or 2;
(l) X1 is (each independently) O or S;
(m) X2 is (each independently) O, S, =NR9, or =NOR9; and
(n) Z is CN, $NO_2$, $C_1$-$C_6$ alkyl(R9), C(=X1)N(R9)$_2$.

3. A molecule according to claim 2 and isotopes and stereoisomers thereof, wherein
(a) X is CR8;
(b) R1 is H;
(c) R2 is H;
(d) R3 is H;
(e) R4 is Cl or $CH_3$;
(f) R5 is H or unsubstituted $C_1$-$C_6$ alkyl;
(g) R6 is O;
(h) R7 is (unsubstituted $C_1$-$C_6$ alkyl)$S(O)_n$(unsubstituted $C_1$-$C_6$ alkyl), (unsubstituted $C_1$-$C_6$ alkyl)$S(O)_n$(unsubstituted $C_1$-$C_6$ alkenyl), O(unsubstituted $C_1$-$C_6$ alkyl), or ($C_1$-$C_6$ alkyl);
(i) R8 is H or F; and
(k) n is 0, 1, or 2.

4. A molecule according to claim 1 or 2 wherein said molecule having a formula according to Formula I is further in the form of a pesticidally acceptable acid addition salt, salt derivative, or solvate.

5. A molecule according to claim 1 or 2 wherein said molecule having a formula according to Formula I has at least one H that is a $^2$H.

6. A molecule according to claim 1 or 2 wherein said molecule having a formula according to Formula I has at least one C that is a $^{14}$C.

7. A molecule according to claim 1 or 2 wherein said molecule having a formula according to Formula I is a resolved stereoisomer.

8. A composition comprising a molecule according to claim 1 or 2 or 3 and at least one member of an Insecticide Group, Acaricide Group, Nematicide Group, Fungicide Group, or Herbicide Group.

9. A composition comprising a molecule according to claim 1 or 2 or 3 and at least one biopesticide.

10. A composition comprising a molecule according to claims 1 or 2 or 3 and at least one of the following compounds:
(a) 3-(4-chloro-2,6-dimethylphenyl)-4-hydroxy-8-oxa-1-azaspiro[4,5]dec-3-en-2-one;
(b) 3-(4'-chloro-2,4-dimethyl[1,1'-biphenyl]-3-yl)-4-hydroxy-8-oxa-1-azaspirol[4,5]dec-3-en-2-one;
(c) 4-[[(6-chloro-3-pyridinyl)methyl]methylamino]-2(5H)-furanone;
(d) 4-[[(6-chloro-3-pyridinyl)methyl]cyclopropylamino]-2(5H)-furanone;
(e) 3-chloro-N2-[(1S)-1-methyl-2-(methylsulfonyl)ethyl]-N1-[2-methyl-4-[1,2,2,2-tetrafluoro-1-(trifluoromethyl)ethyl]phenyl]-1,2-benzenedicarboxamide;
(f) 2-cyano-N-ethyl-4-fluoro-3-methoxy-benenesulfonamide;
(g) 2-cyano-N-ethyl-3-methoxy-benzene sulfonamide;
(h) 2-cyano-3-difluoromethoxy-N-ethyl-4-fluoro-benzene sulfonamide;
(i) 2-cyano-3-fluoromethoxy-N-ethyl-benzenesulfonamide;
(j) 2-cyano-6-fluoro-3-methoxy-N,N-dimethyl-benzenesulfonamide;
(k) 2-cyano-N-ethyl-6-fluoro-3-methoxy-N-methyl-benzenesulfonamide;
(l) 2-cyano-3-difluoromethoxy-N,N-dimethylbenzenesulfon-amide;
(m) 3-(difluoromethyl)-N-[2-(3,3-dimethylbutyl)phenyl]-1-methyl-1H-pyrazole-4-carboxamide;
(n) N-ethyl-2,2-dimethylpropionamide-2-(2,6-dichloro-α,α,α-trifluoro-p-tolyl) hydrazone;
(o) N-ethyl-2,2-dichloro-1-methylcyclopropane-carboxamide-2-(2,6-dichloro-α,α,α-trifluoro-p-tolyl) hydrazone nicotine;
(p) O-{(E-)-[2-(4-chloro-phenyl)-2-cyano-1-(2-trifluoromethylphenyl)-vinyl]} S-methyl thiocarbonate;
(q) (E)-N-1-[(2-chloro-1,3-thiazol-5-ylmethyl)]-N2-cyano-N1-methylacetamidine;
(r) 1-(6-chloropyridin-3-ylmethyl)-7-methyl-8-nitro-1,2,3,5,6,7-hexahydro-imidazo[1,2-a]pyridin-5-ol;
(s) 4-[4-chlorophenyl-(2-butylidine-hydrazono)methyl)]phenyl mesylate; or
(t) N-Ethyl-2,2-dichloro-1-methylcyclopropanecarboxamide-2-(2,6-dichloro-alpha,alpha,alpha-trifluoro-p-tolyl)hydrazone.

* * * * *